US008722865B2

(12) United States Patent
Ryan

(10) Patent No.: US 8,722,865 B2
(45) Date of Patent: May 13, 2014

(54) ISOLATED GENOMIC POLYNUCLEOTIDE FRAGMENTS FROM THE P15 REGION OF ISOLATED GENOMIC POLYNUCLEOTIDE FRAGMENTS FROM THE P15 REGION OF CHROMOSOME 11 ENCODING HUMAN TUMOR SUPPRESSING SUBTRANSFERABLE CANDIDATE 4 (TSSC4)

(75) Inventor: James Ryan, Augusta, GA (US)

(73) Assignee: Kyoger, LLC

( * ) Notice: Subject to any disclaimer, the term of this patent is extended or adjusted under 35 U.S.C. 154(b) by 0 days.

(21) Appl. No.: 13/244,468

(22) Filed: Sep. 24, 2011

(65) Prior Publication Data

US 2012/0053232 A1 Mar. 1, 2012

Related U.S. Application Data

(62) Division of application No. 09/999,121, filed on Oct. 31, 2001, now Pat. No. 8,039,602.

(60) Provisional application No. 60/244,705, filed on Oct. 31, 2000.

(51) Int. Cl.
*C07H 21/02* (2006.01)
*C07H 21/04* (2006.01)
*C12Q 1/68* (2006.01)
*C12P 19/34* (2006.01)
*C12N 5/00* (2006.01)
*C12N 5/02* (2006.01)

(52) U.S. Cl.
USPC ..... 536/23.1; 536/24.3; 536/24.33; 536/24.5; 435/6.1; 435/91.1; 435/325; 435/375

(58) Field of Classification Search
USPC ........ 536/23.1, 24.3, 24.33, 24.5; 435/6, 325, 435/375, 91.1
See application file for complete search history.

(56) References Cited

U.S. PATENT DOCUMENTS

| | | | |
|---|---|---|---|
| 5,582,979 | A | 12/1996 | Weber |
| 5,591,623 | A | 1/1997 | Bennett |
| 6,150,092 | A | 11/2000 | Uchida |
| 6,184,212 | B1 | 2/2001 | Miraglia |
| 6,537,751 | B1 | 3/2003 | Cohen |
| 6,566,135 | B1 | 5/2003 | Watt |
| 6,812,339 | B1 | 11/2004 | Venter |
| 7,125,858 | B2 | 10/2006 | Fillion |
| 8,039,602 | B2 | 10/2011 | Ryan |

FOREIGN PATENT DOCUMENTS

| | | |
|---|---|---|
| WO | W095/20678 | 8/1995 |
| WO | W09844152 | 10/1998 |
| WO | W099/18198 | 4/1999 |
| WO | W000/15795 | 3/2000 |
| WO | W001/62778 | 8/2001 |

OTHER PUBLICATIONS

Examiner'S Interview Summary dated Oct. 6, 2005 for U.S. Appl. No. 09/999,121.
Examiner'S Interview Summary dated Mar. 4, 2009 for U.S. Appl. No. 09/999,121.
Examiner'S Interview Summary dated May 21, 2010 for U.S. Appl. No. 09/999,121.
Examiner'S Interview Summary dated Mar. 31, 2011 for U.S. Appl. No. 09/999,121.
International Preliminary Examination Report from counterpart international application PCT/US01/45381, reported completed on Jul. 27, 2009.
Office Action dated May 14, 2012 for U.S. Appl. No. 13/235,404.
Office Action dated May 10, 2012 for U.S. Appl. No. 13/239,243.
Office Action dated May 11, 2012 for U.S. Appl. No. 13/239,327.
Office Action dated May 11, 2012 for U.S. Appl. No. 13/244,463.
Office Action dated May 11, 2012 for U.S. Appl. No. 13/244,465.
Sequence: GenBank Accession No. AC002536.1 Evans_Dec. 10, 1997.
Sequence Alignments from Office Action dated May 11, 2012 for U.S. Appl. No. 13/239,327.
Sequence Alignments from Office Action dated May 11, 2012 for U.S. Appl. No. 13/244,463.
Sequence Alignments from Office Action dated May 11, 2012 for U.S. Appl. No. 13/244,465.
Wade-Martins et al. "Long term stability of large insert genomic DNA episomal shuttle vectors in human cells." Nucleic Acids Res. 27:1674-1682. 1999.
Alders et al. "The human Achaete-Scute homologue 2 (ASCL2, HASH2) maps to chromosome 11p15.5, close to IGF2 and is expressed in extravillus trophoblasts." Human Molecular Genetics, 6: 859-867. 1997.
Altschul et al. Gapped BLAST and PSI-BLAST: a new generation of protein database search programs. Nucleic Acids Res. 25: 3389-3402. 1997.
Andria et al. "Genomic organization and chromosomal localization of the TAPA-1 gene." J. Immunol. 147: 1030-1036. 1991.
Bowie et al. "Deciphering the message in protein sequences: Tolerance to amino acid substitutions." Science 247: 1306-1310. 1990.
Burge et al. "Prediction of complete gene structures in human genomic DNA." J. Mol. Biol. 268: 78-94. 1997.
Examiner's Interview Summary dated Jul. 14, 2009 for U.S. Appl. No. 09/999,121.
International Search Report from counterpart international application PCT/US01/45381, report completed on Jul. 27, 2009.
Itoh et al. "Proportions of cells with paternal 11p15 uniparental disomy correlates with organ enlargement in Wiedemann-Beckwith syndrome." J. Med. Gen. 92: 111-116. 2000.
Kenmochi et al. "A Map of 75 human ribosomal protein genes." Genome Research 8: 509-523. 1998.
Koi et al. "Tumor cell growth arrest caused by subchromosomal transferable DNA fragments from chromosome 11." Science, 260: 361-364. 1993.

(Continued)

*Primary Examiner* — Terra Cotta Gibbs
(74) *Attorney, Agent, or Firm* — Cheryl H. Agris

(57) ABSTRACT

Provided herein are isolated genomic polynucleotide fragments from the from the p15 region of chromosome 11 encoding human and tumor suppressing subtransferable candidate 4 (TSSC4) and methods of use.

32 Claims, No Drawings

(56) References Cited

OTHER PUBLICATIONS

Lee et al. "Two novel genes in the center of the 11p15 imprinted domain escape genomic imprinting". Hum. Mol. Gen. 8: 683-690. 1999.
Ngo et al. "Computational complexity, protein structure prediction, and the Levinthal Paradox." in the Protein Folding Problem and Tertiary Structure Prediction Merz, Jr., K. and LeGrand, S. eds. Birkhäuser. Boston. 1994.
Notice of Allowance/Allowability dated Jun. 3, 2011 for U.S. Appl. No. 09/999,121.
Office Action dated Aug. 24, 2004 for U.S. Appl. No. 09/999,121.
Office Action dated Sep. 8, 2005 for U.S. Appl. No. 09/999,121.
Office Action dated Jul. 27, 2006 for U.S. Appl. No. 09/999,121.
Office Action dated Oct. 6, 2008 for U.S. Appl. No. 09/999,121.
Office Action dated Jul. 7, 2009 for U.S. Appl. No. 09/999,121.
Office Action dated Jan. 5, 2010 for U.S. Appl. No. 09/999,121.
Office Action dated Nov. 8, 2010 for U.S. Appl. No. 09/999,121.
Oren et al. "TAPA-1, the target of an antiproliferative antibody, defines a new family of transmembrane proteins." Mol. Cell. Biol. 10: 4007-4015. 1990.
Pileri et al. "Binding of Hepatitis C Virus to CD81" Science 282: 938-941. 1998.
Reik et al. "Imprinting in clusters: lessons from Beckwith-Wiedemann syndrome." Trends in Genetics 13: 330-334. 1997.
Segade et al. "Differential Regulation of the Murine Ribosomal Protein L26 Gene in Macrophage Activation." Life Sciences 58: 277-285. 1996.
Sequence: EMBL Database 'Online' 1997 "Human chromosome II pac pdJI075f20" see nucleotides 17080-34380.
Sequence: GenBank Accession No. 003693 (version 003693.1) Human Chromosome 11 p15.5 PAC clone pDJ915f1 containing KvLQT1 gene, complete sequence, PRI Sep. 30, 1995, downloaded on Jul. 2, 2009.
Sequence: GenBank Accession No. ACO26645 submitted by Waterston, R. H. et al. Mar. 22, 2000 bases 2312-4001.
Sequence: GenBank Accession No. BE295955 (version BE295955.1) 60117424SF1 NIH_MGC_17 *Homo sapiens* cDNA clone Image: 3529954 5-, mRNA sequence, Entry Created: Jul. 5, 2000 (Entry Updated: Jul. 20, 2000).
Sequence: GenBank Accession No. BE560890 (version BE560890.1) 601346329F1 NIH_MGC_5 *Homo sapiens* cDNA clone Image: 3679567 5-, mRNA sequence, Entry Created: Aug. 10, 2000 (Entry Updated: Aug. 10, 2000).
Sequence Alignments from Office Action dated Sep. 8, 2005 for U.S. Appl. No. 09/999,121.
Sequence Alignments from Office Action dated Jul. 27, 2007 for U.S. Appl. No. 09/999,121.
Sequence Alignments from Office Action dated Jul. 7, 2009 for U.S. Appl. No. 09/999,121.
Sequence Alignments from Office Action dated Jan. 5, 2010 for U.S. Appl. No. 09/999,121.
Siebert et al. "An improved PCR method for walking in uncloned genomic DNA. Nucleic Acids Res." 23: 1087-1088. 1995.
Virtaneva et al. "Chromosomal localization of three human genes coding for A15, L6, and S5.7 (TAPA1): all members of the transmembrane 4 superfamily of proteins." Immuogenetics 39: 329-334. 1994.
Westerman et al. "The human Achaete-Scute Homolog 2 gene contains two promoters, generating overlapping transcripts and encoding two proteins with different nuclear localization." Placenta 22: 511-518. 2001.
Witherden et al. "CD81 and CD28 costimulate T cells through distinct pathways." J Immunol. 165: 1902-1909. 2000.

SEQUENCE LISTING

```
<160> NUMBER OF SEQ ID NOS: 14

<210> SEQ ID NO 1
<211> LENGTH: 193
<212> TYPE: PRT
<213> ORGANISM: Homo sapiens

<400> SEQUENCE: 1

Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
                20                  25                  30

Arg Cys Ser Arg Arg Arg Arg Pro Ala Thr Ala Glu Thr Gly Gly Gly
            35                  40                  45

Ala Ala Ala Val Ala Arg Arg Asn Glu Arg Glu Arg Asn Arg Val Lys
        50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
                100                 105                 110

Arg Asn Ala Leu Ala Gly Gly Leu Arg Pro Gln Ala Val Arg Pro Ser
            115                 120                 125

Ala Pro Arg Gly Pro Pro Gly Thr Thr Pro Val Ala Ala Ser Pro Ser
        130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
                180                 185                 190

Tyr

<210> SEQ ID NO 2
<211> LENGTH: 132
<212> TYPE: PRT
<213> ORGANISM: Homo sapiens

<400> SEQUENCE: 2

Met Gly Arg Thr Trp Cys Gly Met Trp Arg Arg Arg Pro Gly Arg
1               5                   10                  15

Arg Ser Ala Val Pro Arg Trp Pro His Leu Ser Ser Gln Ser Gly Val
                20                  25                  30
```

```
Glu Pro Pro Asp Arg Trp Thr Gly Thr Pro Gly Trp Pro Ser Arg Asp
            35                  40                  45

Gln Glu Ala Pro Gly Ser Met Met Pro Pro Ala Ala Ala Gln Pro Ser
 50                      55                  60

Ala His Gly Ala Leu Val Pro Pro Ala Thr Ala His Glu Pro Val Asp
 65                  70                  75                  80

His Pro Ala Leu His Trp Leu Ala Cys Cys Cys Leu Ser Leu Pro
                 85                  90                  95

Gly Gln Leu Pro Leu Ala Ile Arg Leu Gly Trp Asp Leu Asp Leu Glu
                100                 105                 110

Ala Gly Pro Ser Ser Gly Lys Leu Cys Pro Arg Ala Arg Trp Gln
                115                 120                 125

Pro Leu Pro Ser
    130

<210> SEQ ID NO 3
<211> LENGTH: 290
<212> TYPE: PRT
<213> ORGANISM: Homo sapiens

<400> SEQUENCE: 3

Met Val Thr Leu Thr Tyr Phe Gly Ala His Phe Ala Val Ile Arg Arg
 1               5                  10                  15

Ala Ser Leu Glu Lys Asn Pro Tyr Gln Ala Val His Gln Trp Ala Phe
                 20                  25                  30

Ser Ala Gly Leu Ser Leu Val Gly Leu Leu Thr Leu Gly Ala Val Leu
                 35                  40                  45

Ser Ala Ala Ala Thr Val Arg Glu Ala Gln Gly Leu Met Ala Gly Gly
 50                      55                  60

Phe Leu Cys Phe Ser Leu Ala Phe Cys Ala Gln Val Gln Val Phe
 65                  70                  75                  80

Trp Arg Leu His Ser Pro Thr Gln Val Glu Asp Ala Met Leu Asp Thr
                 85                  90                  95

Tyr Asp Leu Val Tyr Glu Gln Ala Met Lys Gly Thr Ser His Val Arg
                100                 105                 110

Arg Gln Glu Leu Ala Ala Ile Gln Asp Val Phe Leu Cys Cys Gly Lys
                115                 120                 125

Lys Ser Pro Phe Ser Arg Leu Gly Ser Thr Glu Ala Asp Leu Cys Gln
                130                 135                 140

Gly Glu Glu Ala Ala Arg Glu Asp Cys Leu Gln Gly Ile Arg Ser Phe
145                 150                 155                 160

Leu Arg Thr His Gln Gln Val Ala Ser Ser Leu Thr Ser Ile Gly Leu
                165                 170                 175

Ala Leu Thr Val Ser Ala Leu Leu Phe Ser Ser Phe Leu Trp Phe Ala
                180                 185                 190

Ile Arg Cys Gly Cys Ser Leu Asp Arg Lys Gly Lys Tyr Thr Leu Thr
                195                 200                 205

Pro Arg Ala Cys Gly Arg Gln Pro Gln Glu Pro Ser Leu Leu Arg Cys
                210                 215                 220

Ser Gln Gly Gly Pro Thr His Cys Leu His Ser Glu Ala Val Ala Ile
225                 230                 235                 240

Gly Pro Arg Gly Cys Ser Gly Ser Leu Arg Trp Leu Gln Glu Ser Asp
                245                 250                 255

Ala Ala Pro Leu Pro Leu Ser Cys His Leu Ala Ala His Arg Ala Leu
                260                 265                 270
```

```
Gln Gly Arg Ser Arg Gly Gly Leu Ser Gly Cys Pro Glu Arg Gly Leu
        275                 280                 285

Ser Asp
    290

<210> SEQ ID NO 4
<211> LENGTH: 145
<212> TYPE: PRT
<213> ORGANISM: Homo sapiens

<400> SEQUENCE: 4

Met Lys Phe Asn Pro Phe Val Thr Ser Asp Arg Ser Lys Asn Arg Lys
1               5                   10                  15

Arg His Phe Asn Ala Pro Ser His Val Arg Arg Lys Ile Met Ser Ser
            20                  25                  30

Pro Leu Ser Lys Glu Leu Arg Gln Lys Tyr Asn Val Arg Ser Met Pro
        35                  40                  45

Ile Arg Lys Asp Asp Glu Val Gln Val Val Arg Gly His Tyr Lys Gly
    50                  55                  60

Gln Gln Ile Gly Lys Val Val Gln Val Tyr Arg Lys Lys Tyr Val Ile
65                  70                  75                  80

Tyr Ile Glu Arg Val Gln Arg Glu Lys Ala Asn Gly Thr Thr Val His
                85                  90                  95

Val Gly Ile His Pro Ser Lys Val Val Ile Thr Arg Leu Lys Leu Asp
            100                 105                 110

Lys Asp Arg Lys Lys Ile Leu Glu Arg Lys Ala Lys Ser Arg Gln Val
        115                 120                 125

Gly Lys Glu Lys Gly Lys Tyr Lys Glu Glu Leu Ile Glu Lys Met Gln
    130                 135                 140

Glu
145

<210> SEQ ID NO 5
<211> LENGTH: 236
<212> TYPE: PRT
<213> ORGANISM: Homo sapiens

<400> SEQUENCE: 5

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
            20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
    130                 135                 140
```

```
Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
            165                 170                 175

Ser Gly Ser Asn Ile Ile Ser Asn Leu Phe Lys Glu Asp Cys His Gln
            180                 185                 190

Lys Ile Asp Asp Leu Phe Ser Gly Lys Leu Tyr Leu Ile Gly Ile Ala
            195                 200                 205

Ala Ile Val Val Ala Val Ile Met Ile Phe Glu Met Ile Leu Ser Met
            210                 215                 220

Val Leu Cys Cys Gly Ile Arg Asn Ser Ser Val Tyr
225                 230                 235

<210> SEQ ID NO 6
<211> LENGTH: 329
<212> TYPE: PRT
<213> ORGANISM: Homo sapiens

<400> SEQUENCE: 6

Met Ala Glu Ala Gly Thr Gly Glu Pro Ser Pro Ser Val Glu Gly Glu
1               5                   10                  15

His Gly Thr Glu Tyr Asp Thr Leu Pro Ser Asp Thr Val Ser Leu Ser
            20                  25                  30

Asp Ser Asp Ser Asp Leu Ser Leu Pro Gly Gly Ala Glu Val Glu Ala
            35                  40                  45

Leu Ser Pro Met Gly Leu Pro Gly Glu Glu Asp Ser Gly Pro Asp Glu
50                  55                  60

Pro Pro Ser Pro Pro Ser Gly Phe Leu Pro Ala Thr Val Gln Pro Phe
65                  70                  75                  80

His Leu Arg Gly Met Ser Ser Thr Phe Ser Gln Arg Ser Arg Asp Ile
            85                  90                  95

Phe Asp Cys Leu Glu Gly Ala Ala Arg Arg Gly Pro Ser Ser Val Ala
            100                 105                 110

His Thr Ser Met Ser Asp Asn Gly Gly Phe Lys Arg Pro Leu Ala Pro
            115                 120                 125

Ser Gly Arg Ser Pro Val Glu Gly Leu Gly Arg Ala His Arg Ser Pro
130                 135                 140

Ala Ser Pro Arg Val Pro Val Pro Asp Tyr Val Ala His Pro Glu
145                 150                 155                 160

Arg Trp Thr Lys Tyr Ser Leu Glu Asp Val Thr Glu Val Ser Glu Gln
            165                 170                 175

Ser Asn Gln Ala Thr Ala Leu Ala Phe Leu Gly Ser Gln Ser Leu Ala
            180                 185                 190

Ala Pro Thr Asp Cys Val Ser Ser Phe Asn Gln Asp Pro Ser Ser Cys
            195                 200                 205

Gly Glu Gly Arg Val Ile Phe Thr Lys Pro Val Arg Gly Val Glu Ala
            210                 215                 220

Arg His Glu Arg Lys Arg Val Leu Gly Lys Val Gly Glu Pro Gly Arg
225                 230                 235                 240

Gly Gly Leu Gly Asn Pro Ala Thr Asp Arg Gly Glu Gly Pro Val Glu
            245                 250                 255

Leu Ala His Leu Ala Gly Pro Gly Ser Pro Glu Ala Glu Glu Trp Gly
            260                 265                 270

Ser Pro His Gly Gly Leu Gln Glu Val Glu Ala Leu Ser Gly Ser Val
            275                 280                 285
```

```
His Ser Gly Ser Val Pro Gly Leu Pro Pro Val Glu Thr Val Gly Phe
        290                 295                 300

His Gly Ser Arg Lys Arg Ser Arg Asp His Phe Arg Asn Lys Ser Ser
305                 310                 315                 320

Ser Pro Glu Asp Pro Gly Ala Glu Val
                325

<210> SEQ ID NO 7
<211> LENGTH: 17290
<212> TYPE: DNA
<213> ORGANISM: Homo sapiens

<400> SEQUENCE: 7
gcccctgcct ggatcacaac aggcaggacg gctgagcagg cacacatctg tctctccctc     60
tgctgatctg tggccttgga caggggctac tctgggggag ctgacaggtg accccccag    120 gaggcccctc cctgcctctg gctgggaat ccacctctgt ggagccctg ggaatggcct    180 gtttcaaata cgtaagtggg agcaaggtct catcctcagc gggggacatc gctgggggca    240
aggccagtgg gtgggtggga aggtttctgt ggcactgggg cctcctgttg attgattcac    300
ccaattaatc acagccagca gctggggagg gggtaggaag gcggtgaagg gaaaaggagc    360
ccacagccgg gaggccctgg gaggttggca gaggcctgca cctgcctgca gccagccctc    420
cggcccagcc ctcttccctc ctttcggagg ggccagagca tggggtgcta agggctcagt    480 cttaacccc tccccagctc tcagggagcc cctcccatgc tccccaggcc tctgccccac    540
ttgcacctcc ccgggcccca gggcacagga cgctttcccc acccttggg aggctgaggg    600 tgtcaggagg cctgggctga gtgctggctt ccgtctcact ggcttgcaga caagaccctc    660
catttcggtg gaaaaacagc aagaacagca ccccctcca ggcagaccca agggaggcat    720
cggtgtgagg gcttcaagct ctgtactgtg gtttaagcc ttgcacctct ggatacctgt    780
gggcctcggg cagatcactg agcctccctg catctggaag tcgggtgag accctcaga    840 ggggctggg aggaggaagg gcccctcttg atgggcagcc cccaccctcc acctactgcc    900
ctgccctccc agccttcagg gtcctcccca gcttctgtgg gctcccaggt ggacctgggc    960 caccctgag accccgaaga gctcaaggcc agctaatagc ccacaggctc aggacagcac    1020
tggacaggcc tctgggccca cctggcccca ctcccgattt ttatgggaac aaagactgaa    1080
ggtgtggccc caaaggaacc accctcccc cagtgccccg ctgctgggaa aagggtcagc    1140
agagtttggg tctccccca caagcccct gggctgtgcg tgctacagct gaggacatgg    1200
cgttgagggg caggccgcct ccaacccgt ccaccttgcc ctgtctagct ctgtccaagg    1260
ctctctccgg ctggctaatc acctctgggc acagctgtgc tgctgaggtc tctgggatga    1320
ctgaaggtct ttgaaggcca cttgggaga agcgaaggtg catggacacc agggaccctg    1380
ctcacagcga gtgtccctgc ccatcccctt tctgcattga gtgggacaag cttgcttcca    1440
tttgggggat cgccatctga ctattccact tgtcttaggg tggggcagag attaggtgat    1500 gtggagggc ttctctacat ggcccccctg ccccagctct gagggtagc accagagtgg    1560 gtttcaccag cgtagggcac gtaggcccg ccatgaacag ggcccaacc ttggtttaat    1620 gctttgctac tgccatctta aagttctttt tttattttt attttgcttt attttttatt    1680 agagatggg tctcccagtg ttgcccaggc tggtcttgaa ctcctggctc aagcaatcct    1740
ccggcctcag cctcccaaag cactgggatg acacgtgtga gccaccttgc ctggcctttg    1800
gaatctgact acttttatct tctaacttgt tttgcaggtg caggccaacg gcatacagca    1860
gcactcacat aagcaaagga gagcgtgcac aaggcgccaa atgtatatcc accctcactc    1920
```

```
gtcccccccac ttgagtagcg catccacgat gcccacagac accaggccac acagaaaagg    1980
tgccagggac ccacagcagt gcaaggcagc gtgtcacacc tacgcatgag caagccgggc    2040
gctgatggcc accgagcagc cacgttttcc attcaaatcc gcacttgcta aggatgcagc    2100
aggaagccag tggtgttcta caaacgtgc aggacccggg aacctgtcat gtcctttctt    2160
acttgtgcga cttctctgtg ttagccgagg tctcttgctg atggatctac ccacagtgcc    2220
ttttgtcttt gaacttgtcc cttccctcct tcctcgccca tcagcgagca ggaggtggag    2280
ggtgctggtg gaacaagcct gcgtcaagga gtgaaatcag ctgatttcat ttttgtgcag    2340
tttccactgt tctagtagca aatgaaatag agacgcctgt gccaggacaa aacacacact    2400
gtgtcattcc agtgattccg catagaagtt aaatgctctt atgcttgcat tttaaactgg    2460
catcacataa tataaagatg gataactaca ttcacgctag tcacttaaat tcctaatctt    2520
tcttactcag aatggcatta aatagtgagt ataaaataag aagtataaaa tagtaagtca    2580
agaggttgac tatagaagaa agaaaaatgc tttatatttt agcaccttga acatgacatc    2640
acgatcacct tctccctgga atcagtttct aacttccagg tggggactag gcctggacca    2700
tgagctccta gcagagccct gctgcccca cagcagagcc caggacaggc tggcacctgg    2760
gccaggtgag gctctgtcca ggctcactga tctcaaatgc tgaactgcta aggatgtcat    2820
gtccccaaag gagccgccag gctcagcctc acttcctgga aggcgtgaac attgcaagaa    2880
tgtggaagtg aaagagtcca gggcttaaat ctcaattctc atcattttca agctgagtcc    2940 aaggagaga agacagtcat ggattcttag tttctgtttc tggttgagcc agcagggtcc    3000
cttcctcatc cctctttct gcttatcact agagacagaa actaaaacca tgactttagg    3060
ctgctgagag cctaaaacaa aacgacagca agagaaggtg ggttggacca gcttgcctgt    3120
gacttcaggc acttcatctt tactgggcac tgggtgaatg acagtgtggg gaggggtctt    3180
cataacacgg caatcagcag cccactgtgc ccaggagact cgcctgtggt cctggttatc    3240
aaccacagcc cttttccagtc tcaaaaatgt ccccgctggg acagcaagtt acatcgtcgc    3300
tacaagtcct gtctcctggg agatgcagtc cagcagcact acatcctctg agcagcaggt    3360
gccaagtggg atgaactgga taaggactgc attcggggaa acgcccgtgt gaaaggaaat    3420
acacaggaag gaggtggcaa cgggtgggaa gccactagac cacgacgcga ttctgcccca    3480
gtgaaggcga gggatagcc tgggcctaga tcgctgtgag gtctatggaa gtttccacaa    3540
gcttgctggg tagttctcga ggcaaactcg gaaagggagt cccttgtctc cctggaacgg    3600
atctttcttg gcatctctgt cacactcatt aggtgggcct ggtgtcaacc ccatttgcag    3660 gccacccca acttgatcaa aggtccgctt ctggcacccc ataccctgtc ctacaggaaa    3720
tacagggaca ggctcccaat aacaacaccc agcacggtgc catcaacacc accacgcaca    3780
cgggggctca acggaacaga catctccgct tcttcaatga agacactgga gggaaattgc    3840
ttacaaggcg cttaagagac ctattaagca aacttgatgt gtggacctgc ggcggatccc    3900
gattctataa ggccaactgc acaaaaccac gagacccct gaggactgcg ccattggctg    3960
ggtccccgat gatatgaaag aacggtggtt catttgagcg ggtgatgttt ttgcggtttc    4020
ctttagaggc acacgtgaaa catgacgggt gaaaggattc aaagtctggg atttgcttca    4080
aagcaacgca gggatggcgt gggggatgga tgggcagga agggccttga aactggtgct    4140
ggaggcttcc cagggctgcc ctggagccca gtgcgtcctc caccggccag actgtacaac    4200
ggttggatcc tgtgtccact gctaggaccc aggctccacg agcacgggct tgtgtggcac    4260
acggatgcac cctaagtcct ggcacagaga ctgctcaaca aaggcctcgg tgcttttgtg    4320
```

```
tatgtttgaa attttccata ataaaatgaa aaatgggaaa atgggaaaac aaaaatggca    4380
gcactactta ccctctgcag agttttgtcc gcttcacgcc agtgggtggc agtcgtttcc    4440
tctgccctgg ccttccatcg tttccccccct accctcttca cccacccaac agccccctgt   4500
ggtcctggca gctgtgggcc tttccttgag gtcaaggtgt ggagtcctgg ggagggctca   4560
gggaggccac cgacccgggt gtggattctg ggagaagcct gtgggatgtc cctccctggg   4620
tgaccacggc aatgtgcccc ctcctgtccc ttggccaagg ccagttccct gagccctgca   4680
gccccaagcc acagctggtc cactgacccc agttgagcct ggtcctcatc agaccagctg   4740
acccctttga cccccgctac agactcggct ttgaccttgg ctgctgagga gcccccacct   4800
ggactgagc tgcagctggc gagagaggag ccctgagctc ctctgataag aagggacctg   4860
gccagcctga cgtttgagac ccaggcatcc cggtagcctg ggtgtcctgt tgccgtggtt   4920
attcaggagc cacccactct gggacaacac cagctgctcc cacctcgcag ggctcccacg   4980
gctctgtccc aaccactcct ttctgaagga aggggtgcct ctgcgcccta aagaaaccgg   5040
gggagcccca caaccctcc cccaccagga cactaaaagg cagctttcgg tacagtgaga   5100
catcaaagcc tcctaggccc tgagtcaaag gtatagccgt gtaatatccc agtgccagct   5160
ctccggctgc ggggagcctg gcgcaaagct tccaagcctt ccttgttcct ttcaagagcc   5220
gctcttagaa ttcaggtgag cggagacctg cagggcctcc ccagtgcggg caaaacccaa   5280
agctagcgag agggcagcct ccaggcacct ctcactaact cctcccagag gccgttgagg   5340
tgggtctggt caaacccatt tgcaagttaa cccacttgcc ctgggctgcc cagctgccac   5400
gttagtggag atctgagcgt ggtggcctgc gcaggagccc atgccctcag ccccacagcc   5460
ggtgctctct ggtcagacca cctcagccta gccccacacc cagcacttac cccagccctc   5520
gggatgggtc agcagcctcc agcctgcagc ttccaagcca gcgagtagcc ctgtctggac   5580
aaccccaccag cccaccacct cctggaggat gcccccagcc tcacaaggtg tcccaatggc   5640
tccgctatca acggcctggc tgcactccag atctcaccca gacccacccct acggaggagg   5700
cagcagggtt tgaggagtag tgaccacgga agtctggccg tcacctggga agtgtaggtg   5760
ataggagcca ctggtaaaca gaactgattt atttataaag ttcacgctcc cttgaagagg   5820
tgtgccccac acaggcttct ccctagcaga gcagcagtgc ccacaaaccc accccagggt   5880
gggctgtcac gggggcctca cgccagggac cccgcccctc agggactgct cgtgtccaga   5940
tcttggccag catggaaaac tccagatagt gggggcaggg gtccaggtca tctttattac   6000
gccccaggtc aagggttctt tgtacaaaaa taggtctccg tttgccagca gtgtccctcc   6060
agcagctcaa gttaatgtgt agaaaatgga ttctctgtgc ccttagaaaa tcctctcccc   6120
tccggaaaaa tctccaagtg ttggtgcccc ccgcccact gcagtcgaga agctgtgggg   6180
aggggcggcg tcgaggaag ccgccagccc ttatggggcc agctccaagc ccgtttccac   6240
cgcggcattg gtcaggctgg gccggacgaa cgaggcggcg tcggcggtgc ggggggtggt   6300
gggtgggtcc ccggctcgct gggggcggag cgcggggccgg tccacctggc gggctccccg   6360
gcgatgagcg cgccggccgc tcgctcggct tccgggggctg aggctgcggg gggaaggtgg   6420
ggaaccaaac gcgcgtcaac gcgggcgcgg gcccggggca gaccccgccc gggccggccc   6480
tgcccgcacc tcccccaagc gaactcggca gtttcgtttg ctcggttggt tttggagtct   6540
tgagtccgtg ggtgccgcga ctcggtctga gacacggcgg gggcggggcg ggcgctcgga   6600
gccgcggtga gtcagggctc cgcgcccgcc gactcatttc tgccgccccg gcccgggagc   6660
gcgatttgca atgcaaagtc accccgcctc cagcacccca atctgcccca ggatccgcca   6720
```

```
gcactagaga ccctcaacggc ccgacggccg ctcccctccc ctcgtctacc cctccctcgt   6780
cggcggctga gccgcgaggg gaagttttgc aatcccggac aaacaaacgc cggtcttgca   6840
cgggcttgaa aaactttggg ggaaatgaag agtgagcgaa atcgaagcca tcgctcgggc   6900
ctggcgctcg gctccgcggg ctcctggggg cgcgacccgc cgggcctgcc caccccgtcc   6960
ctccaccccg gcccccggcc ctccctcctc cctgcctccc ggctgttacc tcataggtcg   7020
agggcgctca gtagccccct aaccagctgg agaagtcgag tagctcgcgc tccgcaggac   7080
tcagcgcgcc ttcgcagccg ctgtcgtccg acgagtaggc ggaacgcggg gagccgggct   7140
ccgagctgcc cccgcggccc ggggacgaag aagcgcggga gggcgaggcg gcgaccgggg   7200
tggtccctgg cggcccgcgg ggcgcagacg ccgcacggc ctgcggcctc agccctcccg   7260
ccagcgcgtt gcgcacggcg tcgtgctcgg ccagcaggcg ctgcagcgcg cggatgtact   7320
ccacggctga gcgcagcgtc tccaccttgc tcagcttctt gctggcgccg ccgtgcggca   7380
cgtgctgccg cagcgcctgg aagcccaagt tcaccagctt cacgcggttg cgctcgcgct   7440
cattgcgccg cgctacggcc gctgcgccgc ctccggtctc tgcggtggcc ggtcgccgcc   7500
gccggctgca gcgcaacagt tccggggacg cgggtctccg ccgggcagcg cagccgacag   7560
ggacgggggg cgcaggggc gcggacctgg gcagtgtgcc gccgtccatc gcgcctgcat   7620 ccaccgccc gctccaggtc ccggcgcgcc gcaggaaggt gcaggcagag gaaccggagg   7680
cgacggggaa aactgtggcg ccccaagggg gcttctggca cggcgccgcc aggcaactcc   7740
ccagggcacg cgtcctaggt cgtctggagc ccggggatag gaggcctagt ggtggcaggc   7800
cgtacgcgcc agggagcgtg ggacgctcgt gtcccgcgcg tgcggccgga ctctcccagg   7860
tctccgcagg cgcggcgcag gcggctggtt tttaaatgta tagataaccc tcctccgcgc   7920
cgccgccgtc gccttctca cgccctcctt ccttcgcctc gccctcccgc cacgcttcgc   7980 cctcccctc gcgcgatcac attctgtaag gcccaaagcg tgcgcatgtc cccctagccc   8040 atccccgga cgcagtccac agatccccag tgcgcccaac tggcgaaatc tgcgagttcc   8100
cggtgcgccc cctgctcccg gcaggtgctt agtgcgcccc caaagcaagg tacgcaggtc   8160
ctgggttgag ccttcccgta cccccaccct aacccgcgc gcagccccgc cagtcccaag   8220
agccgccaga ccttcgcacg cgcagcgcgc gctgtgggag ggaaggcgcg gccctggcga   8280
caacacggct gttcgggagg cgcgcaagat ccccggggc agcacgcgcc gcgcagccca   8340
cacccacgcc ccaccctcct ggggccgagg aggcgggggc cagggtctca gccaatcgtg   8400
ggccacccgt ttggccaatc gcgcagggcg cggctccacg cccggcccca ttgaggaagc   8460
gcgtacgcgt ggcgcgtggc tcacggggag catcgctaac aaagctgggt tcctgctggg   8520
ccccgccctg ctcctcgccc ccgcgactgg gctgggcgcg ctgtccccta gcgcagctat   8580
gtcccgagcg cgccccacc tgtgcgttaa tctactggga atgggggtgg actgcgcctt   8640
acctggggcg gggtggggct taaggagtgg tcgagactga ggcggggtgg gaggttcagg   8700 ttccgggc gccttcccca acccgccccg ctttccccgt ccctccacgc gcaccctgcc   8760
tgtggtttcc gtgcgccccc ggcctgaggg ctctgggcgg caccttaacc cggagggcct   8820
ggaggtctgc acccgaccgc cttgtgccag gacggtcagg tccacgccct ccccaccgt    8880 ggctccctcc atctgcagta tccccacct ccagcccgtc ctgccctcct gttctccgtc   8940
tcgcttcccg tcggtgcctc cgggatctca cagccctcgc acctctttg tgacccaggc   9000 tgttttttctg cacccccctc tccctgagg gcactgagat tgggccattg gcctgaaggt   9060
ctctgggagc agcaccttc caggggaggt gggacgtcga gaacttctcc ctaagagatg   9120
```

```
cggggaaatg gtggggcctg agagtgcaaa cactgcagaa atgcgaaaaa tgtagtgtta      9180
acggaagagt ttaggtcctg cctcactgtc cgggaaacgc gtgccctcgg gggagccttt      9240
gccaagccgg ttttcccga aggtgaccag atgctcctgg ccactgcct ctgagacctc       9300 agggaacgga gattttgtg acccagctg cctggagctg ctttcctgtt ccggccggag       9360
gaggtgaggc caagacccc tcctgggagc tggggcag atagccagtg tttactgcca        9420 gcctcgggt gcccacctgc tcccattacc ctgcaggatg ctgctggctg cccacctgg       9480 gcccccagca cacctgtgtc tcgagtacgc ctggccctcc tgccttggga ggggccggaa     9540
gagtagcacc tgcctgggag ctggtggtct gcggtctcta tttggcagat gaggaagccg     9600
acttggagag aaccctggat gtgtccacag tcactcctcc gcccagtgga gcgatccagg     9660
cagaaatcgg ggccctgagt ctgaatccgg gttctgcaac cagggcagat gcgggcttgc     9720
ctctgctccc tgtccctggt ctgagagccc attcttccca gatggtcact tggcaaatca     9780
cagcctggca tggattgttc tgccctcctt ctgctgcctc cctccttccc cttgtcaagg     9840
ctgcaagacc aggatctagg aacgatcctg gagccctgca aactaggcct tggaaatccc     9900
tgctggattt ccacctcccg ggctgggagc ccctcggtca tctgttgctg tgtaaggagc     9960
caccaggatt ttagcggtct gaacaacgat gtattatttc tcaggattct gtgacttgat    10020
gggtgggccc tctgctgctc tgggtgtggc tgcatacacc ccggggggtca acagggacga   10080 gcggtacagc ggctgggttg ctctctaccc ggtcttcgtc caagcccctc cacagctggt    10140 aagatcccg gagcaggacc tgcaagccct cttcagatca ccccagaact tcctgtctaa     10200
aaactgaagc ctctcactgc ccaggcatgg cttcttgcta ccctgccctc aggcacagtc    10260
ctgcacccac ctgcgtctgc tgtgccatgt ccaggccagt ccccccccac caccaacacc    10320
tctctctatc ttcatcctct tcccaatctg gtcctccac cgctgtggaa accccgtctg     10380
cccccaaagc ctagcttaaa aataattccc tagggacctg tgtctctccc tgcctcggcc    10440
cctccttcat tcctgggtgc ctccggctgt gcagcatttg acactgcagc accccccctta   10500 attcggaagc atgctgtctc ctggactggt gagtctccac actatctgag ccgtcttctc    10560
tggaactctt ggcctctcag tccgttctga gaatacagcc ttggtaagca cggtgcccac    10620
atgaatgttt ccagcagcag gattcaaaat agccacatgt ccatcaacag atgagtggat    10680
aaacaaaaca tggtccagaa taatggaaga ttactcagcc ctaaaaagag acgaagctgg    10740
tgaacctcga gaacacgagg ccgcgtgaac gaagccagac accgaggacc acgtagcgtg    10800
agactctcag tctatgaaat gtgcggagtc gataaattca cagagacaga aaggagattc    10860
acggttgcca ggggctgggg agtgacaaca gagggatggg ggtgactgtg aaagggtacg    10920
tggtttcttt cccagaggat aagaacgttc taacatggcc tgtcctgttg gcttcacagc    10980
tctgtacaac acacaaaaaa accattgaaa tgtacactt gtggaatgtg aactgtatct    11040
tgataaagca gttagaagac cttcgaacat aagcatgcgg cctcatgggg cctttgcctg    11100
ggcaccctgg cacctctccc aggctctacc tatctccgac ttcattcctg agctcttgaa    11160
caggggtaag gcaaactttt tctgcaaagg aacacgtggt aagtattttc ggccttgacg    11220
gtcacatgtc tctgccacga gtcgtctgcc ttggggcgca aatgcaggct gggcaggga    11280 agaaataaca aaacttgctt cctggtcact gaaacatgaa gtccaggtca cactcactgt    11340
tacaaaatac tccgaatttt cagactgtgg ttcaatacac atgacataaa atggaccttc    11400
ttaaccattt gtaagtgcac ggttccgtgg aattcagtat attcatgtgg ctgtgcaatc    11460
atcaccacca tccatctcca aaagtttctc attttcccaa accgaaagtc tgtccccatt    11520
```

```
aaacagcagc ttcccatgac ccttccccca gccctggca cccaccatcc actctgtgtc    11580
tgtagatttg actgctctgg agacctcctg taagtggaat cctacagcat ctgtcttttt    11640
gtggaccggc ttcttacact gatgctgatg ccctcgagct tcatccatgt cgtagcctgc    11700
ataaggattt cctctctttt tatgggtgaa taatattcca ctgtatgggt agaccacggt    11760
gttgatccgt tcctccgtca gtggatgctg gggtggtttc cacccttggg ctaccgtcag    11820
tgacgctact gtggacatgg gggtacaaat atctctttga gatcctgctt tcagttcttt    11880
tggggataga cggagaagcg gagttgccag gtcatacggc aaacctctgt ttaaccttt    11940 gagggaccac catgttgttt tccgcagtgg ctgcccacag tacattcctg ctgcgcacga    12000
ggttctgatg tctccacatc cccgcccaca cttggtgctt tctgggtttg tttcgtttcg    12060
ttttgttttt gtttgttttt gagacggagt ctcgctctgt ctcccaggct ggagtgcagt    12120
ggcgcaatct tggctcactg cgacttctgc ctcccgagtt ccagccattc tctagtttca    12180
gcctcccgag tagctgagac tacagatacg tgccaccatg cccggccaaa ttttattt     12240 ttgtagagat agagtctgac tatgttgccc agcctggctg aggtgataat agttttttga    12300
tgatagctaa tgggtatgga ttttaatttt ttaaccactt aagaatttaa agaaaattcc    12360
tagcttttgg gcaatacaaa agcaggccag gggctggatc tggcccatgg gcctcggtct    12420
gctgacagct gctccagagg actggtatgt ccacgtgaca cctggcccga cccccatcct    12480
cctgcagctc ctcaaaactca acttgttgca ggttgaactc ggcctccttt cctctaagga    12540
aagatcccct ccgcagcaga gaacaccagg tcggcagtgt gggcactgcc cttcctctcc    12600
cctgccctct gctgtacgtc agcccagccg cttctccagc caggtcccca tcttgccttg    12660
gacactgccc ctgcctctgc cctggtctcc tgggttctca gtttgctgct tctgtctgtg    12720
caccgcctgg aagtgggggg gccttaccca gcatccagcc cagctagatc atgtccgggc    12780
cctcggggtt caggcccagc accctcacgt gccatcactc actgcctcct ctccagctcg    12840
gacgttgtat ctcctggaag ccttccctga tcccagtggc ctcctgaagc ctcctcgccc    12900
ctgtgctcca cagggagctg tgctgccgg gcctgctctg tccaataggc taacctgacc    12960
tgctccttcg acatctaagg tgctgctcat gtgtattcat gacctgggtg gatgttgggg    13020
agcccaggcc cagcaaagag gggcaggagc aggcagttcc ggggttggcg atggcccagg    13080
ggaagctttc ggcctggttg gtcagagctc ctggtgacca agggtgactt caaagtcaac    13140
gtgagcctca ctcacatgag atgagcctag agcgtccaag aacagctctg tagctggcca    13200
gccgggagct gcagccctcg gtcctgctgt cccccggg agccggctcc tgctccaggg     13260
atgagcaagg ctcaaattga ctttgaagtc tcccacaggc cgtttggaac tggggtgcag    13320
gagctggaag tgtgggcac cctggggagt cacgaagcct gactgattgt caggcagatg    13380
tgtggcggga gttggggaga tgcggtagga cacagggggg atctggggg tgccagtgtg     13440 ggccgcgggc tgggaggtat catcagtaac ttcagatcgt ttcgtagcga cacttaaaaa    13500
atacctgaag agggacgggt ggaatgaact tcaacatcat acccaaaata ttagcatttc    13560
aacatgtaat cagtataaaa attacttgag agctgtttca cattttcttt tcataccaag    13620 gttttgaaa tccggcgtgc gtcttttac actcacagta cctctcactg tggaccggcc      13680
acgtctcaat gctcagtggc acccagggct ggtggctccc gtcttagaca acacacatct    13740
ggaccgggag agcctcaggt cccctgtgat accagttttc tagtctctgt atctgacagt    13800
gtgacatctt ggggacttgc tgactatgaa gggccacccc tcccaggata aactaattcc    13860
tagagacagt gaaggagacc cttttcatgg gcaaacccac caacgcagag cccaaccct     13920
```

```
tcctctatca gggtcttacc tttgagggca ctacacctgc ccttgttacc ccaagggaag   13980
gtcccagaca accagcagcc cctaggccct agagttctga acttatgtca gcctggccaa   14040
tcctaaaccc atatccctg ccttgcccat tccttctaca gaaaccacaa gaaaggttct    14100
tgcccaggtc tccctgtggc tcccccacct tctgaccgac cctgtgcctg tgcccgcccc   14160
gctgcctgtg gcatgccacc cgctttgaga actgtgagct aacaattatc tcttctatgg   14220
caattgactc tcgatctgtt ggcctcacca tacctgaata taacggaac tacattttag     14280 aaagccagta gaaagccatt gcctcgcatg acagaccagg aagctggggc ccagagaaaa   14340
gccacgtgct caaggctggc cagtgagtga gaggcagaga ctcaggagtg gatcatgggc    14400
ttcccttggt tcagcctcct ttacatccgt ccccttaccc caccgtggag gcttggggct     14460
gagagggaga ttctgtggct gcactccaag gactggccag ttccaggcag gaggcggcac    14520
tcccagctgg ctggaaaaga agaggctgct tctctgtcaa gctcatgtca ttccccatg     14580 aaactgaaag ctgcccgggt atgagaccat ggagaagaca ggtctcattc tctgggccac    14640
gtttcctaac cacagtacaa taaggctaga agaaaaccc caaagtccca gctctaacat    14700
ggcaaatgca tgaagaaaag aacagtcttc taaacaactc ttaggtttaa gaagaatgaa    14760
aacagtgatc atgggccttt cgaaaatcaa cagccaaaaa actttataac ctcaaacaaa    14820
ttcctccgaa acaagaaact ctgaacaaaa gtgaacaaag cattcaactc taggagatca    14880
ggaaaacaaa acccgaaata tgtgtgaaag aagtaataag ggctaattaa tgatgaggag    14940
gagagaaatt aacaaggcag aaaagtgaac tgttaactaa gttgatataa tgaaaaactg   15000
ctgtttttta aaagaccaac aaaataggcg catttaaata agaaagaaga cacattttta    15060
aaataccaga aagggtgaaa ggtgacttaa gtacaaatat gtaaaagatt aaaaacagga    15120
tgttcattta tgaccacgat ggagtaacag ggactgaatt tactgctctc ctcccgcccc    15180
ctccaaaaca acaataacaa caaaaaggat caaattcagg aaacaacagt tttcaataca    15240
ctgcacatac gacaacaaag gacagtagtc ctcaagagat ggcaaacagg tgaacggggc   15300
cctacagctt cccagctgct ccctgagtt tcccaaccat ggcccagaag gaggtacctg      15360
ggcagagccc agtggagtac ttggaggagg agacagagct cagagccaag gaggcccagg   15420
cagctgggtt ctcaggacag aggagtggat tggagagagc tgcatagagg gagagcccta   15480
gagagctgca gaaagttcct ccaaggactc agcagagaac tgatcaggga tgtgtgtgaa    15540
gagccagagg ctagggaaga aattgtccgg aaggatcaga gagaagtgcc cagttctcac    15600
tcaggactgg aggagggctg tcctaaccag cccacatggg aaactcatag ttcatgaggc    15660
cgtggacaga gtatacagca ggctcttgcc tcactggcgg ggatcatttg ccctagactg    15720
gacaccgttc caatcccacc tcaccccaaa aaatcaagtg tttctaagta actcaactat    15780
gccccaggca aaactaaaaa ataggaatac aaaaatatct ggcatctaaa aagataaaga    15840
ttacaatgta tgatatttaa taaaaaatgc caagcatgca taaagcagaa aaatatgcca    15900
tctaataagg atatagataa aaagtaaata aatatccaga gctgacaaag gcattaacaa    15960
ggaaagaaca tcaaaacagg tgttatgact gtatttccta tgttgaaagc caagtggaga   16020
catggaagag atgtatatat attacatatg tctcttctat gtctctagtt aggggattc     16080 tatggctgca ctccaaagac tggccaatca ctggccagag gcagcacccc cagcctgctg    16140
gaagaggaga ggctgcccct ctgtcaacct catgtcattc tcccatgcaa ccagaagctg    16200
tccggatatg agatcatgca gaaagtgacc atatactcag gacaggacag gttcatttgg   16260
gactatttat ttatttattt agagatgata gctacaatgt ctgagacaaa gaatacactg    16320
```

```
agctggaaaa acagtaagga tattatgaaa gaaaaggtta atgaacttga agacattgca    16380
atagataata ttcaaaatta agcatagaga gaaaacagaa ttgtttaaaa gtgaagagag    16440
cagcagtgag ctatggaaaa attcaagtgg tctaatatac atgtaatcaa agtccctgaa    16500
tgaaaggaca gaagagacag aaaaagtatt tggagaaaat aaatgacaga aaattttcca    16560
aagttgatga aaattataac acacagatct gcaaagctca acaaattctg ataaggagga    16620
acttgaagaa aatgacagca tcaagacaca tcttctttgt atatcttcat cttttctgag    16680
atagggtttc actcttgtcg cccaggctgg agtgcaatgg tgcgatctcg gctcaccgca    16740
acctctgcct cctaggttcc agcgattctc ctgccttagc ctcccgagta actgggatta    16800
caggcatgca tcaccatgcc cagctaattt tgtatttta gtagagatgg ggtttctcca    16860
tgttggtcag gctggtctca aattcccgac cttgggtgat cctcccacct tggcctccca    16920
aagtgctggg attacaggaa gacatatctt aatcaaattg cttgaaacca gtagtaaagc    16980
aaaataaaat aaaatgaaat aaaaccttaa aagcaaccag aggaaaaaag atacatttac    17040
atatgtacaa aagaatgact tatatacaga ggaatagaaa taaggatgaa acaatatttg    17100
tacacctgtg ctcatagcag cactatttac aatagccaaa aagtgaaagc aaccgactat    17160
ccattgatga tgaatgaata aacaaaatgt ggtccatcca tgcagtggaa tattatccag    17220
ccttaaaaag caagggaatt ctgatacatg tcacaacata gatgaacctg gaggacatta    17280
tgctgagtag                                                           17290

<210> SEQ ID NO 8
<211> LENGTH: 25970
<212> TYPE: DNA
<213> ORGANISM: Homo sapiens

<400> SEQUENCE: 8
aataagccag acacaaatat tgtatggttc cgcttacatg aggtagcatc attaaatcca      60
taaaggcaga cagtaaaatg gtggttgcca aggcctagga gttagtgatt aatgggatcg     120
agatacagtt tggaaagatg aaaaagttct ggagatggat ggtgataatg gctgcacaac     180
aatatgaatg tacttaatac cattgagtta tatacctaaa aatgattaag gtagtaaatt     240
tgtatgtcat gtatatttta ccacaattaa aaaattagac aaaatacaaa aataaaaaag     300
gatgatacaa atttctcact ggaaacaatg caaggagaag acaatggagc aacatctttta    360 aagaactaaa aaaatactgt caacctagaa ttctataccc agtgaaaata tctttcaaaa     420
gtacagatga aatcgtttgt tcagacattc aaaagctgaa agaattcatc accagcagac     480
ctgcactaca aaaatattaa aggaagtctt tcaggaagaa ggaaaattat atgagataga     540
attatagaat tagcaaacgg atgaagagca ccagaaatgg taactatatg gataaataca     600
tataaatttt tgttgctatt taaatatttt taaaaaatag gtgactactt aaacaaaaac     660
agtaactgat agggagttga taccatatgt aaaaatagat catatggcaa taccacaaag     720
gcaaggaggg gagaaatgga ggtatactat cataaaattc tcatactgta tgtgaagttg     780
tatcatttca ctttaaggtt gactgtgata agttgaagat gtaagctata taccctacag     840
gaagcactaa atttaaaaaa aagaattaca gtaaataaat taattaaaaa ttaatggaat     900
cattaacaaa ttattcaatt aattcttacc accaaaaaaa aaaaaaaaag aaacagaaaa     960
agagacgaaa tgggacaaag acagatagaa cgaatagaaa tgacaggttt atatactcag    1020
gcctaaccat aacaataaac acattaaatg tcaatggtct aaatacccag ttaaaacctc    1080
atagtcaggt tggataacaa agtaatacct aactgtctgc tgccttcaag aaacatgctt    1140
```

```
caaatataaa tatataaata tgtttaatgt aagatggtgc tatggtaagt ggcttttaag    1200
gaggcccgaa gcatcttagt attcacatcc atggctggga ctaggggag gcaagtaagc    1260 cacttgcctc ggtcatgaaa ttcaaagaag gaccacaaaa ttcagtaatc aagacaaata    1320
atatttcaat gcaatatttt taaaaataca aattaatgca aaaatatatg aagaccaaat    1380
tttcagaatt ttaaataaag acaggatgag taacagtacc atactatgct gagcctctgt    1440
tggagcctga agcaaaaggg aaaattcagc cttctgagaa gccctgattc ggaggcacca    1500
agataaactg tgcttagttt cctggcccac aggaatctgt gagataagta tctgttgttt    1560
taagctacta agttttgggg tatttgttag acagcagtag atagtatgaa gttcaggatt    1620
ctatgtcaaa accaatcaaa agaaagcaga agtggccatt ttaatagatt tcaggataaa    1680
gaatattacc aggcattaag aaggtcactt cagaacaatt aaggggccat tcatgagggc    1740
atgacaatcc caaatgttaa cgaataaagc aaaagcatca tgatagacct acaaggagaa    1800
atagattaac ccacaattac agtcagagtc ttcaacactc ctttctagat acttgataga    1860
ataaatagac agaacatcat aaaaaatata gaaaaggtaa acaacactat caacttgctt    1920
gacctaattg acattaatgg aaaatcccac ctgttaacag caaaatacac attcttttaa    1980
agtgcacgtg aagtatttac caaggtaaat tgtcttatgg gcaatagaac aagtcttgga    2040
aaatgtaaaa gaggattcaa gtcatacaaa gtatattctc tgaccataat gaagttaaat    2100
tctgctaata acagagatat atgaaaaatg cccaaatatt tggaaataaa taaaatagat    2160
ctaaataacc catggtttaa caaataaatc aaaagagaaa ttagaaacta ttttaaacca    2220
agtaaaaatg aaaacacagc atttcaaaat ttatgcaatg cagtacttgg agggggattt    2280
agacagctaa acacatatat tagaataaaa taaaagcctg aaatcaatga caccagctcc    2340
ttagaaacta ggaacacaaa cccaatgtaa gtgcaaggag tacaaaataa gaatcagagt    2400
agaatcagtg aaacagaaaa aaatagagct atcagtgaaa cacaaagctg gttcattgag    2460
aaggtcagta atatcaataa aagccagaat ggtcaggagg aaaaggaaaa agatgctatt    2520
tgccaatatc atgaatgagt gagaggtcat cattacagat cctacaggta ttaaaagtat    2580
aataaaagaa tattaggaac aactttatac caataaattc accgacttag atgaaataga    2640
caaaatcttt gtgagacaca aactaatagc acttacttaa gaagaattga ataaccagaa    2700
tagcaccata tttattcagt aaattaaatg tgtaggtaaa atccttcctt caaagaaaac    2760
cccaggccta tgtgatatca ctagtgaatt ctatcaaata tttaaggaag agataaaacc    2820
aattctacat aaataaatcc agaagaattg aaaaagatgg aatacttta aattcattct    2880 ataagaacag cattaccctg ataccaaagc cagacaatca caacacaagg gaagaactac    2940
aggctgatat tcctcatgaa cgtagatgca agaattctaa aaaaaagttt agcaaattga    3000
acccaaccat atacaagtgg ggcctattca aggaatcaag gtgcgtttaa cattcaaaag    3060
atcaactcaa cgaattgacc atattaaatt taaaagaag gaccatataa taatgtcaat    3120
agcacagaaa aagcatttga caaaatccag tggccattca tgattttttaa aatctcagcg    3180 aactaggaat agaaagaagg acaatttctc agcctgtaaa gggtatcaaa cttaatggta    3240
caagactggt tactttcctg ctaaaacaca tagacaagac aaaggtgtcc tcataatttc    3300
tatttagcaa tgtcctagag gttttagtca gtggaacaaa gcaagaaaaa ggaacaaaag    3360
ccttccagtt tggaaggagt aaaactatcc tcattcacag aaaatgatca gctgtgaaga    3420
aaatctgacc aaatctgcaa aaacactaca ttaattaaag tgagtttagc aaggttgcag    3480
gatacaagat caatctagat aatcaattgt atttccatat agtagcaaag aacaattgga    3540
```

```
aattgaagta aaaaatgcca tttgcaaaaa catcaaatat taaatactca gctataaata   3600
tggcaaaaga tttgcaaacc tgtacactga aaactgaaaa acattgatga gggacattaa   3660
agaagactta tctaagtgga gagatatgct gtgttaatgg attggaaaat tcagtattaa   3720
gatgtcaatt ttcctcacgt taatctatga attcaacaca attcaaataa aaaaaatatc   3780
agaaggcttc tttgtagaaa ctggcaaaat ggttttaaaa tctgtaaatt cttaatttcc   3840
catacgaatg tattttcgtt cttcaactga cattttatct gtaaaaatct gagaagtgtc   3900
aggttggcat ggagcatatc ataatttttc acattaaaaa tattggaaat attttttgttt  3960 aattgctttt tctttcacag aagggcagtt atgaatgaat gtatatctct ataatacaa   4020 tatacatata tataatacat atatagtata cataatatat atataatatg tattgcatgc   4080
atatattcag agacagaatc tcactgtgtt gcccaggctg gagtgcagtg gtgcgatcat   4140
agctcactgc ggcctcaaac tcctgacttc aagatatttt cttgcctcgg cctcccaaag   4200
cactgtgatc acaggcatgt gagccactgc acccagccta aatggatgtt tgtaagtgtg   4260
gaatatgtgc atacaggagt ctgcctccaa actctctacc cctctgtctt tggtctaact   4320
ttcctcttat gccaatccca tgggattttc ctattaggct tcactgtatg tcttcatatc   4380
agacagagca aattcctctc ttttgttct tttcaatcaa agttgacatg taacaggcat    4440
atgccagaca tcactgtgga aacgctatac tcaactgagg actttggtag atttacggag   4500
agtacgcaga cagacatttc gtgtgggaat gccttaatat tacaaagctg tcaaaccccc   4560
ctacatgaac gtaaggatcc agtgcaatcc cagtccacat ctcagctggg gtgtggcaaa   4620
cgctccacga ccttactcca acactaagat cgaagtgtag aagtccgtga gtagctcagt   4680
cagctttgag tgtttgcaaa gtgagtgttt cagtggcaaa tattcctaat attctctgag   4740
gcttggtgtg cctaagggta ttttcatctc gctgctgcat ttaaacaata atcatacccg   4800
taaaatcctg tgttcaaagt taccttccac gcctttgaaa tattattctt ttgtcttctc   4860
acatccggta tcgctcttga gaagaatgat gcgattcttt cttgctcttt ttaggcaatt   4920
ctgccgattc tctatgggcc aattcaggac tttgatattt taaaacttca ccgtaacgca   4980
tctatgttct ttcttatctg tcctcgccgg cctgtcaaga gcccttgcgt gtgtttctgt   5040
aattctgggg tatttatttt cattatttct ttaaatacct cctctcttcc tctgctttct   5100
gagactcttc ctagccaatc cactactttc tccttttctc ctcaaacgtc tctgcttccc   5160
ttttaagttt ttttctcatt attgctcctg aaccttctag aacaattcca ccacacttga   5220
tattttatct cacttgtttc ctagcagcac ccatgctgtg atgtacccca ttcactgttg   5280
aactggcatc ttccctcacac tcagtatttt cccccagctc cttgtatatg cctcttcatc   5340
ccatttcaca ctgtgccagc accatcccctt atgttttga gggtttttt ctttcaagtc   5400 tggagtgcag tggcacaatc ttggatcact cagcctcaat ctcctgggct caagcaatcc   5460
tcctgcctca gcctcccaag tagctgggac aacaggcacg aaccgccatg gttggttaat   5520
gtttgtatgt tttgtagaga tgggatcttg ctacgttacc caggctggtc ttgaactcct   5580
cagcccaagc gatgcgctca cctctgcttc ccaaaatgct gggattatgg catgaatcac   5640
tgcacccagc catgttttg agttctacc aggattgctt tagcctcaca gttcatgttt   5700
ttcagcagtt cttgtctgta tgcaatgtga tgatcagatt gctgcctttc cattctcgca   5760
ggtatgccca tgagttcagg ctccacctga agtgacggtg actgcgtcgg gcagtgtgtt   5820
gggggaggaa ccagggcctg gcctggctg ggccatccca ggccgtggaa tgtagggacc    5880
agccccacag ggtcggtggg tctctccccg tgtgcggcga cgagagagtg taaaaataaa   5940
```

```
gacacaggac aaagagataa aagaaaagac agctgggccc gggggaccac taccaccaat   6000
gcgcggagac cagtagtggc cccgaatgtc tggctgtgct gatatttatt ggatacaaag   6060
caaaaggggc agggtaaaga gtgtgagtca tctccgatga tagataaggt cacgtgggtc   6120
acatgtccac tggacagggg gcccttccct gcctggcagc cgaggcagag agagagggga   6180
gacagagaga gaaacaactt acaccattat ttctgcatat cagagacttt tagtactttc   6240
actaatttgc tactgctatc tagaaggcag agccaggtgt acaggatgga acatgaagga   6300
ggactaggag cgtgaccgct gaagcacagc atcacaggga gacggttagg cctccggata   6360
actgcgggtg agcctgactc atgtcaggcc ctccacaaga ggtggaggag cagagtcttc   6420
tccaaactcc accagggcaa gggagactcc ctttcccggt ctgctaagta gcggatgttg   6480
ttccttgact ctttttgcta ccgctagacc acggtccgcc tggcaacggg cgtcttccca   6540
gacgctggcg tcaccgctag accaaggagc ccttctggtg gccctgtctg ggcataacag   6600
aaggcttgca tgcttgtctt ctggtcactc ctcactatgt cccctcagct cctatctctg   6660
tatggcctgg tttttcctag gttatgatta tacagtgagg attattataa tattggaata   6720
aagagtaatt gctacaaact aatgattaat gatattcata tataatcatg tctatgctcg   6780
agatctagta taactcttgt tgttttatat attttattat actggaacag ctcgtgccct   6840
cggtctcttg cctcggcacc tggatggctt gccgcccacc gtggaagaag aggaaagcgt   6900
tcctcttccc ttcccttccc ctttcctttta acacttaaaa catatttatc cctcccctcc   6960
catctcccct cccaactcat aaatatagta ggattccaac taataaacat agaaggcatt   7020
tggcaaccag cacagcaatt atttaggcac aaatcctcaa ctgatgctaa aacgagtgag   7080
taaaagtcta agaagcaaca ggaagttaca cggcatcacg tttctcccca caaactggaa   7140
attacaaagc acagaacatc aacgtgacat tggagaaacc tgccagctac aattttaacc   7200
gtgttccaag ttaacactgc cgggtccttc ttcctctttg ggccgtgata gagcagttag   7260
gaccacacgt ggccttcact gcacacaacc agcaaccagg atgcagtcac acagtttgtg   7320
aggcaagttc tcaaacgctg gacagcgcgc cgtgggtggt ctgtgaagga cgtgaaacca   7380
gccgggggag cctggtgatc ttccagccga ccgagagtct ctgggctggg ccctgggtct   7440
cactgaggtg aggagacaga ggtcagagct cagcgaggat gaggcaacta gaattttcag   7500
ggtagatctt tgaagaggag gtgggggaaa gagagaaaga cagaggagag agacagaggc   7560
agagatacgc agagagggag agagagagag cgggagaggg agagaggggg aagagaggga   7620
ggaagagatg aagaaagggg gagaaacagg gatacagaca gggagagaga taactaggca   7680
gagagagtta gaaaggggag aagagagaga tagagaaaga cagagagaga gagagaaaga   7740
gatacagaga gagagagaga gaaaaaaaaa aactccaggg atctgcagag accctcaggt   7800
ccttggctga atatggatcc acacatgcat gaagataaac cacctgaggc cagagaaaaa   7860 accccgtag ctcaggtcac acggtctgga gacagtttgt gttcccacaa aactatataa   7920
tacacaggat gtcgggaagg gtcctcataa gagcctctct tgagtgctga ttctaaacca   7980
accctagact aaaggcagcc ctggattcac cctacaaagc atagaagcaa agctccaaag   8040
atccgatggg tatcaggaac tcatggatgc cagaacaaaa tccgacagca attaaaggaa   8100
tacaacaaaa tctagcaacg gactgtgcaa tatttgcaaa aaaaaaaaaa aaggccaggc   8160
atgcagagga acagggaaac gtgacccaga accaggagaa aagccagtca gtggaggcag   8220
gtgcagaaag gccagaggtg ctactgtgac cagacaagga ttgaaacagc tgttttagag   8280
gggccctacg tgtaagaagg tccagtaata gaaagagggt gataaagcaa tggtggtagg   8340
```

```
gtgctcacag ttggagaata ggcggaggta caggaatcct ttgtactatt aatgaagctt    8400
ttctgcacat tggaaatgat acaaaacaaa aagttaaaaa atgaaagaga ggtggggtga    8460
gcctagagca tggagcccca ggacccatag aattttgttg attcctctta gtgttcctgc    8520
tagccaggca ccttgtgtga aatttgccat taactctctg gaaaaaatcc gctttgggag    8580
gaggccactg cccgtgtggc cacctccagc cttgagacca gagcagaagg atacaggagc    8640
aactgcttgg agacggctgg cagatctgca cgtgtttcta tccatcccac ttcccctctg    8700
taaggttcta actctgccct gctgttctcc ctgctgtcca ggccattgct gctgatttct    8760
gcagtgacgg ggccagcaac aactgtctca aggcagcttg ggaaaagaca agcctgcctc    8820
caactgttgc tcttgtcact gcttctagct gtctcctccc caggttgcag ttcccaacac    8880
cacacacacg tgtgcacaca catgcatgca tgcacacaca tgcacatata gcacagcatt    8940
catgcataca catgtaccca cacacgcaca cacttgcaca cacatgcaca atgcatacac    9000
atgcacatac atgtgcacat gcacaccagc tcaccacagc ctgtagtctt ttttttttga    9060
gacggagtct cactctctcg cccaggctgg agtgcagtgg tgcaatcttg gctcactgca    9120
agctccgcct cccaggtttc caccattctc ctgcctcagc ctcccgagta gctgggacta    9180
caggcacgcg ccaccacgcc cggctaattt tttgtatttt tagtagagac ggggtttcac    9240
cgtgttaacc aggatggtct cgatctcctg acctaatgat ctgcccacct ggcctccca     9300 aagtgctggg actacaggcg tgagccaccg cgccctgccg cctctagtat cttagagat     9360 gtgccacatt gttgattttt cctcaaggct gtttctccct ctagatgctg agcttctcc     9420 agcattgatt ttggggacgg aagcctgggc gaggtacaca ttccggcagc cagtgccagc    9480
tcttagaagg tcacactgcc tattgtgtgg acagattaga tggggtgggg gtgggacttg    9540
tgagtccagc aaggggcta ttgtaggcag agctgcaaga ggcaccagca ggctgcatgg     9600
gctccaggag agaggtgcga cctgagagcc attctggaca ctgggctcag tgaaagaagc    9660
cggtcagaaa aggacaaatc ctgtgtgatt ccctgggtag aaggtcccta gggtggtcaa    9720
atccatagag acagaaagtg gatggtgggt gccaggcct aggagagggg atggggaacg     9780 agtgttaat ggggatagag tttcagtttg gaagatgag aaagttctgg agatgaaggg      9840
tggtgacagc tgcacaacag cacgaatgtg tctaatgacg ctgaagtgta gtttaaaatg    9900
gttaagatgg tcagttttgt attatgtcga ttttaccaca ctgttttttaa aaagaagcat   9960 cctggagaaa gcgtcagtac tgctcatggg ggtggggtga ggagtcagct ccagtggctg   10020
ctgggctctc gtccgagagg agaagggagg ctggccctcg ggggaagggc tgcagggatc   10080
cagggttcct gggtggatgt gcggagtctg gggtacctgg gaactatccc cacagaaatg   10140
ggaggccacc actgaaattc caatgagggg ctcgaagtta aaacttaaca catgaaagat   10200
aagtggggtg acagcgtgga gccccaggac ctgttgattc ctcttaccgt tgctgagggg   10260
ctaatggaag gggctgggct ggagggtccc ctgcagtcag tggcaactca gcccctgggc   10320
actgagggac catgcaagaa gcgggagaga gaacagaaaa ggcaggaaga gcccttttcc   10380
tccactgagg gagtaggcag agtcagggag tggctgagaa agggcaacac agtcagcaac   10440
gggaaatgca aggaagacat gaggacccgg tcccccatg cctggagggc tggagtgagg    10500
acagaggggg cctgctggac ccaggagcgt ggagctcact ggtgactcct gagagtcagg   10560
ggactcccag gaatggcgtg gaatccagga tgccacttcc tcctgcctgg cagcagggca   10620
ggcagctggc tggggcccag actcccagga ggatgccact gctgcccaga cctactgcag   10680
tgcacagcag agcggcaagg gccccctggtg cgttgagcaa acttccaggc ttaaaaagag   10740
```

```
cgtggctgcc tcatccctcc accacccaga gctggctcag gccacgtgtg acccacccta   10800
cccttaacaa ggcagctccg ggagtcctgg aagatgaaca tcccgctcag ctagggcgac   10860
actgtgccaa tccctcccat gggcttccac ctgtacctct tgttttctac acagctttat   10920
tgaaatataa ttcacatact ataaaattca ctgttttaac tgtaccattc aggggctttt   10980
agtatattca cagaagcatg cctccctcag caccccaaa aacaactccc cgctttagta    11040
tattcgcaga ggcgtgccac ccgcagcacc cccaaaaaca actccccact ttattcgcag   11100
aggcgtgcct cccgcagcac cccaaaaac aactccccgc tttagtatat tcgcagaggt    11160
gtgcctcccg cagcaccccc aaaaacaact ccccgcttta gtatattcgc agaggtgtgc   11220
ctcccgcagc accccaaaaa acaattcccc gctttattca gagggcatg ccacccgcag    11280 caccccaaa aacaactccc cgctttagta tattcagagg cgtgccaccc gcagcacccc   11340
caaaaacaac tccctgcttc agtatattca cagaggcgtg cctcccgcag caccccaaa    11400 aacaactccc tgctttagta tattcagagg cgtgcctccc tcagcacccc caaaaacaac   11460
tccccgcttt agtatattca cagaggcgtg ccacccgcag caccccaaa aacaactccc    11520 cgcttcagta tattcacaga ggcgtgccac ccgcagcacc cccaaaaaca actccccgct   11580
ttattcacag aggcgtgcca cccgcagcac cccaaaaac aactcccac tttattcgca     11640 gaggtgtgcc tcccgcagca ccccaaaaa caactcccg ctttagtata ttcacagagg     11700
cgtgccaccc gcagcacccc aaaaacaac tccccgcttt agtatattca gaggcgtgcc    11760
acccgcagca ccccaaaaa caactcccg ctttagtata ttcagaggcg tgccacccgc     11820
agcaccccca aaacaactc ccgctttag tatattcaca gaggcgtgcc acccgcagca     11880
cccccaaaaa caactcccg ctttagtata ttcagaggcg tgcctccctc agcacccca    11940 aaaacaactc cccgcttcag tatattcaca gaggcgtgcc acccgcagca cccccaaaaa   12000
caactcccta cttcagtata ttcacagagg cgtgccaccc gcagcacccc caaaaacaac   12060
tccccgcttt agtatattca cagaggcgtg cctccctcag caccccaaa aacaactccc    12120 cgctttagta ttttcacaga ggcgtgccac ccgcagcacc cccaaaaaca actccccact   12180
cactagcagc cgctcccctt gccccagcct ctgccaaaca ctgacccact tcccacctcc   12240
atggagttgc acgttctgga catttcatac aaatggggtc ctctgattcc ccacccacaa   12300
tttttaatca tacttaactt ccaaataaag acaaagtcaa atccctcttc cacccaacaa   12360
gatgtggcca agcgtataca agagaacagc atgtcccct ctcccccaga gaagaggaga    12420 gccctgatc ctgattcatc tctgggtgtt cttccctta aaaaaaaaa aaaaaatca       12480 aagggggaat aggattcagc tggaatggga ttcagctgat tctcattctc cctttgatat   12540
cctaattttt tttttttttt tttttttttt ttttgagac agactctgtc agccaggctg    12600
gagtgcagta gtgcaatctc ggctcactgc aacctccacc tcctgggttc aagcaattct   12660
cctgcctcag cctctcacat agctgggata caggcacgg gccatcacgc ccggctaatt    12720
tttgtatttt tagtagagac ggggtttcac cacattggcc aggctggtct caaactcctg   12780
acctcaggtg attcgcctgc ctcagcctcc caaagtgcta agattacatg cctgagccac   12840
cgtgcccagc ctgatagcct aaaatttaaa cactgagatg tttgaaataa ttaaatatca   12900
actactatca aacgtacact tcatacacta gtaccgtatg aagtggtagg gaatggaaga   12960
ggagaagaaa cagtggctaa tgtggtccta cccaatacac tcggatcaaa ataagaaaca   13020
cgcacacctg tgataggctt cgtttctgca gcagccgagc agcgggaact agcgtttcag   13080
cctccgtctc ccgcatagcc ttcgcctccg caagcactca gctgatgtgg ctctttgcct   13140
```

-continued

```
ggtgggatgc cctaagcctt cattcctgga gagcctgggt cctgaatgac cctgcttgga   13200
tcaggggtga tggttttcca tgattttaat cacaggacat gggaaccttg agaggcgctg   13260
caggggaccc tccgcattcc agacgtgctc ctcctcatcc tccttgtgca acccggccga   13320
ttccgcccga taaaatcagt cccgtggccc gggcagtaac tgccttttt acctattgat    13380
tctctgcagt gaggatccca aaatggcctg gtgcaatctc accttccagt ctggtggagc   13440
cgttggtgtc tctgcgggaa actctcctcc ctcgagaact cagacttcta caccaagagg   13500
acctagagtt gtggggacag ggagcaaaca catcaccagc agaatgtcat gagggtgaag   13560
agaagccatt gccacttccc cttctggact cccagaaccg tgaggtctgg gcggcaggag   13620
aaaccgctcc atagactgac tctaattcag agcctggacc gcctcctgga ggacacggcc   13680
ctctctgcaa agcgtcccca ctcagcaggc gccgtgtgag tctcccgaag gccattccac   13740
ggtcctgttc gtgagctgct tcggggagag gaggaccacg gaagacctcc aaggtcacaa   13800
gcattgggcc tttgccctac tccattaact gtggtgaatt ccttgagcag cagtgtgaga   13860
atgccgaatg aggcgctcca gagtccacag gtggtttcgg caaaagcacc gtgggcaagg   13920
agggccagtc cacctgcaga gcaagcctct atcctggtga agcgcagcg gtgccagttc    13980
catgccggca gctgtctcat atcatccact ccacctggag gctggcagat cccctgcaac   14040
actgggcag gcgggcactt agtggatggg ccttggtgag tggagcccct gtgccgatcc    14100
catgtgtgac ctccatccct gctaccacag tctctatctt caccagcctg ctgacaatga   14160
cagggtggct ggggaaggag cctgactgat gcccaaagaa agggccatct tgtctacctg   14220
gtcactgagc ttctcctcgg ctgaggcggt tgcccttgg caaatgtcac atgggctgcg    14280
aggatcttca cgctctgccc tttcagagac ctctaaccac acaacacttc cccacacctc   14340
ctgctaccgt ttcccaaat gtgttccttt caagtccctg accatccatc tggccaagcc    14400
aggagcaact gaccatgagt gggtggcacc tgtagctccg aactctcctt ccaggaaaaa   14460
tgaaaacacc taggggccct gcccagagta tggaccacgg gtgttggaac cacttttttca  14520
tgtaacttgc ttgtgacttc agggcctgcc tgagccccgg gttgtatatt gctgcttcca   14580
cttgaagaca gaacacagct gtgcatgccc aactctgtgg ctcgctgggt ccagcaacat   14640
cccactcatg acgtacagtt cagatcacgt ggcgacttag tggcctgtcc agtctctatg   14700
gaggcctgga cgcaatccac agagttatcc agagaggatg gcagagcttg actccaaaat   14760
cctaagggcc ctgggctgtg attcacctgc aggagcctat catggccccc acgcagcatc   14820
cttacctgcc acagacacct caaatgccat gggatctgtt ggtcccgtgg ctcaagtggc   14880
tcagcagctt tcatgaccac atgcacttgc tgcagagcct tctcttgttc tgggactccc   14940
agaaagcaga cagcatttta ggtcattcct acatggtttt tcctacccat gtcttcctac   15000
ctacccgtgg gtcatatggc ccatgttgca aacattttg gaaaaggcaa aactatgcag    15060
acaatgaaat gatcagtggt ttccaggagt cagtggggag ggagggaaga ataaatggag   15120
cacagacgga ttttagggca gtaaaataat tctgtgtgac actgtaatag tggagatatg   15180
ccattacaca tttgcccgaa ctcacagcat gtacaacaag aagagtgaac cctcatgtaa   15240
cctgatcaat gactaggtca atattggttc atcaattgca aagatgtatc acagtaattc   15300
aagatatgaa taataaggga aactgtgtgt agggagagat gctatatgag gactctcaaa   15360
tatgctcaat ttctctgtaa acatgaaact gctctgaaaa ataaaatcta tattaaaaat   15420
taaagctttc accagatcaa tggctgtaga ccaggtgtcc ggggatgctt tgatttgccc   15480
cagtgatcag tagtcatatc tggaacagca gttgcaattg gagtcctggt taagtttacc   15540
```

```
aggattcact gtccttcttt ctccgggacc ccctgtctt ccacacaagc caattagacg   15600
agtggaacga ggctgcagtg ggggtcacca ccctgcatct tccaagtcct cgatggcggc   15660
actgaccttt gcagtccctc cagggctgca ggttgctttt gactgacaat tttcctaggc   15720
agagttcacc ccaatggctt ccacctggcc tttcccagca tagtagcccc caccctcagg   15780
tcagggaaca aatgtgggggg ctctgctggc tgccacatac gtctgtttac tcacccatct   15840
gaggctaggg aagtgacctc tgcacccacc gagggttgga cctgagctag aactccgtga   15900
gcccactgac ctccatacgc ccctcctctg actattagat ccgatgggtg tttgtgtccc   15960
caggagtggg tgtcaggtta gagttagagt ccagtaatcc ccctgagtct gatgatcccc   16020
ctttccacta gccaccccag caaatggctg caggtccctg aggggagact ggggaaagaa   16080
gaataatgta aatttgtagg agtatggcaa ggtccttcct caggggcacc cagtcctcct   16140
tcactcaggc accaggcaag ggaggccacc cattgctcca gctcccgtgg caccgtgagc   16200
caccggccaa ggccacaggg ctccatgggc tggactgttc caatcactgc cggtgccagt   16260
tgccatctca gccacaggcc cggggcctcg tggccacccc cactgggctg tgccctgcct   16320
ccttaaagac tgtgagcgag ctcccaactg ggacacccct gaccagctca ctcttatttt   16380
gtctgccctg gcctgatgc tggtgtttga gatatcagaa ctcacctcaa accaccctaa   16440
gcagagatca ctccggctga cgcaggggtg cggcccacat gtgagggacc ctcaggctgg   16500
gcagcattgg ctgagccccc accgcaccctt ccctcccacc ctgggtcct cagcctccgc   16560 ccaaggcagg ggggacactg ctggcaactg gtcacccaga gagcatgggc tgcagggatg   16620
gccctgagta ggacacacag ctcccgagac ccctcactgg ggacacaggg gggccctgca   16680
gccagggtgt cagtgtgggg acagcccagc agacccccaag ccaccactg aggttgcttc   16740 tcaggggagc accactggtg ggctgtcagc tcctgcctgg gccccggcct cttgccctg   16800 tcccacctcc cacctgcacg gcctccagca ttgcccaaat tcactgcctt cactcccaag   16860
tccacagagg tgtctcatcc aggcgggtga acactcgtgt gttgggaggc tggtgaagcc   16920
tggcattggg gggcaccacc catctcccctt ctttgtctca ctgccttgaa acacccaca   16980 tctatcacct ctgcccccga ggctccccag gttcaccccca tgccagcctc agcccaacaa   17040
ggcctgtgct tctgaccagc accgctgggg ttctcagggc atctaccctt tccgctgtag   17100
cccactgtct ctaaacatat ttcacacgtt gctgggggca gtgtgtgtga ctcactgctt   17160
cccagagcca gcccagagct gtttagtaga catgaggtga gtgaatgaat gaatgaatga   17220
atgagtgctg ggagctgtct cagttagctc caatctgcca taaggaagca ctgcaggctg   17280
ggcatgtaaa cagcaggtgc ttatttcttg cagttctgga ggctggaagt ccaatatcaa   17340
ggtgctgctg attccagtct tggtgagggc tctcttcctg gcttacagat ggctgccttc   17400
tctctgtgtc ttcatacagc tgtccttcag tgcatgtaag gagagagaga gagaagaggg   17460
agctcctaaa tgtctcttgg tataagggca ctaatcctat gggaccaggg accttcatgt   17520
cctcatctgt ccctaattac ctcccagaga tccacttcct aacactatct cattgcgggg   17580
cagggcttca acctatgaat tttgcaggaa cacgattctg tccatagcga acactgacac   17640
tgaacccgcc tcctaaagcc ttctctcacc atattcctca tgctgctcaa agatcctctg   17700
caaccttgtg cccctcccaa gggtccctgc acctgtccca gagagagggc agcctggcaa   17760
tgggcctggg ccctgacgct tgagcatcgg ggtctggcct gaaggggat gggcgttcac   17820 ttctaggttc ctgagagagg caacactgca ccttttaaagg tgtcaggagc tcactgcccc   17880
agctggtcat gaaacagtct cttcatcaag ggctaaataa agcacgctga ccaccaggaa   17940
```

```
tggggcagga agcttctgcc ctgcagcctg ccttgtctgc acagggagtg tggggaccat    18000 taggggagg gtccgatgtg cattttctg ccagcgggac cttcccctgc ccccagtcct     18060
gcccaggccc gggggtcac tctgaaggca tctggctctt accccaggca tctcctgcct    18120
ctgccccact cctccacccc cacggggtgc cgagtctcag cccaggctgg ggtggcccag   18180
gcaggacagc aggcttggtg gtgcccggcc ccacatacta gtgggtggca cagcgtggat   18240
gtggatagag acgcctcccc tacagtctgt ccctggtatc tgtgacgcag gtgtggggtc   18300
cctttagact cccctgggag acagctgtgt ctatgaaggg gcagccatcc ctgggtcccc   18360
tctgccctca ctgagggcag agcctaggct ccttggggg ggaagcaggg tgcccctcag    18420
tgcccactgg agttggccag cggaggcagc agcccacggc actgagaggg aaggcccggg   18480
cagccatgcc ccagaaactc ccttggttgg gagcagagca gtgcccagag cccagaaccc   18540
agtttgagta tggtcttggc tctcaaggga caggccaggg tgcctccagg ggaaggggc    18600 tgcccaggca gtaggggttc aaaggtcccc tggggcccac ccagctgacc caggcctagg   18660
gtaatccaga aggggagctg ccctcctcct ccctgggctc aggagaggct gcaaaggcag   18720
ctcctgggac gtggatttca gaatcagggc aaaggacaga catgagccag attcaggtgc   18780
ccgcgtggcc cccacaggtc tcttcaagct ccaggcccca ctcgctgtga cgcaggtggg   18840
aagctcttga gtgcctcccc ggtgggaggg gccgcgctca cagacagcac aggggccccc   18900
aggctccagc ctcagagccc ggctgctcac ctctgatgga cagaaaaggg tccctgtctc   18960
aggaaggtag aggctgccac ctcctggccc gaggacacag ctttccagag gaggggcctg   19020
cttctaagtc caagtcccat cccagccgga tagccagggg caactgccca ggtaaactga   19080
gacagcagca gcaggcaagc cagtgcagag ctgggtgatc cacaggttca tgagcggtgg   19140
caggtggaac aagggcacca tgggcggagg gttgggcagc tgcaggtggc atcattgagc   19200
caggggcctc ctggtgggta aggacattgt agagtgagcg ggcgcacctg gacccagga    19260 attcacagga aggagagagg aaaaaggaag tccctggcgg gtaaacacat atgcatgcac   19320
acacatccac gtctgcacac gcatccacgc ctgcacacgc atccatgcct gcacatgcat   19380
ccacgcccaa tctcttccct ggaaataaag ccaggggccc ttaggccagc ttgcagtggg   19440
gcccagccct taggacaggc tccttggtgg ggtaggggtg ggggcagctg tcctcctggg   19500
ccagctcctt ggggctgaac ccgctgctcg aggggtcttc caggctccca gcggccggca   19560
ccacctctag agcaggtggg caggggtgtg tggggtgggc aggggtttgt gagggtgggc   19620
aggggtgtgt ggggtgggca ggggtgtgtg gggtgggcag gggcatgtgg ggtgggcagg   19680
ggtgtgtgag gttgggcagg ggcgtgtggg gtgggcaggg gtgtgtgagg gtgggcaggg   19740
gtgtgtgggg tgggcagggg tgtgtaaggt tgggtagggg tgtgtggggt gggcagggat   19800
gtgtggggtg ggcagcggtg tgcggggtgg gcagggtgt gcgggtggg caggagggtg     19860 tggggtgggc agcagcctgc acagtggctt cccctcaaca agccacttcc tcttgcagag   19920
ggaatgttgg ggtgggaggg tgtggctcag caaaggcgt gggggttcca ccggctccct    19980 gccccgctg gtggggcaca gtgagggggg ctgtggtcag acctggtctc tggagggcca   20040
gccgggggtt cccgtccacc tgtcaggggg ttcgacgcca ctttgagatg acaagtgagg   20100
ccacctgggc acagcgctgg tgtgagaagg aggccatcag gacaggtcaa gaacccaggc   20160
ccgccctgct ccgaaattct tcagacctga tgaagaggtg tcccagaagc gggtggtgct   20220
ccaggcccgc ctcaccagct ccaggaggt caaggttgga gagagacaat tctagggcg     20280 aaccagacat agccaagagc agctcatctt ccctggagag gacgggctgc ccacttgcac   20340
```

| | | | | |
|---|---|---|---|---|
| agcccggggg | cctcctgccc | ctagacctgg | taccttcact | cttgttgcca ccctacatt 20400 |
| catacctgcg | cccagtctg | agccacacct | aggcccccag | ctgaagtgac actgtgggtg 20460 |
| ccaggcatct | gaggtctcca | caagccccca | cagactcagg | gtgggaattc ctgggggcca 20520 |
| gagctgcaga | gggtgctgcc | tgggggtgct | gggctggacg | ggggtcctgg ttgtccctcc 20580 |
| tggttctcct | ggttctccct | ccgcagaggg | agggaggcgg | tggcctcagc agttcctcca 20640 |
| gcagcgttcc | tgagcgggcg | gcagctgggc | cctcttccca | cagccacgct ggggttgcca 20700 |
| tgcctgcagg | tcttgggcc | ccctcccct | tgatgaggtc | ctgaccaaat gcaggaggag 20760 |
| caattccagc | accgagggc | gagcagagcc | gcctgttagc | actcctggga gggcccggag 20820 |
| tggtccctga | atgatggatt | cacctggaac | attttcaccc | tcttcaggcc caccctgccc 20880 |
| cagaggccca | cggaaaccct | gcctgtactg | gggccgcagc | gctgccccca cccatacgta 20940 |
| attacacggc | tcggtgtaat | tgcaaattcg | aggtttacaa | agcctccccc tggaggcccc 21000 |
| acgtgagtgt | gagcgaggcc | ccagcccacc | cctgtggccc | caagaaggct ctgcgacaaa 21060 |
| atatccatga | gtgccgccca | cgaaggcatt | aaaaccaacg | accttctcaa aacttaagct 21120 |
| gtcacaggac | atttcaaagg | gtgtttccta | agaaacacctc | aataatgatg ttccaaggag 21180 |
| accccatcca | aattcctcca | aggattacgc | ccccaaggcc | cagtccacac ttgctcactc 21240 |
| ccaggacggg | gagctcacct | cctcctcccc | gggcgccgtc | tcctccacat cccacaccag 21300 |
| gtcctgccca | tgactttccc | cctctcagcg | ccgtcctcag | tggccacacc aagaacgagg 21360 |
| ccatgtcttc | ctgggaaggg | cctcagatgt | cagcaaatgc | cctggtgtct tgggctgggc 21420 |
| tgggggcacc | agggtgaggt | ggtggggga | gccaacctca | ctgcccctcc ccttcctgcc 21480 |
| tgcccttctt | ccggggcacc | cagcagctcg | gtcctagggc | gatgttgaca gacagacaga 21540 |
| ggggcggatg | cagcctacct | cctgggcagt | gagctgcggt | ctgaggcccc tgcccagctg 21600 |
| gaaaccacag | ggaggggaag | ggaggggagg | agaggagagg | agaggaaccg tcatggggcc 21660 |
| ttggagtcga | gtcagggttg | ccaaatgcca | gatgctggtc | acctgcttct ttatcttggt 21720 |
| aacaggcagg | tcgggcagga | gtgggtggtg | ggtggggtg | agcagggggtg aggggtggca 21780 |
| gggcctcagc | acagggatta | tccctcccct | gacacacaca | ccagccctac tgtccctgtc 21840 |
| ctgcccttgc | agacatgtgt | cctgcccttg | cagacagccg | caggcaggca gggaccacca 21900 |
| tgagcaaccc | cgtctctcct | cctgaggggc | agcacagagc | ctggaggagg cctgagtggg 21960 |
| gctgaggcct | ggggcgagct | ggggtggagg | ggcactggct | gccgggctcc agggatcttc 22020 |
| tccccttcct | gccccggagg | gtgctggcac | aggggtgggg | ctcactccca ctccgtagac 22080 |
| acaatgatca | gaggtcctgg | gtgtctgggg | aagctgggct | gtgcgtgtat gcgtctacca 22140 |
| tgtggggtg | cctgtgagtg | tgctggggcg | tctgcagtga | aggcctcctg agaccactcc 22200 |
| acggaaacac | cgggaatccc | tgcagctgag | cctgtctctc | acgggaccgg gaagctggag 22260 |
| agagcccaa | ccctgcccgc | tggggccgag | ctccctgctc | ctgcagcagt cccatgcccc 22320 |
| acactctgag | tctgccctat | ccacagctgc | tgggcctctc | tgtggccacc atggtgactc 22380 |
| ttacctactt | cggggcccac | tttgctgtca | tccgccgagc | gtccctggag aagaacccgt 22440 |
| accaggctgt | gcaccaatgg | ggtaagtgag | gtccaggcct | ggctgcatcg ggagggcct 22500 |
| cgggtgcaag | ggtggctggc | acgagcccag | ctggacgcct | cacagccaga atggtgccag 22560 |
| gccctaggca | ggagccagag | gtggtcaggg | gcagggaggg | gctgccctgg agtcctagct 22620 |
| cccctgggca | gggcctcggg | tctgggtgac | agccagtgtt | cctgcctggt tctcgtgccc 22680 |
| cacaggagcg | tgggcacagt | gtgggtatat | gtcgggcagg | gtcaggaagt ggctctgtgc 22740 |

```
ggtcaggacc tggctctgtg cagtcagggc tcagtcccag gcaggcctgg gactggcctg    22800
gggctgggca cagcaggtcc atgagggctc cacatggctg atgttccact caggacctgg    22860
gatgtgggtg ggaggggggt gggggctgct ctagccagac gcctccctgc agggactcag    22920
cagcgactta tccaacatcc agagagcggg agcgagggcc agagcctgct ggggccactc    22980
aggggtaagg ctgaggaagg ccccttttaat gaggggatgt cagagccaga tctgcagggg    23040
actctcaggc aggagctcag ggggcccagg aaggctgcag cccggtgggc agatgtaggg    23100
aaactgaggc ccaggaggtc agggatactg ccttagaacc caatgctttt ccccaagtcc    23160
taggaccagg gcctccctgg aggaggacgc ctggggccca ggtccaggtc cggactgata    23220
agattacagc tccagtccgg ccacttgtca ctaggacatg gcaggaggat gcctggggcc    23280
caggtccagg tccagactga taagattaca gctccagtcc ggccacttgt cactagggca    23340
tggcagggag catgtggctt ccaagatagc cccacaggca tggagggcag ggaggaaaag    23400
agggaaggag gggcagtccc ccaggctgaa cgagtcccac ctccctcctc cttccctcag    23460
ggccgtctga tggagagaca ggcccattca gagcccccca ggagtccctc acggcccctg    23520
actcccaagt tagatttcac acccaggctg tgtgcactca ggacctgtcc tgggcacccc    23580
taaccctcct cctctctcct cccaaccagc cttctctgcg gggttgagcc tggtgggcct    23640
cctgactctg ggagccgtgc tgagcgctgc agccaccgtg agggaggccc agggcctcat    23700
ggcaggggtg agttcattgt gttcccagat gcccaggccc ccagaaaaga attagaaagg    23760
agtgaagagc tggcagggct gtgtgccacc cccacacctg agtgaccagg cagaaccaga    23820
ggccccaggg atgctggcca gccgagaccc ccacgtcaac cccacacctg agtatctagg    23880
cagaaacaga ggccccaggg atgctagcca gccgagaccc cctacctggg tagccaaggc    23940
ccctccacca ggccctacct caccctgtca tctacacgcc caacaagggt tcctatagga    24000
gctctgaaag agagagacgg ccctcctgac cctgggagct gtttccaaag tccctgggag    24060
ggtctggttc tattgcccag caagctctgg gagggcactg ggagcatccc atttcctgtt    24120
cggaggaggc cgggccaggc tcaggaaacg ccccttgagc tctccagcct gggctctccg    24180
gagctgcaca ctctccttcc cagctgccgg aggtgtctcc ccagcccgga ggtcccatag    24240
gcccctccac cccacccccat agcagtggcc tcttgtcacc ctcattccta ctcctcccca    24300
tgggcttctg tcttggtccc tgccactcga tggtcatcgc agaccccacc tggcggcagc    24360
ctccccacgc ctgtcctgcc cctgctaggc ccacagccct cttctctcac cccagctggg    24420
gcagctcctc cctggcgccc cgggctccca cctgtccctc tagcctcccg tctcccttt    24480 ccagccatga ggagcttgtg ctgggggctt tgcttccctg tttagcctgt gaagctggac    24540
cactctgggg gtccctgagg gcagagcctc ctgggtcccc agggctggca gggttttcag    24600
ctcagccttc aagttcagca aatgcttgtt taatgaccct ggtttataaa tgtctccaag    24660
aataggaata gagtcacctc ctggagctgc tgccgggcca accagccctg ggtgggccca    24720
tggtgggcag aggaggaccc agcagctcca gcactagcca ggattcctgc tccggggcac    24780
acgagcatgg gcaggggacaa ccccggcctg tgctatctgg cttcagggcc aggtgggagg    24840
ccccagtggg gagatgacaa ggcaggtagt ctgccccccc ccccagaggg tgtgtggcct    24900
gcaaagggac acctggatgg aagaaaaggt tggcaacagg gccaggccaa ggggtccagg    24960
tcagagctgg aggcccagaa agaaccagcg ctggggctgc agtaccgtcc accaggggt    25020 gccatggtgc tgggcttgag gccacatatg cagaagccag ccgctgggcc acggggctcc    25080
tgtcccagtc accagccttt cccacccccac cttgccccg tgcacaaacc agtctagcac    25140
```

```
cctcatctgt ggccaaggcg gtcagggagc acctgggctc aggttctgtg tccccagcca    25200
gccccaaggc cagggtgact tgacatgtgg gtcaggcctg tagagcagcc ttggaggccc    25260
ccaactggat gcctgcactg ggctggggtc ctgaggacac tccagtccca gctgggtggg    25320
ctccagcaca gctcccaagc cccaatgcac ttagacccag cctggatggt gagctcagca    25380
tggccacagc agggagctgg gagacccag  tcaagagacc tgctccattg agctgcatgc    25440
atgtgtgtgc atgagggtga gcctatgtgt atgcgtgtgc aaatatacat gtgtgtgtgc    25500
atgtgcatga gtgtgtgtgt gcatgtgtgt gtgcgtgtgc aggtgcctct gtgtgtgtgt    25560
gtgtgtgtgt gtgtaagtat ctgtcaccgg tcttcacctg ccctgttgc catacgggtg     25620 tggtgtctgc gtgttgcatc tggcacatct gtatgtgtgt ctgcacgcat gagcacaagt    25680 gaagggcta gggaagggga gcagggagtg gaaagatttt ttccaatggg ctgggcgcct     25740
ggatgctccc cacaaagccc cttcctgcct gcccccaccc ctccggcctc tcccctagct    25800
ggcctctcgc acaggaaatg aaagagcttg ctgggctgag agagcagagc tggcagcgcc    25860
gcccaaggaa gcacattcaa ttcgcttatg tatctattta tttatttcca tttagaatga    25920
ggagaaagaa aatggccagg gcagacctga ccacccagca gcctctgatg               25970

<210> SEQ ID NO 9
<211> LENGTH: 30196
<212> TYPE: DNA
<213> ORGANISM: Homo sapiens

<400> SEQUENCE: 9
tggtgagggc tctcttcctg gcttacagat ggctgccttc tctctgtgtc ttcatacagc      60
tgtccttcag tgcatgtaag gagagagaga gagaagaggg agctcctaaa tgtctcttgg    120
tataagggca ctaatcctat gggaccaggg accttcatgt cctcatctgt ccctaattac    180
ctcccagaga tccacttcct aacactatct cattgcgggg cagggcttca acctatgaat    240
tttgcaggaa cacgattctg tccatagcga acactgacac tgaacccgcc tcctaaagcc    300
ttctctcacc atattcctca tgctgctcaa agatcctctg caaccttgtg cccctcccaa    360
gggtccctgc acctgtccca gagagagggc agcctggcaa tgggcctggg ccctgacgct    420
tgagcatcgg ggtctggcct gaaagggat gggcgttcac ttctaggttc ctgagagagg     480
caacactgca ccttttaaagg tgtcaggagc tcactgcccc agctggtcat gaaacagtct    540
cttcatcaag ggctaaataa agcacgctga ccaccaggaa tggggcagga agcttctgcc    600
ctgcagcctg ccttgtctgc acagggagtg tggggaccat taggggagg gtccgatgtg    660 cattttctg ccagcgggac cttccctgc ccccagtcct gcccaggccc gggggtcac      720 tctgaaggca tctggctctt accccaggca tctcctgcct ctgccccact cctccacccc     780
cacggggtgc cgagtctcag cccaggctgg ggtggcccag gcaggacagc aggcttggtg    840
gtgcccggcc ccacatacta gtgggtggca cagcgtggat gtggatagag acgcctcccc    900
tacagtctgt ccctggtatc tgtgacgcag gtgtggggtc cctttagact cccctgggag     960
acagctgtgt ctatgaaggg gcagccatcc ctgggtcccc tctgccctca ctgagggcag   1020
agcctaggct ccttgggggg ggaagcaggg tgccctcag tgcccactgg agttggccag     1080
cggaggcagc agcccacggc actgagaggg aaggcccggg cagccatgcc ccagaaactc    1140
ccttggttgg gagcagagca gtgcccagag cccagaaccc agtttgagta tggtcttggc    1200
tctcaaggga caggccaggg tgcctccagg ggaaggggggc tgcccaggca gtaggggttc    1260
aaaggtcccc tggggcccac ccagctgacc caggcctagg gtaatccaga aggggagctg    1320
```

```
ccctcctcct ccctgggctc aggagaggct gcaaaggcag ctcctgggac gtggatttca    1380
gaatcagggc aaaggacaga catgagccag attcaggtgc ccgcgtggcc cccacaggtc    1440
tcttcaagct ccaggcccca ctcgctgtga cgcaggtggg aagctcttga gtgcctcccc    1500
ggtgggaggg gccgcgctca cagacagcac aggggccccc aggctccagc ctcagagccc    1560
ggctgctcac ctctgatgga cagaaaaggg tccctgtctc aggaaggtag aggctgccac    1620
ctcctggccc gaggacacag ctttccagag gaggggcctg cttctaagtc caagtcccat    1680
cccagccgga tagccagggg caactgccca ggtaaactga gacagcagca gcaggcaagc    1740
cagtgcagag ctgggtgatc cacaggttca tgagcggtgg caggtggaac aagggcacca    1800
tgggcggagg gttgggcagc tgcaggtggc atcattgagc caggggcctc ctggtgggta    1860
aggacattgt agagtgagcg ggcgcacctg gacccagga attcacagga aggagagagg     1920
aaaaaggaag tccctggcgg gtaaacacat atgcatgcac acacatccac gtctgcacac    1980
gcatccacgc ctgcacacgc atccatgcct gcacatgcat ccacgcccaa tctcttccct    2040
ggaaataaag ccaggggccc ttaggccagc ttgcagtggg gcccagccct taggacaggc    2100
tccttggtgg ggtaggggtg ggggcagctg tcctcctggg ccagctcctt gggggctgaac   2160 ccgctgctcg agggggtcttc caggctccca gcggccggca ccacctctag agcaggtggg   2220
caggggtgtg tggggtgggc aggggttttgt gagggtgggc aggggtgtgt ggggtgggca   2280
ggggtgtgtg gggtgggcag gggcatgtgg ggtgggcagg ggtgtgtgag gttgggcagg   2340
ggcgtgtggg gtgggcaggg gtgtgtgagg gtgggcaggg gtgtgtgggg tgggcagggg   2400
tgtgtaaggt tgggtagggg tgtgtggggt gggcagggat gtgtggggtg ggcagcggtg    2460
tgcggggtgg gcagggtgtg gcgggtgggg caggagggtg tggggtgggc agcagcctgc    2520
acagtggctt ccctcaaca agccacttcc tcttgcagag ggaatgttgg ggtgggaggg    2580
tgtggctcag caaagggcgt gggggttcca ccggctccct gccccgctg gtggggcaca     2640 gtgaggggggg ctgtggtcag acctggtctc tggagggcca gccgggggttt ccgtccacc   2700 tgtcagggggg ttcgacgcca ctttgagatg acaagtgagg ccacctgggc acagcgctgg   2760
tgtgagaagg aggccatcag acaggtcaaa gaacccaggc ccgccctgct ccgaaattct    2820
tcagacctga tgaagaggtg tcccagaagc gggtggtgct ccaggcccgc ctcaccagct    2880
ccagggaggt caaggttgga gagagacaat tctagggggcg aaccagacat agccaagagc   2940
agctcatctt ccctggagag gacgggctgc ccacttgcac agcccggggg cctcctgccc    3000
ctagacctgg taccttcact cttgttgcca cccctacatt catacctgcg ccccagtctg    3060
agccacacct aggcccccag ctgaagtgac actgtgggtg ccaggcatct gaggtctcca    3120
caagccccca cagactcagg gtgggaattc ctgggggcca gagctgcaga gggtgctgcc    3180
tgggggtgct gggctggacg ggggtcctgg ttgtccctcc tggttctcct ggttctccct    3240
ccgcagaggg agggaggcgg tggcctcagc agttcctcca gcagcgttcc tgagcgggcg    3300
gcagctgggc cctcttccca cagccacgct ggggttgcca tgcctgcagg tcttggggcc    3360 cccctccccct tgatgaggtc ctgaccaaat gcaggaggag caattccagc accgaggggc    3420
gagcagagcc gcctgttagc actcctggga gggcccggag tggtccctga atgatggatt    3480
cacctggaac attttcaccc tcttcaggcc caccctgccc cagaggccca cggaaaccct    3540
gcctgtactg gggccgcagc gctgccccca cccatacgta attacacggc tcggtgtaat    3600
tgcaaattcg aggtttacaa agcctccccc tggaggcccc acgtgagtgt gagcgaggcc    3660
ccagcccacc cctgtggccc caagaaggct ctgcgacaaa atatccatga gtgccgccca    3720
```

```
cgaaggcatt aaaaccaacg accttctcaa aacttaagct gtcacaggac atttcaaagg   3780
gtgtttccta agaacacctc aataatgatg ttccaaggag accccatcca aattcctcca   3840
aggattacgc ccccaaggcc cagtccacac ttgctcactc ccaggacggg gagctcacct   3900
cctcctcccc gggcgccgtc tcctccacat cccacaccag gtcctgccca tgactttccc   3960
cctctcagcg ccgtcctcag tggccacacc aagaacgagg ccatgtcttc ctgggaaggg   4020
cctcagatgt cagcaaatgc cctggtgtct tgggctgggc tggggcacc agggtgaggt    4080 ggtgggggga gccaacctca ctgcccctcc ccttcctgcc tgcccttctt ccggggcacc   4140
cagcagctcg gtcctagggc gatgttgaca gacagacaga gggcggatg cagcctacct    4200 cctgggcagt gagctgcggt ctgaggcccc tgcccagctg gaaaccacag ggaggggaag   4260
ggaggggagg agaggagagg agaggaaccg tcatggggcc ttggagtcga gtcagggttg   4320
ccaaatgcca gatgctggtc acctgcttct ttatcttggt aacaggcagg tcgggcagga   4380
gtgggtggtg ggtgggggtg agcaggggtg agggtggca gggcctcagc acagggatta    4440
tccctcccct gacacacaca ccagccctac tgtccctgtc ctgcccttgc agacatgtgt   4500
cctgcccttg cagacagccg caggcaggca gggaccacca tgagcaaccc cgtctctcct   4560
cctgaggggc agcacagagc ctggaggagg cctgagtggg gctgaggcct ggggcgagct   4620
ggggtggagg ggcactggct gccgggctcc agggatcttc tccccttcct gccccggagg   4680
gtgctggcac aggggtgggg ctcactccca ctccgtagac acaatgatca gaggtcctgg   4740
gtgtctgggg aagctgggct gtgcgtgtat gcgtctacca tgtgggggtg cctgtgagtg   4800
tgctggggcg tctgcagtga aggcctcctg agaccactcc acggaaacac cgggaatccc   4860
tgcagctgag cctgtctctc acgggaccgg gaagctggag agagcccaa ccctgcccgc    4920 tggggccgag ctccctgctc ctgcagcagt cccatgcccc acactctgag tctgccctat   4980
ccacagctgc tgggcctctc tgtgccacc atggtgactc ttacctactt cggggcccac    5040
tttgctgtca tccgccgagc gtccctggag aagaacccgt accaggctgt gcaccaatgg   5100
ggtaagtgag gtccaggcct ggctgcatcg ggaggggctc cgggtgcaag ggtggctggc   5160
acgagcccag ctggacgcct cacagccaga atggtgccag gccctaggca ggagccagag   5220
gtggtcaggg gcagggaggg gctgccctgg agtcctagct cccctgggca gggcctcggg   5280
tctgggtgac agccagtgtt cctgcctggt tctcgtgccc cacaggagcg tgggcacagt   5340
gtgggtatat gtcgggcagg gtcaggaagt ggctctgtgc ggtcaggacc tggctctgtg   5400
cagtcagggc tcagtcccag gcaggcctgg gactggcctg gggctgggca cagcaggtcc   5460
atgagggctc cacatggctg atgttccact caggacctgg gatgtgggtg gggagggggt   5520
gggggctgct ctagccagac gcctccctgc agggactcag cagcgactta tccaacatcc   5580
agagagcggg agcgagggcc agagcctgct ggggccactc aggggtaagg ctgaggaagg   5640
cccctttaat gagggggatgt cagagccaga tctgcagggg actctcaggc aggagctcag   5700
ggggcccagg aaggctgcag cccggtgggc agatgtaggg aaactgaggc ccaggaggtc   5760
agggatactg ccttagaacc caatgctttt ccccaagtcc taggaccagg gcctccctgg   5820
aggaggacgc ctgggcccca ggtccaggtc cggactgata agattacagc tccagtccgg   5880
ccacttgtca ctaggacatg gcaggaggat gcctggggcc caggtccagg tccagactga   5940
taagattaca gctccagtcc ggccacttgt cactagggca tggcagggag catgtggctt   6000
ccaagatagc cccacaggca tggagggcag ggaggaaaag agggaaggag gggcagtccc   6060
ccaggctgaa cgagtcccac ctccctcctc cttccctcag ggccgtctga tggagagaca   6120
```

```
ggcccattca gagcccccca ggagtccctc acggcccctg actcccaagt tagatttcac    6180
acccaggctg tgtgcactca ggacctgtcc tgggcacccc taaccctcct cctctctcct    6240
cccaaccagc cttctctgcg gggttgagcc tggtgggcct cctgactctg ggagccgtgc    6300
tgagcgctgc agccaccgtg agggaggccc agggcctcat ggcagggtg agttcattgt    6360 gttcccagat gcccaggccc ccagaaaaga attagaaagg agtgaagagc tggcagggct    6420
gtgtgccacc cccacacctg agtgaccagg cagaaccaga ggcccaggg atgctggcca    6480 gccgagaccc ccacgtcaac cccacacctg agtatctagg cagaaacaga ggccccaggg    6540
atgctagcca gccgagaccc cctacctggg tagccaaggc ccctccacca ggccctacct    6600
caccctgtca tctacacgcc caacaagggt tcctatagga gctctgaaag agagagacgg    6660
ccctcctgac cctgggagct gtttccaaag tccctgggag ggtctggttc tattgcccag    6720
caagctctgg gagggcactg ggagcatccc atttcctgtt cggaggaggc cgggccaggc    6780
tcaggaaacg ccccttgagc tctccagcct gggctctccg gagctgcaca ctctccttcc    6840
cagctgccgg aggtgtctcc ccagccccga ggtcccatag gccctccac cccaccccat    6900 agcagtggcc tcttgtcacc ctcattccta ctcctcccca tgggcttctg tcttggtccc    6960
tgccactcga tggtcatcgc agaccccacc tggcggcagc ctccccacgc ctgtcctgcc    7020
cctgctaggc ccacagccct cttctctcac cccagctggg gcagctcctc cctggcgccc    7080
cgggctccca cctgtccctc tagcctcccg tctcccctttt ccagccatga ggagcttgtg    7140
ctgggggctt tgcttccctg tttagcctgt gaagctggac cactctgggg gtccctgagg    7200
gcagagcctc ctgggtcccc agggctggca gggttttcag ctcagccttc aagttcagca    7260
aatgcttgtt taatgaccct ggtttataaa tgtctccaag aataggaata gagtcacctc    7320
ctggagctgc tgccgggcca accagccctg ggtgggccca tggtgggcag aggaggaccc    7380
agcagctcca gcactagcca ggattcctgc tccggggcac acgagcatgg gcagggacaa    7440
ccccggcctg tgctatctgg cttcagggcc aggtgggagg cccagtggg gagatgacaa    7500 ggcaggtagt ctgcccccc ccccagaggg tgtgtggcct gcaaagggac acctggatgg    7560
aagaaaaggt tggcaacagg gccaggccaa ggggtccagg tcagagctgg aggcccagaa    7620
agaaccagcg ctgggctgc agtaccgtcc accagggggt gccatggtgc tgggcttgag    7680
gccacatatg cagaagccag ccgctgggcc acggggctcc tgtcccagtc accagccttt    7740
cccaccccac cttgccccg tgcacaaacc agtctagcac cctcatctgt ggccaaggcg    7800
gtcagggagc acctgggctc aggttctgtg tccccagcca gccccaaggc cagggtgact    7860
tgacatgtgg gtcaggcctg tagagcagcc ttggaggccc ccaactggat gcctgcactg    7920
ggctggggtc ctgaggacac tccagtccca gctgggtggg ctccagcaca gctcccaagc    7980
cccaatgcac ttagacccag cctggatggt gagctcagca tggccacagc agggagctgg    8040 gagacccag tcaagagacc tgctccattg agctgcatga atgtgtgtgc atgagggtga    8100
gcctatgtgt atgcgtgtgc aaatatacat gtgtgtgtgc atgtgcatga gtgtgtgtgt    8160
gcatgtgtgt gtgcgtgtgc aggtgcctct gtgtgtgtgt gtgtgtgtgt gtgtaagtat    8220
ctgtcaccgg tcttcacctg cccctgttgc catacgggtg tggtgtctgc gtgttgcatc    8280
tggcacatct gtatgtgtgt ctgcacgcat gagcacaagt gaaggggcta gggaagggga    8340
gcagggagtg gaaagatttt ttccaatggg ctgggcgcct ggatgctccc cacaaagccc    8400
cttcctgcct gccccaccc ctccggcctc tcccctagct ggcctctcgc acaggaaatg    8460
aaagagcttg ctgggctgag agagcagagc tggcagcgcc gcccaaggaa gcacattcaa    8520
```

| | |
|---|---|
| ttcgcttatg tatctattta tttatttcca tttagaatga ggagaaagaa aatggccagg | 8580 |
| gcagacctga ccacccagca gcctctgatg gtgaaggccc tggggaggtc tgggtgggcc | 8640 |
| catccaccac ccaagatcct ctctgcgcgg gaggttggtg gtgggggggag agagagaaag | 8700 |
| agagaaagag agaaagagag agagaggccg tggatgctct ttctcctgag gaatgaaatg | 8760 |
| gtttctggaa aatgctggtc tcctgagctg gctcagggcc tcaagcctgg gaggcagcat | 8820 |
| tgagtgatag cttccagatg gggatggtgg ccctcagcca gcaaggagga ggaggaggag | 8880 |
| gacgaagaag gaggagggca gaggagaagg agggagaaag agggagaggg aagaggagga | 8940 |
| aaaggaggga aaaggggga gaagggagag ggagaggggg agggagaggg aggggagggg | 9000 |
| gggagaagaa ggagggaggg ggagaaggga agaggaggga gaaggaggga ggacaaggga | 9060 |
| ggaggagatg gaggaggggg aaggaggaga aggaggaggg agaaggagga ggaaagagaa | 9120 |
| aagaggaaag aaggtgagga gaagaaagaa ggggagggtg gaaggaggag gaggaagagg | 9180 |
| aggaaggagg aggagagaga agagaggagg aggaggcagc tcccaggcca tcccccatca | 9240 |
| ggccttgcag cctccagggc aggcaggagg gccatgagga gccgccagcg ccctgtccct | 9300 |
| gcagggctgg aggcccatg ctcacgcctg tgcttggggg ccagcagggc tccccagctc | 9360 |
| tttccacgcc cctctggccc agcttcccct ggcatgccag cgttgtcgct gcccacctgc | 9420 |
| cagcatgtgt gggtctccgt ctatcccacg gcacccatg ctcctggcat caccctgaat | 9480 |
| ggggccccag ggtttgaagg gcccagaccc aacctgctcc agcctgtgga ccacccaggc | 9540 |
| gggcacagtg ctgcctgagg gggctggcgt ttcaccgggg cctcaggact cctggggag | 9600 |
| ctgcccggtc ggtggctaga ctcaccgtca ggtactccag gtcctcaggg caccagcatg | 9660 |
| aaggcaaagg cggctgccca gaccctgagt gggaggacat ccccagggtt cttagcctgg | 9720 |
| gtgacctctg ccaccatcca taaaactgta tcgggggcat ctgtatgctc tcagaggagg | 9780 |
| ggtctctcgt gttccttagc ttccgcaagg gggctctcaa aagcctggaa gccttgaccg | 9840 |
| agagaacaac gggcaagtgc cgggggcggg tgcgcagacg tttccaccag agaacgcccc | 9900 |
| actccacgac taggggcacg ggcatcagtg agagagaggg gacagtggtt ggccgggcca | 9960 |
| tggagaccca ggcagagtat ggagagaaag tgaggtgagg gaggtgggct caactgcaaa | 10020 |
| gagagaggcc acagcatcct gagcaggcac cacacctgtc ccaagcctca ccagcactgg | 10080 |
| gctagctggt gccttgtttc agaaaagaag gcaaaacaga agatcctaca gccccggccc | 10140 |
| tggagaggct caggctcagg ggagactctg cccggccctg tccaggtcca tgcccctcag | 10200 |
| gaagcagccc cagtgggcag aggtctccat cttctcaggg gtgccctgcc cctgctgggc | 10260 |
| aggggtgcag tgttgccatc aacaggcccc tgggggccaa aatggagaa caagggatga | 10320 |
| attcccaaaa agcgcagggg aaggggatgg gaaggtgcta tggaacccac gcacccagcg | 10380 |
| cccacgctct ccccaggcca agtctccctc tcaggcagtg gggagcggga ctcagaccca | 10440 |
| cacctcgacc aagcatcctg ctgggggcgc agcctgaggg cactgccctg cccaggcctg | 10500 |
| ccaggcccca ccaggccccg cagtgactgc ccccacccc gcagtgacca ccccccaca | 10560 |
| gtgaccggcc ccccgcagtg accagccccc cgcaatgacc agccccccaac agtgaccagc | 10620 |
| cccccatagt gaccggcccc ccacagtgac cagcccccccg caatgaccag ccccccaacag | 10680 |
| tgaccagccc cccatagtga ccggcccccc gcagtgacca gccccccgca atgaccagcc | 10740 |
| cccaacagtg accagccccc catagtgacc ggccccccac agtgactggc ccgcccacag | 10800 |
| tgaccggccc ccccagcag cgaccagccc ccgcagtga ccagccctca acagtgacca | 10860 |
| gccccgctct gccccaggg cttcctgtgc ttctccctgg cgttctgcgc acaggtgcag | 10920 |

```
gtggtgttct ggagactcca cagccccacc caggtgagca ccagctgccc ctaccctgca   10980
gtggagggtc ccccagtaag ccagtgggca cctggggact ggggagcagt cctgggagga   11040
gcagccccag cttccaggct tgtgctgacc gggtggggtg ggggagaccg cagcctgggt   11100
tccctctgcc tgaggcttca gggaggccaa gcgctggagg tgggtgaggg ccagcagctc   11160
cctggtgggg agggacctat gctgtacccc tgccttcgcc ccagtctcat tttcttaaag   11220
cccctcagcc caccccctcc tgagctgatg ccccctcgggt ttgagggagg gaatgaggag   11280
gaagaagaag gaaagccact ggcttggcct taggggttga ctagaaggag cagagtgttc   11340
cagaaaatga gacctgaggg ccagcgctcc tgatggcctg gtggggcaga cggtaccagt   11400
ggggaaggga cctggagacc gcggactgg ggtgtcgcag cctccacccc ctccacggaa   11460
cagcacccat ccttccgtcc tggatgctga cctgcctgga ggagggtccg gcctagctga   11520
ccgtgggcag gggccaaggg cgtccccgtg gaaaggccag cagcttggag aggaaggagg   11580
cctccctggc ccagcagaga atgagagctc ggtagcagag ccagcccac cttccccttg   11640 agagccagac ctggtgagag cccccagggc agccgggcgg caccagggac agccacgggc   11700
agggtcatgg agtggggcag gagagcctgg caggtcacaa gaggtgatt cttggagccc   11760 tagctggagt cctagtggcc tcgtgtattc aagtgcctgg ttgcccaggg ccctcaaaca   11820
caggcttggc catgagagat accgaggctg gtagcaggca ggtcctctgg ctgagctctg   11880 caggggggcct gctgtgcagt ttcttgagct gtgctggcag cctgagtgtg gtggtcccca   11940
ccgtggtttg caaatggggg gactcaggcc ctctgggggt gggggagct caaggttacc   12000 ctggcagtgc cggggctgga tgggggctcc aggcttacga caaaggctct tggccccaaa   12060
gtgcccaccc acccctggca tcatttggga ggaaccgcct gaaccaggtg ggagaaacac   12120
cattttatca ggcccagaag gatcccagag gggctgagcc cccagaagag ggctgtggct   12180
ttgaggactg gcacaggagt cttaccaggg tggtgagctg ggccaggtcc gtgtttcggc   12240
ctcacgtttc ctgtccactg aggggtggtc tggctcattt gaggtctggg tcacagtgtg   12300
ggtggccgag gtcaagacag ctgccagggt tccccgggct cgtctggggc agctgcggcc   12360
catgccccat gcttctgtgt gtttatggct ctgatcgtgg agccacaatt ctggagggga   12420
gggggccata caggggccac aggacagaac gcagctgggg cctgctctcc aggaagggaa   12480
gggggtgcaa gaagatagat gccccagccg ggctcaccta tggcctgtcc cagccccagg   12540
cagcatcccc cacacacatg gtccttgtct ggcccgtgcg cccagctgcc cttcaggggt   12600
cagttctcag ggccttgcct gaccccaggc aggggactgg ggcttcctcc tgggcctctg   12660
gtccccatct gcccctccca gtgggtcttg acttctggca tcatctgtgt caggcctggt   12720
ggccatggag gtggcctggg tgaaggagct ctgaatatga agtcagtgtc cttgggccgc   12780
ccttgggcaa gccactttaa cttcctgggc ctcagtttcc tttctgtga agggagcacc   12840 aagatccagg ggctgcatgg gtgggaatgg ccaggtgtgt gcaaagactc ttcctcctca   12900
cctgcgtgcc tcctgccgtg ccccgttgcc caggctggtc ctccaggacg tgggacttgc   12960
tcgaagctgt cctgggtgtg gatggagtgg ctttggtgcc agggcccggg ccctgagcag   13020
gaggggcggc tgcacatccc gtctcctgcc ctccaccctc agggcccacc agagccgaat   13080
gggcttcaac cttgggctcc ctgtccaaca aagtcctgct ggcagcctag acagtggcaa   13140
aggccaaagg ccccaagctg ttggcaccgg aaacgtcgag gtgagagccg ggggcccaga   13200
gcccagcccg gcccattcac ccattccccc tgtccctccc cacagggcca ctgaggtgtc   13260
ctgaacacag ggtcagggtg actcatgtgg tgcccctgcg gatgggaagg cagaggacag   13320
```

-continued

```
aggagggaag ggaccagcca catgcccttg gtggtgccct gtggccacag acccgggccc   13380
agagctgaaa gtggggtgcc cctccacctc cccaactctt gccccaggga gtcctggctg   13440
ccacttccct gggatgctca tgcgggcagg aggcgtggac cgggcttcag ggatgaatgt   13500
ggagcttgag ggctattaat tacgttctcc tcgagggctg agagccactt tgccttaacc   13560 ctcccctgt gccctgacga gtctgcttcg ggaataattc atgctcaaat taagtacagc    13620 agtgtgggt gcagcctcgt cctcacagtc tgccccaccc tggagccact accctccctg     13680
gatcctccag ccgccgagtg ggctcaggcc agagccagct ctgtacctgt ggggctggtc   13740
cacaggcctc ctgcagctcc tggtccccac ctgccgttca ggacctgtct gtaccttcct   13800
gagcactttc agcagacaca ggatgggtc gccaagccca gcagacacc agggaagatc     13860 tggtcatggg gaaaagcccc cgggcaccgg aagacggagc ttagtgcgtt gatacctgtc   13920
aggcagcacc ttcccccagg tgtcctgaga acacaggcc ccaggctcct tcagagcccc    13980
cagagcctga atggagaca gacggtgaag catcacctag gagcccaggc cccgtggaga    14040
gcagccggcc cggcctccag ggccctccag ggccagacaa ccggctttgg ggtaggaggc   14100
ctacctcgct gagctctgct tccccagtcg tggggagagc tgcttggcag agccaggcag   14160
ggcaggaaga gccaggcagg gcaggcaggg caggcagggc aggcagagcc aggcagggca   14220
ggcagagcag gccctcagc cactagcagg agttgtcact ctcgcccatg ctgtggtaat     14280
aatgacacct tgctcacagc ctcagaggca cctttgtcct ccttgggcca tggcaggcgc   14340
ctgacaatgg gaacagtcat tggagttggg agggaagcag gaggggaggt ccgagccaac   14400 cccgggccc actccgctgg gcctccagtc ctcaccagga cctccaccca cgaggacaca   14460
atggccaggc cagactccac ccccatttca cactcacaga cgctgaggct gaacaaggcc   14520
cccgccctgg ccgacagtgg tgtggccagc ttggtgcctg cccgcccctg ggcactgcgg   14580
ggaggacaag gctggctgag tcggggatga ctcacggaga gtggtctgac ttttattagc   14640
atcaatggga gggatgcatt agggtcagga gccaagtttg gcctggaaag tccatctgac   14700
tcctgttggg gcctccaggc ttgggcaggg ctgaccgaga gcctccactg cccactgccc   14760
gcccagttgg ccgctgtcag ggcctgccac gggggctggg ccccagtgca atgaggaccg   14820
ccgtaagcca ccccttcctt ctggagggca ggtgtgagtg gctagagcgg gcctggggct   14880
tccatcctcc cccagcccctt tggggcagct gctgagcacc cccttcatgt gtcttgactg   14940
tcagcatggc atttggggga gaactgaggg cctctgaggc aggaaggaga catcagaggg   15000
cagggacctc aaagagggcc tcgccctgtg ccaggagacc agcgactcct ggagcagtca   15060
cagaagcctt cctgtaggag gcgagattcc agtttgtctt tgaaggagta acttggcagg   15120
ggagagcatc ttgcttagga gggtggagac atgaggtcca ggtgttggtg aggtgtggag   15180
cgcaggcagc acatccagcc aggccccgtc accttccacc ttcttcaccc cctgccccac   15240
agtggcctcg tccacccaga tctggcctca ggtgcccaag gcttctctgg tcaaaagcct   15300
tacccggagc ccagctgccc gggcttccag aaggcagccg ggtgattctt gggaaagatc   15360
tagaatcccc aagctttctg ggagctgagg tcctggcaca gggtctctca agccttttcc   15420
accaggccca gccccatccc ccatttccgg tcaacagta gcgtgctgga aacttctgtg    15480
ggccaacctt gtaagaccac agcggaggcg gacgcagagc ttggcctctg ctttatcctg   15540
cgggaccctc tgggggcagg agggccactc tgacggccat tgtgtgaagg ccccatcgtt   15600
gatgttggga agcactgtga ctggctgccc agggacccag gttccgcttt ggggagatcc   15660
acctgctaca aggagggcag tgctgggacg tcactcagca ctaagggccc actagcgttt   15720
```

```
gggatgtcgt ggggaggggg ctgtgtcccc ggatctccca ccagggccag gacctccctg   15780
tggtctctcg gtgcaggtgg aggacgccat gctggacacc tacgacctgg tatatgagca   15840
ggcgatgaaa ggtacgtccc acgtccggcg gcaggagctg gcggccatcc aggacgtggt   15900
gagcgtgggg acggctgggt ggcagggcgg tcagcttctg cttggactgc agttcagaga   15960
acaggcgcag ggtggccagt gagaggtctg gccaggcacc gagggggttc caggacacag   16020
gccagagttg cccctcaggg ctgggggcaa aaagctccca ccctctgtct gcccaggaca   16080
aggccgccta ccagattctc gaggcccagt gcaaaacgag agggcagggc cctgtattca   16140
gaaacactga aggatttcaa gagcattaaa gcaaatacgg ggccgaacat agtggctcac   16200
acctgtaatc ccagcacttt gggaggaggt tgaggcaggt gaattgcttg agcccaggag   16260
ttcgagacca gcctgagcaa catagggaga ccttgtctct actttaaaaa aaaaaaaaa   16320 agaaaagaaa aaataaaagc acatacagcg cacaggccct gtgaacaggg cggggaagct   16380
gcctggctcc agcaggtgtt ctgtcaccag caggcaggca gcgcagcttg agagagctcc   16440
ccttaccagg gcccggctgt gcaatggctg gagcccagc agaagcagct gcaataccag    16500
tagccccagc cctggcctgc agggaacccc acctggatac ttgtggtgcc tcagtttccc   16560
catatgtgct gcccgcctcc tggggtctcg ggagcacatc accactccct cccttctgtt   16620
cctgtagttt ctgtgctgtg gaagaagtc tcctttcagc cgtctgggga gcacagaggc    16680
tgacctgtgt cagggagagg aggcggcgag agaggtgagg gggggacctg gatgctggcc   16740
aggcaagacc ctcgggggct ggacaccctg ggcccaacc ccaagaccca gggccatcct    16800
cccaccccac cccttggcct ccccagaccc ttgggaactg ccgctgaagg gctcagggaa   16860
ggttctgatg tgatcggagg ctagttaggg ttcatggtac gccaagccca ttgggtggcc   16920
aggctgggct caagacataa acacaggccc ctttgcccag ctggacgcag gccccatgcg   16980
ccattcactc cttcaagcca gttccagcct ggggacttcc caaggccagc taagtccaca   17040
gaagcctctt ggagtgcacc catgagggct ctgtgccaag ggctgcaggg ctggtgtggt   17100
gggctctgtc tagggggaag ggtgcaggcg tcctgggggg catcagaagg agttgaaggg   17160
cactcagagg agaagaagta ggccagggtg tggccagggc ttcagcaaca acagagcggg   17220
gcccgaggcc aggaagcctt tcctccccag ggccctggga gagactgggc cctcctctct   17280
ttctcctggt gcccggcagc cctcccccag cccaccctgc cccctccctg ctcccctccc   17340
cgctcccctc ccctactgtc ctggaaacaa acccacccta tctcacagtg ggaggcacct   17400
ggcgaccctc caagaaacag aggggaggag agcaaatggc tggaggcctg gtgagggtg    17460 gagccacagc caaggctctg agggcagaag ggctggcgct gaggatggtg ctggggaggg   17520
accagcggca ttgggggcag ggctaacagt caggaccct gtgccaccca aggagagact    17580
gaaaaggccc ccgactgaaa agcaggagcg agggcctgcc tcgagcaccc ttgggatggc   17640
agggccatgg gcccgactgc aaagcctcct ggggagccgg aagagccagc acaggcggca   17700
ggcacggagc cacccagatg ggctggcatg ggcgggaggg aggcagacct gcctgcgggg   17760
gacaggaggg tgagccctga gaccctgcgg aggcctccac aggccgcccc agttgccatc   17820
atctccaggg ttcagagaca ggcctgccac ctccctttc tgaaaagatg cctctggggtg   17880 ccatgccctg gggtggcact ggaagcctgg gatggaacca ggaagctggg actgtgcggg   17940 gaccccctc acacccctcc accagctggc ttcctgccct ccctgttagc catcaccctc    18000
tggtcaccaa ggtgctgtgc ccggccctgg gctggatgct gggaacccag agtgaattcg   18060
aagtggcccg gcccagggga gccaacgtgt ggcccaacat ggacgctcag gacagctggg   18120
```

```
agacggcacc ggccgggccc agggcagtgc cagagtgccc acagaggcca gccctgtccc    18180
actgggcttc acctgctcgt gctgcctttc cctagagccc tgggggcttc ctaggaatgt    18240
gccgcacccg ccgccctgct gccctggcat tggcctaggt gggcgctgca gctccatggc    18300
cccacagagg ccgcttgtcc aggcagggag ggccgctcag ggcgggtacc atgcctgctg    18360
ccctctcaca ggactgcctt cagggcatcc ggagcttcct gaggacacac cagcaggtcg    18420
cctccagcct gaccagcatc ggcctggccc tcacggtacc ctctcgcctc cctcactgcc    18480
ccttcccacc tcctgcccct cagcctgcca gccccgac tcagatggaa gggtgacccg      18540
ggacaggatc tctggtcttg agcctcactg gctgccaacc tcagggagct gctctggtgt    18600
gacagggcct gcctcctaca gctgggccgc ccccttacac tgcagagtcc tgatgcttcc    18660
tggggagggg cgcccgcacc ctgggcagt ggggcagccg cgggtgtctc cctcccaggt     18720
gtccgccttg ctcttcagct ccttcctgtg gtttgccatc cgctgtggct gcagcttgga    18780
ccgcaagggc aaatacaccc tgaccccacg gtagggcccc ctgcctgccc ccacacccctc   18840 tggaagggtc ctccagctct gctcgagagg catctgctct gccagctgct aggagggagc    18900
cccgggacca agccccaggc tgacactgta gaggaaacgc tttgggggtg gctgagcacc    18960
agggtggggt gggagacctg gagagtttcc agacccaatg caccgcaccc catggcccac    19020
atggggaccc cccttttgctt accccaggc cttaccaaga cctggagatg gatgcttctg     19080
ggcctccagg ttatagcccc aggccaggat ctctgtgctt gaataccca gagctcctca     19140 tgcttagggg gcagggaggg tccaacccac agccaggcag ctcttcctgc ccccacggag    19200
cctggcccgt ctctgcctgc catgcccatt aacccaccca cttgctcttc ctggccatcc    19260
aagccctcat ccctgggtcc tctgcattct acaatagcct cacagtcccg tctagaacat    19320
tctgcaacag cctcacagtc ccctagaaac attccacagc agctccataa tcccctccag    19380
aacattctgc aacagcccca tgatcccctc tagaacattc cacaatagcc tcacaggtcc    19440
cctgtagaac attccaccac agccccatga tccccttgct cctcagagca tgtggccgcc    19500
agccccagga gccagcctc ttgagatgct cccagggtgg acccacacat tgtctccact     19560
ccgaagcagt tgctattggt ccaagaggat gctcgggtag tcttcggtgg ctgcaggaga    19620
gcgatgctgc gcctctgccc ctctcctgcc acctggctgc ccacagaggt gaagacgccc    19680
ctgctgtcag ccctcatggg atccctgagg ggagggtccg agctgtgagg agggaaggga   19740
gtgaaggccc agccagagag ccaggctcca ttgggaacag atgcaagggt aaggggtagc    19800
tcaccaaatc cctccatggg aacgggctgg gagcaagcac aaaggaaacc acactggagg    19860
cagcagccca gggcagactg caagacactg gtgggccacg gcctggaggg ctccacccag    19920
acacaagctg cactggtttt ctatgctgcg taagaagcag catggatgta aggactgcaa    19980
gcagtgccca tttatgatct cgcagctctc cagggcagaa gtcgcggtgg gctcagtggg    20040
tgccctgagc ggggtctctc agactgacgt caggccttgg tgggctgcac tctcacctgg    20100
aggctccggg gaagcatctg cctccaggac cattcaggct gttgacaagt caactcctca    20160
tggctgtagg actgaggatc ccaagtcctt gtccctggtc ctgtggtccc tccaccttca    20220
aaccagcaat ggtgcattga gcaaattgtg gtcaaatata catcacatca aatttaccat    20280
cttaaccatt gttaagtgta tggtttgtgg cattaaatac attcacattg ttgtgcaacc    20340
atcaccacca tctatctcca gaactttcca tcttctcaag ctgaacctct gtccccagta    20400
aacaccaact cccattctct gccccggtcc ctggcaccca ccatccactt ttcgtctcta    20460
tggattcagc tgctccagga acctcatatg tgtggggtca cacaggattc atccttttgt    20520
```

```
gtctggttta tgtcacttac tgttatgtcc ataaggtcca tccgtgttgt agcctgtgtc   20580
agaattcttg aaagagaaat cttatcagct ttcccatcat ctcacagcca catggtccgt   20640
gattaaggca ggacatttag tgggaagcgt ggagcatttt agatattctg cctgccacac   20700
ccactcttac tggacgttca gaccacgttg atgacgaatt agctctaatg gtccctaaat   20760
gtttgcacaa tttgctcaaa attctaagtc ctgggtggaa cgccaagttg cccagccta    20820 ggccaaggtc ctaatgaagc cgacaaaaga gaaggaatgt caaggccctt ctaacttcca   20880
tagagggtgt gtggccccat ctcccaccaa caatcctgta atcccaacac tttgggaggc   20940
cgaggcagga gactgcttga agccaggagt ttgagaccag cctgggcaac atggcaagat   21000
cttgtttcta caacaacaac aaaaagaaaa cattagccag gcatggtggc acacacctgt   21060
ggtcccagcc actcagggggg ctgaggtggg aggatctctt gagcccagga tgtcgaggct   21120
gcagtgagcc atgatcacgg taccgcactc cagcctgggt gacagagtga gaccctgtct   21180
caaaatataa acaataggc ggggggcagt ggctcacgcc tgtaatccta gcactctggg   21240
aggccgaggc aggcagatct cttgaggtca ggagttcaaa gccagcctgg ccaacatagt   21300 gaaacccat ctctactaaa aatacaaaaa aaattagcca ggtgtggtgg cgggcgtctg    21360
taatcccagc tactgagcag gctgaggcgg gagaatcgct tgaacttagg aggcagaggt   21420
tgcagtgagc cgagatcgca ccattgcacc ccagcctggg tgacaagagc aaaactccat   21480
ctcaaataaa taaataaata ataaaaataa ataaagtaca aaaaaattag ctgggcatgg   21540
tggtgggtgc ctgtaattcc agctactcag gaggctgagg cagaagaatc acttgaagtc   21600
aggaggtgga gggtgcagtg agccaagatt gcgccactgc actccggcct gggtgacaga   21660
gcaagacacc atctcaaaaa aaaaaaaaaa tttaatatat atatatatat gtgtgtgtgt   21720
gtgtgtgtgt gtgtgtgtgt gtgtatacat atatacacat atatgactaa ctaaataaat   21780
aaatgctaat aaataaaata aataaattaa aataaatctc caaactagaa gagtaaggac   21840
taacagggcc aagaggtaaa cttttgtgaa tgttccaacc ataagtgctg ccctcactct   21900
cacccgtagg ccccccggcct gtggattctg gtttagggga acggcaccat tcaccagggt   21960
ccagggtcat atgctgtagg actctctgca gtcttgtggt ggcatcttcc agctgagctc   22020
ctaaataatc ctgagtggtc ctgagaagcc agatcaccat cccacagggg tgggtcctgt   22080
ggagggacag ggtacatgga accctagtga atcccatggg gtctccccac tgccctgtcc   22140
tttggctgta aaggcgatgc cttggctgga aacagcagta cgtgcaggag caggcagtag   22200
gctgggaagg aaagtgccgg tgccggagga agcagtgcta gtggagggga gtgggtccag   22260
atcaagaagg gttaagtgca gtcatctttc ccatcatctc atagttgcac ggtccaggga   22320
tgaagacagg acagttagca aggagagggg aaccggatca tttaagacca cagctggaag   22380
atgtccctga tgttcgcac aatttgttga aggttctaag tcccgggtcg aacaccaagt    22440
tggcccagcc taggctgagg ccctaatgta gcttggctaa caagagagaa ggaatgttgg   22500
ggcccttcta acctccatag gggggtgtgg cccccccatga agtggaaata gtgccagtgg   22560
gggagcatca aggagcaggg ccatatccta taggacttca ctgcagtctt gcggtggcat   22620
ctcccagctg tgctcctaaa tgattctgtc ccctccgcac taaatgtcct cccttcgtcc   22680
ctgggaaaag ctagaccctc tccatgaagg aaggcgtcca aagccagtca gcccttggcc   22740
aggtgaccaa tcggtctccc atgagatgtg gtgcgcttct gcgggcggg acggcacact    22800 gctgaccttg atcgggcatc ggctgcagtg caggggtgtc tggaagagct tggtaagctg   22860
agtccctgtg gctgggccac ggcggctccc ctcccctcca tgtctgcctc agggcagcaa   22920
```

```
cagctccctt ggggcagagg ctgcctgtct gccacgggtt ccaagaacct tattagagta   22980
cagtacccca tgcgcttgac agtatgccca gcctgtccag ctacaggact cagcagacaa   23040
acaacaccca ggtcagacta cacctgatgc ccatagacag ggctcagtct ccacccaggc   23100
ccaggggaaa ccgagcgctg tatatccaag cgagaagagg tcctggacac agagggcaaa   23160
ctctgctctc ctcgacgggc actgtggcct ccaccatggc ttggctcagg ctccgagggc   23220
gccttggtca gccaagaccc caagaggacc cttaggtccc tgggtcacaa ctgagtggct   23280
cagtccacac aggaacaaga ccacatgggc atcgtcactg gctgtgcctc ctgcagaaag   23340
caggccaccc ctggcgtgcc tggacacagg ggaagcacac acccaaatgc aggctgtgtt   23400
tcctccaaag agtgctgcgc acggatgact caggtgcag gactggtcct tcaccaccac    23460
ggagtaggca tgcccggctt cgttggaccc agagagagc ttcaggagaa agcaggagtc    23520
tctgttttta cagggtttcc ttctcaccct gccactcatg gttttgtta aagcaaccta    23580 caacttcctc acctccaggt catatcagcc caatgtcctg tgggctgggg agacggtcaa   23640
ggtccacatg ggctaaattg tggctgagag ctaggttatt catgtaatcc caggcaggt    23700 ccacgctgct gtccctccca ggtgagagca aaccaccttt atggttttct atatgttggg   23760
atagactgaa aacaacaac aaaacaggtg tttgctggcg aaatagctgc ttgccagtac    23820
aaatgcctgt gctgatttgt tccaattaag aagaaaactg gtgcttgctt cagccacaca   23880
tacactaaaa ttgaaccat acagagaaga ttagcatggt cctccctgcg caaggatggc    23940
acgcaaattc ttgatgcatt ccatattttt ggaacatacc tcaaataat aagagccata    24000 tatgacaaac ccacaaccaa tatcgtactg aatgggcaaa agctggaagc gttccccttg   24060
aaaaccagcg caagacaagg atgtcctctc tcaccactcc tatttaacat agtagtggga   24120
agttctggcc agggcaatca gacaagggaa agaaataaaa agtattcaaa taggaagaga   24180
ggaagtcaaa ctatctttat ttgcagataa catgatccta tatctagaaa accccatcat   24240
ctcagcccaa aagcttctta agctgataag caacatcagc aaagtctcag gatacaaaat   24300
caatgtgcaa aaatcgctag cattcctgta caccaacaac aggcaagcca atgaactct    24360 cattcacaat tgccagaaaa agaataaaat acttaggaat acagctaaga agggatgtga   24420
aggacctcct caaggagaac tacaaatcac tgctcaaaga aatcagagat aacacaaaca   24480
aatggagaaa cattccatgc tcatggatag gaagaatcaa tatcatgaaa atggcctcac   24540
cgcccaaagc aatttatgga ttcaatgcta ttcccattaa actaccattg acattcttca   24600
cagaattaaa aaaactattt taaaattcat atggaatcaa aaaagagcct gaatagccaa   24660
ggcaatccta agcaaaaaga acaatgctaa aggcatcatg ctacccaact tcaaactata   24720
ctacaggaat acaataacca aaacagcatg gcactggtac aagaacagat acgtagactg   24780
atggaacaga ataagaaca cagaaataaa actgcacacc tgcaaccatc tgatctttga    24840
caaacctgac aaaaataagc aatggggaaa ggattcccta tttaataaat ggagctgtga   24900
gaactggcta gccatatgca gaaaattgaa actggacccc ttccttacac catatataaa   24960
aatcaactca aggtggatta aaaacgtaaa tgtaaaaccc aaaactttaa aaaccctaga   25020
caaaaaccta ggcaatacca ttcaagacac aggcatgggc aaagatttca taacaaagac   25080
accaaaagca attgcaacat aagcaaaaat tgacaaatgg gatctaatta aactaaagag   25140
cttctgcaca gcaaaagaaa ctataaacag agtaaacaca cagcctaagg aatgggagaa   25200 aattttttgca acctatgcat ctgacaaagg tctaatatcc agtgtctata aggaacataa   25260
acaaatgtac aagaaaacaa acaaacaaac aaacaaaccc attaaaaaag tgggcaaagg   25320
```

```
acttgagcaa atacttctca caagatgaca tacacgcggc caacatttga aaaaaagctc   25380
aacatcactg accattagca aaatgcaaat gaaaaccaca atgaaatact atcccacacc   25440
agtcagaatg gccattatta aaagtcaaa  aaataacaga tgctggtgag gttgtggaga   25500
aaaaggaatg cttttacact actggcagga gtgtaaatta gttcaaccat tgtggaagac   25560
agtgtgataa ttcctcaaaa acctagaggc agaaatatca ttctacccag caatcccatt   25620
gctaggtata tacccaaagg aatataaatt gttctgccat aaagacacat gcacgtgtat   25680
gttcacttca gcacaattca caatagccaa gacatggaat caagccaact gctcatcaat   25740
gatagactgg ataagaaaa  tgtggtacat atacaccatg tagtactatg cagccataaa   25800
aagaaacgag ttcatgtcct ttgcaggac  atggatggag ctggaggcca ttatcttcag   25860
caaactgaca caggaacaga aaccaaata  ccgcacgttc tcacttataa gtgggagcta   25920
gatgatgaga acacaaggac acatgggggg aaacaacaca cagtgggacc tgttgttggg   25980 ttggggtgg  gaggagggag agcatcagga agaatagcta atggatgctg ggctgaatac   26040
ctgggcgatg gaatgatctg tgcagcaaac cgccatggca catgtttacc tatgtaacaa   26100
acctgcacat cctgcacatg taccoctgaa cttgaaagct ggaattttt  ttttttttt    26160 tttacttt   taagctcttt tgttaaaaac taagacacaa acacacatag cctcggcctg   26220
cacagggtca gaatcatcag tttcactgtc tttcactgtc acatcttgac cagttttgtg   26280
accggaaggt cttatgggca gtgacatgca tgcaactgtc atcttacgtt atagcaatgc   26340
cttcttctgg atacctcctg aagaaactgc ctgaggttgt tttacattta acttgtttta   26400
tatataagta gaaggagtac actctaaata aaaagtatag taaatacata aacgagtaac   26460
gtagttgttt gttatcattg tcaagtactg tgtgctgtgc ataaatatat gtgccagatt   26520
tttatatgac tggtagcacg gcaggtttac ttacaccagc attgcacaaa acacaggagt   26580
aattgatacg gtttggctgt ttccccaccg acatctcatc ttgaatcgta attcccataa   26640
tccccatgtg ttctgaaagg gacccggtgg gaggtaattg aatcatggag gtggttaccc   26700
ccatgctgtt ctcgtgatag tgagtgagtt ctcacaagat ctgatggttt tataaggagt   26760 ttttcccct  ttcatttggc acttctcctt gctgctgcca tgcgaagaaa gacctgtttg   26820 ctccccttc  caccatgatt gtaagtttcc tgaggcctcc ccagccatgc ttaactgtga   26880
gtcaattaaa cctctttcct ttataaatta cccaagttcg ggtatgtctt tattagcaat   26940
gtgaggatgg actaatacaa aatgcattgt gctacaacat cattaggtga taggaatttt   27000
tcagctccac tataatctta tgggaccact atcacacatg tacccgttct tgaccaaagc   27060
atcctcatgc tgtgcacaac tgtactcagc caccggctga gtccccacat tggtttcctg   27120
acgtgtgggg tgagggccac tattgtgggc caactggaag ccattagagg tgcctctacc   27180
tagaaaaata gtcaaaagcg atacaataat agtcagtcaa aagctgcatt tccagaggaa   27240
tttcagaggt tagtgccacc atcaaatacc tgaaagatgc aggggcagtg atccccacca   27300
cagccccatt ccactcacct atttggccag tatggaagac aggcgggtcc tggagaatga   27360
caagggattg tcctaagctt gactccaact gcagctgctg ggccagattt ggttccattg   27420
cttgagcaaa ttagctcatc tcttgctacc tggtgtgcag ttattgatct ggcgaatgtg   27480
tccttctcca cccctgtcca caaggcccag cagaagccag gccagcaatg caccctcact   27540
gtcccacctc aggggcctct cgcctctcca gcctgtgtca gaggtaatcc tcagggtct    27600 ggatcaccct tcccttcccc ggcatgtcac actggcccat tacactgatg acattatgct   27660
aactggacat aaggcacaag aagcagcaat tattctatac ttgttggtgt cagagggtgg   27720
```

```
gaaataaatc caactaaaat tcagaacctt ctacctcggt gaaattttta ggagtctagt   27780
gctgtggggc ctgctctaag gtgatacata gattgttgca actgaaccct cccacgatca   27840
aaagagaacg acaccaggtg agcccgtttg atgtgaggaa gacaggttct tcctcattta   27900
ggtgtctgac tctggcccat ttactgagtg atttgaaaag ctgctagttt tgaatgtggc   27960
ccagcagcag gtccaggctc tgtgcaagct gttctgccac ctgggccaat gacccagcag   28020
atccagtctg aggtgtcagt ggcagacagg gacactgtgt agagcctttg ccaagcccca   28080
gtaggtgact catagctcag gcccttacag ttttggagca aggccctgtc atcatccaca   28140
gataaccact ccgttttgag aaacaggttt tggactgtgt attagtctgt ttcacactgc   28200
tataaagata ttacctgaga ctgggtaatt tataaagaaa aggggggttag ttgactcact   28260 gttctgcatg gctggggagg cctcaggaaa cttacaatca tggcggaagg gaaagcagac   28320
acattttaca tggcggccag tgggagaaga atgagcaaga caggaactac caaaacttat   28380
aaaaccatca gatctcgtga gaactcactc attgtcatga ggacagcatg gaggaaacag   28440
cccccacgat ccagtcacct ccggccaggt ctctcctta acacctgggg attacaattc    28500
aagatgagat ttgggtgggg acacaaagcc taatcatatc agcctgtgtc taggtcttca   28560
tagaaactaa acacttgacc aagggccacc aagttaccac atggcctgag ctgcccatca   28620
tgatctgggg attatctgac ccatgttgct ataaagttgg gcgtgcacag cagcgctcca   28680
tttgaatgaa agtgatgtat tgtgatcagg ctcaagcagg tcctgaaggc aaaagtaggt   28740
tacgtgaaga agtggcccaa atgcctgtgg cccccactcc tgctccaggt gccttctctc   28800
tccccacctg catctgttgc tgcacaggga ggtccctctc atcaattgac atgggaagag   28860
aagactcagg ccatacttac aagtggtctg ctcgatatgc aggtgctatc agaaaatgga   28920
cagctgcagc cctacagccc ctgcggcaga ggcaaaggat ggaaaattcc attccaaaca   28980
cgagaaatgg gaaggaaagg actaactgag catgaccaaa tccaaaaccc aacaggacaa   29040
aattaaatct taaagctgaa gaataatttt ctttgactct ttgtcctacc ttctggacac   29100
actgggacaa ggctcctggt ggccccactc ctacggcttt gtgtgcctgt ggctttccca   29160
ggctggtggt gcatgctggt ggctctacag gtcccgagtg tcctctgctc ccttgggcac   29220
cactacacat tgtcctgtgg ggactctcca tggcccaaac ctgtagcagt tctcggcctg   29280
ggccccaggg tctccatgac acccagtgga atccaggagc aggaactttt cctccacagc   29340
acgtgcactc cgtgcatctg cagagctggc accgtgctga caccatcgag gtttaccgcc   29400
tgcgccttct gggctggcag cccaaggaac acctgtaccc acgtgagcct ccatgggggt   29460
gggccaggag tgatgcacca gcttgcaggg aggaacagag attgaggcaa gtctgggcag   29520
cacgccccga ggtctcatgg aggccctggg cccttctttt gaagccattc tgccctcaag   29580
accccggcac cctgagcctg tgatgggcat gacagtctgg aaggtctcgg aaatgccttg   29640
ggggtcattc tcccattgtc ttgatgagca gcttctgacc tccttctacc cgtactaatc   29700
tccttatcca aatttgcttg actacaccct tgctattctc tcctgaacat gctttcttat   29760
tctttttttt ttttttatta tactttaagt tttagggtac atgtgcacaa tgcgcaggtt   29820
tgttacatat gtatacatgt gccatgctgg tgtgctgcac ccattaactc gtcatttagc   29880
attaggtata tctcctaatg ctatccctcc ccgctccccc cacccaaaa cgggcccag    29940 agggtgatgt tcccccttgac gtgggcaggc taagagtttt ccaagtcttt aagttttgtt   30000
tcctttctat tatcaattct ttaactcatt tctcttttct cgccttttgc tataagcggt   30060
caacagaagt catgcagtac ccggagtgct ttgcttagag atttcttcca acaaatattc   30120
```

```
tagttcatcg cttttaaatt ctgcctccca caaagcccca gggcatggac acaattcagc    30180 caagttctt  gccact                                                   30196

<210> SEQ ID NO 10
<211> LENGTH: 21630
<212> TYPE: DNA
<213> ORGANISM: Homo sapiens

<400> SEQUENCE: 10
tgttgttggg ttggggggtgg gaggagggag agcatcagga agaatagcta atggatgctg     60
ggctgaatac ctgggcgatg gaatgatctg tgcagcaaac cgccatggca catgtttacc    120
tatgtaacaa acctgcacat cctgcacatg tacccctgaa cttgaaagct ggaattttt     180 ttttttttt ttttactttt taagctcttt tgttaaaaac taagacacaa acacacatag     240
cctcggcctg cacagggtca gaatcatcag tttcactgtc tttcactgtc acatcttgac    300
cagttttgtg accggaaggt cttatgggca gtgacatgca tgcaactgtc atcttacgtt    360
atagcaatgc cttcttctgg atacctcctg aagaaactgc ctgaggttgt tttacattta    420
acttgtttta tatataagta gaaggagtac actctaaata aaaagtatag taatacata     480 aacgagtaac gtagttgttt gttatcattg tcaagtactg tgtgctgtgc ataaatatat    540
gtgccagatt tttatatgac tggtagcacg gcaggtttac ttacaccagc attgcacaaa    600
acacaggagt aattgatacg gtttggctgt ttccccaccg acatctcatc ttgaatcgta    660
attcccataa tccccatgtg ttctgaaagg gacccggtgg gaggtaattg aatcatggag    720
gtggttaccc ccatgctgtt ctcgtgatag tgagtgagtt ctcacaagat ctgatggttt    780
tataaggagt ttttccccct ttcatttggc acttctcctt gctgctgcca tgcgaagaaa    840 gacctgttt ctccсcccttс caccatgatt gtaagtttcc tgaggcctcc ccagccatgc    900
ttaactgtga gtcaattaaa cctctttcct ttataaatta cccaagttcg ggtatgtctt    960
tattagcaat gtgaggatgg actaatacaa aatgcattgt gctacaacat cattaggtga   1020 taggaattt  tcagctccac tataatctta tgggaccact atcacacatg tacccgttct   1080
tgaccaaagc atcctcatgc tgtgcacaac tgtactcagc caccggctga gtccccacat   1140
tggtttcctg acgtgtgggg tgagggccac tattgtgggc caactggaag ccattagagg   1200
tgcctctacc tagaaaaata gtcaaaagcg atacaataat agtcagtcaa aagctgcatt   1260
tccagaggaa tttcagaggt tagtgccacc atcaaatacc tgaaagatgc agggggcagtg   1320 atccccacca cagcccccatt ccactcacct atttggccag tatggaagac aggcgggtcc   1380
tggagaatga caagggattg tcctaagctt gactccaact gcagctgctg ggccagattt   1440
ggttccattg cttgagcaaa ttagctcatc tcttgctacc tggtgtgcag ttattgatct   1500
ggcgaatgtg tccttctcca cccctgtcca caaggcccag cagaagccag ccagcaatg    1560 caccctcact gtcccacctc aggggcctct cgcctctcca gcctgtgtca gaggtaatcc   1620 tcagggtct ggatcaccct tcccttcccc ggcatgtcac actggcccat tacactgatg    1680
acattatgct aactggacat aaggcacaag aagcagcaat tattctatac ttgttggtgt   1740
cagagggtgg gaaataaatc caactaaaat tcagaacctt ctacctcggt gaaattttta   1800
ggagtctagt gctgtggggc ctgctctaag gtgatacata gattgttgca actgaaccct   1860
cccacgatca aaagagaacg acaccaggtg agcccgtttg atgtgaggaa gacaggttct   1920
tcctcattta ggtgtctgac tctggcccat ttactgagtg atttgaaaag ctgctagttt   1980
tgaatgtggc ccagcagcag gtccaggctc tgtgcaagct gttctgccac ctgggccaat   2040
```

```
gacccagcag atccagtctg aggtgtcagt ggcagacagg gacactgtgt agagcctttg   2100
ccaagcccca gtaggtgact catagctcag gcccttacag ttttggagca aggccctgtc   2160
atcatccaca gataaccact ccgttttgag aaacaggttt tggactgtgt attagtctgt   2220
ttcacactgc tataaagata ttacctgaga ctgggtaatt tataaagaaa aggggggttag  2280 ttgactcact gttctgcatg gctggggagg cctcaggaaa cttacaatca tggcggaagg   2340
gaaagcagac acattttaca tggcggccag tgggagaaga atgagcaaga caggaactac   2400
caaaacttat aaaaccatca gatctcgtga gaactcactc attgtcatga ggacagcatg   2460
gaggaaacag ccccacgat ccagtcacct ccggccaggt ctctccctta cacctgggg    2520 attacaattc aagatgagat ttgggtgggg acacaaagcc taatcatatc agcctgtgtc   2580
taggtcttca tagaaactaa acacttgacc aagggccacc aagttaccac atggcctgag   2640
ctgcccatca tgatctgggg attatctgac ccatgttgct ataaagttgg gcgtgcacag   2700
cagcgctcca tttgaatgaa agtgatgtat tgtgatcagg ctcaagcagg tcctgaaggc   2760
aaaagtaggt tacgtgaaga agtggcccaa atgcctgtgg cccccactcc tgctccaggt   2820
gccttctctc tccccacctg catctgttgc tgcacaggga ggtccctctc atcaattgac   2880
atgggaagag aagactcagg ccatacttac aggtggtctg ctcgatatgc aggtgctatc   2940
agaaaatgga cagctgcagc cctacagccc ctgcggcaga ggcaaaggat ggaaaattcc   3000
attccaaaca cgagaaatgg gaaggaaagg actaactgag catgaccaaa tccaaaaccc   3060
aacaggacaa aattaaatct taaagctgaa gaataatttt ctttgactct ttgtcctacc   3120
ttctggacac actgggacaa ggctcctggt ggccccactc ctacggcttt gtgtgcctgt   3180
ggctttccca ggctggtggt gcatgctggt ggctctacag gtcccgagtg tcctctgctc   3240
ccttgggcac cactacacat tgtcctgtgg ggactctcca tggcccaaac ctgtagcagt   3300
tctcggcctg ggccccaggg tctccatgac acccagtgga atccaggagc aggaactttt   3360
cctccacagc acgtgcactc cgtgcatctg cagagctggc accgtgctga caccatcgag   3420
gtttaccgcc tgcgccttct gggctggcag cccaaggaac acctgtaccc acgtgagcct   3480 ccatggggt gggccaggag tgatgcacca gcttgcaggg aggaacagag attgaggcaa    3540
gtctgggcag cacgccccga ggtctcatgg aggccctggg cccttctttt gaagccattc   3600
tgccctcaag accccggcac cctgagcctg tgatgggcat gacagtctgg aaggtctcgg   3660
aaatgccttg ggggtcattc tcccattgtc ttgatgagca gcttctgacc tccttctacc   3720
cgtactaatc tccttatcca aatttgcttg actacaccct tgctattctc tcctgaacat   3780
gctttcttat tctttttttt ttttttatta tactttaagt tttagggtac atgtgcacaa   3840
tgcgcaggtt tgttacatat gtatacatgt gccatgctgg tgtgctgcac ccattaactc   3900
gtcatttagc attaggtata tctcctaatg ctatccctcc ccgctccccc caccccaaaa   3960 cgggcccag agggtgatgt tcccttgac gtgggcaggc taagagtttt ccaagtcttt     4020
aagttttgtt tccttctat tatcaattct ttaactcatt tctctttct cgccttttgc     4080 tataagcggt caacagaagt catgcagtac ccggagtgct ttgcttagag atttcttcca   4140
acaaatattc tagttcatcg cttttaaatt ctgcctccca caaagcccca gggcatggac   4200
acaattcagc caagttcttt gccacttgt aagagggaca gccctccccc agtttctaat    4260
aagatagttc tcatgtctgt ctaagacctc acgagaatgg ctttgactgt gtggatctcc   4320
accagcattg tgatcacgac cactgagatc attgctacca gccagaggc tctctctaca    4380 gccctgccct cctcggcctg cactggagtc accttagcac caactccgtt cgcaggagtg   4440
```

```
tgtgcttttc cagcgtgcac ttcaaaacgt ttccagcctc tcccgtgacc cggttccggc    4500
tctgctgcca cattttcagg tgtttgttac agcaacagcc ccgcttcctg gtagcaatgt    4560
ctgtcttagc ctgtttgtgc tgctgtaaca aagcaccata gaataggtca tttatacgtc    4620
atagaaattg attgctcaca gttccagagg ctgggaatcc tgcactgcag gtgatgtctc    4680
gagaggacct tcttgccgcg tcctcacatg gcagaaaggg aaagggcaca caggcaccga    4740
gctcattcct cgcccttttc taaagcactg atcccaccca ggagggcgga gccccacgg     4800 cctcatcgcc ttccaaaggc cccacctctc actaccgttg cgttgggggac ttttcaacat   4860 gaattttgga gggacacaaa tattcagacc acagtaagcc atgactaatg cacacagaaa    4920
actgaagttt caggatgtat ttgctctcat tcctctccat caactcaatg gcagctgtca    4980
gaaggctctc agacttgaat gggccttaat cccatctttg tcttctgttg atcggtccaa    5040
gtcaggcatt ttattgggcc tttgtctccc aaagcttgtt aaaatcctaa ctcttggagc    5100
agttggtttt tctgcccttg cggtgctctg aatttctgga tccatctctc tgttcactt     5160 catctctgct tgtaagctgg gccttctttc tcaagctggt ctccgtctcg tgttgcggga    5220
cctaacacaa aactcgcaat gtggtgtttt cccacttcgc cccttatgct cctggctgag    5280
ccttcttgta ttcagcctgc caggtcacca ggagtgattt tagcaagttt gctgctccag    5340
ctccaccaag tccccatcac tcgggccccc ggtgcctgct ctcttggcag cagctgggtt    5400
tgggggttcc gactgctacc acaatacagc ctggcctgtc ctgactaata cagaagcagg    5460
ctctgtgaag gagggtgctg ccataagaag aaacgcaaat taacgtat ctacacagtc      5520 tccgtggtgc acaacagtca gcttttcctg cttatgtgtc tgggctctgc ttgactgatc    5580
ttggctgggt gcattcccaa gacagcaagt cgtggctggc ctcgggcaca ggaaagggcg    5640
agagactggg gtcacagata caatctagca taggggggaca gataactcaa tgtttaaatt   5700 cataggggtgc tggaccaaga gagggcatat ccaaacctga tgtgctcatc catcggagat   5760
gctgggtctg gagaaggtgt agtgactggg tggactttgg caggtcaaca gagggggtgga   5820 tggcggaaca gacgatacca tgtgttcacc acactgtttc ttcctcctag gcaaatggaa    5880
agactgcatt tcccagtcac ctctatggtt agtgtggttg catgagggtc atgtgaccga    5940
gttctgacct gtgggatatg ggaggaagca acgtaagcta cttcccaatc gcccttccct    6000
ttccaaggtg accttacagg acacacgttc ccaaagtcag ctcaaagatg aagagtcact    6060
tgaccaccat atgcaagtga aaaataaccc cgagacctca gggggtattt gttaactgca    6120
acgtagccta ctttcaaagc atggttcctg gaccagctgc atcacccggg aatgcggtag    6180
aaatgcagat tctcaggccc tgcccaggcc tccaaaatta aggatgctgg ggtggagcct    6240
agcaatctgc gtctaaaaag ctctccaggg caatctgaag gctgttcctg gccaggaaca    6300
gtggctcatg tctgtaatcc cagcactttg ggattacttg agaggacctt cttgccgtgt    6360
cctcacatgg cagaaaatga aagggcacac agggggatcg aggcgggtgg atcacttgaa    6420
gtcaggagtt ggagacaagc ctggccaaca tgatgaaacc ccatctctat taaaaataca    6480
aaaattagcc aggtgtggtg gtgcatgcct atagtcctag ctactcagga ggccgaggca    6540
ggagaattgc ttgaacccag gaggtggagg ttgcagtgag ccgagatcgt accactacgc    6600
tcccgcctgg gcgacagagc cagattccat ctcaaaataa ataaataaat aaaggctgtt   6660
ccaactatat aggagttcag gatactggca agggtgtgat taaagtgaag gaccaggtgt    6720
tcccagctgt gcaggcaaag aagtgcagtg aggaaagcat gcagtacggc tgcgtagagc    6780
actcccagca aagcaggtgg gcaaagcaaa cacacagggc ctggaggtgt ggaaggggtg    6840
```

```
caaggtttgg actttaaatc tcagagagga agcaacccaa aattaaagag accccaggga    6900
tggtgatggg cacagtgggg cagatgaagt tcactggaca ggggaggtca ggggcctagg    6960
ggccgtggtg tggggttgct tgtcccagct gggatggaca caggaattgg gctggagaag    7020
atgtacatga ggtggtcttg tctaaaccct gcacatccag ctccaagcat gcaggtaaat    7080
tcccccggaa ccaactccca tgccaacgtc agactcgaac aagtccaagg atgctgagta    7140
acagtcaggg ttctccagag aaaccgagtc agtaagatgt gtacatacac acagagagag    7200
attattgtaa ggacttggct cacacaatta cagaggctga gcagtcccaa gatccgtagt    7260
tgggaacctt ggagacccag gaggactgat ggtgtaagct cccgtctgaa aggcagcagg    7320
ctcaagaccc aaggagagcc aatgtttcag tttgagtttg aagacaggaa aaaccaatg    7380 tcccagctca cccaggtaag aggacttccc tcttatttgt cacgcgcctc tgtgtgaaga    7440
gaccaccaaa taggttttgt gtgagcaatg aagctttta atcacctggg tgcaggcaga    7500
ctgggtccaa aaaggagtc agcaaaggga gataggggtg gggcagtttt ataggatttg    7560
ggtaggtagt ggaaaattac agttaaaggg ggttttttctt ttgtgggcag gggcgggggg    7620
gttacaaagt gctcggtggg gaccttctga tactcattga ccaggagaag gaatttcaca    7680
aggtcaattg attagttagg gtggggcagg aacaaatcac catggtggaa tgtcatcagt    7740
taaggcagca actgtctact ttcacttctt ttgtggttct tcagttgctt caggccatct    7800
ggatgtatac atgcaggctt gggctcagaa ccctgacacc actcagccat tttgttctat    7860
gcaggccttc agtgggtggg atgaggccct ctagaaaata aaaggtttcg ctctccctct    7920
ccctctcctt ctccctctcc gtctccctct ccctctcccc acggtctccc tctcatgcgg    7980
agccgaagct ggactgtact gctgccatct cggctcactg caacctccct gcctgattct    8040
cctgcctcag cctgccgagt gcctgcgatt gcaggcacgc gccaccacgc ctgactggtt    8100
ttggtggaga cggattttg ctgtgatggc cgggccggtc tccagcccct aaccgcgagt    8160
gatccgccag ccttggcctc ccgaggtgcc gggattgcag acggactctc gttcactcag    8220
tgctcaatgg tgcccaggct ggagtgcagt ggtgtgatct cggctcacta caacctacac    8280
ctcccagccg cctgccttgg cctcccaaag tgctgagatt gcagcctctg cccggccgcc    8340
accccgtctg ggaagtgagg agtgtctctg cctggccgcc catcgtctgg gatgtgagga    8400 gccctctgc ctggctgccc agtctggaaa gtgaggagcg tctccgcccg gccgccatcc    8460
catctaggaa gtgaggagcg cctcttccca gccgccatca catctaggaa gtgaggagtg    8520
tctctgcccg gccgcccatc gtctgagatg tggggagcgc ctctgacccg ccgccccatc    8580
tgggatgtga ggagcgcctc tgcccggccg agacccgtc tgggaggtga ggagcgtctc    8640
tgcccggccg cctgtctga gaagtgagga gaccctctgc ctggcaacca cccgtctga    8700 gaagtgagga gcctctccgc ccggcagcca ccccatctgg gaagtgagga gcgtctccac    8760
ccggcagcca cccgtccgg gagggaggtg ggggggtca gcccccgcc cggccagtcg    8820 ccccatccgg gagggaggtg ggggggtca gcccctgcc cggccagtcg ccccatccgg    8880
gagggaggtg gggggtcag cccccagccc ggccagccgc ccgtctggg aggtgagggg    8940 cgcctctgcc cggccgtccc tactgggaag tgaggagccc ctctgcctgg ccagccgccc    9000
cgtccgggag ggaggtcagg gggtcagccc ccgcccggc cagccgcccc gtccgggagg    9060
tgaggggcgc ctctgcccgg ccgcccctac tgggaagtga ggagccctc tgccctctgg    9120 gcccgtctgg gaggtgtgcc caacagctca ttgagaacgg gccaggatga caatggcggc    9180
tttgtggaat agaaaggtgg gaaaggtggg gaaaagattg agaaatcgga tggttgccgt    9240
```

```
gtctgtgtag aaagaagtag acatgggaga cttttcattt tgttctgcac taagaaaaat    9300
tcttctgcct tgggatcctg ttgatctgtg ccttacccc  aaacctgtgc tctctgaaac    9360
atgtgctgtg tccactcagg gttaaatgga ttaagggtgg tgcaagatgt gctttgttaa    9420
acagatgctt gaaggcagca tgctcgttaa gagtcatcac caatccctaa tctcaagtaa    9480
tcagggacac aaaacactgcg gaaggccgga aggccgcagg gtcctctgcc taggaaaacc    9540
agagaccttt gttcacttgt ttatctgctg accttccctc cactattgtc ccatgaccct    9600
gccaaatccc cctctgtgag aaacacccaa gaattatcaa taaaaaata aattaaaaaa    9660
aaaaaaaaag ttactcagga gacccttta  gaaatactta gggaaagata agctgtctcc    9720
ttgggatgac tgggctggtg tctgtgcata tgccttctct ggatccaagt gactttacca    9780
caccaagcct taagactgcc agactgttct ctccattgaa agccattctg caccactggc    9840
catacagaag gaatctcata ttccaggaga ctggcccaaa caggactgtt gagtggcctc    9900
taaggctttt agacgtcaaa agggtttata agaataatca tcataatata gttatgaatc    9960
agaaacatgc atacattttc ttaaatgacc ctgtggggac tggagttaaa aagggaggag   10020
tacccagatg caggcgtcta gcagaatgga cttgcttgag aatatcaagc aagacagcca   10080
aagaggactc ctaggattgt ctcaccagga cttctgaggc gactctaatg aaatgactta   10140
aaagtgtggt ggagtggctt ctgtggctcc acaccggcc  taatcctggt tgatattgca   10200
caaccagggt gcactgacaa tctctgggaa aaaagcaagg tctaatattc aaagcttggc   10260
aaacatgacc aagactttt  ctctttcctt tgaattattt tagttcccta atttttttgtc   10320
ccatatgcca cttaattctt tttattttgt attaaaagtt gtgctcttgt ctcaaccttc   10380
tttctagatt ggatcctgca tgttttttt  atcattatac ttttggcagc cctaccacta   10440
ggcttcctga aatatagcac ctttgttttt gtttgtttgt tgtttgtttg tgagaccgag   10500
tttcgctctg tcacccaggc tggagtgcaa tggcacaatc tcagctcact gcaacctctg   10560
cctcctgggt tcaagcgatt ctcctacctc agcttcctga gtagctggga ttacaggtgc   10620
gtgccaccac ccccggctaa ttttttgtgtt tttattgaga tggggtttca ccatgttggc   10680
cagactggtc tcaaactcct gatcccatga tctgcctgcc taggccttcc aaagtgctgg   10740
gattataggt gtgagccacc gcgcctgcc  tgcacctttg ttatatagaa aattcttatc   10800
aacattattg tctacttta  gactttattt tgttctattg aactattctg gttctagtac   10860
catacattaa aattatagct ttataatact ttttaacatc tgacaggatg tgctcccctt   10920
atcatcctc  ttttttcaata ttttatcatt ctcacagttt ttctcagatc aacttcacat   10980
gtaatttaca aaagaaatta aaattacatt ggtatttagg tggaaattat gttaaatta   11040
tgtactaatc tggagaagtc ttgttttgta ataataattc ttaccatgaa ggaaaatagc   11100
ttctctctcc gctgattcat gtttttctc  atgtctctca gtagagttta tagcttttt   11160
tgtataagtt ctcataattg cttgaatata ttcctaatta tttaaaaaaa aaaaaagaa   11220
aataaaaggt ttccactttc aaagttcccc ttccttgttaa agaatgaatc ataagtgtta   11280
gaaataacag tttctttttt tttttttttg gaagcatttc ccatttttat tcataaaatt   11340
attacttaaa attgcaaaag tagatttaca gagccacagg taacaaaaca ggaaatgaaa   11400
tgttccagac attccgaaaa gttcgaaaga acacaccct  agcctcaaaa tctccggtta   11460
aaccgtggtt gcacaacagg ttctatttat tcctgcattt tctcaataag ttcttcttta   11520
tatttgcctt tctcttttcc aacttgttga gacttggctt tgcgttcaag aatttttttc   11580
cgatccttgt ccagttttag cctggtgata accaccttgc ttgggtgaat gcccacgtgg   11640
```

```
acagtcgtgc cgttggcctt ctcacgctgc acccgctcga tgtagatgac atatttcttt   11700
ctgtacacct ggattaccct gccaatttgc tgacctttgt agtgtcctcg aactacctgg   11760
acctcgtcgt ccttgcggat gggcatggag cggacattgt acttctgccg cagctccttg   11820
gagagcgggg atgacatgat cttcctgcgc acgtgtgagg gggcattgaa gtaacgtttg   11880
cggttttttac tgcggtccga ggtaacgaag ggattgaact tcatggtgac cctccggcta   11940
ctagctgcct cagaccctca acagtttctt ttaaagacta actttcttca agcctccttg   12000
ctttgtgcta ataactcttt gttaagctct atcctatgta actgttggac atcctcacca   12060
acatattcca gctcacagcc tatgcccctt ccttatttgg tgatgttatt gcctcctgag   12120
acttttcata agcaacttat ttgttcttcc ctgcacttac ctatttagga aagtttcagg   12180
ttattagcaa atcgggtatc actttaagat tgtgaggtcc cactccagcc aatggatgca   12240
ggacatagca gtaaggacaa cccaaatgcg taagggataa atacatctgc tttctctttg   12300
ttcaggtgtg ctctcaccat tgttccatct gcgactgagc accatttctg caaaaagtaa   12360
agatggcctt gctgagagat cttttgtctc tgtgctgact tttcttcacg gcactgatta   12420
tcttttctta acaattttgg tggcaattgt atggggatat acttctcctcc aggggcgtct   12480
ctagtcctct ctcacgaggg ggcactctgc tgcctcttgc agtggcctca ggggtaaggg   12540
accgagaccc atccggtgtg accaataaac ccggactctc agcaatgtgg aaagaaactg   12600
gccaacaacc tggggtaaag gatcctcaca taccgaggtg acgactctgt gcacagacca   12660
acgaaggaga agccacggga gccggtaaag tacttcttgg tggtcagatt ctgggggct    12720
gaatgtgtgt gtgcacgtga atgatcacag acaaccctgc ttgcggtgtt gtgtggatgg   12780
tgacaaatcc tactgctgga cggagtgttt gggtcctctc tgtgcttcca gagcaacctc   12840
agatggctta gggcagatcc tgccatggga tttatactgg cacgccaact ctaagagggg   12900
cctagctctc ccttggggga gtggccagag aggacaacac aagtgggaag tgtgcaaggg   12960
accttcagag gaggaaaggg aggaaacagg tcaacctctc acggcaggca aggcaagaca   13020
cccccctggtt tgagggggtc ttctgcaaat ttcaggagt tgaacctcat acaaacctcc    13080
ggtagtaaga aaatattca gagttctcct ttcccttctt ctcgggggaa gaaagaggct    13140
aagctccact ccgcttgtcc cttccctagg ggaaggggaa ggagaaggga gaatagcagc    13200
ataagcgact ggcagaggca gggaaagacc ggcagaaagg aaagagaaac tgggagagga    13260
agtcagagag agagagagac aaagagggag tcaaagagag agaaagagag agacagagag    13320
tcagagagag agaaagagag agacagagac aaagagggag ttagagagag aaaaagagag    13380
acagagagta agagagagag agtcagagag agagaaagag aagtagtaaa gagaaaacag    13440
tgtaccctat tccttaaaa gccagggtaa atttaaaacc tataattgat cattgaagat    13500
cttctctgtg accctagaac actccaatac tgcctgtaaa gaagcaagac gagtcacacc    13560
agtgactgca agaccctaga gctattaacc agttagtcca aactacccac cctgttgtta    13620
cagtaataga tgtaaaagat gccttctggg cttgtccatt tgcagaggac agccaggacc    13680
tatatgcctt tgagtgagaa gaccctcact ccggtgaaaa atggtaatac caatagacgg    13740
tcttacccca agggtttacg gagtctccaa atttatttgg tcaaatattc aaataagtca    13800
tttaattagc aaaggtaaac agaaaattga gcttgaatgg attgaaggca tcacattctt    13860
gcctctgctg gagactaaat aagagcttag aaaattttgg gattagttgt atggataccg    13920
tcgtctatgg gtagactcat gccctaaaaa caaaactctt acacaaaaag ctcacacgag    13980
acagaccaaa cccctcatg tggcaattac cagaaatcca acaggtggga aggttaaaac    14040
```

```
atctattagt aactgcccct gtcctagctt tactctcctt aagcagccat tccaccttgt   14100
tggtggtgta aacaacggcg tagcccaaaa acactgaggc cactgacaac ccatagcctt   14160
cctaatcaaa aatccttaac ccagtaaccc gcggatggtc caaatgcatt caatctgtag   14220
cagcaacttc tttgctgaca aagaaagta gaaaataac tttgagaaga aacctcattg   14280
tgagcacacc tcaccaggtc agaactatcc taagtcaaaa aaaaaaaaaa aaaaagaaaa   14340 gcaaaaggt agcttactaa ctcaaaaaat ttaaaatatg aagcgattct gtcagaaaaa   14400
gatgatttaa cattaaccac tgatcattcc cttaacccag caggtttgct aacaggggat   14460
ctaactctta atgaattacc atacaaaggt ccaaccagac ctagaaggaa ctcccttcaa   14520
gacaggacaa tagatggttc ctcccaggtg aatgagggaa aaagccacaa tgggtattca   14580
ttaagtaatg gggaaatagg agtagagtta ggaaaattgc ctaggagttg gggagttgtt   14640
tgcactgagc caagccttaa gatactgaca gaatcaggaa ggagtcattg tgaaaagtga   14700
agtagagttt acctcctcaa aagactttcc tcccccatct aatcaggaat aaatagtaac   14760
ttctcttagt agcaaaatgt attcaaagac cagcgctaac attcttaaat atctgctaga   14820
cgtaataaag aaatcaatgt actttatgtc cttagctccc acaatttagt ctaaatgttt   14880
gctctggcat gcttatactg gtccaggcaa gcattaggtc ctatcctgtt cctcttcctt   14940
gtttgtgtct cacatgtccg tgtgaaaaga ccaccaaaca ggctttgtgt gagcaacaag   15000
gctgtgtatt tcacctgggt gcaggcgggc tgagtccgaa aagagagtca gcaaagggtg   15060
gtggattatc attagttcct acaggttttg gggtaggcgg ttgggttagg agcaatgttt   15120
tgccagcagg gggtggatct cgcagagtac attctcaagg gtggggagaa ttacaacgaa   15180
ccttcttaag ggttggggag attacagagt acattgatca gttagggtgg ggcagaaaca   15240
gatcacaatg gtggaatgtc atcagttaag gctattttca cttcttttgt ggatctttgg   15300
ttgcttcggg ccatctggat gtatacgtgc aggtcacagg ggatatgatg gtttagcttg   15360
ggcccagagg cctgacagtt tgaaggtgtt tttaccttc tcagcattcc acgagttact   15420
tcttcctttg ttctcctctg cctttgcctc ttttaaaag ttctaagttg ctagccagtc   15480
gggacaaatg cagaatgtca ggcctctgag cccaagctaa gccatcgcat ccctgtgac    15540 ttgcacgtat atacgcccag atggcctgaa gtaactgaag aatcacaaaa gaagtgaata   15600
tgccctgccc caccttacct gatgacattc caccacaaaa gaagtgtaaa tggccggtcc   15660
ttgccttaag tgatgacatt accttgtgaa atcccttctc ctggctcatc ctggctcaaa   15720
aatctccccc actgagcacc ttgcgacccc ccactctgct cgccagagaa caactccact   15780
ttgactgtaa ttttccttta tctacccaaa tcctataaaa cggccccacc cttatctccc   15840
ttcgctgact gtcttttcgg actcagcccg cctgcaccca ggtgaaataa acagccgcgt   15900
tgctcacaca aagcctgttt ggtggtctct tcacacggac gcgcgtgaaa cagaatgtga   15960
ggtcccgttc cagccaatgg aaaccagaca cagcagtagg gtggacgcgt caggttataa   16020
atgaccctgt ctcctttgct cagtgtactc tcgtggcaaa actgctgccg agtgtaccct   16080
ttctacagaa agtataaaaa tgaccttgcg taggaaatta aatttatgtt caagtgccat   16140
ttctttatgg caccggggag caagcatttc aaacatcatt tgtaccaatt ctaagttaaa   16200
tttggactaa acaaggtctt attaatagca aaggataatt gaaatcccaa acttacaagg   16260
ttttcaacaa aagtaaagtt tgctaaaagt taacagtata acatgtatta tcctaacttc   16320
taatgttgtg accttaggct gtctagtcca cagacataaa ggaagttcgc tttggaaaag   16380
aatggttatc atctttgaga gaaaaaaaat tgtttcgaag gtttaagcaa gttttgaaat   16440
```

```
attcattgta aaggaaacat attggctaaa gttaaagggg tatcttccag ttttctgtg    16500 aactggacat taaaataaaa gcccagtggg tttttcttaa agcgctaacc tgctctttaa    16560
caaaaattac gaaaggttaa aaattataaa agtttaaaaa aagagtctgg aaatctcacc    16620
ttgtggtcag accttaaaat tggatacata tgtctacaag gttttattaa aatgaagttt    16680
aacacgaata acacactaat gtaaaggtga aatttagctg atctggtata aaatcacaca    16740
ggaagcactg tcaaatataa aatggtgttt ggctttcttt ggtctaaaaa ctaataaaaa    16800
taggtactaa aggaaatttc tcagcaagaa ggcactaagg actataaaat ccactgctga    16860
tgtccccacc tttaaaacaa aagatcaatt tttagaaatg atatacttgg tttatcctcc    16920
acccttaaaa caaaggtct tctagcacag gccctgccct gagagtttcc agtacatcag    16980
caccagcctg gggatcccgt tctcatcaaa gggtggaaag aagggaaact ggagccagcc    17040
tgggaaggac cctgccttgt gctgctgact accgagattg ctattcgtac aacggaaagg    17100
gggtggacac gtcccaccag agtcaagcaa gcaccattat caacagaatc atgggccatt    17160
gtttctggat caagccctac caaattaaag ctaaggaaag ctgagtctat ctctttcctt    17220
tcctttccta acccagtgcc tatatccatg actattccta ccactagcaa ctctaacccc    17280
actttagaga gtttctgtgg tttgggagca gaggtcactg gaagggatcc tataggcttc    17340
aaggtgcgct ttgttctccc tcctccacct cctacgactg ccccttccc aaacctacaa    17400 catcaaacta tgcctcgcct catgccaaat gacacaagca agttcttaga agtagaaata    17460
ggagacccaa ggcaaaccct agccattgaa agagggtata aagacataaa tgccggttaa    17520
aacggattaa atatcccgtt cgcactttaa gcaaagtga ccattaagct tgtgggcgcg    17580
gtaggccaga ggctcaggat gcctcctttc cactgggacg gtcctcaaat caagcggaca    17640
tggagtgcgt ggtagctctt ttcgaagatt ccaccacctg gaataacgaa ttgtgccaag    17700
ctctttctct gctatttcct gaagttcagt gccctgtggg tcagccccg agggccatcc    17760 agccttcatc ttccaaaacc aatttaacct cgtgtctcca acaacgaggg gaaaaaactt    17820
ggcattcctt ggagacttaa aaggttgcag taaagtcagg cacctccaaa agctgaccca    17880
tcggtctgcc cttattcatc cctgagcgga tgtatggtgg tattatggag gacctttact    17940
ggacactctg ccaaataatg agagcagtac tgatgctgta gttcagttgg ctatcccttt    18000
tactctggca tttcatcaac cagaaaaaga aaaaaaaatg tagcctcaat tcttacctct    18060
ttaacaacgc taataagtat actctttctt cgtaggtgtt atgtcgtacc atacatccag    18120
gagttcatca aaacaactaa gccaagacat gctaagaaag tttgaagagg aaaactatac    18180
agtaaaagag gagggaattg taggaagtaa aaagtttctg cttcaaagtt ccccttcttg    18240
ttaaagaata aatcataagt cttagaaata atagattctt ttaaagacta attttcttca    18300
agcctccttg ctttgtgcta atagctcttt gttaagccct atcctatgta actgttggac    18360
atgctcacag acacattcca gctcacagcc tatgccccctt ccttaattgg aaatgttatt    18420
gcttcctgaa acctttgta agcaacttct ttgttcttcc ttgcacttac ctatttagga    18480
aagtttcaaa tcgggtatca gtttaagata gtgaggtccc actccagcca atggatgcag    18540
gacacagcag taaggacaac ccaaatgcgt aagggataaa tacatctgct tttcctttgt    18600
tcaggtgtgc tctcaccatt gttccatctg cagttgagca ccctttctgc agaaagtaaa    18660
gatggccttg ctgagagatc ttttgtctct gtgctgactc ttcttcgcag caccgattat    18720
ctatttctaa caattttggt atttctaaca ggcccacaca cactgtgtgg gccaagctgc    18780
ttcactcagt ccactgatca aatgctcatc tcatcctcac agacacaccc aggatactgc    18840
```

```
ttgaccaaat atctggacaa cccatggccc agtcaagtcg acagaccaaa tgaactgtca   18900
cagacagctt ctgtccttgg aacggggtgg gattccacgg actctctccc ttcacagtgg   18960
agatgctcag tcagcaagct gccagaagtt cagagctggg gaagatataa agaggactgg   19020
gcatggaagc tgcaggaact agtcaggaac tgggagtacc taggagtcag ctcctgagtg   19080
tgcaggatca tggtgaaata gaaagttaga gaaggaagag tgtgtcaata tcagagcatt   19140
gtcttatagc acaggactta accctctcct aaggttccag ggagacagtg ccaaatcatc   19200
acttgagtgg tgcttagaag cttcagggca aaagagccaa ccctaagtac atttgtctac   19260
tggggctgcc atcacaaagc accgcagaca gggtggctta tacaacagac tcattgtctc   19320
acaatcctgg cggctggagt ccaagatcaa ggttttgcaa ggctagctcc tcctgaggcc   19380
tctcttggct tgtagatgac cggggccttc tctctgtgtc ctcacagggt cttccctcag   19440
tgcgtgtccg tgtcctcacc tcctcttgta agactccagt cctatgagat taggacccac   19500
tgtcatgaac tcatttactg ttgattacct ttgttttatg tttttttgttt ttttgagaca   19560 gggtcagtct ctgtcaccca ggctggagtg cagtggtgca atcatggctc actgcagcct   19620
caaactcctg ggctcaagga atcctcccac ctcaatctcc caagtagctg ggactacaga   19680
tgcataccac tgtgcctggg tgtattagtc tgttattgca cagctataaa gaaatacctg   19740
agagtgggta acttataaag aaaggaggtt taattggctc acggttcata gctgcttctg   19800
gggaggcctc aggaaagttt cagtcatggt ggaaggtgaa ggggaagcag acacgtctta   19860
cacggccaga cagttcctcc tacactggct gacactctct cctgccacct tgtgaagaag   19920
gtgcctgctt cctttttctgc catgactgta agtttcctga ggcctcccca gccatgtggg   19980
actgtgagtc aattaaacct cctttgttta taaattgccc agtctccggt agtatcttta   20040
taacagtgtg aggatgagct aatacacaca ggaagcagca atgccatcaa agagccaggg   20100
gccttgactg gcagaactag tgagaccatc accaaaacat ggcattcctt gggcaaggca   20160
ggtgcgcagc cagcaaggta ttgcttaatc tacatgatca aaagacatca ggatggttgt   20220
tcaggaggct gagaacagcc atcctattat ggctgagttg tgtcccctca aaatttatat   20280
actgaagtct taaccccca ggacctcagt gtgtaagtat ttggagaaag ggcctttaaa   20340
gatgtagtta aattaaaatg aagacattag ggtgggccct aatccaatct gactggtgtc   20400
cttgtaagaa gaggagatga ggacacatgc agaggcatga ccacatgagg acacagggag   20460
aaggtggcca tctgcaaatc aaggagtgag gcctcgggag gaaccagcac taccaacacc   20520
ttgatctcgg acttccagtc tccagaacca tgagatgatg aaagtctgtg tttaagctgc   20580
ccagtctgtg atattgtttt gcaaccctaa tagatgaata catacccaa tgaaaaagca   20640 tgatctcttg cccagtttct gcacctgaga cagttttcaa acccaaaccc cactgattga   20700
aggagggatt aggtcccagg aggacggacc ctgcagtacc atagcaggct cccccagtcc   20760
ttccccaccc caccactaaa ggtgtatttc agtaactgtg cactaggaaa agggcaatgc   20820
ccagggctgg gggactccgg gaccaagttg acactgagag ctggagtcaa ggtaccatca   20880
tgggcccact agagtagggc gtatggaggc cagcaaagtg caatcctggt ccacctctag   20940
ctcacactga gtcatccctt tgcattccca gaatgctgca tattccccca gaccctaaaa   21000
gtacactcag acaatcttgg tagttggcag aatcctcacg taggctcatt gtcctgtagg   21060
gtaaaaacta tcatagtgtt accaagtaga aacttctgaa actgccacc acccttagcca   21120 aggcaataca ccaaaaagaa aatctcattg gtggggaatg gcagagatgt gggcccccttt   21180 ggaagacttg aaggttgcag gtgaggcgat tcccatcatc tcccccattt tccagagaat   21240
```

```
gctaacagac tactgtcaac ttgtgatggg aaattttatg cgtccacttc actgggccat    21300
ggtgcccaga tgtttggtta acattattc tgggtgtgtc tgcaaggtgt ttctggatat    21360
gcttagcatt tgaatctgtg gactgagaaa agcaggtcac tctctctggt aaaggtgggc    21420
ctcatccaat cagttgaagg tctgactaaa acaaaaagat taagcaagag aaaattcgct    21480
ctccctgcct gtcttagtct gtttatgttg ctataaagga atattggagc ctgggtaatt    21540
gataaagaaa agaggtttat ttggctcatg gttctgcagg ctgtacaaga aacatgacat    21600
ctgcatctgc tgctggtgag ggcctcaggc                                     21630

<210> SEQ ID NO 11
<211> LENGTH: 37113
<212> TYPE: DNA
<213> ORGANISM: Homo sapiens

<400> SEQUENCE: 11
tgtgggctcc cctctgctga tgggttcccc tctccagctg tggcttccct ctgctgatgg       60
ggtcccctct ccagctgggg ctccctccac tgatggggtt ccctctacag ctgtggctct      120
ctccactgat ggggtcccct ctccagctgg ggctccctcc actgatgtgg tcccctcttc      180
agcttgggct ccctccactg atggggtccc ctcttcagct ggggctcctc tccactgaca      240
gggtctcctt tccatctggg gctcccttgg ctgatgaagt cccttctcca ggtgaggctg      300
ctctctgctg acagggtccc ctccagct aggtctcctc tctgttgata gggtcccctc       360
tccgggtggg ctcccctctg ctgacggggt cctctgatgg ggtccctact ccagggggc      420 tcccctccat agatgagctc cccttcctgg gttgggtgac cctccgccc tatctgtgtc      480 tgcaggttgg ggctaggcag tgctggccag catctgacaa cctcccctt ctgttcttgg      540 gcactgctca cttattcagg tctcagccag gcagcccctc caatggtaat cttcagagtc      600
cccttcagca acacagcttc ccctctgtgg cccagctcat gctgaagtaa acaaggcaat      660
gtcattaacg gctggtatca gcttgtacgg ggaaccagtg gccccagaag cctctgggga      720
ggcccaggct gtgaggatca gggtccgga agagcctcta gagcgggaga aagaggcctc      780 agggtccct cctcacaggg gatggtgaca acacggtagg gaatggaggg gtcagggctg      840
ggtccaggac acggtgaccc tggccagaaa aggccgggcc tggctggcac ccgcacgaag      900
ggaacggagc cagtgtggaa aagcaggccc gcgtcctctt ctgcactccc agccccttta      960
aactacacac agcttgtagg aaggggatca gaggcccctg ggcgtcccat ggctatgctg     1020
cacctgggga catgaagcct agggtagctc agccagctct ggtcacggct gacagacagc     1080
ctcaccccaa cagcctcacc catccctcct cagggaacag gtcctaaca agctgctttc     1140 cccatcccag tgttgaacaa aaactcatgg gtttagacaa gagtgaaggt gactcctcca     1200
ccacccatcc cacctccagc aggcagccac cccaaaatt attgatttat taataaatca     1260
atgacaggtg ccagccagcc ccacctgtcc ccaacctgca aatgcagaca ggggtcactt     1320
ggtccaggga gaggagaccc tcagtggagg ggagacaccc tggagagggg acccccatcag     1380 caaagggggag cccagctgg agacagtaaa taggcagact attcactgtc ttcccctca     1440 agccaggccc acagagtcac agagtatagc caccagcctc ctgggccac ccgggaggcc     1500 ccaaccacac tccccctgct cagctcagcc cggatttctg gattctgctg cctgccaggg     1560
atcctgagga ggagatggta tcagagcctc accagccctt ctcataccca ggagtcctca     1620
tgatgataac agtgtgtgcg ccaggctgtg caggtgctgg ccgggatcct ctgagggac      1680 gagatctcca tgggagggca ccactctgat gtccatcctg ggcttccgtg gccctgcctg     1740
```

```
gccactgccc gctgctcttg gtcaagatca tggaccctca gaggccaacc aggcctcagc    1800
ctgtgcctac agcatcctct ctactgccgg gcttctgaat tgctccttcc tcctgtctcc    1860
cacccagagc aagaacgaag gggaggcccc cagagccctg cagcgccggg agagactccc    1920
atccccaccc cgcatgccat caacacaaac tgccggagag tttaggggat cccacgactt    1980
ggggtctcca aagagacccc cgggacatct catcgagacc ccctgggca ctgcatgctc    2040
aggcttccca ccccctggccc accccatggg gtgtgcccag tcccgcatct caccccatat    2100
ccatgcatgc atgcatgaac ctgaaagcac cccacaccct ctggtgctca gtcctcccct    2160
cctccctggg gtcccctccc ctccctgccc cccaagcctt gcatccccct gcaaacctca    2220
caaggggaa ctatttctgt cctgaaagca gagagggccc ttttcttggg acctctccgc    2280
catctctgcc tccactccca gctgctgtca gctctggcct ggcccctgca ggaagcaatc    2340
actggtctcc ctgtttccca tctggcccca aggtctgttc ttgcccttcg accagagagg    2400
tttgaaagca caactcgggc cctgcgtgcc ctgctcccca gggctccaca cctctgagca    2460
cccgcgcagt aacggaggct cccagccccg cctcgcccca gggtcccctc caacactctc    2520
tggccttggg cctttgctat acccgggggcc tggaagggcc ccctcatccc caagtgtca    2580
ggcaaaggtc tcagagcact gtccctgccc ggcgtgcttg gtcctgactg ctaggcccca    2640
aatcattcct tttcccatta cctcttggtt tctctgtagc tggggtcact accccaaatt    2700
cttgaattga ctgacgtgtc caactatttc atgttttccc cctctacact gggagcccta    2760
caagggcagg gccccctggg caagaatagt gccagccagg agcccctgga gaagatagct    2820
acacatgtgc cccaggcccc agatggcact cagccctgcc tgtcaatgct ggacataggg    2880
cagtttttat cctggctttc tacacaagga ggaaagacta accatgccag cgggcagcgg    2940
ccggatcacg tatgtcagta gaactctgac ccctgagaag cctggaagcc aaaccacacc    3000
tctgtagcaa tcacgccaca gactcaggcc acggctaacg gctgccagtt cacctatttt    3060
tgcccccaac tcaagaccaa ctggaggaag gcaaatatgt ccctgacgaa gggtggccgc    3120
ctccagcctc cccagcccag agcctcagcc tccccagccc actgcctcca gcaacacaca    3180
tctgaagcct tctctgttgg ttggttttat tggtattttg gaagattgtt tgttttttgt    3240
tatgagatgg agcctcgctc tgtccccag gctggagtgc agtggcgcga tctcggctca    3300
ctgcaagctc cgcctcctgg gttcaagcca ttctcctgtc tcagcctccc gagtagctgg    3360
gactacaggc acccgccacc gtgccaggct gattttttg tattttttagt agagacgggg    3420
tttcaccatg ttagccatga tggtcttgat ctcctgacct catgatctgg ccatctcggc    3480
ctcccaaagt gctgggatta caggcgtgag ccactgcacc tggcctttgg aaggtctttt    3540
atacctttat tgagataaaa ttcttatgac ataaaactta gcataaactg tagacttagt    3600
tggtgtgact ttagagtagt ctcagaattg tgcaaccatc accactgcct acttttagaa    3660
cattttcaac atcccaaaga cagaaccccg taggcacctg ttagcagcca ctccccaccc    3720
agtccacgaa gccccaggca gccactcacc aatctacttt ccattaattt gcccattcta    3780
aacacttgaa aaaaatggta tcacaatggt cttttgggtt tggcttcttt ccctcagcat    3840
catacccctca aagttcatcc atgttgtagc tcgtatcggt acttcattca tttttatggc    3900
tgaataatat tccactgtat ggatagaccg atattttgtt tatttattta ttcattgatg    3960
aacatttgaa ttgttcccac ttttttagcta ttaaaactag tgctggctgc gtgcagttgc    4020
tcatgcctgt aatcctagca ctttgggagg atgaggcagg cggatcactt gaggccaaga    4080
gtttgagacc agcctggcca acatggtgaa accccccatct ctaataaaaa tacaacaatt    4140
```

```
agccagacac ggtcatgcgt gcctgtaatc tcagctactc aggaggctga ggcaggggaa   4200
tctcttgaat ccggggggca gaggttgcag tgagccaaga tcgcgccact gcactccagc   4260
ctgggcaaca gaccaagact ctgtctcaaa aacaaaaca  aaacaaaaca aaacaaacca   4320
gtactgctat gaacatgcat gtgcatattg ttatacagac atatgctttc atttctcttg   4380
gatacacaca cacacacaca cacacacaca cacacacacg tatatctagg              4440
actggaattg ctgatttta  tggaaactct atatttagca ttttgagaaa cggccagtct   4500
gttttccgaa gtggctgcac tattttgcat tcccaccagc aatgaaggag ggttccaatt   4560
tctccatacc tctgccaaca cttgttattg tctgtctctt ttatttatag ccatcttgat   4620
gggtgcatcg tggtatctcg ctgtgttttg atttgcattt ccctgatgac taatgatggg   4680
gacatctttt catgagctta tcggtcatat gtacatcttc tttggagcaa gctctattct   4740
aatcctttgc ccatcattaa aggtaggtgg tttgtcttct tgttgataag ttagagttct   4800
ttacatgttt agatactagt cccttatcaa atagatgatt cacaaatgtt tgctgtcatt   4860
tcttgggttg tctttccact tccttgatgg tgtcttttca cgcacaaatg tttttagctt   4920
tggccaagtc caatttatct atttttttctt ttgttgcctg tgcttttggt agtgtatatt   4980
aaaaaccatt gtttaacaca aggtcaccaa gatttattcc tatgttcttt cctaaggatt   5040 ttatttttc  ttttctttt  ttttcttttt tttgagacaa agtctctctc tgtcgccaaa   5100
gctggagtgc aacggcacaa tctcagctca ctgcaacccc tgcctcctgg gttcaagcga   5160
ttcttctgcc tcagcctccc gagtagctgg gattacaggc gcccaccacc atgcccagct   5220 aattttgtg  ttttagcag  agacggggtt tcaccatgtt ggccaggctg gactcaaact   5280
cctgatctca ggtgatccac tcgcctcggc ctcccaaact gctgggatta caggtgtgag   5340
ccactgcgcc tggccttcct aaggatatca taatttagt  gcttacattt aggtctacga   5400
tccattttga gttaattttt gtgcacagca tgaggtaggg gtccaacttc attcttttgc   5460
acatggatat ctagttgtcc cagcaccatt ttctgaaaag actattcctt cccccattga   5520
attgtcttgg taccccttgtc aaaaatcaac tgatggccgg tctgaaggta gtgagttatc   5580
tcaattgatt gttcacagtc agttacagat ggaacacctc gttctactct ttcccgcctt   5640
ctcactgctg cacttgaaca gtcttttaaaa aaatcaattg accataaatg caaggatttg   5700
ttcttggagt ctcaacttta ctgcattgat ctgtaggtct atccttatgc cagtaccaca   5760
ttgtcttgat tactgtagct ttgcagtaag tttgaatcag gaaatgtgag ccctccggtt   5820
ttgctcttct cttttctagat tgttttggct attctgaaac ccttgtattt ccttatgaat   5880
ttgaggatca gcttgtaaaa agacagatgg gattttgata gagattgtga agctatagat   5940
gaattcggga gtttggccat cttaacatta tgtctcctga tccatgactg caggatatct   6000
ttccatttaa ttcgatactc tttgattcct tcaaaaata  ttttgtattt ttcagtacac   6060 aagtttatg  catcttttgt tgcatttatt tctaggtatg ttcttttgc  caatattata   6120 aatgagattg tcttcttcac ttcatttttg gatggttcat tgctagtgta tagaaataaa   6180
atcgatgttt gtatattgat cttgtatcct gccacattgc tatgcatgtt tattagtttt   6240
aagggtttta gtggatttc  tatatataat gtcatataat cagcaaatag aaagtttaat   6300
gtcttagtcc ttttgagctg ccacaacaga ctaccataaa ctgagtggct tataaacaac   6360
acaaatgtat ttcccacagt tctggagact gggatgtcca agatcaagac acccgtaggt   6420
ttggtgtctg gtcggggcct acttctgggt tcatagatga ctgtcttctc gctgtgtccc   6480
ccccatagtg aaaggaaggg gcccagggtc tttctaaggc ttcttttata aggacactaa   6540
```

```
tccaatatag gaaggctctg ccctcataac ctaatctccc aaaggcctca cttccaaatt    6600
ccatcacctg gggagtaaga atttcaacac tgggggaca cagatattca gacatagcat    6660
ttttcttctt cctttctaat atgggtgccc ttgacatctt tttcttacct aattgccctg    6720
ccagagcctt ccagacagtg ttgaatggaa gtggggagca ttcaccccac cttactcctg    6780 atcataggg  aagaactatc cggctttcac cactgagcac cacgttagct ggggtatttt    6840
tgtcagcgct ctttatcagg tggaggcagg tcccttctat ttctagtgag ttcagtgctt    6900
tttttttttt ttaatcaggg aagagtgtga gcttgtgttt gggtgccttc cctgcgtctg    6960
ttgagatgat cttacggttt ctgtctctta ttctattgat atggcgtatt tattaccttg    7020
gttgcttttt ggatgttgat aacatccaaa ctcttctgcc accccttta ataggaaagct   7080 gtacaactcc ccaacctgcc tgggcgtgtc tgcccaagat gagtgctagt ggccgactcc    7140
ctgctagagt gagcactgca taaacagcct ctgcttgtcc tcatttgagt gatcttcatg    7200
tattccacga gaaatcaagg cacaggggtc tcatggtctc atgaatggct ccaccaactg    7260
aaggtgtgct ccatcggggc tgtgagtcac ctcacgccag gcagaaaggt ctctctgtca    7320
aacatggctt caaggaacca gggacctggt tcctcccaca ggccaggccc tgcccctaag    7380
tgcaatggga atatatgcac atgtcacctg tcccaaaatg ctgggagatg gcacttctgc    7440
agatggggaa actgagggac cagcccgaag tcacggggag gggaagactc ctacacacag    7500
ggaggagaag aacccagccg ggctgcaaac gcctgccctt cctcaacgtg cctccggctg    7560
tgcccacatc gctccagcag ctctgccttc tcaggcata agccttctca gggcagggga    7620
ggcccaggga gcggcgctcc catcccaggc cgggctgctg agcaagcccc tccccttctc    7680
cccctcatcc tctgacagag tccacctgaa tatttgtcct ggagccagga tggaagctcc    7740
accaggccca gctaacaaca ggaacccttt cagacgcact tctgggtgcg tactgtgcca    7800
gtatcacaca gacacaagcc atgtccttgt cagccatggg atccccaagg tccccatgag    7860
gtcacaccag tgggccactg ggaagggcac ttcagatgtg gagctcccat gggccaggcc    7920
ctgcgaagtg gtcctcctac cccctcatag ccagtcttcc ctgtgagcct gcaagtgact    7980
gtgaatgtga gttccactct ggagctaaga cgggctgctg cccccgcaat cagatgtcag    8040
gcccatgaag ccctccatca tcccactgca gtcagaataa aatgcagcct ccctctggcc    8100
tccaggtccc aaggccagcc cccctgcctc ccaggctcac acctgcccct aacctgtgtc    8160 cagcccctt cccctggctc tgtctcctgc ttcccttgtg ttcctccaac ctcacctgtc    8220
tgtctggagt gctcctcccc ggctctgcct agctggctcc ttctcaggca tcagggcctg    8280
gatccactgt ggctcttcca agcctctgca cttggagtgc ctcagcccg  tggttgagga    8340 gtgccccaac cctgtgaccc tctagcaagc atcctaggaa ttccgtccct ccccagcact    8400
gatatgacca tcgtgctgtg acacgtgtca tctccgccag agttgcagat cctccagggg    8460
aggggtctgc tgcctggctc ccacagccag ggcctggaac agtgcctgac acacagcagg    8520
cacccactaa atatttgatg catggctgaa gaggacaggc aggctggctg ctggctgggc    8580
atggcctgct tctgaggctg gtggtcaagg acacagtgtg catggatctg cccctcctc    8640 ccacttcctg agagtggagc cagtgtctcc ctccacctac cacccctgc tgaggacaca    8700 gctcacacct ttaacgggaa atgtcccat cactgggac agcagggagc tgatgggaga    8760
gcaggtgtcc aggacatcca gagaaatgtt tcctcacact ggaaccctt tctattccct    8820 tctaaacaaa aagaatcctc gaagactctc aagtgaccat atagtgtctt ttcttataat    8880
gtcacttcga caggcacaaa atgtaaaacc aggcataaac tactagtgct tgcagttctt    8940
```

```
acgcaggcat gaagccaaaa ccagtttaca aattaaccac caagaaaacc ggtagagcac    9000
agatgatgac gatagagctg tttttgtccaa tgtgagcgct actggccacc cagggccatg    9060
tgaatttaaa ttacgatgaa acacaatgaa aaatttggtt ccttgtggcc acatttccag    9120
tacccagtag tcatctgtgc caggggggtta tccaggtaca gaacattccc atcgttgcag    9180
aaggttctat cagctagcac tgggttggac gacacttgcc aagacgagct ggctagagga    9240
tggttctccg gacctggtcc cacgtggttc ccaggtaagc ccccgcccag gatgcagccc    9300
cgttgtccat cagttttctt ggagagggca tgggaaacct tcgtcagtgt gtcatctcct    9360
gcaaaggcct tcgctccttc ctctggggag aaagcaccct tcactctctg aatcattagc    9420
ccaaagcagt aagtgcagca ggcctggccc cacaccttcc ggaagagcca cggtgtgagg    9480
ctggcatccc tggggcacga cacaaccagg atgtagacga aatagatgca atatctggag    9540
gttctcctat aggtgtctct ggcctcctgg acacttcaca ctgttctggg agctgccctc    9600
tcaggcccca gtgaccttt cagatgcaga ctcccacagc atgggtcagc aattctcccc    9660
ttccgtgaga cagggattgg ttacctgtac taggaccttg aggccaacac tgactagggg    9720
gcctcatgcc tgcccaggtt ccagcccgg agagcaatgt gagcaaagct tgctgtcttt    9780
gcaaagccaa ccactgtggc atcaactcct tcaggaagcc ctcccggatt gtccaaggtg    9840
ctcacctcct ttggggagcc ctcccagatt gtccaaggtg cttgagggag ggaggaatgg    9900
gttgttctcc cggcaccggg gctgcactcc tgggcagacg ctgcatgcct gtcctcaggc    9960
gcggccctgc tgccacccc ttgggggctc ggagcgcgac agcagcttgg ggacgcctcc    10020
cgcgcccagc acggtgcacc tgggccctga ggtcctggcc gaaacgcgcc aagttggggg    10080
taggtgcagc gaccccatac ccctcggctg cgcgccctgg cggcaggagg cggggccggg    10140
ggcggggcgt gagctggccg ggggcggggc ctatggaggg gcgggaccgc ggcgccctat    10200
aagtactgcg gagcgcaggc gcgcgcccgg ccagagagcg agcgcgcaac ggcggcgacg    10260
gcggcgaccc caccgcacat cctgccaggc ctccggcgcc cagggcgcac ggcgcgcccc    10320
cgtgccggcg gccctgcgc ccatttcttg gcgcccccgc ccggtcggcc cgccaggccc    10380
ctttgccggc caccagccag gcccgcgcc ggccgcccg ccgcccagga ccggcccgcg    10440
ccccgcaggc cgcccgccgc ccgcgccgcc atgggagtgg agggctgcac caagtgcatc    10500
aagtacctgc tcttcgtctt caatttcgtc ttctgggtaa gggctgcgcc gggggccggg    10560 gcggagggg gcaggcacac actccacgtt gggcaggtcc cgcggcagcg tgctaggccc    10620
cgcgggcgca gcgcgggccg cgaagttgtg gggccacctg tgggctccag gagcggggtg    10680
gggggtcgcc cggggccacc gcgcccccg acattgggc tgagggctgc gagccgagtt    10740 tcgggggcctc tgtgctcggg ggcccacctc tgcggccggg ccggggcttc tggggggccgc    10800 cgggcagttc ccgctgtggt ggtgatgggt gcgtggtcg cgggtcggga cccgagtacc    10860
cggccgcccc tcagctaagg aggggcctgc gcgggtccct ggccgcggat tccggactgc    10920
tgcttcgcgg ggacgagggg ggggctcgcg ggcgggactc ctggcgcccc gcccccatga    10980
gctcatcaag agccgccgcc cctggatggt ggggcgggg cgcacacttt gccggaggtt    11040
gggggcgatc cgcctcactc tttccccagc ccagctcact ctccaatctg cggtcaccac    11100
ccgagacctt cctgggggtc gcgcctaaaa ggagcgcaga ctcccgccgg gatggcccag    11160
aagctggggt gcgcgcaccc tggccgtccc tgcctgggag ccgatctccc tctcctcacc    11220
cagacacgtt ccagcggagg cctcctccca gaagggctct ggaggcctcg caggagtggg    11280
gatcccgcgg ttctgagttg gcacaaggaa gagagtggca ccaggggcct ggagtggatg    11340
```

```
gcagggtccg ggagtggggc cgctgctttg caagaggggc ccccacgctg ggcatctttg   11400
ggtgccagcg tgggtggagg agggtctttt gctgagaatg gctttctcct gaccgcagtc   11460
tttgctgctg ggaagtgact gatgggcttt cgccttttgt ttccatttcc tgtcggtgtt   11520
agaattgggg aggggtgga aatcccttct tggcctggaa ggactggagt gggtgtccat   11580
ggccgcggcc tccccgtggc cacgcccctg gcatagact gcaagcccct ccccgtgccc   11640
cccaggctgt caccccttc tcgtggaaga ctcggctgat gtcccagtgg accgagtgtt   11700
tctcaagttg aggcagggag ggcaaacttt ttaaatggcc cctggagcca gtgtgtggga   11760
ccagagacat ctgtttccca tctggacggc tgaggatccc agtgcggatg attatttgga   11820
gggggaagga cggaggctga actgaactct cagctgggag atgagtgggg cagtcacatc   11880
ccaccttccc caagccgggc tgttctgcac agcctgcttg gacgctggt gggagtcact   11940 gtggctttcg gcactgccct ggcagtgggg gcagctaggc catttgggag gggctcgctt   12000
tccccaggcc gggccctggg acctcagccg ttgcttagtg gtggcctgct tcagcccagg   12060
catgtgggag aggcaccaga cacaggatgt ccctctgcca gccctgaag cccgtcccc    12120 tgacgaggcg agtgtggacc tggggtggg ggctgaggga gactgtggac ctgggggtgg   12180
gggctgaagg aaggtgtgga cctgggggca ggggccgagg gaaggtgtag gcctggggt   12240 agtaggggct gagggagagt gtggacctgg gagtaggggc tgaggagggg tgtaggcctg   12300 gggtgggg ctgagggaga gtgtggacct ggggtaggg gctgagggag agtgtggacc    12360
tgggggtggg ggttgaggga gggtgtgga ctggggggcag gggctgaggg agagtgtgga   12420
cctaggggca gaggctgaag gggagtcacg ggaggggact tctccggagg tggatttttg   12480
ctctctggac ggtgtgtcag cactgggtga gcccctcctg cctgcccagg ctgagaggtc   12540
tccctggcag cccctggga gtgtcgccag ggcgggcctg gaagtttccc aggcagctgg   12600
ggtggagacc tgacacatcc caagggtgct tgttattaag gctcaaggaa atgtctctga   12660
ggcctcaccg ctcctctccc cagggcctgc tccctgcaaa gcattgagaa ctgagtccgt   12720
ccacagtcac tgtggaccca cccatccact ggggctcagt ggtagccagc aatgccaggc   12780
tgggtgaggt ggggttggtg ggcaccaccc tggtggaccc ccctccaccc tggtgtcgca   12840
gggtgtgtgg ctgagagcac agtgccatgg gcttgggcct ccttggtgga gtccccaaca   12900
cactgctctg gtcctgggcc tcggccttcc ccgtctgcag tggggccca cagtgagcct   12960 acctcctggt ggtgttggtg gatttgctga catgcctgag tgttgacagg gggcttggtg   13020
caggaagggc tcagggcgtg ggtgttggcc agggtccaa agggacctct gcctcagaga   13080
gcccagccca gacaggcagg atgtgcagtg gggaagggc tgcgggaacc ctgcagggtc   13140
cagaaggaca cagtgcagtc ctgtgggctc tggggaggct ggtggggagg aggttgacaa   13200
tggatatctg ggtggggcac ttgttagaag ttccatttta gagaggaaag aggccttgcc   13260
tgtgggagaa ggcagctggg gtagcctgac ctctttccca ggaaggagcc cacacacaca   13320
cgcacaggca ctcacacaca cgaatgtgca cacacacaca ctcccaccctt cacacacact  13380 cacactcttg ctgtctccct tcccaagcca aggtgcgagg gggaaggtct gggcagcatg   13440
cacctgcgcc ctgaccgctt tggggccag tgagaactgg gctccctggg tgcgcggcgg   13500
gcccaagcag ggaggacatt gcagatgccc tggccaagca gcgtggaaat cctgtccctt   13560
gggtgggtct cggagcctcc atcagaggcg gctggcacct gagacccacc tgctgccagg   13620
agcagggcag gagagtttgt gtcccgggac agggaactgg cctgtgggag ccttgccttc   13680
ctcatctgtg taatggatat aagagtcttc tcctcggggg ctggccaggg agtccagaag   13740
```

```
aggtgtcacc agtccccgca gggagaagag cggtgtcccc cgcctgggac tggctgctcc   13800
cccaagctaa tgcagctggt agccacctcc cagtggcagg gcagccaaac ccggccggga   13860
aagagactga ttagaagcct cgctcacggg tatttctcgc ttccagacag cacatgactg   13920
tcatttggca cgtctttcgc cgtccttccg ggagagggc tgcaaccctg gcaggcgctg    13980
tgggggaggg ggctaggaca tcctgtgcct ggtttcacca agtgggtgtg tggacttttcc  14040 ctggctcccc caggctgtct ggctgcacag ctttgggaa acggccactg ggtcaagcgg    14100
gccgagaaga ggaagtctgt ggtttgtctc tgctacagac tggccccagt gaggctgtcc   14160
agcagtgcag ggcacagagc aaaagcaggg aggtatgggc ctacttcccc ggtcgcccct   14220
gtggctggct gtggctctgc cgggtgctga caagtcactc gccctccctg cggtcaccag   14280
ggtgcatgcc cgaaagccct ccattctttc ctgggtttga gggtccttct cctgcaccca   14340
ccccagcgcc cagttcagct caactttcag aaatctggtt caccccaat ccctttctca    14400 taactgcttc caagcccaga caaggagaca gaccccaaaa gatccctacc cctatttccg   14460
cacctgaaat cgcaccacgg gaagagcttt gctcatagag tcaataaggc ttagagtcca   14520
ggcgcctgtg cgagggagca ggtcatcacc cttgtaccca ccgtggtttt agacaggacc   14580
ctgaggttgg ggtggggctg gggctggaga ggagccaggt gccctgcccc ttgcttgggc   14640
cccgtgtccc tgtgatccag gctgggcgtg ctatgggtgc tgggtgatat tccagccctg   14700
caggtgtccg ccttgttccc agcaccccctc tgggcaagaa gaaccaggct ctcccagaaa  14760
tgggcttcag tgatctccac ttccaagtcg tccccacctg ccttgtagga cacagtggta   14820
cctggtatgc tgggcagcct tccaggaacc tctggactta ctcagtgtcc cccagcccta   14880
cacaccattc tttgtgtttc tgggcccaaa ctaagcccc caacctgggc tgcagagcaa     14940
gtgctgaatc atgagagacc cttgagggtc ctccaggtag gccccagtg ctggaggagt    15000 cccctcaggc aggggccac gcccaagggt gtggaaggtc agctggcagc cggatctcac    15060 tttggggct gtaggcttcc tgcactggcc gccaatgcca tggccgtggg atggccagga    15120
taaggcatct gccccccacc cccacccccc gcacaaggtc tttgagggct gcgggctcaa   15180
ggagttggcg gtagggctgg gggaccaggg gcacagagct tgtaagcgcc tctctccagg   15240
atgtgggtgg cccagcaggg gagctttgag agtccaggtg tgagattcca aatgctaggg   15300
gcctgagagg agggagccac cagcttggcc agagcctggt ggatcacgcc cccaccacgc   15360
cttgcccttc tctctggtca tgtgctctcc caccacgttt ggaaagttac tgcttccctc   15420
ttcctcagcc cctcgggctc ccagttatgg aagtggcgtg attcagagaa ggtaaaggat   15480
gggagggaga gggctgggtg atgggggacc ccgcagggcg ccctgtgctg ttacatggag   15540
ctccaggatc agggcaggtg ggcagcctgg ggtcctcact tctctcccca gccaggccag   15600
gtccctcaca gccctgccag gagcatgata tccgctgcgg tgcagaacta atctcaaagc   15660
tcaaacccag gtaacagtgt aggtaaaaca gatgacaggg catgagactc accccaggac   15720
aggcgaagga cccaggccga tggggcccca gaacagtcct gatcctggag ctccttcccg   15780
agtgggaccc caggggttttc cgaggggctt agagtagggc ttagaggctt agagtagggc   15840
tagggacttc ctggcttccc tgcctcggga acagctggtc ctggaagggg cttggtcctc   15900
ggggcactgg tgcccaccac ccctgatgcc tgggagacac cagcatcctc tgagcatgtg   15960
tgcgtcctcc tggtcccgag ggaagtgact cctcacatcc cccagctggc ggggccagag   16020
ggccagcatc ctcgcctgac acctattttt agatgctgag acaggcggct tcctcggggc   16080
caggggccct gtgagtggag cttccgcttc ctggcctagg agagaattcc tgctcctctt   16140
```

```
ccctccatgc tgccttttcg ccsctggagg ccacaacggg gtcagagggg cagctgctca   16200
ccacctagga gggcctgaga gggccctacg tcacccaggg aggagtctgg ccccgtcccc   16260
aacctccaca cccaggcctg gcactgcccc ttcttggtgg gcagagagtg aggggttggc   16320
ctgcagggac ccaggctgga ggggccgttc acctccggcc cccagcgtcc cttcctggaa   16380
gcaccttggt gagcccctcc cctccttcac ccagtatctc caggggtact tcctcctttc   16440
cttcctgcct cagggcctca ctgtcctcct ggggagggtg tctcaggccc cagcacctcc   16500
cagtggctga gccgaatggg cacttccggg tgtgtttccc atatgtgcag tcctaggtg    16560
tcggtgagca ggcacagagc ccgcagcgtg gccctgcctg gtgaccccc  tccccaagag   16620
catcaaggga gggcctggac tagagacaca cagatgccca gcctgtacgt aaaggcgggt   16680
gagctgatgt accatcgtcc tcgtccccca ctggggtgcc tgggcaggac ttggggtgac   16740
cacttggccc gtctgggtgg gggtaaggta tgggtggggc gaccagatcc ctgccctttc   16800
ctgcagctgt gggggtgtgt gtgctggcct ggagagctcc cacccgaagt tctggctcct   16860
ggctgtccgg ggcctgcggg ggcagcgagc agctggcatg ggtaggggag ctgacctagg   16920
cctgcccggg cagcgcctgc tgccttttgc tccctttcag ctgcttcttg gaaacagcgg   16980
acaggctggg caggaaccca gtgtgcttgg cagccccccct tttaaagtcg attctgttat  17040
ttattaattc ccaggaagga gaaagaaaga aacaatcctt catagagtac aaacactgct   17100
tttagtagcc ttgcaaggag ccctccagga accccacagg ttacctgggc tccatcctga   17160
gagccaccct ccatccccaa tccccagcag agcatcttgt ggggtggggc ggcttgtggg   17220
gcggggcgcc ttgggaggcg gggtgtctcg ggaagcgggg cgtctcggga ggtggggtgg   17280
cttgtggggt gggcatttc ctggggtggg gcgtctcgtg gggtgggaca gcttgggggg    17340
tggggcatct cggggaggcgg ggcgtcttgt ggggtagggc ggcttgtggg gtggggcatc   17400
ttgtggggta gggcggcttg tggggtgggg catcttgtgg ggtgggacgg cttgtggggt   17460
ggggcatctc gggaggtggg gcatctctgg ggcccggcca cttgggaggc ggggcatcct   17520
ggggggcgggg catctcagag ggcgcctccg gaggctggag tatcttggga ggtgggagca   17580
ggtggcagag aggcttccca caggtgagct ttgagcaggg aggtgcctgt atggatggct   17640
ctgtggggag aggggtgaca ggagttccag attccggcac ttatgaaacc tcacagtgat   17700
ggagagccga gtgctgctgt gcaggctaag ttgtgtgcat gtcagcttct gcacttttat   17760
ttccttgttt gtagacaagg cagagagaag ctgagatggg cctgaggtcg ccttggtgaa   17820
aggcactcag cagccagggc cttgggctgc cctccctcat caccgtgaaa gcgggactct   17880
cttttaactg acatcgggct ccatagttac tccagtccta actttgatgg atcctaaaag   17940
tgcacttcta aggacgcggc ttcggtgttt cccatgccgc tgcttgcccc tgggaagcgt   18000
tggctctgcc tcggaagaag ttagcgccaa gatggcagcc tggggtcttt ggggcccaga   18060
agaaacactg gccccgggga gttcagtcat cagggactta ggatgtgggg gcttttcaaa   18120
cagctttatt tagacgtgat tgacacacag taaatacaga tgtttaaggg tacaacttgg   18180
taagttttga caaatttata ccccgtgaa  accatcacca actccccagg tgcccctggg   18240
gcccttggga tctctgcttc ctgccctcc  tccccgtccc agggcaacca cgggccgtcg   18300
ctgtgggtgc acacagcatg catttcttca acaagcggac tcagaaggca cttgcacatc   18360
gttgctgttc tgcctctttg cttcagcatg attacccaga ggcgcacccg tgccgtggcc   18420
tgcccgtcgt ctatgcaccc gtgctgtggc gtgcccgtcg tctgtgtggc atgcctgtct   18480
gtgcacccgt gctgtggcgt gcccgtcgtc tgtgtggcat gcctgtctgt gcacccgtgc   18540
```

```
tgtggcgtgc ccgtcgtctg tgcacccgtg ctgtggtgtg cccgtcgtct gtgcacccgt   18600
gccgtggcgt gcccgtcgtc tgtgcacccg tgctgtggtg tgcccttcgt ctgttccttt   18660
tattgccggg cagggttgca cccacatgtg caagccagcg acggacccca ggttcacccg   18720
ttcaccggtc agtgggcata tgggttgttt cagtttgggg catttacaag aaacgtgcta   18780
gaacatttgt gtacaagtct tgtgtgaacc taagttcatt tctcttgggt aaatacctgt   18840
gcgtggagca gctgggtcat gtggtgaatg tgggtttcac tgcttaagca gcagttttac   18900
ataactgcca aactgttatt caaggtggct ggaccgtttt acagcccccg ttgtatgcgt   18960
cccagttgcc tcccccagca gcatgtggtg tggttggtct ttttcgtggc agccagtcca   19020
ctgggtgcgc tcggcatgtg gctgcagctt gacctgggtt tcctggtccc tgcaaggtg    19080
gagcatctct tcatgtgctt ttttgctgtg tgtggatctt gcggggaagg gtctgttcct   19140
gttttttgcc catctttcaa agattgggtt gccagttttc ttgctgttga gtttggaaag   19200
ctctgcatac gttcagggca caggtccttt accaggctct gccccaggtc tttcggagag   19260
caggtgtctt tcgcattcct gactctgggg aacctctagc cctgccacat ggggtttgtt   19320
atggggcagg ggcacctgtg cctttcccac cacgggggctt ggggatttgg tgctgccatt   19380
gccctccctc gtaggtggcc ctaggggggt ccctccgcct ccgtttcctc atccagaaac   19440
cggcagtgac catcaccacc attgttgtca cctagctcca gctcaaggtc cctgctgaag   19500
gtcggagagc ttggcatggc cccgtttgtc catgctaggg ctgggaagac caaggctcag   19560
gtgaggcctc tgcccagtgc ctggcactcc ttcttgcccc attttccac ccagggtggc    19620
tcccgactac ttctggtagc ctcggggaca gttgaggtgg acaggctggc gtcaccccca   19680
tttccggctg tccctcccac cccctcctgg cccagctgtt ctgccctatt aaaagtcaca   19740
tgggccctcg ggtccttcct ggtgttggcc caggctcttt caggccctgc aggccaggac   19800
cagccttccc tgcaaccctc ggcagaggcc tgggccgggg gcttgtctag ggcagcctc    19860
cccatacggc cctggagtct gaacagaagc cccttcccag agcacagcaa gaagctgcaa   19920
cgtggcctga agtcccacca ttagcaggtt tggggtttag gctgagcttt gccatcacta   19980
cctttctgtt aggacggtat gcccattaga tgggatcatc cctcagcgc ccaggctaga    20040
ggaggggtgg tccctgccca gccagggagg gctggggtg gatgggcctc tacagagcag    20100
cttccgagcc aggcacggtt ccatgatcag ctctgtttta tagaggggga cactgaggaa   20160
ccggggagcct ggggaccttc cagtggcccc acagctcctg tggctgagtc agggtttgtc   20220
accaggcctc tgtggggatg aggctccccc atccacctgc cccactctgt cctggaacag   20280
ctctcaaaac ggtctctgga ccacagtttc aaaagaaaat aagcaatgtt ttcaaaggcc   20340
ctggaggaag ccagagttac cacggcaact ctcggcctcg ccacctcctc ccgccaggct   20400
gcatctggag ccagctcagg agggcagcag ggtgaggaca gccaggctct ctggggccac   20460
cccccagccc ccaccccttcc tgcctctcct gcactgtcca cggccctccc tgtgctccca   20520
cgggtataat gggcacagaa gaaccaggag ctgtctgccc ctgcaggatt ctggaagcca   20580
ggggcccctg gcctccctgg ggccttgtca tgtgaggggc acacgtgggg tcccagctgc   20640
cacatggctt ccagcgctgc ccgcaggtgt atgttgggcc cttggtgact ctaatgcacc   20700
ttccactcgg cacagaagag cttcagtctg gggcctgggg ggggaagta ggctgccatc    20760
ctcgctaaac caaagtgtga aaattgagtt gaaactccca taggagggca ggaggcacag   20820
ctcctcagaa gaaggtctga gaaaccacag cccaggttgt tgtttcgggt gtgtggagaa   20880
ggtgctctgg cagtcctgct acaggggggac catcaacagc ccctttgggg tgagagcccc   20940
```

```
gtggctgctg gcaccagcag cccctatgag gcttatttta tttttgagac agggtcttgc   21000
tctgtcaccg aggctggagt gcagtggcac aatcataact cactgtagcc tcaacctcct   21060
gagctcaagc gatcctcctg cctcagcctc caaaggtgct gggattacag gcgcttgcta   21120
ccacgcccag cccctctggg ccttattgtt tgccaggccc agctcaggtc ccggaggagg   21180
ggagacagga gtgtgaggga aaggggaag aggtatagag cccccagctc ctccacccac   21240
ccgaaccctc accgaggccc tagaccctag accggcctga ccgggggtc ctcaggccgg   21300 ggacttgggt gcaggccatg gtgctggggc ctgaagctca cgctctgctg agcacagccc   21360
cctgcccaac cccacccctgg ggccctgctt ccctggccag ggccattgga acaggagtgg   21420
ggctgtccag gtggtgttct tgggtccagc cctcagtttc tcttctgcag ttgaccggca   21480
gccctgcatc tgtggtgggg tcggcgcctg gtgctggtga ggcaaggcct cagctgctgg   21540
gacaggacct gcctggcacc cagctggtgg cagagccaag cattccgact cagctctggg   21600
agcagctgcc ttctgggctg gcattctccg ccagggggt tgtgccctcg tggcccccc   21660 cgggtgcctc ctcacctggc tgatttcatc tcctgtcccc ctgcctcctc ctccaggaag   21720
cccccagggc ctggccctcc ttgagagtgg catggaggag gaagaagact cgcccaggcc   21780
catgggagtc ggatggtggc cgcacttgtg gggccctgac cccataggct tcttcagcac   21840
gccctggcct gggtgatccc tgcctgaggg ctgtgcacgg ctcatctgcc agaccagatt   21900
ttaggggatt cttgtactgt cctcctggag cagcaggggg taaagcctga cccacccaga   21960
ctgtccagca acaagggcct cctgctgtgg gccaggacc ctggaactga ccaattgtgt   22020
cctagggacg cagagtcccc aggctgctag agggctgtgg ggccctgttt catgcctgaa   22080
gcaggaagaa accccaggag aggtctgaag gggacccagc ccccaccctg tctagcaggg   22140
aggagcctct gcaagaggcc gagggtgct gaagtggagg aggatagagg cagcaggact   22200
cagggtcact ggtcattat ggggatcaca cggctgcagt gtgccctgca tggtgctagg   22260
caccagggac agcagaggac aagcctgtgt cctctcccac caccagaggg ctgggcactg   22320
cccctaggga gagaggggc cttggtgtgt gcagagggg gctgggca cgtgcctggc   22380 ctggtcagat gatcagagtg ggctgggctg ggcctggtct ggggcccagt ctcaagggca   22440
gaccccacct ggctagagtt gattgtgtgc acaccggatg accggcgtt gaaggcctct   22500 cctctctgtg agcctcatcc ccacctgcca gactcccagc acagcctgct tcctgcccca   22560
gctgctgagc gacagcgctg gccggcttc tgcgcgcccc ttccccagc ccatcttgga   22620 aaccacagca gcgtccttcc tcccaagtcc cttcccaggg ctgacatccc acagcaggga   22680
tgtatcccac aaacccgca ggccctggtg cctacagctt ggcctggtaa catcaaatcc   22740
taccctctcc tcctggcagc aaagatgggg tgcccccacc ccagagttct cagcaccccc   22800
agacagaagc agtcccccag cgacctcaga actcttgggg cgctgccaca cccttgcagg   22860 aggggcagt gttcctggga tgctcaggtc ctggtatcac ctctggccag atacggaagg   22920
tgaaactaca gggcatccaa ttcaccttga acttcagata aacaccagat tattttttg   22980 tatgtcccgt gcaatatttg ggacacactt accctaaaga agtattctgt tttcatctga   23040
gaggcagatt taaccggcgt cccgtgtctt cctggcagtc ctgccctgga gtcacactcc   23100
acaggtgcag ggcagggcca ggctccaagt agatggcggc caaagcaccc gccccatgct   23160
cctgactccc ggggctcttc agggcattgc gaaaccagc agcagagctg acacctggtc   23220
cctgctcggg agccagcaag gcaggaggct gcttaggcct tgcgtgtggg gtgggcgcac   23280
tccctgctgc agtgctcttc gtacatgtga cactgttccc gctctttccc agctggctgg   23340
```

```
aggcgtgatc ctgggtgtgg ccctgtggct ccgccatgac ccgcagacca ccaacctcct   23400
gtatctggag ctgggagaca agcccgcgcc caacaccttc tatgtaggtg agtgcacatg   23460
tggccgcaga cgcattcagg gagggcttct aggaggaggc aggtcctagc cttttggatg   23520
gggacatgga gggtgaaaga cagtcgggca tggcgtgtcc gggcagggag gcggccctgg   23580
aaagggctct gggcacaagg gttgagatgg aggtgggcct gtggcctgct ggcccttctg   23640
gtctgagcca gggcagggg tggcagctag gcctgggcag ggactgtgtg gagaccttgc    23700
ttattttaag tgtgggtta tttcggggga ggctccctga aagggtggg gctggatgcc     23760 tgggccacac agagcagccg aggcagctgg cgctgtggag cccgggaggg agggagggat   23820
ggagctcaag ggatggaacc cagtgagggg tggagacggg gcaggggagg ggtggagagg   23880
ggtggagacg ccccagaggc ggtgtgactc agctgcccct gcaggcagct gcaccttgct   23940
gccttattag gctgcgtgtg ggggactggg ctgccctccc tgcccccagg agcaggagca   24000
ggagtgatgg aggaggagga ggggaggggc aaggccagga ggaggaggag ggccatctca   24060
ctgtgcagag agcagcaccc ttcctcctgg tgcccctggc agggctggtg ctggtggggc   24120
tctgggagca tttgttgaga tgcttctggc cttgaaagga ggccctggg atggctctgt    24180 tgccctcaca ggctgagggg tgggtgaggt gggcagcctg tgtgtcccca gtcctcaggg   24240
cttccctcag ccggcaggtg ccccaggcc tggagctgca gggccaggcc cctgccagt     24300 tacggaggct gcttggcttg gttgctgaac cagggcccca ggaggccgaa atagccccac   24360
acctgcgccg tcccacctct ttgtccagtc accccagggc caggtgaggg ccctggccac   24420
acagcgtgcc cgttccttct tccccatgcc ccgctcatgg gtcagagggc cggtgctggg   24480
gtccagatgg tgtcaacagg gatggtccct gtcctcccca gagacagaag cctgtggccc   24540
acggagggtt tctgggccca gccgatccta gggagggtcc catggccctg cccataggtt   24600
cctggcctct ctcggggccg tggtgccctc acaggtggtg tcaggaagga cgggaaaggc   24660
tgcttgtccc aggggctcat gtggagacca ccccctgcac gcagctgggg cgctcctgcc   24720
tgtgtcctca gaagcactcg gcttagcttt gcccatgtgc ctgggctgtg ggtggcagag   24780
cccggccagc atcctccgat ctccaagggt gcatctctac tggaggcccc tcctgggcct   24840
cttgctcccc gcttcccaga tcattaggat atttggggtc cagaagggcc tcccagccat   24900
cctgggcctt gtcctccggg gccaccagtc cagccagtga caaccacagc atccccggcc   24960
tggaacgagg ctgcccccag cacgttcctc gtactcctgt ccaggacag gaggggctgc    25020 ccctgccacc gagtcccctt ctccaggacc tggggcctgt gggtgtgagg caggtgttct   25080 tggaagggt cactctccag gcacccggcg gccaaggctt gtggctggag cagctcccgc    25140 tgtgggtcg gcgtcgggcc ccgtgtggcc ggagaggagc tgaagggtca cttagcttcg    25200
ggctggggcg aggacagggg acaccccaga gaggtatgcc aggcctcctt cctgcgcccc   25260
actctcggca gaagcagagg tcacaggctg tgctgaggcc ccatggtgct gccccatga    25320 tgccagggtg aggctggcgt tggaagcagg tgtctgacct gcatggtgtc accgtggcca   25380
catcagagct ccagccccag agccgcccac cctcggtcct tggctgtggt ttccctgggc   25440
tggaggagcc tgccgttgtg ttggccacac gaccacagga cctgccaccc ccgacgtggg   25500
ctctgcctgg gcccccactg gacagggacc ccttggagct cctctggcca ccaagtcctc   25560
gcccattcca gaatcggcct tctggagcct cttgctgtcc ctgatgcggg ctgggccttg   25620
ccaagggctt tttttcctgc gccgggaaca gggtggattt gctgggctca ctcccctcag   25680
agacgctgcg ggtgcggtgg gttaggccca agggcgttaa gagaggaggc tggggtgggg   25740
```

```
ctggggcctg gcaggggtc tggcagccct gggcctccca cctcctgtca ggaccaaaaa    25800
aggcaacgcg cctctcctga cctgtacccc ggagtgaacc caaccttgca acccaggagt    25860
gtcagggcct gaggggaggg agacctggct cctgggtgcc gtgcccgtaa ggaggtggcc    25920
acctgcaggg cattcctggc agaggcttca tctggccagg taggaggctg ggtggccgag    25980
ccccaaatct gggtgtgttc tctgcctggc ggtgggtcct gccccaggca ccttctcctc    26040
tgggctggct gggcagggac aatgggcctg gctgcgagga gggggcctgg gctgccttct    26100
gcattgcctc ggtgacggga gatgcccct gcctgctgag ggataggga gtgggcaggc    26160 agtgagagac actgacagct gtcccgcggg tacagggccc tgtctgggtg gccaggccca    26220
tgtctcgggc ccacagtgcg ccccccaccc ttggacggcg ccttctccct ccccaggtgc    26280
atgctgccca gccagggagc gtgggggagt tcgggagggc tggcctacac gccctggtcc    26340
agctgtccca ggtggggtgc tgggcttcag ccctcagccc agggcctagg aatccaactt    26400
gatcctcccc acacagcagc caggttcaaa tgcaggtccc gtaacggaag tgctgctgtg    26460
cagcccagat tggggggcag gagccagcag ggcccccca ccctcttctc gcaccacact    26520
ggggaggcag cattggttcc agttccggtt cctgggctgc cctctcaacc ccggcctaca    26580
gtggggccca ccctgtgcct tctgatgcca ctcccacccc acgccaagtc ccagaggctt    26640
tgggagcggg tgaaggcggt gggtggcggg tggcaggtgc aggcggtggg tggtgggtgt    26700
ggcaggtggc gggccccacc gcaggtgtca tccctgcgaa gcacctgtcg ccagcactca    26760
gagcgctcat gaggtgccca gtccccatgt ggcctcctta gtctccgtcc tgtgtcatgg    26820
aagaggtaac tgaggcacag aaaactcacc aggccaggct gggatgtgag gtcccttgct    26880
gctcatccct ggcagtcagc aaccctacat cttcccagct gggcggcccg tggtgggttc    26940
ggcacccagg accctccggg gtcttgggct gtggcgagtg tgtaggcacc cacctggtgt    27000
ctctctcccc gcaaggcatc tacatcctca tcgctgtggg cgctgtcatg atgttcgttg    27060
gcttcctggg ctgctacggg gccatccagg aatcccagtg cctgctgggg acggtaaggc    27120
agggaggcgg gcctgtgcct gggccgggga ggggctgggg gctgcgtctg gccctgagga    27180
gggggcagag ctggtgctca gggcggagcc tagaattctg ggggaggtgg ctcctgtgcc    27240
ctgcttttcc cgtttggttt ttaaattaaa tcccaccgtg cttggtctcc atcgtggcca    27300
gttcctacgt gaccgctttt ctttgtcaaa aaatagccac aaatataaca gggagcaagc    27360
ctcagctctg aggccagcct cggcgtcccg ggcacaccgc ccctgtggg aagcccaggc    27420 ctggctgtgc catccagggc ctggccagtc caggaagagg gagcctatgc ccgtgtctcc    27480
agtgggggaa actgaggcag atcccatggc tcccccttcc gtggggagca ggaacaaggg    27540
ggtggggaag atcagtcagg ggtcatgctg ctgcacacgc ctccctgggg gctgcagaca    27600
tcctggactc accagcctgt gaccccaaac cacacgcccc gccccatcca ccccgtcctg    27660
tggagcctgg tgccgcgtgg ggacatcctg ggctttgacg gctcctccct gcgctgagtt    27720
ttagcctctg tgccccaggg ctccacacaa gccgctcact cctggtcagg tcgtgggctg    27780
gtggctccca ctagcccctc acagacacgc ctgctgggca cctgggtgtg tgtccttggg    27840
ccccgcctac agcctgccct ctttcctccc tctggccact gcccggctcc agttcttcac    27900
ctgcctggtc atcctgtttg cctgtgaggt ggccgcggc atctgggct ttgtcaacaa    27960 ggaccaggtg agcctgggtg tgcagggaca gggtggggtg ggtgacgggg gcaccctcct    28020
ctcctgtcgc gggtgggggt tgggctgact catggcttgt gggagctctt tgggctcttc    28080
ctgggtccca cttgccagga ggatctccag gggctttatg gaggaggcag cattgggct    28140
```

```
gagcaccagg ccagcctccc gtgtcccagc actcccgggg cagctgagag tgcagagtcc   28200
ttgtcctctg gggtctagcc tcgaagccac cctgcccagg gagagcctgg gaaaagtgcg   28260
tccgcctggg gcggggcggg gtgggggcaa ggagggggag gttcccctg tgcatgtgac    28320 cgcacccctc ccccagatcg ccaaggatgt gaagcagttc tatgaccagg ccctacagca   28380
ggccgtggtg gatgatgacg ccaacaacgc caaggctgtg gtgaagacct tccacgagac   28440
ggtgcggccc cgggggcga gggcggggag cagggccccg gaacccggc ggggtgtgtc     28500 tcgtcctgga tgaatcctgc ctacgcccag acctcaggag caggaggtgc ccttgggacc   28560
tccaggaccc ctggtctcaa ctggtcctcg ggtgggaacc tagtgggcca gggtggccca   28620
gggtgcggaa agctctgagc agcgcagctg aggaggaaga aggctggccc ctggatgcat   28680
tctgcagtgg ggagcgctgc gtaccctgg ccacctcccc atgggttccc tagagccacc    28740 gtcccctgg gcacatccag ggctgacctt gcacccctgc tctctgcagc ttgactgctg    28800
tggctccagc acactgactg cttttgaccac ctcagtgctc aagaacaatt tgtgtccctc  28860
gggcagcaac atcatcagca acctcttcaa ggtgcgcgag gccggtgggg ccgcgcctga   28920
ccccccgcat gtcccgcccc tgggtggggt cctaggggtg ggcaggtcac acggcagccc   28980
cacagggagc gaccacactg ggtggcatgg cccctgtcag ggctgctctg ctgggagggt   29040
tggggtggga ccgcatctgg cccacgagga aggcaggcgc cctgtgctgc gcattccggg   29100
tgaagaaggt ggaggctctg gggggtggga actcacctgc accccagct ccacgtgtgc    29160 actcgtgggt gtggacgccc ctgacagcct gtagctggca gggcctgcag gccatatagt   29220
gccctgtgga agtttcctgc tgaggcctca gtggaagtcg tcatcagtga tgctttaggg   29280
gtctagtgac accaatgacc gtgatctcag tggaaaaggg cacagtgtgt cccaggcatt   29340
tcgcgtttat gttaaaacgg gtggaagata gcaagccggc agaggccggg ccgctgcacc   29400
cgcctgttcc gaggtgggta gggggtgggg ggctgttccc aggattcccc tctacgcttt   29460
ctgtggtgac cacggattac tgcgtgacaa cgggaagccg ggagccgagg cccggtccct   29520
gaccacgcgt gcctggccac ccctgcagga ggactgccac cagaagatcg atgacctctt   29580
ctccgggaag ctgtacctca tcggcattgc tgccatcgtg gtcgctgtga tcatggtgag   29640
cgggcggggg cggagggcct gctctctggg ctgccccttc cgcggggcct tgtgctgact   29700 gcgccccca ccaccctcct gcagatcttc gagatgatcc tgagcatggt gctgtgctgt   29760
ggcatccgga acagctccgt gtactgaggc cccgcagctc tggccacagg gacctctgca   29820 gtgccccta agtgacccgg acacttccga gggggccatc accgcctgtg tatataacgt    29880
ttccggtatt actctgctac acgtagcctt tttacttttg gggttttgtt tttgttctga   29940
actttcctgt taccttttca gggctgacgt cacatgtagg tggcgtgtat gagtggagac   30000
gggcctgggt cttggggact ggagggcagg ggtccttctg ccctgggtc ccagggtgct    30060 ctgcctgctc agccaggcct cctgggag ccactcgccc agagactcag cttggccaac     30120 ttgggggct gtgtccaccc agcccgcccg tcctgtgggc tgcacagctc accttgttcc    30180
ctcctgcccc ggttcgagag ccgagtctgt ggcactctc tgccttcatg cacctgtcct    30240
ttctaacacg tcgccttcaa ctgtaatcac aacatcctga ctccgtcatt taataaagaa   30300
ggaacatcag gcatgctacc aggcctgtgc agtccctcag tgccagtggt gtctgagacc   30360
taggggttgg ccggagggca ggggaatctg acatcggtgg ggcttggctc tgtggactct   30420
gtggggtcca gggtgagggt gggtgggtcg ggatccctgg tgttcaccaa aggagtcact   30480
ctgtaaaatt tggggagtta tttattctga gccaaatatg agcaccggtg gcctgtgaca   30540
```

```
cagccccagg tcctgagaac ttgtgcccaa ggcggtctgg ctacttaatt gtatacattt    30600
tagggacata ggacattgat cattacatct aagatgtacg ttggtttagt cggaaaggtg    30660
ggacgatttg aaggggaggg actttcaggt cataggcgga ttaaaagatg ttctgattaa    30720
taattggttg atttatcta aagacctgaa atcaatagaa tggactatct gggttaagag     30780
gagttgtgga gaccaagatt attatgcaga tgaagccgcc agattgtaaa tgtttcttat    30840
cagacttaaa aaggtaccag aatcttagtt aattctctcc tggatcagga aatagacctg    30900
gaaagggagg gggattctct atagaatgta gattttccca agagacagct ttgcagggcc    30960
atttcaaaat acatcagaga aatatatttt ggggtaaaat acttcggttt ctttcagggc    31020
ctgctgtcac gttggtatct tattactaca gagtctgttt tgtgagtctt aaggtctttt    31080
tatttttaga cagagttttg ctcttgtcac ccaggttgga gtgcaatggc gtgatctcag    31140
ctcactgcag cctcccctcc acctcccagg ttcaagcgat tctcctgcct cagcctcctg    31200
agtagctggg acaacaggca tgcaccaccc acccagcta atttgtatt tttagtagag      31260 acggtgtttc gccacggtgg ccaggctagt ctcgaactcc tgacctcacg tgacacacca    31320
ggttttggga ttacaggtgt gagccaccac accggactaa ggtctctgtt ttaatgtgaa    31380
tgctggtcag ctgtgcctat gaggcatgtt cggccaccca cagtcatcat ggcctcaacg    31440
agcttttcag gttacttta gaatgcattt ggccaagagg tgcccattca gttggttggg      31500
gttgcttaga attttacttt gggtttaaac cagggagcaa ctccaggtag caagggccct    31560
ttttgggagc gttctctcta ttctcttttg ggagaggccc tgtgttgcct gcagccactt    31620
ccaccctgcc ccttgggcac acaaggggca cacagtgtaa gcaggtgggc aggaggggtc    31680
gggcagccag ggaatgcagt gagatgggct tggggtaggg gctgggtgcg ctgcaggact    31740
cctcttcctc ctgagggatg gtaaaggatg gacacactgc cccctcccga gcatttgagg    31800
gtctctgccc tgcccatctg ttacctgtaa atgttccttt gaggagctga tggctcaggc    31860
ctgagccaca tctcagaggg tctggagggg aagaaagacc tcatcctact agggagcccc    31920
cccagcccac cagcgagcgg tggttggggg cagacaggct gtggggctaa ggagcccctg    31980
cactcccccg tccttttccc tttgtctgag cacctccagc cagtgggctt ggtctagact    32040
ctcctatctt tccccacatc gtggggtggg gcttgctctg ggttaggcta cttttcccta    32100
gttgtgggga gggggtgct ggcacatttc actgttccct ggaggaaatg agtgcctggg      32160
aattcatatc tagggctccc agcagcctct ttgcaggcca atttggaaac tgtccccagc    32220
cctgcatttt aggggttac agagtctctc agcaggccct cctcccctgc tgctcccaac     32280
ttgcaagcct gcactggttg ggagaacata atggtccaag gagccccctc tctactttcc    32340
gctgtgttcc ctgtggggag ggaagagcag tttaagaaat aaggaatccc aaaggcgcac    32400
agcagaccgg gggccgagga gtgggtcctg cttcccctcc ttttttctag gctgagccac    32460
agcaggtcct tgaatcctat ttcccagcgg atgccaggac agcaggccct gggggagttc    32520
tctctcgagc ctttcagagg gaccagaggt ctagcagcca aggagaactc agaatccttg    32580
agtgtgtggg gcaggaactc tcccagctga aaggggcac aagtgccaa ccatctaggg       32640 cccagtggcc aaggaagacg cggcttgtcg cagggagaat ctgggccctg gtcctccctt    32700
tcagggcggg cagctgacct gccccctgct gcggacaggc gaggccaggc tgctggctcg    32760
caagcatggc ggagcccaaa ccttccctgc tgccgcccgc ccagccacgg ctgacttgga    32820
agcttgagga gcgttcagca gcctccatcc tgcccgggag gaccggggac ctggaagggc    32880
ctggccctcg cttccctgca gcgccctagg gggacgtctc agtgcctccc ggagcccgga    32940
```

```
ccaatgcacc agagctgagg gcccaagggt gtgagggtgg ccgggcagtg ccccgagga    33000 cggcgcccca caagtttgcg gccagggccc agcaaacccc tagggtggg aaagcgtcgg    33060 cccagctagc gggtccagca gggctgcccc cttcaccgtg gcccagcggt cacgacccca    33120
cgtcctcatc gcgggctggg actgcctctg cgtctggcct gagcgggacc gtgggatcct    33180
ggggagcccc gcctcggtgc actgacagag cccagaagga gtgacggtta ccgcttccgg    33240
tcaggaccgg aagtgccggg aacggcattc gtcctccgtg cgagatgacg cacttcctgc    33300
ctgaggcggc cgctgttctc gcggcttccg gcaggtggcg ctgagaccac gggaagccag    33360
cctggctgtc ggttagccct cgagcattct gggaattgca ggcctggccc ctcctcttcc    33420
tgttcttggt caattccggt cttgtttccc aacaaatgc cgtcgtttcc ggggctgctt    33480
ccgagccgga cccaagggcc ggggcgtgga ggagtagagg ggcgagcgca tgcgcacagg    33540
actacacgtc ccgacaggcg tcgggagcgg cggcccagtt ccttgtggga gctgtagttc    33600
tgcaggcgcg gaagccgtgg tgctcggccg gcagagcact cggtttccca gagggctgag    33660
cgcgccgcac ggaggtgcgg cgccgaccaa gatggagact gccgagcagc cttgagccgg    33720
taggtttgtg gtgagggagg acgggccgcg cgggccggcc gagcctccgg gaggtcaccg    33780
agcgcagctt taatacctga gctcgaaggc cccgctgtgc tcgccgaccc ccgtacctcg    33840
cggccgggcc cttgggaccc acagcatcct tgtgaggccc ggaggcctgt ccagcccgac    33900
tggacagtgc cgaggggcac cgagagccag cttggcaccg agagttcgtt tgttctctgg    33960
cggggaggtc ttgctggcac atatagtgga gaaaggccgg gctctgcgtt catgtggaga    34020
aagagacggc ttccttcagc ctacggacat gaaggagtca actctacctt ccactcgttg    34080 ccggcttttcg ccgagaaccc cgagaaacgg actaccggag tccctatctt gcagcccgat    34140
ccccgctacc cgtcggagtg ccccgctgac caggctgctt ctggccgcgg cggcgttccg    34200
ctgcagagga cgggagtgcg aatctgggaa gcagggttct ggttgaactc cagcttcgtc    34260
tgcaacatac tgtgtgactt gggcaaatta tttccccgc cccgttcctg ccagctttaa    34320
aacggtcatc agtgggggt gctgcgtatc cctttcact ggggtggctt cttcactgag    34380
gagagtcgcg cctcagagga actgaggtcc tgcctgtgtt cgacctggtg ggggcacta    34440 agagcccctg atagtacccc tgaccccatc cttattgggt gcacaagaca caggtcactc    34500
tgggcgggca aggagttttg gtagcaggag aggagtcggt ggatggatgg ctgaggacag    34560
tgcagaaggg tgtggctggg ccgtcttttt ttgcctggaa attcaagttc tgaggcaccc    34620
agtcactcca gcactaaatg ggtgcaggag gcagcacttg tctgcccagc tggaaaggca    34680
gggtatgtgc tgagtgttac aggtggaagg ccactggagg tcgctccagg agccgcgggg    34740
atttacctct gcctaacagg gctgctcaag gtgatggtcg acaccccact ttcctgagag    34800
cttgaccctc agatgccagg gccttggctg cagattcctt gggagctccc gggatcttc    34860 cagcaaatag gagcaaatct tttcccgtg gatcaggaag gtgcacgctc tttgtggaat    34920
acgactgctc acccgcaca gcaagcagct tataagtggc cctcctgcct gatttcagcc    34980
ctgggttcaa gccctgggtg gctgcttact accaaaatcg ctcagtagct ccaagcctgc    35040
ctgcagaggg ttggcaccat taaatgaggt aacgagtcaa aagtccctac cctgggtcct    35100
agcctgtcag gggctccgaa aacccaggct caggtcggtc ctgcccggca cctgtttcac    35160
acatgtacac tccggtctga ggttggtcct ctccccacc ccacccacct gcagttgagc    35220
agctgaacag aggccatgcc ggggcactcc gaggcctgag acgaccacgc ctgtgccgct    35280
gaggaccttc atcagggctc cgtccacttg gcccgcttgg ctgtccaatc acactccagt    35340
```

```
gtcaaccact ggcacccagc agccaagaga ggtgagagga gggcttggag ggggaggcgg    35400
gactccaccc tgtgtgggac agttctgtca gttgaccctc cacttgtcca ggggcagtgg    35460
atctgcaggg ggaactcatt ctcaatactg ttcctcctga gaaacaaatt ttctgggctg    35520
ttttggttta ggtgtggcgt ggccctgggg acgcatggct gaggcaggaa caggtgagcc    35580
gtcccccagc gtggagggcg aacacggac ggagtatgac acgctgcctt ccgacacagt    35640
ctccctcagt gactcggact ctgacctcag cttgcccggt ggtgctgaag tggaagcact    35700
gtccccgatg gggctgcctg ggaggagga ttcaggtcct gatgagccgc cctcaccccc     35760
gtcaggcctc ctcccagcca cggtgcagcc attccatctg agaggcatga gctccacctt    35820
ctcccagcgc agccgtgaca tctttgactg cctggagggg gcggccagac gggctccatc    35880
ctctgtggcc cacaccagca tgagtgacaa cggaggcttc aagcggcccc tagcgccctc    35940
aggccggtct ccagtggaag gcctgggcag ggcccatcgg agccctgcct caccaagggt    36000
gcctccggtc cccgactacg tggcacaccc cgagcgctgg accaagtaca gcctggaaga    36060
tgtgaccgag gtcagcgagc agagcaatca ggccaccgcc ctggccttcc tgggctccca    36120
gagcctggct gcccccactg actgcgtgtc ctccttcaac caggatccct ccagctgtgg    36180 ggagggagg gtcatcttca ccaaaccagt ccgagggtc gaagccagac acgagaggaa      36240
gagggtcctg gggaaggtgg gagagccagg caggggcgag cttgggaatc ctgccacaga    36300
caggggcgag ggccctgtgg agctggccca tctggccggg cccgggagcc cagaggctga    36360
ggagtggggc agccaccatg gaggcctgca ggaggtggag gcactgtcag ggtctgtcca    36420
cagtgggtct gtgccaggtc tcccgccggt ggaaactgtt ggcttccatg gcagcaggaa    36480
gcggagtcga gaccacttcc ggaacaagag cagcagcccc gaggacccag gtgctgaggt    36540
ctgagaggga gatggcccag cctgaccca ctggccactg ccatcctgct gccttcccag     36600
tggggctggt caggggcag cctggccact gcctagctgg aatgggagga agcctgcagg     36660
tggcaccggt ggccctggct gcagttctgg gcagcatcct cccaagcaga gaccttgctg    36720
aagctcctgg ggtgtgggt gtgggctgga agcactggct ccctggtagg gacaataaag     36780
gttttgggtc tttctgagac tttgtgtcta tctgggccct gcttacccaa agggctcagt    36840
tggcagcaag agctccccac acctgaccct cggtgccgga ccactcgagg gtggctgaca    36900
cctgcatccc tcaccagcac atcacccagg tgacagtgag aattggaaac cccaggcctc    36960
ctctagggct tgtggctcag tggcaggtgt ccagtgagtg ccctcaatgg gcctgagtgg    37020
gtacagaatc tgccctcccc caaccaaagc ccacatgatg ccatcagccc caggcctagt    37080
gcagaccaca gcttgggaag cgaaagggag atg                                37113
```

<210> SEQ ID NO 12
<211> LENGTH: 15540
<212> TYPE: DNA
<213> ORGANISM: Homo sapiens

<400> SEQUENCE: 12

```
agccaagcat tccgactcag ctctgggagc agctgccttc tgggctggca ttctccgcca       60 gggggttgt gccctcgtgg ccccccccgg gtgcctcctc acctggctga tttcatctcc       120
tgtccccctg cctcctcctc caggaagccc cagggcctg gccctccttg agagtggcat       180
ggaggaggaa gaagactcgc ccaggcccat gggagtcgga tggtggccgc acttgtgggg      240
ccctgacccc ataggcttct tcagcacgcc ctggcctggg tgatccctgc ctgagggctg      300
tgcacggctc atctgccaga ccagatttta ggggattctt gtactgtcct cctggagcag      360
```

```
caggggtaa agcctgaccc acccagactg tccagcaaca agggcctcct gctgtgggcc      420
agggaccctg gaactgacca attgtgtcct agggacgcag agtccccagg ctgctagagg      480 gctgtgggc cctgtttcat gcctgaagca ggaagaaacc ccaggagagg tctgaagggg      540
acccagcccc caccctgtct agcagggagg agcctctgca agaggccgag gggtgctgaa      600
gtggaggagg atagaggcag caggactcag ggtcactggt catttatggg gatcacacgg      660
ctgcagtgtg ccctgcatgg tgctaggcac caggacagc agaggacaag cctgtgtcct      720
ctcccaccac cagagggctg ggcactgccc ctagggagag aggggggcctt ggtgtgtgca     780 gaggggggcc tggggcacgt gcctggcctg gtcagatgat cagagtgggc tgggctgggc      840
ctggtctggg gcccagtctc aagggcagac cccacctggc tagagttgat tgtgtgcaca     900
ccggatgacc cggcgttgaa ggcctctcct ctctgtgagc ctcatcccca cctgccagac      960
tcccagcaca gcctgcttcc tgccccagct gctgagcgac agcgctgggc cggcttctgc     1020
gcgccccttc ccccagccca tcttggaaac cacagcagcg tccttcctcc caagtccctt     1080
cccagggctg acatcccaca gcagggatgt atcccacaaa ccccgcaggc cctggtgcct     1140
acagcttggc ctggtaacat caaatcctac cctctcctcc tggcagcaaa gatggggtgc     1200
ccccacccca gagttctcag cacccccaga cagaagcagt cccccagcga cctcagaact     1260 cttgggcgc tgccacaccc ttgcaggagg gggcagtgtt cctgggatgc tcaggtcctg      1320
gtatcacctc tggccagata cggaaggtga aactacaggg catccaattc accttgaact     1380
tcagataaac accagattat ttttttgtat gtcccgtgca atatttggga cacacttacc     1440
ctaaagaagt attctgtttt catctgagag gcagatttaa ccggcgtccc gtgtcttcct     1500
ggcagtcctg ccctggagtc acactccaca ggtgcagggc agggccaggc tccaagtaga     1560
tggcggccaa agcacccgcc ccatgctcct gactcccggg gctcttcagg gcattgcgaa     1620
aaccagcagc agagctgaca cctggtccct gctcgggagc cagcaaggca ggaggctgct     1680
taggccttgc gtgtggggtg ggcgcactcc ctgctgcagt gctcttcgta catgtgacac     1740
tgttcccgct cttccccagc tggctggagg cgtgatcctg ggtgtggccc tgtggctccg     1800
ccatgacccg cagaccacca acctcctgta tctggagctg ggagacaagc ccgcgcccaa     1860
caccttctat gtaggtgagt gcacatgtgg ccgcagacgc attcagggag ggcttctagg     1920
aggaggcagg tcctagcctt ttggatgggg acatggaggg tgaaagacag tcgggcatgg     1980
cgtgtccggg cagggaggcg gccctggaaa gggctctggg cacaagggtt gagatggagg     2040
tgggcctgtg gcctgctggc ccttctggtc tgagccaggg caggggtgg cagctaggcc      2100 tgggcaggga ctgtgtggag accttgctta ttttaagtgt gggttatttt cggggaggc      2160 tccctgagaa gggtggggct ggatgcctgg gccacacaga gcagccgagg cagctggcgc     2220
tgtggagccc ggagggagg gagggatgga gctcaaggga tggaacccag tgaggggtgg     2280 agacgggca gggagggggt ggagagggt ggagacgccc cagaggcggt gtgactcagc      2340 tgccctgca ggcagctgca ccttgctgcc ttattaggct gcgtgtgggg gactgggctg     2400
ccctccctgc cccaggagc aggagcagga gtgatggagg aggaggaggg gaggggcaag      2460
gccaggagga ggaggaggc catctcactg tgcagagagc agcacccttc ctcctggtgc     2520
ccctggcagg gctggtgctg gtgggctct ggagcatt gttgagatgc ttctggcctt       2580
gaaaggaggc ccctgggatg gctctgttgc cctcacaggc tgaggggtgg gtgaggtggg    2640
cagcctgtgt gtcccagtc ctcagggctt ccctcagccg gcaggtgccc ccaggcctgg     2700
agctgcaggg ccaggccccc tgccagttac ggaggctgct tggcttggtt gctgaaccag    2760
```

```
ggccccagga ggccgaaata gccccacacc tgcgccgtcc cacctctttg tccagtcacc   2820
ccagggccag gtgagggccc tggccacaca gcgtgcccgt tccttcttcc ccatgccccg   2880
ctcatgggtc agagggccgg tgctggggtc cagatggtgt caacagggat ggtccctgtc   2940
ctccccagag acagaagcct gtggcccacg gagggtttct gggcccagcc gatcctaggg   3000
agggtcccat ggccctgccc ataggttcct ggcctctctc ggggccgtgg tgccctcaca   3060
ggtggtgtca ggaaggacgg gaaaggctgc ttgtcccagg ggctcatgtg gagaccaccc   3120
cctgcacgca gctggggcgc tcctgcctgt gtcctcagaa gcactcggct tagctttgcc   3180
catgtgcctg ggctgtgggt ggcagagccc ggccagcatc tccgatctc caagggtgca    3240 tctctactgg aggcccctcc tgggcctctt gctccccgct tcccagatca ttaggatatt   3300
tggggtccag aagggcctcc cagccatcct gggccttgtc ctccggggcc accagtccag   3360
ccagtgacaa ccacagcatc cccggcctgg aacgaggctg ccccccagcac gttcctcgta  3420 ctcctgtcca gggacaggag gggctgcccc tgccaccgag tcccttctc caggacctgg    3480 ggcctgtggg tgtgaggcag gtgttcttgg aaggggtcac tctccaggca cccggcggcc   3540
aaggcttgtg gctggagcag ctcccgctgt ggggtcggcg tcgggccccg tgtggccgga   3600
gaggagctga agggtcactt agcttcgggc tggggcgagg acaggggaca ccccagagag   3660
gtatgccagg cctccttcct gcgcccact ctcggcagaa gcagaggtca caggctgtgc     3720
tgaggcccca tggtgctgcc cccatgatgc cagggtgagg ctggcgttgg aagcaggtgt   3780
ctgacctgca tggtgtcacc gtggccacat cagagctcca gccccagagc cgcccaccct   3840
cggtccttgg ctgtggtttc cctgggctgg aggagcctgc cgttgtgttg ccacacgac     3900 cacaggacct gccaccccg acgtgggctc tgcctgggcc cccactggac agggaccct     3960 tggagctcct ctggccacca agtcctcgcc cattccagaa tcggccttct ggagcctctt   4020
gctgtccctg atgcgggctg ggccttgcca agggcttttt ttcctgcgcc gggaacaggg   4080
tggatttgct gggctcactc ccctcagaga cgctgcgggt gcggtgggtt aggcccaagg   4140
gcgttaagag aggaggctgg ggtggggctg gggcctggca gggggtctgg cagccctggg   4200
cctcccacct cctgtcagga ccaaaaaagg caacgcgcct ctcctgacct gtaccccgga   4260
gtgaacccaa ccttgcaacc caggagtgtc agggcctgag gggagggaga cctggctcct   4320
gggtgccgtg cccgtaagga ggtggccacc tgcagggcat tcctggcaga ggcttcatct   4380
ggccaggtag gaggctgggt ggccgagccc caaatctggg tgtgttctct gcctggcggt   4440
gggtcctgcc ccaggcacct tctcctctgg gctggctggg cagggacaat gggcctggct   4500
gcgaggaggg ggcctgggct gccttctgca ttgcctcggt gacggagat ggcccctgcc    4560 tgctgaggga taggggagtg ggcaggcagt gagagacact gacagctgtc ccgcgggtac   4620
agggccctgt ctgggtggcc aggcccatgt ctcgggccca cagtgcgccc ccacccttg    4680 gacggcgcct tctccctccc caggtgcatg ctgcccagcc agggagcgtg ggggagttcg   4740
ggagggctgg cctacacgcc ctggtccagc tgtcccaggt ggggtgctgg gcttcagccc   4800
tcagcccagg gcctaggaat ccaacttgat cctccccaca cagcagccag gttcaaatgc   4860
aggtcccgta acggaagtgc tgctgtgcag cccagattgg ggggcaggag ccagcagggc   4920 cccccaccc tcttctcgca ccacactggg gaggcagcat tggttccagt tccggttcct    4980
gggctgccct ctcaacccg gcctacagtg gggcccaccc tgtgccttct gatgccactc    5040
ccaccccacg ccaagtccca gaggctttgg gagcgggtga aggcggtggg tggcgggtgt   5100
caggtgcagg cggtgggtgg tgggtgtggc aggtggcggg ccccaccgca ggtgtcatcc   5160
```

```
ctgcgaagca cctgtcgcca gcactcagag cgctcatgag gtgcccagtc cccatgtggc    5220
ctccttagtc tccgtcctgt gtcatggaag aggtaactga ggcacagaaa actcaccagg    5280
ccaggctggg atgtgaggtc ccttgctgct catccctggc agtcagcaac cctacatctt    5340
cccagctggg cggcccgtgg tgggttcggc acccaggacc ctccggggtc ttgggctgtg    5400
gcgagtgtgt aggcacccac ctggtgtctc tctccccgca aggcatctac atcctcatcg    5460
ctgtgggcgc tgtcatgatg ttcgttggct tcctgggctg ctacggggcc atccaggaat    5520
cccagtgcct gctggggacg gtaaggcagg gaggcgggcc tgtgcctggg ccggggaggg    5580
gctgggggct gcgtctggcc ctgaggaggg ggcagagctg gtgctcaggg cggagcctag    5640
aattctgggg gaggtggctc ctgtgccctg cttttcccgt ttggttttta aattaaatcc    5700
caccgtgctt ggtctccatc gtggccagtt cctacgtgac cgcttttctt tgtcaaaaaa    5760
tagccacaaa tataacaggg agcaagcctc agctctgagg ccagcctcgg cgtcccgggc    5820
acaccgcccc ctgtgggaag cccaggcctg gctgtgccat ccagggcctg gccagtccag    5880
gaagagggag cctatgcccg tgtctccagt gggggaaact gaggcagatc ccatggctcc    5940
cccttccgtg gggagcagga acaagggggt ggggaagatc agtcaggggt catgctgctg    6000
cacacgcctc cctgggggct gcagacatcc tggactcacc agcctgtgac cccaaaccac    6060 acgcccgcc ccatccaccc cgtcctgtgg agcctggtgc cgcgtgggga catcctgggc    6120
tttgacggct cctccctgcg ctgagtttta gcctctgtgc cccagggctc cacacaagcc    6180
gctcactcct ggtcaggtcg tgggctggtg gctcccacta gccctcaca gacacgcctg    6240 ctgggcacct gggtgtgtgt ccttgggccc cgcctacagc ctgccctctt tcctccctct    6300
ggccactgcc cggctccagt tcttcacctg cctggtcatc ctgtttgcct gtgaggtggc    6360
cgccggcatc tggggctttg tcaacaagga ccaggtgagc ctgggtgtgc agggacaggg    6420
tggggtgggt gacgggggca ccctcctctc cgtcgcggg tggggttgg gctgactcat    6480 ggcttgtggg agctctttgg gctcttcctg gtcccactt gccaggagga tctccagggg    6540
ctttatggag gaggcagcat tgggctgag caccaggcca gcctcccgtg tcccagcact    6600
cccggggcag ctgagagtgc agagtccttg tcctctgggg tctagcctcg aagccaccct    6660
gcccagggag agcctgggaa aagtgcgtcc gcctggggcg gggcggggtg ggggcaagga    6720
ggggagggtt cccctgtgc atgtgaccgc accctcccc cagatcgcca aggatgtgaa    6780
gcagttctat gaccaggccc tacagcaggc cgtggtggat gatgacgcca acaacgccaa    6840
ggctgtggtg aagaccttcc acgagacggt gcggccccgg ggggcgaggg cggggagcag    6900
ggccccggga accggcggg gtgtgtctcg tcctggatga atcctgccta cgcccagacc    6960
tcaggagcag gaggtgccct tgggacctcc aggacccctg gtctcaactg gtcctcgggt    7020
gggaacctag tgggccaggg tgggcccaggg tgcggaaagc tctgagcagc gcagctgagg    7080
aggaagaagg ctggcccctg gatgcattct gcagtgggga gcgctgcgta cccctggcca    7140
cctccccatg ggttccctag agccaccgtc ccctgggca catccagggc tgaccttgca    7200
cccctgctct ctgcagcttg actgctgtgg ctccagcaca ctgactgctt tgaccacctc    7260
agtgctcaag aacaatttgt gtccctcggg cagcaacatc atcagcaacc tcttcaaggt    7320
gcgcgaggcc ggtggggccg cgcctgaccc cccgcatgtc ccgcccctgg gtggggtcct    7380
aggggtgggc aggtcacacg gcagccccac agggagcgac cacactgggt ggcatggccc    7440
ctgtcagggc tgctctgctg ggagggttgg ggtgggaccg catctggccc acgaggaagg    7500
caggcgccct gtgctgcgca ttcgggtga agaaggtgga ggctctgggg ggtgggaact    7560
```

```
cacctgcacc cccagctcca cgtgtgcact cgtgggtgtg gacgccctg acagcctgta   7620
gctggcaggg cctgcaggcc atatagtgcc ctgtggaagt ttcctgctga ggcctcagtg   7680
gaagtcgtca tcagtgatgc tttaggggtc tagtgacacc aatgaccgtg atctcagtgg   7740
aaaagggcac agtgtgtccc aggcatttcg cgtttatgtt aaaacgggtg aagatagca    7800
agccggcaga ggccgggccg ctgcaccgc ctgttccgag gtgggtaggg ggtgggggc     7860
tgttcccagg attcccctct acgctttctg tggtgaccac ggattactgc gtgacaacgg   7920
gaagccggga gccgaggccc ggtccctgac cacgcgtgcc tggccacccc tgcaggagga   7980
ctgccaccag aagatcgatg acctcttctc cgggaagctg tacctcatcg gcattgctgc   8040
catcgtggtc gctgtgatca tggtgagcgg gcggggggcgg agggcctgct ctctgggctg   8100
ccccttccgc ggggccttgt gctgactgcg cccccacca ccctcctgca gatcttcgag    8160
atgatcctga gcatggtgct gtgctgtggc atccggaaca gctccgtgta ctgaggcccc   8220
gcagctctgg ccacagggac ctctgcagtg cccctaagt gacccggaca cttccgaggg    8280
ggccatcacc gcctgtgtat ataacgtttc cggtattact ctgctacacg tagccttttt   8340
acttttgggg ttttgttttt gttctgaact ttcctgttac cttttcaggg ctgacgtcac   8400
atgtaggtgg cgtgtatgag tggagacggg cctgggtctt ggggactgga gggcaggggt   8460
ccttctgccc tggggtccca gggtgctctg cctgctcagc caggcctctc ctgggagcca   8520
ctcgcccaga gactcagctt ggccaacttg ggggctgtg tccacccagc ccgcccgtcc    8580
tgtgggctgc acagctcacc ttgttccctc ctgccccggt tcgagagccg agtctgtggg   8640
cactctctgc cttcatgcac ctgtcctttc taacacgtcg ccttcaactg taatcacaac   8700
atcctgactc cgtcatttaa taagaagga acatcaggca tgctaccagg cctgtgcagt    8760
ccctcagtgc cagtggtgtc tgagacctag ggggtggccg gagggcaggg gaatctgaca   8820
tcggtggggc ttggctctgt ggactctgtg gggtccaggg tgaggtggg tgggtcggga    8880
tccctggtgt tcaccaaagg agtcactctg taaaatttgg ggagttattt attctgagcc   8940
aaatatgagc accggtggcc tgtgacacag ccccaggtcc tgagaacttg tgcccaaggc   9000
ggtctggcta cttaattgta tacattttag ggacatagga cattgatcat tacatctaag   9060
atgtacgttg gttagtcgg aaaggtggga cgatttgaag gggagggact ttcaggtcat    9120
aggcggatta aaagatgttc tgattaataa ttggttgatt ttatctaaag acctgaaatc   9180
aatagaatgg actatctggg ttaagaggag ttgtggagac caagattatt atgcagatga   9240
agccgccaga ttgtaaatgt ttcttatcag acttaaaaag gtaccagaat cttagttaat   9300
tctctcctgg atcaggaaat agacctgaa agggaggggg attctctata gaatgtagat    9360
tttcccaaga gacagctttg cagggccatt tcaaaataca tcagagaaat atattttggg   9420
gtaaaatact tcggtttctt tcagggcctg ctgtcacgtt ggtatcttat tactacagag   9480
tctgttttgt gagtcttaag gtctttttat ttttagacag agttttgctc ttgtcaccca   9540
ggttggagtg caatggcgtg atctcagctc actgcagcct cccctccacc tcccaggttc   9600
aagcgattct cctgcctcag cctcctgagt agctgggaca acaggcatgc accacccac    9660
ccagctaatt ttgtattttt agtagagacg tgtttcgcc acggtggcca ggctagtctc   9720
gaactcctga cctcacgtga cacaccaggt tttgggatta caggtgtgag ccaccacacc   9780
ggactaaggt ctctgttta atgtgaatgc tggtcagctg tgcctatgag gcatgttcgg   9840
ccacccacag tcatcatggc ctcaacgagc ttttcaggtt tactttagaa tgcatttggc   9900
caagaggtgc ccattcagtt ggttggggtt gcttagaatt ttactttggg tttaaaccag   9960
```

```
ggagcaactc caggtagcaa gggccctttt tgggagcgtt ctctctattc tcttttggga    10020
gaggccctgt gttgcctgca gccacttcca ccctgcccct tgggcacaca aggggcacac    10080
agtgtaagca ggtgggcagg aggggtcggg cagccaggga atgcagtgag atgggcttgg    10140
ggtaggggct gggtgcgctg caggactcct cttcctcctg agggatggta aaggatggac    10200
acactgcccc ctcccgagca tttgagggtc tctgccctgc ccatctgtta cctgtaaatg    10260
ttcctttgag gagctgatgg ctcaggcctg agccacatct cagagggtct ggaggggaag    10320
aaagacctca tcctactagg gagcccccc agcccaccag cgagcggtgg ttggggcag     10380 acaggctgtg gggctaagga gcccctgcac tcccccgtcc ttttcccttt gtctgagcac    10440
ctccagccag tgggcttggt ctagactctc ctatctttcc ccacatcgtg gggtggggct    10500
tgctctgggt taggctactt ttccctagtt gtggggaggg gggtgctggc acatttcact    10560
gttccctgga ggaaatgagt gcctgggaat tcatatctag gctcccagc agcctctttg    10620 caggccaatt tggaaactgt ccccagccct gcattttagg gggttacaga gtctctcagc    10680
aggccctcct cccctgctgc tcccaacttg caagcctgca ctggttggga aacataatg    10740 gtccaaggag ccccctctct actttccgct gtgttccctg tggggaggga agagcagttt    10800
aagaaataag gaatcccaaa ggcgcacagc agaccggggg ccgaggagtg ggtcctgctt    10860
cccctccttt tttctaggct gagccacagc aggtccttga atcctatttc ccagcggatg    10920
ccaggacagc aggccctggg ggagttctct ctcgagcctt tcagagggac cagaggtcta    10980
gcagccaagg agaactcaga atccttgagt gtgtggggca ggaactctcc cagctgagaa    11040
ggggcacaag gtgccaacca tctagggccc agtggccaag gaagacgcgg cttgtcgcag    11100
ggagaatctg ggccctggtc ctcccttca gggcgggcag ctgacctgcc ccctgctgcg    11160
gacaggcgag gccaggctgc tggctcgcaa gcatggcgga gcccaaacct tccctgctgc    11220
cgcccgccca gccacggctg acttggaagc ttgaggagcg ttcagcagcc tccatcctgc    11280
ccgggaggac cggggacctg aagggcctg gccctcgctt ccctgcagcg ccctagggg    11340 acgtctcagt gcctcccgga gcccggacca atgcaccaga gctgagggcc caagggtgtg    11400
agggtggccg ggcagtggcc ccgaggacgg cgccccacaa gtttgcggcc agggcccagc    11460 aaaccctag gggtgggaa gcgtcggccc agctagcggg tccagcaggg ctgcccctt     11520 caccgtggcc cagcggtcac gacccacgt cctcatcgcg ggctgggact gcctctgcgt    11580
ctggcctgag cgggaccgtg ggatcctggg gagccccgcc tcggtgcact gacagagccc    11640
agaaggagtg acggttaccg cttccggtca ggaccggaag tgccgggaac ggcattcgtc    11700
ctccgtgcga gatgacgcac ttcctgcctg aggcggccgc tgttctcgcg gcttccggca    11760
ggtggcgctg agaccacggg aagccagcct ggctgtcggt tagccctcga gcattctggg    11820
aattgcaggc ctggcccctc ctcttcctgt tcttggtcaa ttccggtctt gtttccccaa    11880
caaatgccgt cgtttccggg gctgcttccg agccggaccc aagggccggg gcgtggagga    11940 gtagagggc gagcgcatgc gcacaggact acacgtcccg acaggcgtcg ggagcggcgg    12000
cccagttcct tgtgggagct gtagttctgc aggcgcggaa gccgtggtgc tcggccggca    12060
gagcactcgg tttcccagag ggctgagcgc gccgcacgga ggtgcggcgc cgaccaagat    12120
ggagactgcc gagcagcctt gagccggtag gtttgtggtg agggaggacg ggccgcgcgg    12180
gccggccgag cctccgggag gtcaccgagc gcagctttaa tacctgagct cgaaggcccc    12240
gctgtgctcg ccgaccccg tacctcgcgg ccgggccctt ggacccaca gcatccttgt    12300 gaggcccgga ggcctgtcca gcccgactgg acagtgccga ggggcaccga gagccagctt    12360
```

```
ggcaccgaga gttcgtttgt tctctggcgg ggaggtcttg ctggcacata tagtggagaa   12420
aggccgggct ctgcgttcat gtggagaaag agacggcttc cttcagccta cggacatgaa   12480
ggagtcaact ctaccttcca ctcgttgccg gctttcgccg agaaccccga gaaacggact   12540
accggagtcc ctatcttgca gcccgatccc cgctacccgt cggagtgccc cgctgaccag   12600
gctgcttctg gccgcggcgg cgttccgctg cagaggacgg gagtgcgaat ctgggaagca   12660
gggttctggt tgaactccag cttcgtctgc aacatactgt gtgacttggg caaattattt   12720
cccccgcccc gttcctgcca gctttaaaac ggtcatcagt ggggggtgct gcgtatcccc   12780
tttcactggg gtggcttctt cactgaggag agtcgcgcct cagaggaact gaggtcctgc   12840
ctgtgttcga cctggtgggg ggcactaaga gcccctgata gtacccctga ccccatcctt   12900
attgggtgca caagacacag gtcactctgg gcgggcaagg agttttggta gcaggagagg   12960
agtcggtgga tggatggctg aggacagtgc agaagggtgt ggctgggccg tcttttttg    13020 cctggaaatt caagttctga ggcacccagt cactccagca ctaaatgggt gcaggaggca   13080
gcacttgtct gcccagctgg aaaggcaggg tatgtgctga gtgttacagg tggaaggcca   13140
ctggaggtcg ctccaggagc cgcggggatt tacctctgcc taacagggct gctcaaggtg   13200
atggtcgaca ccccactttc ctgagagctt gaccctcaga tgccagggcc ttggctgcag   13260
attccttggg agctcccggg gatcttccag caaataggag caaatctttt ccccgtggat   13320
caggaaggtg cacgctcttt gtggaatacg actgctcacc ccgcacagca agcagcttat   13380
aagtggccct cctgcctgat ttcagccctg ggttcaagcc ctgggtggct gcttactacc   13440
aaaatcgctc agtagctcca agcctgcctg cagagggttg gcaccattaa atgaggtaac   13500
gagtcaaaag tccctaccct gggtcctagc ctgtcagggg ctccgaaaac ccaggctcag   13560
gtcggtcctg cccggcacct gtttcacaca tgtacactcc ggtctgaggt tggtcctctc   13620
cccaccccca cccacctgca gttgagcagc tgaacagagg ccatgccggg gcactccgag   13680
gcctgagacg accacgcctg tgccgctgag gaccttcatc agggctccgt ccacttggcc   13740
cgcttggctg tccaatcaca ctccagtgtc aaccactggc acccagcagc caagagaggt   13800
gagaggaggg cttggagggg gaggcgggac tccaccctgt gtgggacagt tctgtcagtt   13860
gaccctccac ttgtccaggg gcagtggatc tgcaggggga actcattctc aatactgttc   13920
ctcctgagaa acaaattttc tgggctgttt tggtttaggt gtggcgtggc cctggggacg   13980
catggctgag gcaggaacag gtgagccgtc ccccagcgtg gagggcgaac acggacgga    14040 gtatgacacg ctgccttccg acacagtctc cctcagtgac tcggactctg acctcagctt   14100
gcccggtggt gctgaagtgg aagcactgtc cccgatgggg ctgcctgggg aggaggattc   14160
aggtcctgat gagccgccct cacccccgtc aggcctcctc ccagccacgg tgcagccatt   14220
ccatctgaga ggcatgagct ccaccttctc ccagcgcagc cgtgacatct ttgactgcct   14280 ggaggggcg gccagacggg ctccatcctc tgtggcccac accagcatga gtgacaacgg    14340
aggcttcaag cggcccctag cgccctcagg ccggtctcca gtggaaggcc tgggcagggc   14400
ccatcggagc cctgcctcac caagggtgcc tccggtcccc gactacgtgg cacacccga    14460 gcgctggacc aagtacagcc tggaagatgt gaccgaggtc agcgagcaga gcaatcaggc   14520
caccgccctg gccttcctgg gctcccagag cctggctgcc cccactgact gcgtgtcctc   14580
cttcaaccag gatccctcca gctgtgggga ggggaggtc atcttcacca aaccagtccg    14640
aggggtcgaa gccagacacg agaggaagag ggtcctgggg aagtgggag agccaggcag    14700 gggcggcctt gggaatcctg ccacagacag gggcgagggc cctgtggagc tggcccatct   14760
```

```
ggccgggccc gggagcccag aggctgagga gtggggcagc caccatggag gcctgcagga    14820
ggtggaggca ctgtcagggt ctgtccacag tgggtctgtg ccaggtctcc cgccggtgga    14880
aactgttggc ttccatggca gcaggaagcg gagtcgagac cacttccgga acaagagcag    14940
cagccccgag gacccaggtg ctgaggtctg agagggagat ggcccagcct gaccccactg    15000
gccactgcca tcctgctgcc ttcccagtgg ggctggtcag ggggcagcct ggccactgcc    15060
tagctggaat gggaggaagc ctgcaggtgg caccggtggc cctggctgca gttctgggca    15120
gcatcctccc aagcagagac cttgctgaag ctcctgggt gtggggtgtg ggctggaagc     15180
actggctccc tggtagggac aataaaggtt ttgggtcttt ctgagacttt gtgtctatct    15240
gggccctgct tacccaaagg ctcagttgg cagcaagagc tccccacacc tgaccctcgg     15300
tgccggacca ctcgagggtg gctgacacct gcatccctca ccagcacatc acccaggtga    15360
cagtgagaat tggaaacccc aggcctcctc tagggcttgt ggctcagtgg caggtgtcca    15420
gtgagtgccc tcaatgggcc tgagtgggta cagaatctgc cctcccccaa ccaaagccca    15480
catgatgcca tcagccccag gcctagtgca gaccacagct tgggaagcga aagggagatg    15540

<210> SEQ ID NO 13
<211> LENGTH: 25760
<212> TYPE: DNA
<213> ORGANISM: Homo sapiens

<400> SEQUENCE: 13
gatcacgata gccaagaaat agactcacac atgaggacag ctagtttgac aaaggtgcaa      60
agtcagttta atagagaaat tgtatctttt caaccaatga tgctggaaca attggatatc     120
cacctgcaaa aagacaaaat aactttgacc aattcctcaa gctgtattca aattcattaa     180
tgtaaaatga attagtaacc taatataaat gtaaaactgt gaaactgtta gatgaaaaca     240
tggtggaaaa tctttgtgac cttagattag tcacagaaag gatatgacgg caaaggcaca     300
attcataaaa gaaaggtggc taaatggaat gtcatcaaaa tttaaaaatt ccactctttt     360
gaaaggcagt cataagagaa taagaaagc aagccatcag ctgataggaa atattcacaa      420
atcatattac gatgaaggac ttatatccag aatattcatt gcatattctc tgtgtatttt     480
caaaaatgaa tagtaagaaa acaaccctat aaaaatgagc aaaaaagata tacagatatc     540
tcctacacac ttgaccaaag aagatatatg gataataaat aaggtcatga aaacatgctc     600
aacatcatta atcattagga aaatgaaaat taaaaatcgt aatgagatat cgctacacac     660
ctattagaat ggttaaattt tcttgcttta aaactgatca taccaacttt tggcaaaggt     720
aggagaaact gtaattctca tgcactgtga gtgggaagat taatggtaca accccttaaa    780
aaaatgattt ggtagattct taaaaggtga aacacacacc ggccggccat atgatccatc     840
cattccactc ctaggtattt attcaagaaa aatgaaagca tttgtctcca caaagacttg     900
ttcatgaatg tttatagcat tggatcatag atagcccaaa ccagaaacaa tccaagtgac    960
gcctaacaag tgaaggtata agcaaatata cccattcatg ttatttatca ataaaaataa    1020
atgaacgatt gatacctgca acaatatcaa tgaatctcaa ataagtata tggcatgaga    1080 taagccagac aaaagaatac atcctgtatg tgtccattga cataacaccg tagaatgcaa    1140
agaatacctg atagaaggcg gatcagtggt tacctaaggc tggggaggag gggtgggagg    1200
aagggattac acagttgtaa tttaattacg aatttaaaac ttacaagaaa ttgttgacgg    1260
tgatgatggt ctcactgttg tacacatatg tcaaaattca taaaactctg cattttggcc    1320
cagtgtggta gctcacgcct gtaatcccag cactttggga ggctgaggca ggtggatcac    1380
```

```
ctgaggtcag gggttccaga cctgcctggc aacgtggtg aaacctcatc tctattaaaa      1440
atacaaaaaa cttagccggg cgtggtggca cgcacctata gtcccagcta ctcaggaggc      1500
tgaggcagga taattgcttg aaccctagat gcagaggttg cattgagccg agattgcacc      1560
actgcactct agcctgggca acagagagag acctatctaa aaaaaaaaaa aaaaaaaaaa      1620
aaaaaaaaaa acaaaaaaaa acctctatat tttaaatatg tgtagtttat tgtatgtcag      1680
ttagcccccca ataaacctat aacttcccag gggaaatggc tgagattgat gccaccttca     1740
aagagttaaa gaaggcctag gtagtaaccc ccaccatctc tctcgtgatt tccctctct       1800
ggcctctctg cagactggct gaatcagaat agatgattgc agacctcaaa ctcaaccaag      1860
tagcaacacc aaatgggctg ccaggccaga tgtggtatct tcgtttaatc ttagattaaa      1920
ttagattcat ttaatctaag attaaattaa cactgcccct ggtacccggt atcagtagct      1980
acggattctg tgaatgaatt ctcttccatc tcatcaggag agagtgtgag aagcaatttg      2040
cattcgcaca ggagggacaa cagtacacag tcacagtttt gccccaggga tatgttaatt      2100
cttctgctct ttgtcacagt atagtccaaa gggaaaaggc cctctggaca ttccacagat      2160
tatcacgtta gttcactata ctgatggcag tctgttaact ggatctgacg agcaagcagg      2220
ggaaagtact ctggacgccc caagtaaggc acacgagcca ggctgggaga taaattccac      2280
gaagctttag aggcctgcta catcatgatc ttattaccat gaagttattg ccataaaatc      2340
tggcaaatcc catggtacaa gaggtatttg caatggagaa agacaccaca cacacagagc      2400
ccctggagaa cttcaaagaa gagtcatggc ccagactcct tgggctctgg aagaaggccg      2460
tgcagagaac gataccattc agaaagaggt tcctgctctc ctgtgggaac ctctagagaa      2520
agagtttctg gtcatggacg ttaagtgacc atgtggtcag agatgcccat cttgagctag      2580
gatctgttaa acccaccaaa tcagaaggtc aggcaagccc agcagcatcc agtatacatg      2640
ggaaaagaca cctcctggga ctgcgaacaa gcagagggca aaagaaagcg acataatccg      2700
gggatcggaa cccccacgtc atctaccagt gttgcactga cacctcttct tcagtccaca      2760
cctgtggcct cctgcagagg tccctctgac cagccgatgg agaaggaagg ggcctgagct      2820
tcactcattg gcaggttagc tagaaacgtt agtgagcccc caaaggactg ctcctgcact      2880
gcagcccact caggtggtgg tgatggtggc gatggggtaa ccctcccagg gggccgagct      2940
ttgagtgcag gacctggtcg tgcacttgta gggagagaag cgaaccaaat cagtggttct      3000
atttctagca gttttaggct ctacagggcc attcccagag cgggacgctt ccaccggaag      3060
acgctattaa gacagcttcc acctggtcac ttcgggctcc tggtatcaac aatctggcag      3120
agagaatgaa gttcccatac tggcaggggt aactggctgg gagcatcatg agaaggtatg      3180
aatacagtca tcaatggggg cgggcaggtg acccaccagg ggcatctctt ggtgctgcca      3240
tgcacagatc ttcccgcaag tagcaagcgc cacagtgtga gcatgataag gccatggtga      3300
ccacaggctg ctcaaggtcc cggctatctg acacggatgg aggaggaagg ggcggtggct      3360
atcagtcagg gccccaggca atgaaaatgg caatggcaat ggcaggagta ggcactggcg      3420
ttcatcccac tcagcctgtt agtgtcaatt tcccctggtt ttgggaccaa tttgatcctg      3480
gagaagctct cctcagggga gcaaacctcc tacacaggtg ggctgtgcgg ggggtggggg      3540
tggagtaagg cgtgttgggt catgggtgct actggtgtcc tccccaactc cttttatctg      3600
gaccgtgtgc ctatccccca gctgttaagt gttgacaact aatggctcaa tgaagagctc      3660
tttagctaaa gggaagcccc acatcccgga cgtgtgtgcc ctgggggaca cacagcaaat      3720
gactgacaag gaggaacaga aggcagcctc ttgcttccag tcctgggaga ccatgctgaa      3780
```

```
gccctgcctc ctggcttatc tgtatctcct gcacaagaat tccagcccag gctctgtttc   3840
tagggagtgt gccctgagat gccagcgctt gagcttcgag agcacgaggg ggtaggttct   3900
ggtggacagg gacccggtg tgacgacaac tgcaaggttc accttggacc ctggcactat    3960
cctcccacca ggctggaaaa ggagaccagg acatggcccc agcacagccc ccaggtgggc   4020
aaaccggcag gctgggctgg ctaagctctt ggtgttcttt gtgtggggt aggtggggct    4080 ggtgagggcg ggactggctg caggtccttc agcgggtccc tgctggacct ccgtggcggg   4140
gacagggatg aaattaaaac agacccgact ccattcaatc tcagcgatcc atgactcagt   4200
gatgcccgga gctgcctccc tttctcctcc ctgggctccc accccgccgc gccccacccc   4260
attatgatcc cccccaaaat gcagagagcc cactagaggg aggaggctga gggctccagg   4320
ctgccctggt cagacaacac atcatgttcc ttcacctgca gatagaccct gagcccatca   4380
gtgaaacaag gggcccccag gagaatcaga atcctgaccc catcccaccc tccacaccag   4440
ctcaacggac tcccaggctg ccagaaaggc ctcatacgtc aaagtcagcc tcccagtcgg   4500
cctccgtttc caggtgtggg cctggagtgc cgtggcccag gtggtatcag aagctcgcag   4560
ggataggcct aagaggtgac cccaggggag gccaggcca aggagctgca gagagggctg    4620
gggaagctcc agatccccca cctccttcaa aacacacctg aaacaccagc cagcaccagc   4680
accaccaaga tgagaaaggg ccctggaccg tctccaccag tgtcatgcag cagctgggct   4740
ggtcccctcc cttgggtccc catctgcccc acttgtacag gagctaacga cgcctgctgc   4800
ccacccagga ggacctagca ggagcccagt gtgaaggtgt ttgcaaaact ctggggaaag   4860
tgaaggtcag aggtgactcc cagcttccac ttaggacata gagagctgga aagagcccgg   4920
ctcccatcct taaactgcag cagcaacaaa aggcaccaag caacctgaaa agtcaggact   4980
tttctcaaaa ctctctgaga gctgaggtca cagggcaacc aactaaccca aaacaaaggg   5040
aaggcaggcg cctgcaggag gagacgggat gcaggctgtc accgagacag acgaggccag   5100
acaccaggaa gaagaacaca gccaaaatgt ttaatgagtt ggcaagggtc ggtgtggggt   5160
aatgggagag cacagaagcc ccaggggctg cggagtgaag ggaaatccac atccactgga   5220
aggtccccgt ggatttcacg ggatgctctc tttgtggtgt aggcccagca gaggggaaca   5280
gcagccactg tcccaaaggt acaaaaccta cataggttat tctcctcaat ggaacaaaac   5340
ccttagattg ctggaggaaa ggcaaaaaag gcaaaaaaca ctgtcacact tagggcacga   5400
gtagaaacca tcgaaactgg gggaatccta aaagccctgt gccctgggga gggataagct   5460
acatggtggg cccagagcta cagctgagcg tagggcagga gtcccaagaa tgcttcaccc   5520
acaagaccca aaggacatag ggttaatcag aaaaaaccga acagccccc acctccagca    5580 cctgctgaca agcaccatgt aacaagtgac cctggagtgg gagaggccgc agagtgtggc   5640
ctgggagagt ctgcggagtg tggaaaccct ctccaaggta agcttatagc cgaaggctgg   5700
ttggacactg ggaaaagcct ctctatggta aacacaaagt agtgctggag ggatttgatg   5760
actgtggtgc tccagagata accatgacaa ccaaactg aaaccagct caactctgga     5820 cgagattagc cccaagcccc gcagtaaagg aacagcaaaa agaagggtat gcccatttcc   5880
aaaagcacaa aacgaatttc ttcagtctct actgtcctct gcacgatgtc tggatttcaa   5940
aaaattgatg aggcctatta aaaaataaa taaataggcc agggtctgtg gctcacgcct    6000
gtaatcccag cactttggga ggccgaggca ggtggatcac gagttcaaga gatcgagacc   6060
atcctggcca atatggtgaa accccatctc tactaaaaat acaaaaatta gccgggtgtg   6120
gtggcacacg cctgtagtcc cagctacttg ggaggctgag gcaggagaat cgcttgaacc   6180
```

| | |
|---|---|
| cgggagacag aggttgcagt gagccgagat cgcgccactg cgctccagcc tgggcaacaa | 6240 |
| gtgagactcc gtctcgaaaa ataaataaat aaataaataa taaataatag atgaatagat | 6300 |
| aacgtgctat caagacaaag caagcaaaat aatcagactg aaaggctggt ctcagtggct | 6360 |
| cacacctgga atcccagcac tttgggagac tgaggtggga ggatcgcttg agcccaagag | 6420 |
| tttgagacca gcctgggcaa cacagagaga cctacctcta caaaaaataa aaataaaaaa | 6480 |
| atcaactgtg catggtggtg cccacctgtg gttccagcta ctcgggaggc tgaagcagga | 6540 |
| gaatcacttg agcccaggag gtcaagcctg cagtgagtta agattgtact tctctactcc | 6600 |
| ggcccggggc agcagagtga ggccttgtct caaaataata atgataaaaa aagaaacaga | 6660 |
| ctcagatatg acacagccgt cggaactgtc agacaggaca ttttaaatac aataaatatg | 6720 |
| ctaaagactc taaggaccct aatggagaag ggggaaaata tgcaagctca gataggtcac | 6780 |
| ttcagcaaag agatggaaac tagaagaaga aatcaaatgg aaaagctaaa ataaaaaaca | 6840 |
| gtaacagcca tgagaagaag cctctggtgg gctcatgaat gtactagaca cagcaggaca | 6900 |
| gggtccgtga acttgaacac agttcagtaa aaaataccta aaatgcagag gaaaaaatat | 6960 |
| tgaaaagggg gaaaagatgc cccaaatctt tccaagaagt gtgggacata ttaagtgatc | 7020 |
| taacatatgt gtgaatggaa atctcagaaa gaaagatag aaaacacagt gaaaagaca | 7080 |
| gagttgaaga ataatgggt aagaatttta taaaatcatt gacaaacaat aagccacatg | 7140 |
| gccaagttca gagaatacca agcaagataa gtaccacatt ttttttttt ttttgagaca | 7200 |
| tagtttcgct cttgtcgccc aggctggagt gcaatggtgt gatctcggct cactgcaacc | 7260 |
| tctgcctcct gggtccaagt gattctcctg cctcagcctc ccaagtagct gggattacag | 7320 |
| gtgcctgcta ccaggcccgg agtagagaca gagtttcacc atgttggcca ggctggtctg | 7380 |
| gaacccctga cctcaggtga tccacccacc tcagcctccc aaaggctggg attacaggtg | 7440 |
| tgagccactg tgcccggccg gtaagtacca ttttttaaaa actgaaggca tatcacattt | 7500 |
| aaactgctga aaacccaaga caaaagcgaa atcttgaaa gcaaccagag aatacaggta | 7560 |
| cattccatag agacacaaga aaaacagaaa tatggtagca gacttctaaa cttctcgtca | 7620 |
| gaaacaaagt cagccaggga tgaaagaaaa acaacaacaa aaaaactgtt gattcagaat | 7680 |
| tctatatccg gtacaaatat cttttcagaaa aaaggagaa ataaagtctt tctcagacaa | 7740 |
| acaaaaactg tagaatttgt tactgaaaga ccttcactat aagaaatgtt aaaggaagtt | 7800 |
| cttcaggcaa aaacatgata ccagacagag acttggatct acacaaagaa gcaaagtgca | 7860 |
| ctagaaatgg aataaatgaa agtacaaata gaatttcttt cttt ctcatt tttaattgct | 7920 |
| ctaaagata actgactaaa gaaaaaattg tggtcacgta ttatatgtct atagtataat | 7980 |
| gtaaaataga atgtatgaca ataatagcac aaacagtggg aggaaggaat tgagaatatg | 8040 |
| cagttgtaaa tttattatat aacacacaga gcaaggtaat atcatttggt agacaatgat | 8100 |
| tatttaaaga tgtatattat aaaacctaag acaactatta atttaaaaaa taagatataa | 8160 |
| atgataagcc aatagtggaa actaaatgga atcataaaaa gtactcagtt aatccaaaag | 8220 |
| aaggcagaaa agggagtggg gggacaacag acggaataaa tagaaaagag ttagcaagat | 8280 |
| ggtaaattaa atccaagcat atggccagaa gcagtggctc gggcatgtaa tcccaacatt | 8340 |
| ttaggaggct aaggtgggag gattccttaa gcccaggagt tcagaggcta taatgagcta | 8400 |
| tgatcatacc accgcactcc agcctgggca acagaatgag atcccatctc taaaaaaga | 8460 |
| aaacactcc aaatacataa ataaataatt atattaatct caacacacca atgaaaagag | 8520 |
| atgatcaatt tgaataaaca aaagacccaa ctatatgcta tctatatgaa acccacttta | 8580 |

```
aatataaaga cataaataag gttaaagtaa aaggatggaa aatatgtgac acagaagcat   8640
gcgtcaaaat aaagatgcag cagctacatt catctcagac aaagtaggct tcagaacaag   8700
gactattaca agggataagt gagacctcac ataacaataa aggagttgca ttttctgaga   8760
aaacaatcct cagtgtgtag gcacctacca acaaaggctg aaaacacaga aagcaaaaaa   8820
tgataaaata aaatgtaaca ctcattcatg attttttaaaa aactgtcaac aaacaaggaa   8880
tgtaagagaa ctgaacctaa taaaaggcga agctgaaata caaaaaaaaa aaaaaaaaaa   8940
gctaacatac taaatggtga aaggctgagt acccctaaga ttgtaaagaa ggtatgatat   9000
cccctctcac acttcttttt tttttttttt gagagtctcg ctctgtcgcc caggctggag   9060
tgcagtggcg cgatctcggc tcactgcaag ctccgcctcc tgggttcacg ccattctcct   9120
gcctcagcct cccaagtagc tgggactaca ggcgcccacc accacgcctg gctaattttt   9180
tttgtatttt tttagtagag acggggtttc accatgttag ccaggatggt cttgatctcc   9240
tgacctcatg atctgcccgc ctcggccttc caaagtgccg ggattacagg cgtgagccac   9300
tgcacccggg cccctctcac acttctattc catattttac aggaaggcct agccaagata   9360
ttaaggcaag aaaagaaag aaatggtata caaatttgaa aggcagaaat aaaactaagt    9420
caattcacaa tgacatgaat gttgcataga aaattcccca aacaactaga gaaaactcct   9480
caaatgaaca ggagagttga gcaagatctc agtataaagt caatatacaa aagtgagttg   9540
tattaatatt tctgtttgct agcaacaaac aattagaatt ttacattttc aaaatagatc   9600
cacttataat aatgctcccc atatgaaaaa cttgggcaca gatgtaacaa aaaaagtatt   9660
ctgatctaaa cgaacagaaa aatatactat gttcatggat tagatgagtc aatattatta   9720
agatgtcagt tctccccacg ttgatctaga tattcataca tcccaataat tttcccagca   9780
gaatgttttg tagatgttga caagttgatt caaaaattca tatggaaatt aaaatgctct   9840
aggatagtca aaataattta ggaaaattat tttctggtca ctatctgatt tcactgatat   9900
gttactatat atttactatt tactacctga tttgactata aagctatagc aatcaagaca   9960
ctgaggtatt ggtgaaggcg tagactcagc tcagtgggat tgaatagaga gcccagaagt  10020
ggatccatat aaatatagtc aagtcaattt tggcaaagat gcaaagggaa atcagtagag  10080
aaagggcagc cttatcaaca aacggaactg gatctattgg atgtccatat gcaaaaaatg  10140
aacctggaca cacatatatc acaccttaca caaaaattaa ctctaaatga atcatagacc  10200
ttaacgtaaa atatacaact ataaaacttc tagaagaaaa cagagaaaat ctttgtgcct  10260
ataggaaagc cagggtcttc agcctcggta ctgttgccat ttggggatgt agctcctgtg  10320
tgggggctgg tctgtgcacc agggaggttt agcagcggtg tgctccagtt gtgacaacta  10380
acaatgtccc cagacactgc ccaatgtcct ctgggggcaa aacaggcctg aattgagaag  10440
agaaagttct cagctgtgac gtggaagcat aacccataac aggaaaaaaa aaagttaata  10500
cacgggactt tgttaaatgt aaaacttttc ttctgtaaat ggccatgtta agatattgaa  10560
aagacaaacc acaggctggg aaaaaatatt tgcaattaca ttatcagatg cagaatttgt  10620
attcagaata cacaaagaac tcgaaactca acaatcagaa aacaaacagc ccaattaaaa  10680
aaatcggcaa agggcttgac agacatgtca ccaaagaagg gaggcagatg gcaaagaagc  10740
cccaaaagat gtgccacagg gttcgtttca gggaaatgca aaccgcaaga gacctgtgtg  10800
ctcctgcgtg ctcccgtgtg ctcctgctta ctcctgtgtg ctcccgtgtg ctcctgtgta  10860
ctcctgctgc gaagggtaaa atgaagcaaa acagcgaaaa ctcacagcac acaacctagt  10920
gccagcgagg atggggagca agtgggcctc acgccctgct gcagagtgca ctatggcaca  10980
```

```
gccoctgtgt gtgcctgggg ggcctgtggg tgacagggggg acaaagaaga ggttggcaga    11040
gatggcagag cagcctcctg gtgctggact tcctcaccca gccaggatgg cctgggcctg    11100
caccagtgct gcctgagaca gcgagtctca acctgctcca ggggcgtgtg cgtttctgcg    11160
tgtgtgtgtg tgtgtgtgtc catgcatgtg tctctatgaa tatatgtgct gtatttgcat    11220
gtgtgtgtgt gtctatgtgt gcatatgtct gtgtctgtgt gtctttctgt gtgtgcggtc    11280
tgtgtctgtg ggtctacacg tgtatatgtg catgtgtctg tgtgtgtcgc agtgtgttac    11340
tgtgtctgcg cgtgtgtgca tgcatatgtg caggagggag ggagggctca ggccttagca    11400
gagtccctgg ggctctggga gtggagggca gtgaggctga ggctggtgca aaggtggttt    11460
caggcgctca ggtgaagtgg agcagaaaca gaagttggaa tccagcccca gcgggcgggc    11520
ggcagcagca gtgccggccc tgcccagaac aggttcgacc tgagccggca ctgcccggct    11580 gccctgggc tagggaggct gagacagaga agggaagcca gagggtgggg gtggggggccc    11640 ggcactggca gagctgcctg ccctcaacga ccgcccctgc cggagacccc cgccccaccc    11700
gctgtggttc tgctggccca ggtttcgctg ggcccactcc cagggtttgg catcactgga    11760
gcccagggtc ccccccgcac cctccccaca gccttggccc tgctgctgcc tgcctcctcc    11820
agggtacccc gaggcccacg tcaggagacc cgcctcaggc agcagtggcc cggtggctgc    11880
ttctgcctag cccgcagcac gtgccaccct gggcgcactg ccttcccgaa ggctctcctc    11940
cctccccggg gcgctccctc ccactctgga atgcctccct gcctgcacag caggagtgtt    12000
tggctgaggt ctgcagcccc gacacaggtc acctcccacg cctatggggg cttcagaaag    12060
tcccggaatc ggccgggcgc cctggctcat gcctgtaatc ccagcacttt gggaggccga    12120
ggcgggcgga tgatgaggtg aggagatcga gaccatcctg gctaacacag tgaaaccccg    12180
tctctactaa aaatacaaaa aattagccgg gcgcggtggc gggcgcctgt agtcccagct    12240
actcgggagg ctgaggcagg agaatggcgt gaacccggga ggcggagctt gcagtgagcc    12300
gagatcgcgc cactgcactc cagcctggga gacagagtga gactccgtct caaaaaaaaa    12360
aaaaaaaaaa aaaagaaagt cccagaatcc cagacatcta acaggatggg gtcccagaga    12420
ccctccaccc acccatctcc ctgacttcca cacaggcagg gatgaaggac tgagggagag    12480
tgggagaggg taactgtggc ggtcacgaag ggtcctcagg tccccgtcct tatcccaagc    12540
cccatccagg ccagaaccgc ggagtgggtg tgcagagcac tcaggcagcc tgtgaatccc    12600
cacagccact tccctaccct gagacctcag agaatgacct ggcctctgtc tttctgtttc    12660
attttattta tttttatctc cagcttgttt gtgaagttca ggggtaccag tgcaggatgt    12720
gcaggatcct tgtcacaagc atccttctca cgaccctgcc tcactccaaa aggggtatca    12780
ggtaggtgag cagaaacgcc ccttcctgaa tgcctgtcct tgtcccacca caaggatgag    12840
gatgcctgct cagagggcac agggagaagc caatggcata gggtgcacag cagcgagggc    12900
caagggacaa ggagtggggg gcccccacct gcccagcgtg acctgctgac cacagctcct    12960
cagcggcggg acaaagcctg cccatggggc cctcagtggc caccctggat gcaaacacgg    13020
ttaatggtca ggcccagcct gtccctcct gcgcacaaac tcaggcaga gcagagagct    13080 tacatccacc aagacccaga caaagaaag ccccaagaac acccttaaag gcagccaaac    13140
cctggagctg cctcggccc atcgatggga gcacaagagg tgaatcctgc tacgggcacc    13200
gtggccgtct acgcgaccgc agcaaagagg aacatggacg actcacagac gcagagacgg    13260
ggggtccatg ctgtgtggtg atgttcacct gcagctcagg gacaaccct acctacggtg    13320 acagatgtca ggagggtga aggtgaggg agggagggcc tgttagctgg agcgggtctc    13380
```

```
agggatgcct gctgctgctg ctggaaacat tctgcacagg ggttcgggtg gaggttctgg   13440
gagtgtcacc cgtgcacact tgtcagcatg ctctccaggt cctgcatttg aggtgcctgt   13500
accccagtgg aaagatgacg gacagagctg ctcaaccact gccctggacc gcattctgca   13560
gggtgcctta gaaggcccag gaggaaaggg gactccaggc tgggcaccgg tggtccacag   13620
gcttccagag cagcccagct tggccgttgt gtcccagtca ctgggagcta acgaggacgc   13680
accctcatgg gggtatgtgc ccacccagtc ccctccgtag agagcctggg agcctctgtg   13740
atagggcgtc ctggcccagg gctcccaagg ccaagtatga agtctcattc ccccagacaa   13800
ccttcacctc caggctgcat aacctctact gaccccctctc aatcccacct cttcttttg   13860 tccatgaagg cagtcgggaa atgcagcctg tgcttcggag aggcgggcag ggctggggtc   13920 accccgccc caggcagtgg gataggagat gcgccagggt caggtccctt gctgcaagcc   13980
tgcaacccgt gcctgtatgt gccagccggg cctgccaatc catccttcac cctgcaggac   14040
cctcccgtct acaggtccca gctctgtgtg ggcctggcca gccctggggc catggctgag   14100
acctgagtcc tcaaaggact gccccttctg agagcagaat cctgctgccc ccagaagacc   14160
aggtgttcaa cctgagccct gatcctaaaa cccatggtcc tctctctcct ccagaatccc   14220
tctgccagcc tccaagagcc gcctgctgct ctcctggtgc ttctcacacc cctggggat   14280 ggcagggggg cggggagccc agcagaaatt ggagcagaga ggacatggag ggctgagggg   14340
tgagggggca gaccgaatgt atcctctctg cccatgcgtc ttcccccagg atgctacctg   14400
aggtctcggg agaggggcat ctgggaaggc ttcctggagg aagatgagtg cctctctctc   14460
atgagggagg ggctccaggg aggtcagtgt gaacttgtgt tggcacaaag gcagccctgg   14520
ccgagggggc gaaggcagtg tgaagtggga ctcacttccc ccaaagatgc agagggatgt   14580
cgggagacct ggcaggcggc cctgggcagt tcagttgacc ccaccttacc ctaccaggct   14640
gcaggaagcc cctgccccca cctggagccg ctacgggttt tcctagctca gccctaaagg   14700
ctcagcccga ctagatacag gccaactaga gaggtcatgt cagggctgag ggggtggctg   14760
ccaggggtgg ctgctgtggg gaagagcatc ccagcccgca ggccctgcta ccccaggcag   14820
agctgcccgt tgtgtcccgc acgaagagct ttccctgcct gggaatcccg ctctgccccc   14880
caccagccag tggctttgga agttcgtcca gcaaccctgg agtctcagtt tccatgcctg   14940
taatatgggc acagcactca ctccaggatg aacagaagcc gggccaggaa agcagtccct   15000
ggcctggcac cacagcaggg gctgtgaggg ggatggttcc acagttgctg gaggtcgaca   15060
gggaccgaag cacacatgag tgccagatgg gccccacgat gggattccgg cgagggtggt   15120
gcagggagcc acctatacag aggacaattg actgcagaag tgccaggctc atgccctcca   15180
cggatggaga ggccgtcacc tccgggggat gcccagggc cgcatacccg tgcagtggcg   15240
ctggagtggc agtgggcgcc tgccccacac taatgcacac acacatcagt gcacacccac   15300
agccacgcca gagaaagcca caggccctga ggggctgccc catgccagcc tgccagctgc   15360
cacacccctc ccacaaagcc tggctctggc ccgggacaca gggagcccag acccatccag   15420
ctttcccctc aatgccccgg gtcctcccac aaattcatcc tgcctcaagc ctcagtctcc   15480
acttccgaca aatgggtctc aagctctctg ctctgtccac cctgcatggc ggtgtgggca   15540
gcacagagcc agcctggtgg gggctgggga ctctggaagg ggtgctcagg gaggggccgg   15600
gctctggggc ccagaaggcc ttggaaggta gtccaggcgg gtcccggaac aagtgttgca   15660
tgagcaccaa atggctcaga gctcccgaaa cctggcgtgc ctgtgagagc cgttgagacc   15720
ccttttcaag gccctgcctg acagcccaca aaagacattc aaatgagaga caaatatttg   15780
```

```
gggcccaag gttgagccca gcccagcctc tcaggcccag cccaagctgc tcccaggctc  15840
tcatttgggt attaattgca tttcgtttag agatttgcat gcttatcacg cgggtggtgg  15900
ccagccgtgg gggcctggcc agcctggaca gaatcccaag gctcgtaggc aaatgccagg  15960 aggaggggt gggcagagga cccaggagcc tcccgaatgg tatcaggaga gcaagcctgg  16020
gctaggctgc gggccatcag cgtgggccct gggccacgac ctggcatcca tgtggacctg  16080
agcacgacaa caggacaagc agagaaaaaa gtggatccca aaaacagggc tcccaggcca  16140
acttctccct aacaccagct cccagcaccc caccggggac tgcagcccct ccatggtcaa  16200
tcagggtagc cctggggtcc ctgtcacatg acgtatgccc accctccgac agccctgcag  16260
cctgtgggac ggcccgtgtg ctcgccgagg cgcttggaac cttggagggc aggctctcag  16320
aagattggct cagggaccct ctggtccacc ctctcggcat cccagggtgt cctggtccca  16380
ggagatgcct catcccaggc cacacggggc cctaggcctt tccgtcctca gccctgtcta  16440
ctctaccctc tacaagagag gtccagaagg ggcagtgctt gacccaagaa gaagaggctg  16500
taactatgga gaggttggga gggggaagtg gccctaaggg ctggagtttt agaaagccct  16560
cttgttcctg cccattatgg gttggatttt atgccctcca gactcacatg tggctgtttt  16620
tggagccagg gcctttaaag aggtaattaa gttaaagtga ggtcattggg gggaccctaa  16680
tcccatgtga ccgatatcct tagtaagagg aggtgaagac acagacacgc acagagggat  16740
ggccacgtga agacacaggg agaaggcagc gtctacaagc caaggagaga ggccttcgga  16800 ggtgggggc ctgcggaatg tgtgagagact aatttctgct gtgtaggccc cctagtgtgc  16860
ggggcttttt cacgcagcac aggccaaccc attgcagcct ctcctgctgt taggaccca  16920 agtccatcct cagggacatt aattaacata ggaactttt atcctgatgg tgtcacctcc  16980
taggcagaac agggacccgg aggcaggcct agctgcgaac cccagccct ccctgtcctt  17040 ctcgcaggac agcgggtctg gggctgaagg ctgtgacgct gccctgcct ggatcacaac  17100 aggcaggacg gctgagcagg cacacatctg tctctccctc tgctgatctg tggccttgga  17160
caggggctac tctgggggag ctgacaggtg acccccccag gaggcccctc cctgcctctg  17220
ggctgggaat ccacctctgt ggagcccctg ggaatggcct gtttcaaata cgtaagtggg  17280
agcaaggtct catcctcagc gggggacatc gctgggggca aggccagtgg gtgggtggga  17340
aggtttctgt ggcactgggg cctcctgttg attgattcac ccaattaatc acagccagca  17400
gctggggagg gggtaggaag gcggtgaagg gaaaaggagc ccacagccgg gaggccctgg  17460
gaggttggca gaggcctgca cctgcctgca gccagccctc cggcccagcc ctcttccctc  17520
ctttcggagg ggccagagca tggggtgcta agggctcagt cttttaacccc tcccagctc  17580 tcagggagcc cctcccatgc tccccaggcc tctgcccac ttgcacctcc ccgggcccca  17640
gggcacagga cgctttcccc acccttgggg aggctgaggg tgtcaggagg cctgggctga  17700
gtgctggctt ccgtctcact ggcttgcaga caagaccctc catttcggtg gaaaaacagc  17760
aagaacagca ccccctcca ggcagaccca agggaggcat cggtgtgagg gcttcaagct  17820
ctgtactgtg ggtttaagcc ttgcacctct ggatacctgt gggcctcggg cagatcactg  17880 agcctcctg catctggaag tcggggtgag acccctcaga gggggctggg aggaggaagg  17940
gcccctcttg atgggcagcc cccacccctcc acctactgcc ctgccctccc agccttcagg  18000
gtcctcccca gcttctgtgg gctcccaggt ggacctgggc caccctgag accccgaaga  18060 gctcaaggcc agctaatagc ccacaggctc aggacagcac tggacaggcc tctgggccca  18120
cctggcccca ctcccgattt ttatgggaac aaagactgaa ggtgtggccc caaaggaacc  18180
```

```
accccteccc cagtgcccg ctgctgggaa aagggtcagc agagtttggg tctccccca    18240
caagcctct gggctgtgcg tgctacagct gaggacatgg cgttgagggg caggccgcct    18300
ccaaccccgt ccaccttgcc ctgtctagct ctgtccaagg ctctctccgg ctggctaatc    18360
acctctgggc acagctgtgc tgctgaggtc tctgggatga ctgaaggtct ttgaaggcca    18420
ctttgggaga agcgaaggtg catggacacc agggaccctg ctcacagcga gtgtccctgc    18480
cccatccctt tctgcattga gtgggacaag cttgcttcca tttggggat cgccatctga    18540
ctattccact tgtcttaggg tggggcagag attaggtgat gtggagggc ttctctacat    18600
ggcccccctg ccccagctct gaggggtagc accagagtgg gtttcaccag cgtagggcac    18660
gtaggccccg ccatgaacag ggccccaacc ttggtttaat gctttgctac tgccatctta    18720
aagttctttt tttattttt attttgcttt attttttatt agagatgggg tctcccagtg    18780
ttgcccaggc tggtcttgaa ctcctggctc aagcaatcct ccggcctcag cctcccaaag    18840
cactgggatg acacgtgtga gccaccttgc ctggcctttg gaatctgact acttttatct    18900
tctaacttgt tttgcaggtg caggccaacg gcatacagca gcactcacat aagcaaagga    18960
gagcgtgcac aaggcgccaa atgtatatcc accctcactc gtcccccac ttgagtagcg    19020
catccacgat gcccacagac accaggccac acagaaaagg tgccagggac ccacagcagt    19080
gcaaggcagc gtgtcacacc tacgcatgag caagccgggc gctgatgcc accgagcagc    19140
cacgttttcc attcaaatcc gcacttgcta aggatgcagc aggaagccag tggtgttcta    19200
acaaacgtgc aggaccggg aacctgtcat gtcctttctt acttgtgcga cttctctgtg    19260
ttagccgagg tctcttgctg atggatctac ccacagtgcc ttttgtcttt gaacttgtcc    19320
cttcctcct tcctcgccca tcagcgagca ggaggtggag ggtgctggtg aacaagcct    19380
gcgtcaagga gtgaaatcag ctgatttcat ttttgtgcag tttccactgt tctagtagca    19440
aatgaaatag agacgcctgt gccaggacaa aacacact gtgtcattcc agtgattccg    19500
catagaagtt aaatgctctt atgcttgcat tttaaactgg catcacataa tataaagatg    19560
gataactaca ttcacgctag tcacttaaat tcctaatctt tcttactcag aatggcatta    19620
aatagtgagt ataaaataag aagtataaaa tagtaagtca agaggttgac tatagaagaa    19680
agaaaaatgc tttatatttt agcaccttga acatgacatc acgatcacct tctccctgga    19740
atcagtttct aacttccagg tggggactag gcctggacca tgagctccta gcagagccct    19800
gctgccccca cagcagagcc caggacaggc tggcacctgg gccaggtgag gctctgtcca    19860
ggctcactga tctcaaatgc tgaactgcta aggatgtcat gtccccaaag gagccgccag    19920
gctcagcctc acttcctgga aggcgtgaac attgcaagaa tgtggaagtg aaagagtcca    19980
gggcttaaat ctcaattctc atcattttca agctgagtcc aagggagaga agacagtcat    20040
ggattcttag tttctgtttc tggttgagcc agcagggtcc cttcctcatc cctcttttct    20100
gcttatcact agagacagaa actaaaacca tgactttagg ctgctgagag cctaaaacaa    20160
aacgacagca agagaaggtg ggttggacca gcttgcctgt gacttcaggc acttcatctt    20220
tactgggcac tgggtgaatg acagtgtggg gaggggtctt cataacacgg caatcagcag    20280
cccactgtgc ccaggagact cgcctgtggt cctggttatc aaccacagcc ctttccagtc    20340
tcaaaaatgt ccccgctggg acagcaagtt acatcgtcgc tacaagtcct gtctcctggg    20400
agatgcagtc cagcagcact acatcctctg agcagcaggt gccaagtggg atgaactgga    20460
taaggactgc attcggggaa acgcccgtgt gaaggaaat acacaggaag gaggtggcaa    20520
cgggtgggaa gccactagac cacgacgcga ttctgcccca gtgaaggcga ggggatagcc    20580
```

```
tgggcctaga tcgctgtgag gtctatggaa gtttccacaa gcttgctggg tagttctcga   20640
ggcaaactcg gaaagggagt cccttgtctc cctggaacgg atctttcttg gcatctctgt   20700
cacactcatt aggtgggcct ggtgtcaacc ccatttgcag gccacccaa acttgatcaa    20760 aggtccgctt ctggcacccc atacctgtc ctacaggaaa tacagggaca ggctcccaat    20820
aacaacaccc agcacggtgc catcaacacc accacgcaca cggggctca acggaacaga    20880 catctccgct tcttcaatga agacactgga gggaaattgc ttacaaggcg cttaagagac   20940
ctattaagca aacttgatgt gtggacctgc ggcggatccc gattctataa ggccaactgc   21000
acaaaaccac gagacccct gaggactgcg ccattggctg gtccccgat gatatgaaag    21060 aacggtggtt catttgagcg ggtgatgttt ttgcggtttc ctttagaggc acacgtgaaa   21120
catgacgggt gaaaggattc aaagtctggg atttgcttca agcaacgca gggatggcgt    21180 gggggatgga tggggcagga agggccttga aactggtgct ggaggcttcc cagggctgcc   21240
ctggagccca gtgcgtcctc caccggccag actgtacaac ggttggatcc tgtgtccact   21300
gctaggaccc aggctccacg agcacgggct tgtgtggcac acggatgcac cctaagtcct   21360
ggcacagaga ctgctcaaca aaggcctcgg tgcttttgtg tatgtttgaa attttccata   21420
ataaaatgaa aaatgggaaa atgggaaaac aaaaatggca gcactactta ccctctgcag   21480
agttttgtcc gcttcacgcc agtgggtggc agtcgtttcc tctgccctgg ccttccatcg   21540
tttcccccct accctcttca cccacccaac agcccctgt ggtcctggca gctgtgggcc    21600
tttccttgag gtcaaggtgt ggagtcctgg ggagggctca gggaggccac cgacccgggt   21660
gtggattctg ggagaagcct gtgggatgtc cctccctggg tgaccacggc aatgtgcccc   21720
ctcctgtccc ttggccaagg ccagttccct gagccctgca gccccaagcc acagctggtc   21780
cactgacccc agttgagcct ggtcctcatc agaccagctg accccttga ccccgctac     21840 agactcggct ttgaccttgg ctgctgagga gcccccacct ggactgaggc tgcagctggc   21900
gagagaggag ccctgagctc ctctgataag aagggacctg gccagcctga cgtttgagac   21960
ccaggcatcc cggtagcctg ggtgtcctgt tgccgtggtt attcaggagc cacccactct   22020
gggacaacac cagctgctcc cacctcgcag ggctcccacg gctctgtccc aaccactcct   22080
ttctgaagga aggggtgcct ctgcgcccta agaaaccgg gggagcccca caacccctcc    22140
cccaccagga cactaaaagg cagctttcgg tacagtgaga catcaaagcc tcctaggccc   22200
tgagtcaaag gtatagccgt gtaatatccc agtgccagct ctccggctgc ggggagcctg   22260
gcgcaaagct tccaagcctt ccttgttcct ttcaagagcc gctcttagaa ttcaggtgag   22320
cggagacctg cagggcctcc ccagtgcggg caaaacccaa agctagcgag agggcagcct   22380
ccaggcacct ctcactaact cctcccagag gccgttgagg tgggtctggt caaacccatt   22440
tgcaagttaa cccacttgcc ctgggctgcc cagctgccac gttagtggag atctgagcgt   22500
ggtggcctgc gcaggagccc atgccctcag ccccacagcc ggtgctctct ggtcagacca   22560
cctcagccta gccccacacc cagcacttac cccagccctc gggatgggtc agcagcctcc   22620
agcctgcagc ttccaagcca gcgagtagcc ctgtctggac aacccaccag cccaccacct   22680
cctggaggat gccccagcc tcacaaggtg tcccaatggc tccgctatca acggcctggc    22740
tgcactccag atctcaccca gacccaccct acggaggagg cagcagggtt tgaggagtag   22800
tgaccacgga agtctggccg tcacctggga agtgtaggtg ataggagcca ctggtaaaca   22860
gaactgattt atttataaag ttcacgctcc cttgaagagg tgtgccccac acaggcttct   22920
ccctagcaga gcagcagtgc ccacaaaccc accccagggt gggctgtcac gggggcctca   22980
```

```
cgccagggac cccgcccctc agggactgct cgtgtccaga tcttggccag catggaaaac   23040
tccagatagt gggggcaggg gtccaggtca tctttattac gccccaggtc aagggttctt   23100
tgtacaaaaa taggtctccg tttgccagca gtgtccctcc agcagctcaa gttaatgtgt   23160
agaaaatgga ttctctgtgc ccttagaaaa tcctctcccc tccggaaaaa tctccaagtg   23220
ttggtgcccc ccgccccact gcagtcgaga agctgtgggg aggggcggcg tcggaggaag   23280
ccgccagccc ttatggggcc agctccaagc ccgtttccac cgcggcattg gtcaggctgg   23340
gccggacgaa cgaggcggcg tcggcggtgc gggggggtggt gggtgggtcc ccggctcgct   23400
gggggcggag cgcgggccgg tccacctggc gggctccccg gcgatgagcg cgccggccgc   23460
tcgctcggct tccggggctg aggctgcggg gggaaggtgg ggaaccaaac gcgcgtcaac   23520
gcgggcgcgg gcccggggca gaccccgccc gggccggccc tgcccgcacc tcccccaagc   23580
gaactcggca gtttcgtttg ctcggttggt tttggagtct tgagtccgtg ggtgccgcga   23640
ctcggtctga gacacggcgg gggcggggcg ggcgctcgga gccgcggtga gtcagggctc   23700
cgcgcccgcc gactcatttc tgccgccccg gcccgggagc gcgatttgca atgcaaagtc   23760
accccgcctc cagcacccca atctgcccca ggatccgcca gcactagaga cctcaacggc   23820
ccgacggccg ctcccctccc ctcgtctacc cctccctcgt cggcggctga gccgcgaggg   23880
gaagttttgc aatcccggac aaacaaacgc cggtcttgca cgggcttgaa aaactttggg   23940
ggaaatgaag agtgagcgaa atcgaagcca tcgctcgggc ctggcgctcg gctccgcggg   24000
ctcctggggg cgcgacccgc cgggcctgcc caccccgtcc ctccacccct gccccccggcc   24060 ctccctcctc cctgcctccc ggctgttacc tcataggtcg agggcgctca gtagccccct   24120
aaccagctgg agaagtcgag tagctcgcgc tccgcaggac tcagcgcgcc ttcgcagccg   24180
ctgtcgtccg acgagtaggc ggaacgcggg gagccgggct ccgagctgcc cccgcggccc   24240
ggggacgaag aagcgcggga gggcgaggcg cgaccggggg tggtccctgg cggcccgcgg   24300
ggcgcagacg gccgcacggc ctgcggcctc agccctcccg ccagcgcgtt gcgcacggcg   24360
tcgtgctcgg ccagcaggcg ctgcagcgcg cggatgtact ccacggctga gcgcagcgtc   24420
tccaccttgc tcagcttctt gctggcgccg ccgtgcggca cgtgctgccg cagcgcctgg   24480
aagcccaagt tcaccagctt cacgcggttg cgctcgcgct cattgcgccg cgctacggcc   24540
gctgcgccgc ctccggtctc tgcggtgcc ggtcgccgcc gccggctgca gcgcaacagt   24600
tccggggacg cgggtctccg ccgggcagcg cagccgacag ggacgggggg cgcagggggc   24660
gcggacctgg gcagtgtgcc gccgtccatc gcgcctgcat ccacccgccc gctccaggtc   24720
ccggcgcgcc gcaggaaggt gcaggcagag gaaccggagg cgacggggaa aactgtggcg   24780
ccccaagggg gcttctggca cggcgccgcc aggcaactcc ccagggcacg cgtcctaggt   24840
cgtctggagc ccggggatag gaggcctagt ggtggcaggc cgtacgcgcc agggagcgtg   24900
ggacgctcgt gtcccgcgcg tgcggccgga ctctcccagg tctccgcagg cgcggcgcag   24960
gcggctggtt tttaaatgta tagataaccc tcctccgcgc cgccgccgtc gcctttctca   25020
cgccctcctt ccttcgcctc gccctcccgc cacgcttcgc cctcccccctc gcgcgatcac   25080 attctgtaag gccaaagcg tgcgcatgtc cccctagccc atccccgga cgcagtccac   25140 agatcccag tgcgcccaac tggcgaaatc tgcgagttcc cggtgcgccc cctgctcccg   25200
gcaggtgctt agtgcgcccc caaagcaagg tacgcaggtc ctgggttgag ccttcccgta   25260
cccccaccct aaccccgcgc gcagcccgc cagtcccaag agccgccaga ccttcgcacg   25320
cgcagcgcgc gctgtgggag ggaaggcgcg gccctggcga caacacggct gttcgggagg   25380
```

| | |
|---|---|
| cgcgcaagat cccCggggc agcacgcgcc gcgcagccca cacccacgcc ccaccctcct | 25440 |
| ggggccgagg aggcggggc cagggtctca gccaatcgtg ggccaccgt ttggccaatc | 25500 |
| gcgcagggcg cggctccacg cccggcccca ttgaggaagc gcgtacgcgt ggcgcgtggc | 25560 |
| tcacggggag catcgctaac aaagctgggt tcctgctggg ccccgccctg ctcctcgccc | 25620 |
| ccgcgactgg gctgggcgcg ctgtcccta gcgcagctat gtcccgagcg cgcccccacc | 25680 |
| tgtgcgttaa tctactggga atggggtgg actgcgcctt acctggggcg gggtgggct | 25740 |
| taaggagtgg tcgagactga | 25760 |

<210> SEQ ID NO 14
<211> LENGTH: 38360
<212> TYPE: DNA
<213> ORGANISM: Homo sapiens

<400> SEQUENCE: 14

| | |
|---|---|
| tgtgcaaggg accttcagag gaggaaaggg aggaaacagg tcaacctctc acggcaggca | 60 |
| aggcaagaca ccccctggtt tgaggggtc ttctgcaaat ttcagggagt tgaacctcat | 120 |
| acaaacctcc ggtagtaaga aaatattca gagttctcct ttcccttctt ctcgggggaa | 180 |
| gaaagaggct aagctccact ccgcttgtcc cttccctagg ggaaggggaa ggagaaggga | 240 |
| gaatagcagc ataagcgact ggcagaggca gggaaagacc ggcagaaagg aaagagaaac | 300 |
| tgggagagga agtcagagag agagagagac aaagagggag tcaaagagag agaaagagag | 360 |
| agacagagag tcagagagag agaaagagag agacagagac aaagagggag ttagagagag | 420 |
| aaaagagag acagagagta agagagagag agtcagagag agagaaagag aagtagtaaa | 480 |
| gagaaaacag tgtaccctat tcctttaaaa gccagggtaa atttaaaacc tataattgat | 540 |
| cattgaagat cttctctgtg accctagaac actccaatac tgcctgtaaa aagcaagac | 600 |
| gagtcacacc agtgactgca agaccctaga gctattaacc agttagtcca aactacccac | 660 |
| cctgttgtta cagtaataga tgtaaaagat gccttctggg cttgtccatt tgcagaggac | 720 |
| agccaggacc tatatgcctt tgagtgagaa gaccctcact ccggtggaaa atggtaatac | 780 |
| caatagacgg tcttacccca agggtttacg gagtctccaa atttatttgg tcaaatattc | 840 |
| aaataagtca tttaattagc aaaggtaaac agaaaattga gcttgaatgg attgaaggca | 900 |
| tcacattctt gcctctgctg gagactaaat aagagcttag aaaattttgg gattagttgt | 960 |
| atggataccg tcgtctatgg gtagactcat gccctaaaaa caaaactctt acacaaaaag | 1020 |
| ctcacacgag acagaccaaa cccctcatg tggcaattac cagaaatcca acaggtggga | 1080 |
| aggttaaaac atctattagt aactgcccct gtcctagctt tactctcctt aagcagccat | 1140 |
| tccaccttgt tggtggtgta acaacggcg tagcccaaaa acactgaggc cactgacaac | 1200 |
| ccatagcctt cctaatcaaa aatccttaac ccagtaaccc gcggatggtc caaatgcatt | 1260 |
| caatctgtag cagcaacttc tttgctgaca gaagaaagta gaaaaataac tttgagaaga | 1320 |
| aacctcattg tgagcacacc tcaccaggtc agaactatcc taagtcaaaa aaaaaaaaaa | 1380 |
| aaaagaaaa gcaaaaaggt agcttactaa ctcaaaaaat ttaaatatg aagcgattct | 1440 |
| gtcagaaaaa gatgatttaa cattaaccac tgatcattcc cttaacccag caggtttgct | 1500 |
| aacagggat ctaactctta atgaattacc atacaaaggt ccaaccagac ctagaaggaa | 1560 |
| ctcccttcaa gacaggacaa tagatggttc ctcccaggtg aatgagggaa aaagccacaa | 1620 |
| tgggtattca ttaagtaatg gggaaatagg agtagagtta ggaaaattgc ctaggagttg | 1680 |
| gggagttgtt tgcactgagc caagccttaa gatactgaca gaatcaggaa ggagtcattg | 1740 |

-continued

```
tgaaaagtga agtagagttt acctcctcaa aagactttcc tcccccatct aatcaggaat    1800
aaatagtaac ttctcttagt agcaaaatgt attcaaagac cagcgctaac attcttaaat    1860
atctgctaga cgtaataaag aaatcaatgt actttatgtc cttagctccc acaatttagt    1920
ctaaatgttt gctctggcat gcttatactg gtccaggcaa gcattaggtc ctatcctgtt    1980
cctcttcctt gtttgtgtct cacatgtccg tgtgaaaaga ccaccaaaca ggctttgtgt    2040
gagcaacaag gctgtgtatt tcacctgggt gcaggcgggc tgagtccgaa aagagagtca    2100
gcaaagggtg gtggattatc attagttcct acaggttttg gggtaggcgg ttgggttagg    2160
agcaatgttt tgccagcagg gggtggatct cgcagagtac attctcaagg gtggggagaa    2220
ttacaacgaa ccttcttaag ggttggggag attacagagt acattgatca gttagggtgg    2280
ggcagaaaca gatcacaatg gtggaatgtc atcagttaag gctattttca cttcttttgt    2340
ggatctttgg ttgcttcggg ccatctggat gtatacgtgc aggtcacagg ggatatgatg    2400
gtttagcttg ggcccagagg cctgacagtt tgaaggtgtt tttacctttc tcagcattcc    2460
acgagttact tcttcctttg ttctcctctg cctttgcctc ttttaaaaag ttctaagttg    2520
ctagccagtc gggacaaatg cagaatgtca ggcctctgag cccaagctaa gccatcgcat    2580
cccctgtgac ttgcacgtat atacgcccag atggcctgaa gtaactgaag aatcacaaaa    2640
gaagtgaata tgccctgccc caccttacct gatgacattc caccacaaaa gaagtgtaaa    2700
tggccggtcc ttgccttaag tgatgacatt accttgtgaa atcccttctc ctggctcatc    2760
ctggctcaaa aatctccccc actgagcacc ttgcgacccc ccactctgct cgccagagaa    2820
caactccact ttgactgtaa ttttccttta tctacccaaa tcctataaaa cggccccacc    2880
cttatctccc ttcgctgact gtcttttcgg actcagcccg cctgcaccca ggtgaaataa    2940
acagccgcgt tgctcacaca aagcctgttt ggtggtctct tcacacggac gcgcgtgaaa    3000
cagaatgtga ggtcccgttc cagccaatgg aaaccagaca cagcagtagg gtggacgcgt    3060
caggttataa atgaccctgt ctcctttgct cagtgtactc tcgtggcaaa actgctgccg    3120
agtgtaccct ttctacagaa agtataaaaa tgaccttgcg taggaaatta aatttatgtt    3180
caagtgccat ttcttatgg caccggggag caagcatttc aaacatcatt tgtaccaatt    3240
ctaagttaaa tttggactaa acaaggtctt attaatagca aaggataatt gaaatcccaa    3300
acttacaagg ttttcaacaa agtaaagtt tgctaaaagt taacagtata acatgtatta    3360
tcctaacttc taatgttgtg accttaggct gtctagtcca cagacataaa ggaagttcgc    3420
tttggaaaag aatggttatc atctttgaga gaaaaaaaat tgtttcgaag gtttaagcaa    3480
gttttgaaat attcattgta aaggaaacat attggctaaa gttaaagggg tatcttccag    3540
tttttctgtg aactggacat taaaataaaa gcccagtggg ttttcttaa agcgctaacc    3600
tgctctttaa caaaaattac gaaaggttaa aaattataaa agtttaaaaa aagagtctgg    3660
aaatctcacc ttgtggtcag accttaaaat tggatacata tgtctacaag gttttattaa    3720
aatgaagttt aacacgaata acacactaat gtaaaggtga aatttagctg atctggtata    3780
aaatcacaca ggaagcactg tcaaatataa aatggtgttt ggctttcttt ggtctaaaaa    3840
ctaataaaaa taggtactaa aggaaatttc tcagcaagaa ggcactaagg actataaaat    3900
ccactgctga tgtccccacc tttaaaacaa aagatcaatt tttagaaatg atatacttgg    3960
tttatcctcc acccttaaaa caaaaggtct tctagcacag gccctgccct gagagtttcc    4020
agtacatcag caccagcctg gggatcccgt tctcatcaaa gggtgaaaag aagggaaact    4080
ggagccagcc tgggaaggac cctgccttgt gctgctgact accgagattg ctattcgtac    4140
```

```
aacggaaagg gggtggacac gtcccaccag agtcaagcaa gcaccattat caacagaatc    4200
atgggccatt gtttctggat caagccctac caaattaaag ctaaggaaag ctgagtctat    4260
ctctttcctt tccttttccta acccagtgcc tatatccatg actattccta ccactagcaa    4320 ctctaaccccc actttagaga gtttctgtgg tttgggagca gaggtcactg gaagggatcc   4380
tataggcttc aaggtgcgct tgttctccc tcctccacct cctacgactg ccccttccc      4440 aaacctacaa catcaaacta tgcctcgcct catgccaaat gacacaagca agttcttaga    4500
agtagaaata ggagacccaa ggcaaaccct agccattgaa agagggtata aagacataaa    4560
tgccggttaa aacggattaa atatcccgtt cgcactttaa gcaaaagtga ccattaagct    4620
tgtgggcgcg gtaggccaga ggctcaggat gcctcctttc cactgggacg gtcctcaaat    4680
caagcggaca tggagtgcgt ggtagctctt ttcgaagatt ccaccacctg gaataacgaa    4740
ttgtgccaag ctcttttctct gctatttcct gaagttcagt gccctgtggg tcagcccccg   4800
agggccatcc agccttcatc ttccaaaacc aattttacct cgtgtctcca acaacgaggg    4860
gaaaaaactt ggcattcctt ggagacttaa aaggttgcag taaagtcagg cacctccaaa    4920
agctgaccca tcggtctgcc cttattcatc cctgagcgga tgtatggtgg tattatggag    4980
gacctttact ggacactctg ccaaataatg agagcagtac tgatgctgta gttcagttgg    5040 ctatccctttt tactctggca tttcatcaac cagaaaaaga aaaaaaatg tagcctcaat    5100 tcttacctct ttaacaacgc taataagtat actctttctt cgtaggtgtt atgtcgtacc    5160
atacatccag gagttcatca aaacaactaa gccaagacat gctaagaaag tttgaagagg    5220
aaaactatac agtaaaagag gagggaattg taggaagtaa aaagtttctg cttcaaagtt    5280 cccccttcttg ttaaagaata aatcataagt cttagaaata atagattctt ttaaagacta   5340
attttcttca agcctccttg ctttgtgcta atagctcttt gttaagccct atcctatgta    5400
actgttggac atgctcacag acacattcca gctcacagcc tatgccccctt ccttaattgg   5460 aaatgttatt gcttcctgaa acctttttgta agcaacttct ttgttcttcc ttgcacttac   5520
ctatttagga aagtttcaaa tcgggtatca gtttaagata gtgaggtccc actccagcca   5580
atggatgcag gacacagcag taaggacaac ccaaatgcgt aagggataaa tacatctgct    5640
tttcctttgt tcaggtgtgc tctcaccatt gttccatctg cagttgagca cccttttctgc  5700 agaaagtaaa gatggccttg ctgagagatc ttttgtctct gtgctgactc ttcttcgcag    5760
caccgattat ctattctaa caattttggt atttctaaca ggcccacaca cactgtgtgg    5820
gccaagctgc ttcactcagt ccactgatca aatgctcatc tcatcctcac agacacaccc    5880
aggatactgc ttgaccaaat atctggacaa cccatggccc agtcaagtcg acagaccaaa    5940
tgaactgtca cagacagctt ctgtccttgg aacggggtgg gattccacgg actctctccc    6000
ttcacagtgg agatgctcag tcagcaagct gccagaagtt cagagctggg gaagatataa    6060
agaggactgg gcatggaagc tgcaggaact agtcaggaac tgggagtacc taggagtcag    6120
ctcctgagtg tgcaggatca tggtgaaata gaaagttaga gaaggaagag tgtgtcaata    6180
tcagagcatt gtcttatagc acaggactta accctctcct aaggttccag ggagacagtg    6240
ccaaatcatc acttgagtgg tgcttagaag cttcagggca aaagagccaa ccctaagtac    6300
atttgtctac tggggctgcc atcacaaagc accgcagaca gggtggctta taacagac     6360 tcattgtctc acaatcctgg cggctggagt ccaagatcaa ggttttgcaa ggctagctcc    6420
tcctgaggcc tctcttggct tgtagatgac cggggccttc tctctgtgtc ctcacagggt    6480
cttccctcag tgcgtgtccg tgtcctcacc tcctcttgta agactccagt cctatgagat    6540
```

-continued

```
taggacccac tgtcatgaac tcatttactg ttgattacct ttgttttatg ttttttgttt   6600
ttttgagaca gggtcagtct ctgtcaccca ggctggagtg cagtggtgca atcatggctc   6660
actgcagcct caaactcctg ggctcaagga atcctcccac ctcaatctcc caagtagctg   6720
ggactacaga tgcataccac tgtgcctggg tgtattagtc tgttattgca cagctataaa   6780
gaaatacctg agagtgggta acttataaag aaaggaggtt taattggctc acggttcata   6840
gctgcttctg gggaggcctc aggaaagttt cagtcatggt ggaaggtgaa ggggaagcag   6900
acacgtctta cacggccaga cagttcctcc tacactggct gacactctct cctgccacct   6960
tgtgaagaag gtgcctgctt ccttttctgc catgactgta agtttcctga ggcctcccca   7020
gccatgtggg actgtgagtc aattaaacct cctttgttta taaattgccc agtctccggt   7080
agtatcttta taacagtgtg aggatgagct aatacacaca ggaagcagca atgccatcaa   7140
agagccaggg gccttgactg gcagaactag tgagaccatc accaaaacat ggcattcctt   7200
gggcaaggca ggtgcgcagc cagcaaggta ttgcttaatc tacatgatca aaagacatca   7260
ggatggttgt tcaggaggct gagaacagcc atcctattat ggctgagttg tgtcccctca   7320
aaatttatat actgaagtct taaccccca ggacctcagt gtgtaagtat ttggagaaag   7380
ggcctttaaa gatgtagtta aattaaaatg aagacattag ggtgggccct aatccaatct   7440
gactggtgtc cttgtaagaa gaggagatga ggacacatgc agaggcatga ccacatgagg   7500
acacagggag aaggtggcca tctgcaaatc aaggagtgag gcctcgggag gaaccagcac   7560
taccaacacc ttgatctcgg acttccagtc tccagaacca tgagatgatg aaagtctgtg   7620
tttaagctgc ccagtctgtg atattgtttt gcaaccctaa tagatgaata catccccaa   7680 tgaaaaagca tgatctcttg cccagtttct gcacctgaga cagttttcaa acccaaaccc   7740
cactgattga aggagggatt aggtcccagg aggacggacc ctgcagtacc atagcaggct   7800
cccccagtcc ttccccaccc caccactaaa ggtgtatttc agtaactgtg cactaggaaa   7860
agggcaatgc ccagggctgg gggactccgg gaccaagttg acactgagag ctggagtcaa   7920
ggtaccatca tgggcccact agagtagggc gtatggaggc cagcaaagtg caatcctggt   7980
ccacctctag ctcacactga gtcatccctt tgcattccca gaatgctgca tattccccca   8040
gaccctaaaa gtacactcag acaatcttgg tagttggcag aatcctcacg taggctcatt   8100
gtcctgtagg gtaaaaacta tcatagtgtt accaagtaga aacttctgaa actgcccacc   8160
accttagcca aggcaataca ccaaaaagaa aatctcattg gtggggaatg gcagagatgt   8220
gggccccttt ggaagacttg aaggttgcag gtgaggcgat tcccatcatc tcccccattt   8280
tccagagaat gctaacagac tactgtcaac ttgtgatggg aaattttatg cgtccacttc   8340
actgggccat ggtgcccaga tgtttggtta acattattc tgggtgtgtc tgcaaggtgt   8400
ttctggatat gcttagcatt tgaatctgtg gactgagaaa agcaggtcac tctctctggt   8460
aaaggtgggc ctcatccaat cagttgaagg tctgactaaa acaaaaagat taagcaagag   8520
aaaattcgct ctccctgcct gtcttagtct gtttatgttg ctataaagga atattggagc   8580
ctgggtaatt gataaagaaa agaggtttat ttggctcatg gttctgcagg ctgtacaaga   8640
aacatgacat ctgcatctgc tgctggtgag ggcctcaggc tgcttccact cctgacagaa   8700
gatgaagggg agccagtgtg tgcagaggtc acatggtgag agaaacaagt gaacatggga   8760
ctgccaggtt gttttcaaca accagctgtc aggggaactc agagtgagaa ctcactcact   8820
accatgagga tggcaccaag ccatccatga gggatctgcc ctcacaaccc aaacacccca   8880
attagacacc acctccagca ctgaggacca aatttcaaca tgattgatag cccagctcaa   8940
```

```
agagccgctt gtctttgagc tgggatatca gtgttctgcc ttcacactca gattggaact    9000
tacaccatca gctctcctgg gtctccagct tgcagatggc agatggggat actttccaac    9060
ctccataatc acaggagcca attcccccta aaaagcccct gtgtatatgt acagctaatc    9120
ccaagctcca ctgagcagta gcccagtgga ttgttgctgt gccagctgtg ctatatttgc    9180
tggagcagag ggctgtggaa tggggtacat gttaagcacc cattagtggg tggatttgtt    9240
ctatgccatc cctatttaaa aagagccctg gacacctttt gggggacatc atcattctgc    9300
ccaccacccc gggacaggag gcacatgaat gaactcacag gtgtggccat gagaggtgaa    9360
gagcttggta tcacgtgttc attcccaaca gagagcatcc accagggagc cactaagcaa    9420
ccagttagac agaatggccg cagtccttga cttcagccag cctctgtccc cgaccacctg    9480
agtgctggcc ccctgggtgc atgcatggag cagctttggt ggtagaaagg gatgctgacc    9540
atgaaatcaa cagcacagct ccacccacca aggctggtct agccactgct gccacaaatg    9600
cccaacctgt ctgcaacatg ggctgctgag aagcccccac taggcactat ccatagagaa    9660
agttgacaag gcaacagaag catccatccc attgggggca gcaattcaac tccactagaa    9720
ttgacacata acccaggctg atccccaggc cttattaagt gttgatccac caaacagggc    9780
atgcgtagca gtgccttgga ccaagggacc cactttacaa cacagggagg aggtgcagcc    9840
atggcacatg gcacatggca catggccatg gcatctgctg gtcctatcac agcccacacc    9900
actcagacgc agccagcacc acagagcagg ggagcagcct tttcagagct ccatgaaggc    9960
cccagcgtgg gggtgatact gttcaaggat ggggtgtcac attgtggaac tcagtagtca   10020
ctccaactca acagccacca tggggtgcta tgtccccaac aggcctcgga accaaggggc   10080
agaagcagca gcggccccctg taccaccact gccagtgacc tgctgtgggt tttgtgcatg   10140
ctgttccctc cactctaggc tgccagtccg gggtcgtggt ttccacaggg gacaacgcca   10200
ccagtggaca gataggagac ccactgaaat ttaggctaca gccgatgcct tgtcactttg   10260
gattatttgt ccctggagac caacagtcat gacaacgagc ccccaaactg ggagggaggt   10320
gggccgtggc catcaggagg cagtagaact gctactccat gagggggacag gaaagaatac   10380 atttggtgcc tggtgatcca agtggtggga cttgggggac ttggtgttcc ctcaactgct   10440
ttattcatga gtggacaagt acaacagcca tggcctgagc agggatggtg accagggccc   10500
cagacccctc actgaggagg gtcccagttg gcccactggg taggccacag agactagaag   10560
aggtgcccac tgacagggaa ggaaccaaac atgagtcagg gaagaacaag ggtcatgaca   10620
gccatggcca agacgctatg gggcacaggc tgtagttggc tgtttctcta aacttgtaaa   10680
cccaggtatt agtcagcgtt ctccagaaa tcagaacccc aggatatata catcacagaca   10740 tatgagagga tttatgaggg gaatcggctc acatgattat gcaggctgag aagtctcatg   10800
acaggctgtc tgcaagctgg aaacctagag aagctggtgc ggggctcatt ccaagtccaa   10860
aggcctcaga accaggggag cggattgtgt aactctgagt ccgaggccaa aggcctgaaa   10920
actggtggtg gtggagtggc tactggtgtg agtcccagag cacaatggct ggagaacccg   10980
gagttccgat gtcacagtc aggagaagat gggttgccta gccctggaga aaggagaat   11040 tcgtcattcc ctgccttttt tctctctcta ggccctcaac ctattggatg gtgccaacca   11100
catcaagtga gggtagatct tccttattca gtccatggat tcaaataaca atctctttca   11160
aatctaccct cacagatacc cagaaataat gctttgcaag atgtgatggt taattttggg   11220
tgtcaacttt actagattaa gtgatacccca ggtatctgga aaagcattat ttctgggtgt   11280
gtctgtaata taggttggat gtcaccctct accccctacc caaatctcat gttgaattgt   11340
```

```
aatccttcat gctggaggtg gggcctggtg ggaggtgatt ggatcacgag gtggatcctt   11400
catagcttga tgatgtcctc atggcagtca taagatcagg ctgttttgaaa gtgtgtggca   11460 cctcccccac ctctctcttg ctcctgcttt tgccatgtga tgtgcctatt cccccttttgc  11520 cttccaccat gattggaagt ttcctgaggc gtccccagaa gcagatgctt ctatgcttcc   11580
tgtacagcct gcagaactgt gagccaatta aacctctttt cttataaatt atccagtctc   11640
ttttatctca ggtctttctt ttcttttctt ttcttttctt ttctttcttt tctttctctt   11700
ctctttctct ttctttcttt ttctttcttt ctgtctttct ttctttcaga cagatttccc   11760
tcagtctcct acagtgcagt ggcgcaatct cagctcactg caacctccac atcccaggtt   11820
caagccattt tgtgcctca gcctctcgag tagctgggat tacagtcatg caccactgtg    11880
cccagctaat tttgtgtttt tggtagacac agggtttctc catgctggcc aggcttgtct   11940
caaactcctg acctcaggtg atccacctgc cttggcccct caaagtgctg ggattatagc   12000
caccatgcct ggccccaggt attttttac aggagtgcaa gaatggccta atacagaaac    12060
ttggtaccag ggagaaagat atttctataa agatatctga aaatgtggaa gcaactttgc   12120
aactgggtta caggcagaag ttggaagatc ttgaaaggct cacaagaaga gaggaagatg   12180
aaggaaagtt tggaacctct tagagactgg ttaaatggct gtgaccaaaa tgctaatagt   12240 gatatgggaca gtgaaggaca ggctgatgaa gtctcagatg gaaatgagaa acttatttgg  12300
aactacagca aaagtcacat gtgttatgcc ttagcaaaca cttgactgca tcctgttcat   12360
gccttaggga tctgtggaag tttgagcttg agagtgatga ctcaaggtat ctggcagaag   12420
atatttctag gcagcaaagc attcaagatg tggcctggct gcttctaaca acctacacac   12480
agatgcggga gcaaagaaat gacctaaagt tggaatttac atttaaaagg aaagcagagt   12540
gtaaacattt aaaaaaattt gcagcctggt caagtggtag agaaagaaac agcttttttca 12600 ggaaataaat tcaagcacac tctggagcta ccgcttacta gagaaatttg cacaactgaa   12660
acagagccaa gtgctaatat ccaaagacaa tggggaaaag gcctcaaagg catttcagaa   12720
acttccaaag aagcccctcc catcacaagc tcagaggcct aggaggaaag aatggtttca   12780
tggaccaaac ccagggccca gtgccctgca cagccttggg acactgttcc ccacatctcg   12840
gccactctgg gttcagcctc agctaaaacg ggtccaggta caacttgggc tgccattaca   12900
gctccagaga gtgcaagcca taagccttgg cagcttccgt gtagtgttaa acctgcagcc   12960
acacagaatg taaaagtgaa ggaggcttag gagcctccac ctagatttca gaggatgtat   13020
ggaaaagcct gggtgcccag gaggaagcct gccacagggg cagttacctc acagagaacc   13080
tctactaagg cagtgcaggg ggggaatgtg gggctgagg ccccacacag agtctccagt    13140
ggggcacttc ctagtggacc catgggaagg aaggggggcca ctgtcctcca ggccccagga  13200
tggtagatcc actggaagct tgcactctgc acatagaaaa gcagcaggca ctcaacaacc   13260
tgtgacagca gccacaagag ctgcaccctg cagagataca ggggcagagt ggcccaaggc   13320
ctggggtggc acacccctcg caccagcatg ccctggaaat gggacatgga gtcaaaggag   13380
actaccctag agctttaaga tttaatgact gccctgctgg gttttggact tgtatgcagc   13440
ctgtagtccc tttctttttgg ccaatttctc ccttttggaa catgaatgtt tacccaatgc  13500
ccatatcccc aatgtatctc agaagtaaat aacttttta atttacagg cttgtagatg     13560 gaagggactt gccttgactc agttgagaca ttgaacttttt gagttaatgc tgaaatgagt  13620
gaagactttg gaggactatt aggaaggtat gattgtattc ggcaacagga gaaggatatg   13680
agatttggag gcccaggggc taaatgatat agtttggatg tccttttccaa acttcatgtt  13740
```

```
gaacagtaat ctccaatgtt ggaagtggag ccttggtggg aggtgattgg atcacagggg    13800
cagatcccac atggcttggt gatgtccttg atctggacac aagatctggc tgtttaaaag    13860
tgtgtggcac ctcccccccac ctctctcttg ctcatgcttt tgccatgtga catgcctgct   13920 cccccttttgc cttttgccat gattggaagc ttcctgaggc ctccccagaa gcagatgctg   13980
ctgtgcttcc tatacagcct gcagaaacat gagccaatta catctgtttt cttataaatt    14040
acccagttgc aggtctttcc taatagcagt gcaatgacag cctaatacag tctgtgaagg    14100
tgttctcaga agacatcggc acttgaatca gtggactgag tgtcttagtc catttgtgct    14160
gctataagaa aatgcctgaa actgggtact ttatagagaa gataaactta ttttctcaca    14220
gttctggagg ccgggaagtt caagatcaag gtgccagcaa gtatattgtc tggtgaggga    14280
ccctatctct gcgtccaaga tggtgtgttg tggcagcctt ctccagaggg aacgaatgct    14340
ggggtcctcg catggaggat agtggaagag caatacaggg tgaactgtcc ttgaagcctt    14400
tttgacaggg tagtaattca gttatgagga cagagcctgc ataacttaat cacttcccaa    14460
aagccctact tcttaatacc accacaatgg gattacattt caacatgaat ttctaggggg    14520
tatgttcaaa tcatagcatt ctactcctag tcccccaaaa tgtatgacct tatcacatta    14580
aaaatacata cattccatcc cagtaactcc aaaagtctta actcattcca gcatcaactt    14640
taaaatcaaa gtccaaagtc ttatttaaac atcgtctaca tcagatatga ttgacactct    14700
aggtaacatt catcttgagg caaattgctc tccagctgta aacctatgaa atcaaacaag    14760
ttacatgctt ccaaaatatc atggtaggac agacagggga tagatatttc cattgcaaaa    14820
gggaacacta ggaaagaaaa aagcgataat agatcccaag taaatccaaa atccaacaag    14880
gcaagcaaaa tcagatcttg aaacttgaca atgatctcct ttgactccct gtcatgcctt    14940
ccagataccc tagggtggga gttgggcccc caagtctcca ggtggtcctg cccccatggc    15000
tttgccggct gtggctccca agcatgacag tccctgcttt ttggctgtcc caggctggag    15060
ttgcacagca gtgtttctac tggcttgtgg ttgaggggc cctgacccca tggctctatt     15120
aggccatgcc tccatagcac gtgctctgtg tgtgcctgca gaagatgctg ccaaggcgta    15180
ttgcctgtgc ctctggaggg gcagcctgag ccacacctgg gcccatgtga gccatagctg    15240
aggcagctga ggagtgctac actgaatgc agggagcaga gacttgaggc agtactgggc     15300
atgaaggccc aaggtcccat aggtactcag ggaccctcca gagccctggg ttcctcccttt    15360 gactccattc tgccctcaaa gcaaatgcag ggagcagaga cttgaggcag tactgggcat    15420
gaaggcctaa ggtcctgtag gtacccaggg accgtccaga gccctgggtt cctcccttga    15480
ctcccttctg ccctcaaagc cctagaactc taagcctgtg atggccatgg cagcctggaa    15540
gagctttgag atgccgtcag ggcctttctt ccattgtctt aacggacagc acctgacttc    15600
cctctatcgc caggaatctt atcaaatggt ccctgggcca cacctttgt tttctctcct     15660 acacgcgtgg ccaagctgag actcttccaa accttttaagt tctgcttctc ttttgattat   15720
agattctgtc tttaactcat ttctctcttt cttgcatttt accatacaca gttgagagaa    15780
gccatgcagc tcccttagcg ttttgcttag agatttcttc ctctgaatat tctagttcat    15840
cactgttaaa ttctgcctcc cacaaagccc tcaggcacag acacaattca gcctagttcc    15900
ttaccacttt gtaacaggaa cggtctttcc tccagattcc aataagatat tccttgctgt    15960
gatctaacac ttcatcttta ctattcatat ttctaccagc attgggatca tgattactta    16020
aacatttctc ttttttttt agatggagcc ttgctctgtc gcccaggctg gagtgcagtg      16080
gtgggatctc ggctcactgc aagctccacc tcccgggttc acgccattct cctgcctcag    16140
```

```
cctcccgagt agctgggact accggcgccc gccaccacgc ccagctaatt ttttgtattt   16200
ttagtagaga cggggtttca ccgtgttagc caggataatc tctatctcct gaccttgtga   16260
tccgcccacg tcggcctccc aaagtgctgg gattacaggc gtgagccacc gcgcccggcc   16320
cacttaaaca ttcctaagaa gactgaggct ctgtctacag atctcctctt cttctaaacc   16380
tgcaccagaa ttgcctttaa tactctgttc atagccattt aggcttttc tgccatgcac    16440 tctgaaacac ttccagactc taccagcagt ttgaaatctg cttccacatt ttcaggtatt   16500
tataacatca acaccccact tatgtttagc aaattatgtc tccgtcccct tgtgcggcca   16560
taataaaata cctgtaactt ggtcatttct acaacagatt tattatgtca cagtacggga   16620
ggctggaaaa agtgcaagat caggacactg gctgttttgg tgtctggtga gggtcccagt   16680
ctcttcttca agatgaagac ttgttgctgc ctctcctgaa ggggacaaat gctgtgtcac   16740
cacactgtgg atagtggaag agcaatacaa ggtgaactgt ctctgaagcc ttttttataa   16800
gagcgttggt ccattcatga ggactgagcc ctcatgactt aatcacttct caaaaaacgc   16860
taccgcttaa taccaccaca gcggggatta agtttaaata taatgtttgg aggccaggtg   16920
cagtggctca tgcctgtaat cccagcactt gggaggggtg aggcgggcag atcgcttgag   16980
gtcatcagtt caagaccagc ctggccaaca tggagaaact ctatctctac aaaatacaaa   17040
aattaactgg gcgtggtggt gcgtgcacac ctatggtccc agctactcgg gaggttgagg   17100
catggcttaa agccaggagg ttgcagtgag ctgagatcgc gccactgcac tccagcctgg   17160
gcaacagact gagactctgt ctcaaaaaaa aaaaaaaaa acttggagaa ggcaaattca   17220
aagcacgaca gtagagaagg tccatcctcg cccaacgtga gtgggcactg tccaatcagc   17280
agtgggccca gataaggaaa aaaggtagaa gaaaggcgaa ctctccctct ctgcctctcc   17340
ccactctccc ttctgcagct gggacaccca tcttctcttg cctttggata tcagaactcc   17400
agattcttca gccttcgcac tctgagactt gtaccagtgg cctccgggtc tcaggccttc   17460
agctgcagac tgagagttac ccaactggct ttcctgattg acgcttagac tgtaccacat   17520
aaatggcttc cctggtcccc agcttgcaga tggcctattg tgggaatttt cagcctctgt   17580
aatcattgta atcatatgag cccattccca taataaatcc cttctcatgt atctatgtat   17640
ctatacctgt atcaatccta tttctttctt tttttttttt ttgagacaga gtcttgctct   17700
gtcacccagg ctggagtgca gtggcgtgtt ctcagctcaa tgcaacctcc gcctcccagg   17760
ttcaggcgat tctcctgcct cagcctcccg agtagctggg actacaggca cccgccacca   17820
cgcccagcta ttttttgtat ttttagtaga cggggtttt catcatgttg gccaggatag   17880
tctccatctc ttggcctcgt gattcacccg cctcggcctc ccagagtgct gggattacag   17940
gcgtaagcca gcacacctgg cctcgatgct atttctatcc tatcggttct gtttacctga   18000
agaaccctaa cataggtttt ggtatcagga tgattctaga gaaacagaat cataagaatg   18060
agttttctga atgtgtattg tgtttttcgg aattggtttt ctaatatgac ttgacttaaa   18120
agtgagaaga actctacttc caacagtaca caggacactg atggtccatg gtgtgaatag   18180
tttatgaaaa tatgcaaatt tctgcattgt atactcctag taaaccactt acaagaggca   18240
aggagcttag tgactctgta tatgatattt tcgaacattt gtggaaaacc agggaatata   18300
gtgacgtggg ctggttacca gttggttgct ggacaaagtg atgaaatcac aggatgtgct   18360
cagtgattca aattcccagt tccagctctg tataaataac ctgtgagtgg ctgagtgaac   18420
cctgaaggag aacctccttt cctgtagccc tgggccaag actgctgaaa agcaaccaca    18480
agtcctcgtc ctgaaactgg atgaattaca acgcaagttg aactctcagc cttgcgggt    18540
```

```
gtccactgtt ccagtgaggg cattggctgg gaaacagagg atcctgtaag ttgggatgaa   18600
gacatatgga aggaccctga tgaagctggg gacggtcagc ctctaagtta ggatgagtca   18660
ttttgtcagc agaagcagcc tccctgcacc cagtggcagt gctacaccca cccccagtgc   18720
tacacccctc ccccagtggt actggccttt ccaccttctc tgaggcatta atctgtgttg   18780
cctgaggaaa gggtaaggac ttcccctaag gcagttgctg attctcctcg ggtccctccc   18840
ccaacccttc cctttgcttt aagacctata acaagactca cagcccagca ggcccctgaa   18900
ggtgaggccc acagtgtgac acaggaggag gcgagccaca ccccagaaga gccactcgac   18960
ctctctgatt tatacagaca gacacctggg agcatgagtg ggaacggacg ttgggtgtag   19020
ggcactgggg gaggaacatg gaggtggagg gaccaggtgt gcaggcatgt ccaccaagta   19080
gagcctgaat tccaggctgc aactcaggga cttggaaaag ctctaactgg ctggtcggtt   19140
gaaacatgga tcaaaggatg cctgcagtga gcgagctgga gatgcctaaa ctcccttggc   19200
ttaacataga ggaagggggtt caaaggctca ttcccaaagg agatcagaat gtgacaatga   19260
aaacctcctc acctaccctg ggagggccca aaacgcagac cttttcacaac agggatcccc   19320 aaccccccgg gccatggact ggtactggtc catggcctgt taggaactgg gccacacagc   19380
aggaggtgag cggtgggtga gtgagtgaaa tccgtattta tagccactcc ccatcacttg   19440
catgaccacc tgagcttggc ctcctgtcag atcagcagca gcatcagatt tcatagggag   19500
tgcaaaccct actgtgaact gcacatacga aggatctagg ctgcaacgct ccttatgaga   19560
atctaatgcc tgatgatgtg tggctgtctc ccatcctccc cagatgggac tgtctagttg   19620
caggaaatcg agcgcaggcc tcccactgat tctacatgat ggcgagttgt ataattattt   19680
ccttacatat tacaatgtaa taataataca gataaagtga acaataaatg taatgtgttt   19740
gaatcatccc aaaaccatcc tccaactccg ggtctgtgga aaaatattct gccatgaaac   19800
tagtccctca tgccaaaaag gttgaggact gctgtctcac aacactgaaa tatagacttg   19860
tgagggagcc cagtctcctt gaagagctct gagattgttc ttctctgtag gccagactca   19920
ctgtgggaac tgcagtcaat caactgagaa acttacatgt gatgggaata attggatcct   19980
ggggtagcag tggccaagtg ggggcattca agcaccaaag gcaaagttgg catggttacc   20040
atgatagaca gcagaggcaa agtagcagtc agacctgagt tacaggtcca acccatgtag   20100
acctatggca ctggctggtt accatgtttt tcctagcagt gaaacagatg ggaagcctgc   20160
tcaattccta ctggatacaa gcagaaaact tacagatcaa gtggacaaaa ctctaagtcc   20220
aatcataaaa acagagaatc atggcctcag tctttcacag acttgagcca gtctatgaac   20280
ccagaaagag tgaaagaaag gctgggtacc cttgaggaag gaccccagga tggccaaaaa   20340
tgtatatata ctgttaattc tttccctggt cttctccaaa ggggtctatg gccttctatc   20400
tgtgtaactg tgtattggaa aaaagaaaat aatgtggcat ttcaggacga ttggacactg   20460
gctctgtcct gacattgatt ttaggagatg ctggaacgac actgtggccc tccagttagg   20520 gagggggctta gggagccagg tgatcaatgg agttttagct caggtctgac tctgtgggtc   20580
cagcgggtac ccagcccatc ctgtggtcat cttcccagct ccagatgtgt aagtggaaca   20640
gacacactca gcagccagca gagtccccac atgcgtcccg tgacctggtg tgtgaaggct   20700
actgtggtgg gaaaggccaa gtggaagcca ttagagaggt ctctacctag aaccgtcagt   20760
caaaagccat cccacatccc tggagggact gcagacatca gtgccaccac caaggacttg   20820
agaggtgcag gggcggcgat ccccaccaca gcccattctc cccacctatt cggcccacag   20880
gggagacagg tgggtcctgg agaatgacag gggactgtcc taagtttgac tccagctgca   20940
```

```
gctgctgggc cagacgaggt tccatcgctt gagcaaatta gcacatctcc tgctccctgg   21000
tgcgaagctc ttgatccagc aaatgcgttc tcctccaccc ccgtccacag ggcccagcag   21060
aagccaggcc agcgatgcac cctcgccgcc ccacctgagg ggcctctcgc ctctccagcc   21120
cgtgtcagag gtaattctca ggagtctcga tcacctctcc cttccccagg atgtcacact   21180
ggcccattac actggtgaca tcatgttgat gggacgtaag gcacaagaag tagcctccat   21240
cctagacttg ttggtgtcgg agggtgggga ataaacccaa ctggaattca gagccttcta   21300
cctcagggaa atttccagtg gtgtgaggcc tgttctaagg tgaaggacag gttgttgcag   21360
ctgaaccctc ctacaaccaa aagagaagaa cggcactaag tgggcctgtc tgatgtgggg   21420
ttgacacgtt cttctctctt gaggtgtcca actctgtcca tttactgagt gatttgaaaa   21480
gctgctagtt agttttaagc atggcccaga gcaagagaag tctctgcagt aggtccaggc   21540
tctgtgcatg ccgctctgcc acgtgggcca catgacccgg cagatccact ggtgcctggg   21600
gtgtcagtgg cagacagaga ccctgtgtgg agtctttgcc aggcccctgt aggtgaatca   21660
cggctcaggc ctttaggatt ttggaggaag gtcctgtcat cattcacaga taacccactc   21720
tccttcagag aaacagctct tgccctgctt ctgggccttt gtagaaatta aacacttggc   21780
agtgtgaatc tataatccca gcactttggg aggctgaggt gggcaggtca cctgaggtca   21840
ggagttcaag accagcctgg ccaacatggc gaaaccctgt ctctactaaa aatacaaaat   21900
tagccaggtg tggtggcgag tgcctgtaat accagctact gggaggtgg aggcacgaga   21960 atcagttgaa cccgggaggc ggaggttgca gtgagccaaa atggtgccgc tgcactccag   22020
cctgggtgac agagggagac tctgtctcat aaaaaaagaa aagaaaagaa agaaaaaaag   22080
aaaaggaaac taaactagac aagggccacc aagttaccac gtgacttgaa tggctcatca   22140
tgatctgggg actttctgac ccacgtagcc ataaagtcgt gtgcacagca gtgctgcatc   22200
agccagtgga agcagggat aggtgatcag gcccaagcag gtcctgaagg cacaaggaag   22260
ttacgtgaag tagtggccca aagcctgtgg ccccactgct gctcccctgc cttctccctc   22320
cctgtctgca cctgtggctg catggggagt tcctctgatt agttgacgga ggaagagaag   22380
actcaggccg gacttacaaa tggttctgct cagtatgcag acactaccgg aaagtggaca   22440
gctgcagccc tgtagcccct gggggatatc cctcagacag tggtgaagag gaatcttccc   22500
cgtgggtaga acttccggca tgcacctgtg tgtgctccgc ttagaaggag cagatgtgtg   22560
atgatatttc attcatggct gttgccagta atttaagtgg atggaggtgc ttgaaaggaa   22620
catgattgga aaattggtga tgaagaaatg tgtggaagag atgtatagat agccctttct   22680
gaacatgcta atgacatcca gatatttgtg tcccatgtga atgctcacca aagggtgacc   22740
tcagcagagg acttcagtaa tcaggtggac agcatgagct actctatgga caccagtgag   22800
ccttttccca gccaccctc tcatcaccca gtgagctcct gagcgaagtg gctgtggtgg   22860
cagggatgga ggttgtgcgt gggctcagca acatggactt ccactgacca aggccaagct   22920
gagtaccacc agcactgtat gcccagtgtg ccagcagcag agaccaacac tcagcctgat   22980
aagctccatt cctgagtgat cagcccagtg cctgggggca ggtgggtgac actggacagc   23040
tcccatcatg aaggggcgc tgaggctcca ttccccagcg tgttgagccc ggtgcctggg   23100
ggcgggtggg tgacactgga cggttcccat catgggaggg gcgctggttt gttctcactg   23160
ggataggcgc ctgccatgga tatggatttg tcttccctgc acacagtgct tctgtcgtca   23220
ctaccatctg tgggctcaga actcctcatc taatgccgtg ctgtccacac agcattgctt   23280
tgacgaagga actcactttg cagccaaaga agcgtggcag tgggctcatg ctcgtggtat   23340
```

```
tcacgggtct taccgtgttc tccatcatcc tgaagcagct ggcgtgatag aacggtggaa    23400
tgggcttttg cagacacagc tccagcacaa gctgggtggc agtcccttgc agggctgggg    23460
caaggtgctg ctccaggagg ctgtccgtgc tctgaatcag tgtccaatat gtggagctgt    23520
ctctcccaca gtcaggattc acccgtccgg gaaccaaggg gcagaagtgg gagtggcacc    23580
acccaccatc agccccagtg acccactagc agtgtttttg tttcctgttc ccatgacttt    23640
acgctctgct ggcctagggg ccttggttcc aaggtgagga atgctgccac caggagacac    23700
aacaatgact ccattgaact ggaagttaag gtggcacctg ggcagttggg gctcctcaag    23760
cctcagaatc aacaggccga taagagagtt tggatgctgg ctggggattg atccagagga    23820
cccaggggac atcgaactgc actccacacc agaggtgcgg aagagcacgg ggaatgcagg    23880
aggcccctta gggcttcttt aagtgtaacc acaccctgtg gttaagatcc ctggggccag    23940
gctcggtggc tcacgcctgt aatcccagca ctttgggagg ccgaggcggg cggatcacga    24000
ggtcaggaga ttcagaccat cctggctaac acggtgaaac cccatctcta ctaaaaatac    24060
caaaaaatta gccgggcatg gtggcaggca cctgtagtcc cagctacttg tgaggctgaa    24120
gcaggagaat ggcgtgaacc cgggaggcgg agcttgcagt gagccgagat cgcgccactg    24180
caccccagcc tgggcgacag agcaagactc cgtctcaaaa ataaaaaata ataataaaaa    24240
aataatccct gggaaagcac agcaatgcaa gtttccttag gaaactacag caaggccgag    24300
acccttaagc actgaggcct tgggtcacct ggccaggtac agaaccacta ccggctgagg    24360
tgcttgctga gggcaaaggg actacagaat gggcagtggt tataaacacc aggtactcct    24420
gtagcttggc cagtagcaga aatgaggatt gcaactttca cgagtgtttc ctctccattt    24480
tgttaagaaa gcatttgtgc atatgtgtac ataagttaag caaatatctg ttttcttttcc    24540 tctcttactc ctttatcatg taacataaga tctattgatt ttgtctcagt atcaaggtat    24600
cgtgaatttt acatgacagt attgaggtcg tgcgatatcg ggagagtcga catcactcga    24660
ggacttcacc tcctcttcca gggaaggagt cagtgcgtgt ctggttgtat gcgggacagt    24720
catcacatgt tagttggaac catgaccttg ctgctgtcta tttggagatg aagtacggtt    24780
taaggaggtg tgtatgggtt ccaagctgac aaggagtgaa cttgtgacgg ttcgttttcag   24840 ctgtcaactt gactggatga agggatatcc agagagcatg aaagcattat ctctgggtgt    24900
gcctgtgagg gcatttccgg agagactggc gattgaatcc gtgggctgaa taaggaagat    24960
ctgtcttcac ccaaagtggg agggcaccat ccaatccact gagggcccag gcagaacggg    25020
aagatgaatt cgtgctctct tgctctctct tcccccacca gagctgggac acccacctcc    25080
tactgccctt agacatcaga actcctggtt ctctgggctt tggaccctgg aacttatacc    25140
agtggcccct ctgactgcga gttacactgt cggcctccct ggttctcaga tcttcaggct    25200
tgaactgagc cacactacca gcctccctgg gtctccagct tgcacagaca gggcaaatca    25260
tgggacttct cagtctccat actcatgtga gccgattccc atcataaacc cccttttcttc    25320 catccatcca tccatccatc catccatcca tccatccatc catccagcta tctatctagc    25380
taccgagcta gctacctgta tctttactta tctctatcta tgtctaccta tatctatatc    25440
tctgtctaca tctctatatc tatctgatct atctctatct ctatggtaat ctcaatctgt    25500
ctgtctgtct gtccgtctct ctgtctatct gtctccctcc ctgtctgtct atctgcctgt    25560
ctgcctgcct gtctatctgt ctgtctgcct gtctgcctgt ctgtctgcct gtctgcctgt    25620
ctatctgact gtctgcctgc ctatctgtct gtctgtctgt ctttatctct atggatctgt    25680
acttatttat ctatctcatt ccgtgtatct gtctctatat ctatacatct acatcatgga    25740
```

```
ggactatggt agatgctcac tgctgtgcac tgcaccgtcc ctcccagcgg gaccacagca   25800
ctggtccagc cagctgccca cagctctcag cttgctcctc ccgaggaaat gccctcagcc   25860
aaaggcagct gcctcaccca tggcttctcc ctgccctgga agccacctct acccaatgaa   25920
tggtcgatgg aggaagcaac aggtcaggtc cttcacctga attcatggcc tctctaaagg   25980
gccccttcag ctccaaaagc acccgaggca tcatcagaaa ccttctttgc gagtggagca   26040
cagctcagct gcccccacct gctccttccc tctctcacag cctttgtccc caagagcact   26100
tgccacttta cccttgacct acatgtctct atctggcagt gtctcttggg gaaccgaacc   26160
tcagacagtt tgcaagcaac aaattccaaa ggtcgtgcct gggcctggag ctctgctgac   26220
atggaagcca tgcccacctg ggacctgagg gtgtttcttg tctcacaggc ctgatattga   26280
gtggtgtgca tctgcatacc caggtggttg ttaaaacaca gaacggcttc catgctggtt   26340
gaacgacccc taccttgagc ctccaggtgt ccccagagg ccaccccggt tccttccccc   26400
agggtccaag cagggcacga cagacagctt ctggaacatc actcaatgcc gtggccagcc   26460
ccattctgat gggtctgcac caatcggggc tgcttgttaa gcatgactaa agtctcctgc   26520
agtcgtctgc taggactgcc acagcaaagc gccacagtct ggcagccttc acagagacat   26580
ttatctcccc agccctgggg gcctcaagtc caagctcaag ttgttgttgg ggctggttcc   26640
ttcgggggct acgaggtggc ctctgcccag tccctccagc ctctgcccag tccctccagc   26700
ctctggggct cccaggcagc ctcgtgtttc ttggctcgtg gagcatcact ctaatctctg   26760
ccttcacctt cacatggcgt ccttcctgtg tgtgcgtctg catccaactt cccctgttcc   26820
taaggtcacc ggtcagatct gagcaggata ctaatggcca tatcttagtt acatctgcag   26880
tgaccctatt tccaaataag gtcacatatg aggcactgaa ggtcgggact gcaacatgct   26940
tgttctccta tcatggaatc agaccagcag gtgggtcaca ttccgccaga gggagagtgg   27000
gcagacgccc aaagggctgg atgtatacag ctccaggaag aaccgcagtt gcagctgctt   27060
ggacaggtgt gggcactcac agcctcccat gacagccctg gctgggggct ccatccacag   27120
cccctggtgg ggtggggcaa ggcccttcct tctgacccac aggaccttgg acccctgggg   27180
cactgcagag ggactcaggg tcagaccagc agcctttgac atggccaaga gtgaaagtga   27240
tggggaccca cgagccatca gagctctgtc tccagagcct gcacagggag tgttgggaca   27300
aggagcaaag gaatcgggag cacatcaagg caggcaccag atttggaaga acgcccgggg   27360
ggaggtgctc ccaggcgagt ggggcagagg gcagtctcct cctgggcttc cctgggtccc   27420
agcccggccc ggctgggcgt cccactgtct ttggtgtggt gtgctccctg cctgtggccc   27480
tgtgatggga gtcctgcttc tctaaacagt gagaccctca cagaaccgt cagcatgtcc   27540 aaagcacctg gaggagaaaa gatttgtctc ctcattcgtc actaggttca tggttgaggc   27600
tctcacagca aaagacagat taacaagaga aaagcagaca catttattca atataagttt   27660
catctcgtat aggagccttc ggaaatgagg acccagcact tcgggaggcc gaggtggaca   27720
gaccatttga agtcaggagt tccgagacca gcctggccaa catggtgaaa ccccatctct   27780
actaaaaata caaaattagc cgggcatggt ggcatgtgcc tgcagtccca gctaccgggg   27840
tggctgaggc aggagacttg cttgaacccg ggaggtggag gttgcagtga gccgagatca   27900
cgccattaca cttcagccag ggtgacagag tgaaactccg tctcaaaaaa aaaaaaaaa   27960 agaaaaagaa aaggaaaaag aaatgaggac ccaagggaag agggaaaccc gtgtattttt   28020
atgtggagtt tgatggagag tcatgcagag tgtgattgga ttagacaaag tgggtgtact   28080
cgtccgttct tgcactgtat aaagaatact tgagactgcg taattcataa agaaaggagg   28140
```

```
tttacttggc ttacagttcc ccaggctgta cagaaagcat ggtgctgcca tccacatggc   28200
ttctgggggc gggctcagga aacttacaat catggcggaa ggcaaaggag gagctggcac   28260
ttcacgtggc cggagcagga ggaagcccag agggagagag gggaggtgcc atatgccttt   28320
aaacaagcag gtctcatgag aactcactat cacgagaaca gcactggggg gaaatccacc   28380
cccatgagcc aatcacctcc agcaggcccc acctccagca ttggggatta caattcaaca   28440
tgagatttag gcaggtacac agatccaaac cgtatcaggg tgtggcctaa tggtgataca   28500
ctggggagac ttggcctgtg gtcttagtcc atcgtgtgct gttagaacag aaaaccacag   28560
actggctaac ttattggccc ctggtcctag aggctgggag gtccgagatc gacaggccac   28620
ctctggcaag ggtctttgtg ctgccttatc ccatgacaga agggcaaaga gagggagaga   28680
gagacagcca gagagaaggg gaccaaactc atccttctgt cagagcccgc tcccacgaca   28740
atgatgttag tccatcatga ttacagagat gggggacaca ttcagaccac agcagccccc   28800
tcaacccgca cacactgcac attgagggga gggccgggga actggaagga aacatcagag   28860
tctggagaag accaccagga tcaccagggc tatgctctca cccggcaccc agcaccgagg   28920
ggctcatggg aaacaagacg ggtctctcgg tgcacgagtg ctgggcacac atagtccacc   28980
gtgcatcctg ggctgatgat ctggaccctg gtcctgtgca gccctggggt ggggctccag   29040
gctgagatca gccacgtctg ggggaggaga cagtgttccc agtctcacct tgccccacgg   29100
actctgacag gggttgaaga agcaaggagg ctccaaggac tggggagggg gagtctggcc   29160
gacgatctag gagcatcaag gcgcctgctc cctctcggcg tggcccggtc ctgtaggtgg   29220
tcagttatgc aatgccactg ccttcctacc tcacaaggag ggtgggtgga ctcagaagcc   29280
aggcccaggc ttccttcttg gctcaggcaa ggaacatagg gggctttgag ctttgcttat   29340
tcatttaaca actgaacccc tagtctgtgc caggccccca tttaaatggt ccctgggata   29400
cagcagggtc cagaatgggc ccagaccctg cccccatagc tgaccttctg gagagcctga   29460
ggagtgaggg gtgccctcca ggcacggcag acggggcagg ctctgcattc ggggggctcca  29520 gctgctttcc caccacccac ccactccacc cgagcccttc tgggtcagct gggctcctgg   29580
ctctgcccgc ctggggtgca agacgccaag ttccttcctg gacagtgaga gaaccatgcc   29640
aaaaagaaat gaaaggaagg cagacggcga gatgagggag agggtgggca cccagccagg   29700
gaccgcagag acgaggagga ggcacagaga cccactgtcc ccagccactg ccagtgaggc   29760
tggcccaggg ccaggggctg ggcgtccctg gcatgcatgt ggctcccagt gcccccacgt   29820
ccaacaggag tggggcggcc ccctcttctg ccacatcccc atcccacctc ccattccatt   29880
cactggtctc atttttaagt ttttctctcc cagttattca ggattgattt ggagagcaga   29940
gcgatggctg caggtggctc ttcatttttcc ttcacctaag aagcaaacca tcatccaccc   30000
caagcttgtc tctccagcct gcccctaca tgaggacaac ctccctcctc ttccacggtg   30060
gcgctgttcc cactggaggc ccaggcttgg ccatccgttc attcttggag tcctcaagag   30120
attgtcagct ctgcagtggg gagcagccgc tgtcaaagac cctggaactt cctccctgct   30180
gcgtccacca accccactg cccgctgggc actcccaacc tgaaacaagc ttgctcgctg   30240
caaaagcctc acctctgacc caacttccca ctcccaggat acccaacctg gccttccctc   30300 tggataccc tgtgggctcc cctctgctga tgggttcccc tctccagctg tggcttccct   30360
ctgctgatgg ggtcccctct ccagctgggg ctccctccac tgatgggtt ccctctacag   30420 ctgtggctct ctccactgat ggggtcccct tccagctgg ggctccctcc actgatgtgg   30480
tcccctcttc agcttgggct ccctccactg atggggtccc ctcttcagct ggggctcctc   30540
```

```
tccactgaca gggtctcctt tccatctggg gctcccttgg ctgatgaagt cccttctcca   30600
ggtgaggctg ctctctgctg acagggtccc ctctccagct aggtctcctc tctgttgata   30660
gggtcccctc tccgggtggg ctcccctctg ctgacgggt cctctgatgg ggtccctact   30720
ccagggggc tccctccat agatgagctc cccttcctgg gttgggtgac ccctccgccc    30780
tatctgtgtc tgcaggttgg ggctaggcag tgctggccag catctgacaa cctcccctt   30840
ctgttcttgg gcactgctca cttattcagg tctcagccag gcagcccctc caatggtaat  30900
cttcagagtc cccttcagca acacagcttc ccctctgtgg cccagctcat gctgaagtaa  30960
acaaggcaat gtcattaacg gctggtatca gcttgtacgg ggaaccagtg gccccagaag  31020
cctctgggga ggcccaggct gtgaggatca ggggtccgga agagcctcta gagcgggaga  31080
aagaggcctc aggggtccct cctcacaggg gatggtgaca cacggtagg gaatggaggg   31140
gtcagggctg ggtccaggac acggtgaccc tggccagaaa aggccgggcc tggctggcac  31200
ccgcacgaag ggaacggagc cagtgtggaa aagcaggccc cgtcctctt ctgcactccc   31260
agccccttta aactacacac agcttgtagg aaggggatca gaggcccctg ggcgtcccat  31320
ggctatgctg cacctgggga catgaagcct agggtagctc agccagctct ggtcacggct  31380
gacagacagc ctcaccccaa cagcctcacc catccctcct cagggaacag ggtcctaaca  31440
agctgctttc cccatcccag tgttgaacaa aaactcatgg gtttagacaa gagtgaaggt  31500
gactcctcca ccacccatcc cacctccagc aggcagccac cccaaaaatt attgatttat  31560
taataaatca atgacaggtg ccagccagcc ccacctgtcc ccaacctgca aatgcagaca  31620
ggggtcactt ggtccaggga gaggagaccc tcagtggagg ggagacaccc tggagagggg  31680
acccccatcag caaaggggag ccccagctgg agacagtaaa taggcagact attcactgtc  31740
ttccccctca agccaggccc acagagtcac agagtatagc caccagcctc ctgggcccac  31800
ccggaggcc ccaaccacac tccccctgct cagctcagcc cggatttctg gattctgctg   31860
cctgccaggg atcctgagga ggagatggta tcagagcctc accagcccctt ctcataccca 31920
ggagtcctca tgatgataac agtgtgtgcg ccaggctgtg caggtgctgg ccgggatcct  31980
ctgaggggac gagatctcca tgggagggca ccactctgat gtccatcctg ggcttccgtg  32040
gccctgcctg gccactgccc gctgctcttg gtcaagatca tggaccctca gaggccaacc  32100
aggcctcagc ctgtgcctac agcatcctct ctactgccgg gcttctgaat tgctccttcc  32160
tcctgtctcc cacccagagc aagaacgaag gggaggcccc cagagccctg cagcgccggg  32220
agagactccc atccccaccc cgcatgccat caacacaaac tgccggagag tttagggat   32280
cccacgactt ggggtctcca aagagacccc cgggacatct catcgagacc ccctggca    32340
ctgcatgctc aggcttccca cccctggccc acccatgggg gtgtgccag tcccgcatct   32400
cacccccatat ccatgcatgc atgcatgaac ctgaaagcac cccacaccct ctggtgctca 32460
gtcctcccct cctccctggg gtcccctccc ctccctgccc ccaagccctt gcatccccct  32520
gcaaacctca aaggggggaa ctatttctgt cctgaaagca gagagggccc ttttcttggg  32580
acctctccgc catctctgcc tccactccca gctgctgtca gctctggcct ggcccctgca  32640
ggaagcaatc actggtctcc ctgtttccca tctggcccca aggtctgttc ttgcccttcg  32700
accagagagg tttgaaagca caactcgggc cctgcgtgcc ctgctcccca gggctccaca  32760
cctctgagca cccgcgcagt aacggaggct cccagccccg cctcgcccca gggtcccctc  32820
caacactctc tggccttggg cctttgctat accgggggcc tggaagggcc ccctcatccc  32880
ccaagtgtca ggcaaaggtc tcagagcact gtccctgccc ggcgtgcttg gtcctgactg  32940
```

```
ctaggcccca aatcattcct tttcccatta cctcttggtt tctctgtagc tggggtcact   33000
accccaaatt cttgaattga ctgacgtgtc caactatttc atgttttccc cctctacact   33060
gggagcccta caagggcagg gccccctggg caagaatagt gccagccagg agccctgga    33120 gaagatagct acacatgtgc cccaggcccc agatggcact cagccctgcc tgtcaatgct   33180
ggacataggg cagttttat cctggctttc tacacaagga ggaaagacta accatgccag    33240
cgggcagcgg ccggatcacg tatgtcagta gaactctgac ccctgagaag cctggaagcc   33300
aaaccacacc tctgtagcaa tcacgccaca gactcaggcc acggctaacg gctgccagtt   33360
cacctatttt tgcccccaac tcaagaccaa ctggaggaag gcaaatatgt ccctgacgaa    33420
gggtggccgc ctccagcctc cccagcccag agcctcagcc tccccagccc actgcctcca    33480
gcaacacaca tctgaagcct tctctgttgg ttggttttat tggtatttg gaagattgtt    33540 tgttttttgt tatgagatgg agcctcgctc tgtcccccag gctggagtgc agtggcgcga    33600
tctcggctca ctgcaagctc cgcctcctgg gttcaagcca ttctcctgtc tcagcctccc   33660
gagtagctgg gactacaggc acccgccacc gtgccaggct gattttttg tattttagt     33720 agagacgggg tttcaccatg ttagccatga tggtcttgat ctcctgacct catgatctgg    33780
ccatctcggc ctcccaaagt gctgggatta caggcgtgag ccactgcacc tggcctttgg    33840
aaggtctttt atacctttat tgagataaaa ttcttatgac ataaaactta gcataaactg    33900
tagacttagt tggtgtgact ttagagtagt ctcagaattg tgcaaccatc accactgcct    33960 actttagaa catttcaac atcccaaaga cagaaccccg taggcacctg ttagcagcca     34020
ctccccaccc agtccacgaa gccccaggca gccactcacc aatctacttt ccattaattt    34080
gcccattcta aacacttgaa aaaaatggta tcacaatggt ctttgggtt tggcttcttt    34140 ccctcagcat cataccctca aagttcatcc atgttgtagc tcgtatcggt acttcattca    34200 ttttatggc tgaataatat tccactgtat ggatagaccg atatttgtt tatttattta     34260 ttcattgatg aacatttgaa ttgttcccac ttttagcta ttaaaactag tgctggctgc    34320
gtgcagttgc tcatgcctgt aatcctagca ctttgggagg atgaggcagg cggatcactt    34380
gaggccaaga gtttgagacc agcctggcca acatggtgaa accccatct ctaataaaaa    34440 tacaacaatt agccagacac ggtcatgcgt gcctgtaatc tcagctactc aggaggctga    34500 ggcagggaa tctcttgaat ccggggggca gaggttgcag tgagccaaga tcgcgccact    34560
gcactccagc ctgggcaaca gaccaagact ctgtctcaaa aaacaaaaca aacaaaaca    34620 aaacaaacca gtactgctat gaacatgcat gtgcatattg ttatacagac atatgctttc    34680
atttctcttg gatacacaca cacacacaca cacacacaca cacacacaca cacacacacg    34740
tatatctagg actggaattg ctgatttta tggaaactct atatttagca ttttgagaaa    34800
cggccagtct gttttccgaa gtggctgcac tattttgcat tcccaccagc aatgaaggag    34860
ggttccaatt tctccatacc tctgccaaca cttgttattg tctgtctctt ttattatag    34920 ccatcttgat gggtgcatcg tggtatctcg ctgtgttttg atttgcattt ccctgatgac    34980
taatgatggg gacatctttt catgagctta tcggtcatat gtacatcttc tttggagcaa   35040
gctctattct aatcctttgc ccatcattaa aggtaggtgg tttgtcttct tgttgataag    35100
ttagagttct ttacatgttt agatactagt cccttatcaa atagatgatt cacaaatgtt    35160
tgctgtcatt tcttgggttg tcttttccact tccttgatgg tgtcttttca cgcacaaatg   35220
tttttagctt tggccaagtc caattatct atttttctt tgttgcctg tgcttttggt      35280 agtgtatatt aaaaaccatt gtttaacaca aggtcaccaa gatttattcc tatgttctt     35340
```

```
cctaaggatt ttatttttc  ttttctttt   ttttctttt   tttgagacaa agtctctctc  35400
tgtcgccaaa gctggagtgc aacggcacaa tctcagctca ctgcaacccc tgcctcctgg  35460
gttcaagcga ttcttctgcc tcagcctccc gagtagctgg gattacaggc gcccaccacc  35520
atgcccagct aattttttgtg tttttagcag agacggggtt tcaccatgtt ggccaggctg  35580
gactcaaact cctgatctca ggtgatccac tcgcctcggc ctcccaaact gctgggatta  35640
caggtgtgag ccactgcgcc tggccttcct aaggatatca taatttttagt gcttacattt  35700 aggtctacga tccatttttga gttaattttt gtgcacagca tgaggtaggg gtccaacttc  35760
attcttttgc acatggatat ctagttgtcc cagcaccatt ttctgaaaag actattcctt  35820
cccccattga attgtcttgg tacccttgtc aaaaatcaac tgatggccgg tctgaaggta  35880
gtgagttatc tcaattgatt gttcacagtc agttacagat ggaacacctc gttctactct  35940
ttcccgcctt ctcactgctg cacttgaaca gtctttaaaa aaatcaattg accataaatg  36000
caaggatttg ttcttggagt ctcaacttta ctgcattgat ctgtaggtct atccttatgc  36060
cagtaccaca ttgtcttgat tactgtagct ttgcagtaag tttgaatcag gaaatgtgag  36120
ccctccggtt ttgctcttct cttttctagat tgttttggct attctgaaac ccttgtattt  36180
ccttatgaat ttgaggatca gcttgtaaaa agacagatgg gatttttgata gagattgtga  36240 agctatagat gaattcggga gtttggccat cttaacatta tgtctcctga tccatgactg  36300
caggatatct ttccatttaa ttcgatactc tttgattcct ttcaaaaata ttttgtattt  36360
ttcagtacac aagttttatg catcttttgt tgcatttatt tctaggtatg ttcttttttgc  36420 caatattata aatgagattg tcttcttcac ttcatttttg gatggttcat tgctagtgta  36480
tagaaataaa atcgatgttt gtatattgat cttgtatcct gccacattgc tatgcatgtt  36540
tattagtttt aagggttta gtggattttc tatatataat gtcatataat cagcaaatag  36600
aaagtttaat gtcttagtcc ttttgagctg ccacaacaga ctaccataaa ctgagtggct  36660
tataaacaac acaaatgtat ttcccacagt tctggagact gggatgtcca agatcaagac  36720
acccgtaggt ttggtgtctg gtcggggcct acttctgggt tcatagatga ctgtcttctc  36780
gctgtgtccc ccccatagtg aaaggaaggg gcccagggtc tttctaaggc ttcttttata  36840
aggacactaa tccaatatag gaaggctctg ccctcataac ctaatctccc aaaggcctca  36900
cttccaaatt ccatcacctg gggagtaaga atttcaacac tgggggggaca cagatattca  36960 gacatagcat ttttcttctt cctttctaat atgggtgccc ttgacatctt tttcttacct  37020
aattgccctg ccagagcctt ccagacagtg ttgaatggaa gtggggagca ttcaccccac  37080
cttactcctg atcataggg aagaactatc cggctttcac cactgagcac cacgttagct  37140
ggggtatttt tgtcagcgct ctttatcagg tggaggcagg tcccttctat ttctagtgag  37200
ttcagtgctt tttttttttt ttaatcaggg aagagtgtga gcttgtgttt gggtgccttc  37260
cctgcgtctg ttgagatgat cttacggttt ctgtctctta ttctattgat atggcgtatt  37320
tattaccttg gttgcttttt ggatgttgat aacatccaaa ctcttctgcc accccttta  37380 atagaaagct gtacaactcc ccaacctgcc tgggcgtgtc tgcccaagat gagtgctagt  37440
ggccgactcc ctgctagagt gagcactgca taaacagcct ctgcttgtcc tcatttgagt  37500
gatcttcatg tattccacga gaaatcaagg cacaggggtc tcatggtctc atgaatggct  37560
ccaccaactg aaggtgtgct ccatcggggc tgtgagtcac ctcacgccag gcagaaaggt  37620
ctctctgtca aacatggctt caaggaacca gggacctggt tcctcccaca ggccaggccc  37680 tgccctaag tgcaatggga atatatgcac atgtcacctg tcccaaaatg ctgggagatg  37740
```

```
gcacttctgc agatggggaa actgagggac cagcccgaag tcacggggag gggaagactc    37800
ctacacacag ggaggagaag aacccagccg ggctgcaaac gcctgccctt cctcaacgtg    37860
cctccggctg tgcccacatc gctccagcag ctctgccttc ctcaggcata agccttctca    37920
gggcagggga ggcccaggga gcggcgctcc catcccaggc cgggctgctg agcaagcccc    37980
tcccctttct cccctcatcc tctgacagag tccacctgaa tatttgtcct ggagccagga    38040
tggaagctcc accaggccca gctaacaaca ggaacccttt cagacgcact tctgggtgcg    38100
tactgtgcca gtatcacaca gacacaagcc atgtccttgt cagccatggg atccccaagg    38160
tccccatgag gtcacaccag tgggccactg ggaagggcac ttcagatgtg gagctcccat    38220
gggccaggcc ctgcgaagtg gtcctcctac cccctcatag ccagtcttcc ctgtgagcct    38280
gcaagtgact gtgaatgtga gttccactct ggagctaaga cgggctgctg cccccgcaat    38340
cagatgtcag gcccatgaag                                               38360
```

ISOLATED GENOMIC POLYNUCLEOTIDE FRAGMENTS FROM THE P15 REGION OF ISOLATED GENOMIC POLYNUCLEOTIDE FRAGMENTS FROM THE P15 REGION OF CHROMOSOME 11 ENCODING HUMAN TUMOR SUPPRESSING SUBTRANSFERABLE CANDIDATE 4 (TSSC4)

PRIORITY CLAIM

This application is a divisional of application Ser. No. 09/999,121 filed Oct. 31, 2001, the contents of which are incorporated herein by reference. This application also claims priority under 35 U.S.C. 119(e) from provisional application Ser. No. 60/244,705, filed Oct. 31, 2000, the contents of which are incorporated herein by reference.

FIELD OF THE INVENTION

The invention is directed to isolated genomic polynucleotide fragments located in the p15 region of chromosome 11.

BACKGROUND OF THE INVENTION

Chromosome 11 contains genes encoding, for example, KCNQ1, a voltage-gated potassium channel; IPL, a homolog of a mouse apoptosis-inducing entity; human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4). Human achaete-scute homolog 2 (HASH2), human SMS3, human tumor suppressing subtransferable candidate 6 (TSSC6), human ribosomal protein L26 (RIBO26), cluster of differentiation antigen 81 (CD81) and tumor suppressing subtransferable candidate 4 (TSSC4) are discussed in further detail below. Genes for the latter six proteins are located in the p15 region of chromosome 11, a region known to be associated with the Beckwith-Wiedemann Syndrome (Itoh et al. Am. J. Genet. 92, 111-6, 2000) and some childhood tumors.

Beckwith-Wiedemann Syndrome is characterized by pre and postnatal overgrowth up to 160% of normal birthweight, macroglossia, hypoglycemia, hemi-hypertrophy and childhood tumors, such as Wilm's tumor (Reik et al., 1998, Trends Genet. 13:330-334). This syndrome appears to be associated with deregulation of imprinting. Imprinted genes are genes that are predominantly expressed from one of the parental chromosomes. There appears to be two imprinted subdomains, since the imprinted gene domain of 11p15 contains at least two imprinted subdomains (Lee et al., 1999, Hum. Mol. Genet. 8:683-690). Mosaicism may also play some role in the Beckwith-Wiedemann Syndrome phenotype and may explain the variable phenotypes in Beckwith-Wiedemann Syndrome patients (Itoh et al., 2000, Am. J. Med. Genet. 92:111-116).

Human Achaete-Scute Homolog 2 (HASH2)

HASH2 is a basic helix-loop-helix protein that serves as a critical transcription factor for the development of the trophectoderm. Mice deficient in the HASH2 homolog, MASH2, die 10 days postcoitum due to placental failure (Guillemot et al., Nature 371, 333-6, 1994).

Human Tumor Suppressing Subtransferable Candidates 4 and 6 (TSSC4 and TSSC6)

Both TSSC 4 and TSSC6 are believed to function as tumor-suppressing proteins in that the genes are among the genes of a subchromosomal fragment that suppresses in vitro growth of the rhabdomyosarcoma cell line RD (Koi et al., Science 260, 361-4, 1993).

Human Ribosomal Protein L26 (RIBO26)

RIBO26 is one of the approximately 80 proteins that compose the human ribosome (Kenmochi, N. et al., Genome Res. 8, 509-23, 1998). It has been found in mice to be induced by LPS and IFN gamma but is down regulated by TNF-alpha (Segade et al., 1996, Life Sci. 58:277-285).

Human Cluster of Differentiation Antigen 81 (CD81)

CD81 (also called TAPA1) binds the E2 envelope protein of the human hepatitis C virus and is believed to play a role in hepatitis C infection (Pileri et al., Science 282, 938-41, 1998). CD81 also appears to play a role in T cell activation (Witherden et al., 2000, J. Immunol. 165:1902-1909).

OBJECTS OF THE INVENTION

Although cDNAs encoding the above-disclosed proteins have been isolated, their precise locations and exon/intron/regulatory element organizations on chromosome 11 have not been determined. Furthermore, genomic DNA encoding these polypeptides have not been isolated. Noncoding sequences play a significant role in regulating the expression of polypeptides as well as the processing of RNA encoding these polypeptides.

There is clearly a need for obtaining genomic polynucleotide sequences encoding these polypeptides. Therefore, it is an object of the invention to isolate such genomic polynucleotide sequences.

There is also a need to develop means for identifying mutations, duplications, translocations, polysomies and mosaicism associated with Beckwith-Wiedemann syndrome.

SUMMARY OF THE INVENTION

The invention is directed to an isolated genomic polynucleotide, said polynucleotide obtainable from human chromosome 11 having a nucleotide sequence at least 95% identical to a sequence selected from the group consisting of:

(a) a polynucleotide encoding a polypeptide selected from the group consisting of human achaete-scute homolog 2 (HASH2) depicted in SEQ ID NO:1, human SMS3 depicted in SEQ ID NO:2, human tumor suppressing subtransferable candidate 6 (TSSC6) depicted in SEQ ID NO:3, ribosomal protein L26 (RIBO26) depicted in SEQ ID NO:4, cluster of differentiation antigen 81 (CD81) depicted in SEQ ID NO:5, and tumor suppressing subtransferable candidate 4 (TSSC4) depicted in SEQ ID NO:6;

(b) a polynucleotide selected from the group consisting of SEQ ID NO:7 which encodes human HASH2 depicted in SEQ ID NO:1, SEQ ID NO:8 which encodes human SMS3 depicted in SEQ ID NO:2, SEQ ID NO:9 which encodes human TSSC6 1 depicted in SEQ ID NO:3, SEQ ID NO:10 which encodes ribosomal protein L26 (RIBO26) depicted in SEQ ID NO:4, SEQ ID NO:11 which encodes human CD81 depicted in SEQ ID NO:5 and SEQ ID NO:12 which encodes human TSSC4 depicted in SEQ ID NO:6;

(c) a polynucleotide which is a variant of SEQ ID NOS:7, 8, 9, 10, 11 or 12, (d) a polynucleotide which is an allelic variant of SEQ ID NOS:7, 8, 9, 10, 11 or 12:

(e) a polynucleotide which encodes a variant of SEQ ID NOS:1, 2, 3, 4, 5, or 6;

(f) a polynucleotide which hybridizes to any one of the polynucleotides specified in (a)-(e);

(g) a polynucleotide that is a reverse complement to the polynucleotides specified in (a) to (f) and (h) containing at least 10 transcription factor binding sites selected from the group consisting of AP1FJ_Q2, AP1_C, AP1_Q2, AP1_Q4, AP4_Q5, AP4_Q6, ARNT_01, BRN_01, CDPCR3HD_01, CEBPB_01, CETS1P54_01, CMYB_01, CP2_01, CREB_02, CREB_Q4, CREL_01, DELTAEF1_01, E47_01, FREAC7_01, GATA1_02, GATA1_03, GATA1_04, GATA1_06, GATA2_02, GATA2_03, GATA3_02, GATA3_03, GATA_C, GC_01, GFI1_01, HFH2_01, HFH3_01, HFH8_01, IK1_01, IK2_01, LMO2COM_01, LMO2COM_02, LYF1_01, MAX_01, MYCMAX_02, MYOD_01, MYOD_Q6, MZF1_01, NF1_Q6, NFAT_Q6, NKX25_01, NKX25_02, NMYC_01, OCT1_02, PADS_C, RORA1_01, S8_01, SOX5_01, SP1_Q6, STSSC6_01, SRV_02, STAT_01, TATA_01, TCFA_01, USF_01, USF_C, USF_Q6 and VMYB_02, as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (b) with an adjuvant and (c) obtaining antibody from said immunized host animal.

The invention is further directed to polynucleotides that hybridize to noncoding regions of said polynucleotide sequences as well as antisense oligonucleotides to these polynucleotides as well as antisense mimetics. The antisense oligonucleotides or mimetics may be used for the manufacture of a medicament for prevention, treatment or amelioration of a medical condition. The invention is further directed to kits comprising these polynucleotides and kits comprising these antisense oligonucleotides or mimetics.

In a specific embodiment, the noncoding regions are transcription regulatory regions.

The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to diagnose a pathological condition in a subject comprising (a) determining the presence or absence of a mutation in the polynucleotides of the present invention and (b) diagnosing a pathological condition or a susceptibility to a pathological condition based on the presence or absence of said mutation.

The invention is also directed to an isolated polynucleotide from the p15 region of human chromosome 11 selected from the group consisting of SEQ ID NOS: 13 and 14. SEQ ID NO:13 consists of nucleotide sequence immediately preceding the HASH2 gene; SEQ ID NO:14 consists of the gap between the RIBO26 and CD81 gene. Both of these polynucleotides are located in the imprinted subdomains of 11p15. Oligonucleotides derived from these sequences may be used to identify mutations, duplications, translocations, polysomies and mosaicism associated with Beckwith-Wiedemann syndrome. Furthermore, oligonucleotides derived from SEQ ID NO:13 may also be used as a marker for the HASH2 gene and SEQ ID NO:14 may be used as a marker for the RIBO26 and/or CD81 gene.

DETAILED DESCRIPTION OF THE INVENTION

The invention is directed to isolated genomic polynucleotide fragments that encode HASH2, human SMS3, human TSSC6, human RIBO26, human CD81 and human TSSC4, which in a specific embodiment are the HASH2, SMS3, TSSC6, RIBO26, CD81 and TSSC4 genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The HASH2 gene is 17290 base pairs in length and contains a single exon (see Table 1 below). The HASH2 gene is situated in genomic clone AC002536 at nucleotides 17081-34370. The SMS3 gene is 25970 base pairs in length and contains 3 exons (Table 2). The SMS3 gene is situated in genomic clone AC002536 at nucleotides 34371-60340. The TSSC6 gene is 30196 base pairs in length and contains 9 exons (Table 3). The TSSC6 gene is situated in genomic clone AC002536 at nucleotides 51731-81926. The RIBO26 gene is 21630 base pairs in length and contains a single exon (see Table 4 below for location of the exon). As will be discussed in further detail below, the RIBO26 gene is situated in genomic clone AC002536 at nucleotides 77701-99330. The CD81 gene is 21573 base pairs in length and contains 8 exons (Table 5). The CD81 gene begins at nucleotide 120961 in genomic clone AC002536 and extends to nucleotide 3640 in the downstream genomic clone AC003693. Clones AC002536 (140977 base pairs) and AC003693 (155074 base pairs) have a 2084 base pair overlap. The TSSC4 gene is 15540 base pairs in length and contains a single exon (Table 6). The TSSC4 gene is situated in genomic clone AC003693 at nucleotides 3641-19,180.

The polynucleotides of the invention have at least a 95% identity and may have a 96%, 97%, 98% or 99% identity to the polynucleotides depicted in SEQ ID NOS:7, 8, 9, 10, 11 or 12, as well as the polynucleotides in reverse sense orientation, or the polynucleotide sequences encoding the HASH2, SMS3, TSSC6, RIBO26, CD81 or TSSC4 polypeptides depicted in SEQ ID NOS:1, 2, 3, 4, 5 or 6 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time, the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include, on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted (indels), deleted, or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 7, 8, 9, 10, 11 or 12. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The invention also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The amino acid sequences of the variant polypeptides may differ from the amino acid sequences depicted in SEQ ID NOS:1, 2, 3, 4, 5 or 6 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the HASH2, SMS3, TSSC6, RIBO26, CD81 and TSSC4 genes. These include but are not limited to an intron, a 5'-non-coding region, a 3'-non-coding region and splice junctions (see Tables 1-6), as well as transcription factor binding sites (see Table 7). The polynucleotide fragments may be a short polynucleotide fragment which is between about 8 nucleotides to about 40 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600 or about 2000 nucleotides in length may be used.

TABLE 1

Exon/Intron Regions of the human achaete-scute homolog 2 (HASH2) gene, 17290 bp, reference cDNA accession number U77629; reverse strand coding.

| Exon | Location (nucleotide no./amino acid no.) |
|---|---|
| 1 | 7031-7609 |
| | 193-1 |
| | stop codon 7028-7030 |

TABLE 2

Exon/Intron Regions of the human SMS3 gene, 25970 bp, reference cDNA accession number AB029488; reverse strand coding.

| Exon | Location (nucleotide no./amino acid no.) |
|---|---|
| 3 | 18962-19210 |
| | 132-50 |
| 2 | 20023-20118 |
| | 49-18 |
| 1 | 21261-21311 |
| | 1-17 |
| | stop codon 18959-18961 |

TABLE 3

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 1 | 5011-5100 |
| | 1-30 |
| 2 | 6249-6347 |
| | 31-63 |
| 3 | 10879-10953 |
| | 64-88 |
| 4 | 15797-15898 |
| | 89-122 |

TABLE 3-continued

Exon/Intron Regions of the human tumor suppressing subtransferable candidate 6 (TSSC6) gene, 30196 bp, reference cDNA accession number NM_005705; plus strand coding.

| Exon | Location (nucleotide no./amino acid no.) |
|---|---|
| 5 | 16628-16714 |
|   | 123-151 |
| 6 | 18372-18455 |
|   | 152-179 |
| 7 | 18719-18811 |
|   | 180-210 |
| 8 | 19488-19664 |
|   | 211-270 |
| 9 | 20005-20064 |
|   | 271-290 |
|   | stop codon 20065-20067 |

TABLE 4

Exon/Intron Regions of the human ribosomal protein L26 gene, 21630 bp, reference cDNA accession number AF083248; reverse strand coding.

| Exon | Location (nucleotide no./amino acid no.) |
|---|---|
| 1 | 11490-11924 |
|   | 145-1 |
|   | stop codon 11487-11489 |

TABLE 5

Exon/Intron Region of the human CD81 gene, 37113 bp, reference accession number NM_004356; plus strand coding.

| Exon | Location (nucleotide no./amino acid no.) |
|---|---|
| 1 | 10471-10536 |
|   | 1-22 |
| 2 | 23333-23446 |
|   | 23-60 |
| 3 | 27015-27113 |
|   | 61-93 |
| 4 | 27893-27964 |
|   | 94-117 |
| 5 | 28334-28441 |
|   | 118-153 |
| 6 | 28790-28891 |
|   | 154-187 |
| 7 | 29549-29635 |
|   | 188-216 |
| 8 | 29725-29784 |
|   | 217-236 |
|   | stop codon 29785-29787 |

TABLE 6

Exon/Intro Region of the human tumor suppressing subtransferable candidate 4 (TSSC4) gene, 15540 bp, reference cDNA accession number NM_005706; plus strand coding.

| Exon | Location (nucleotide no./amino acid no.) |
|---|---|
| 1 | 13982-14968 |
|   | 1-329 |
|   | stop codon 14969-14971 |

TABLE 7

TRANSCRIPTION FACTOR BINDING SITES

| BINDING SITES | HASH2 | SMS3 | TSSC6 | RIBO26 | CD81 | TSSC4 |
|---|---|---|---|---|---|---|
| AP1FJ_Q2 |  | 14 | 8 | 10 | 16 |  |
| AP1_C | 4 | 6 | 8 | 10 | 8 |  |
| AP1_Q2 | 4 | 7 | 5 | 10 | 6 |  |
| AP1_Q4 |  |  | 4 | 5 | 5 |  |
| AP4_Q5 | 30 | 44 | 55 | 12 | 71 |  |
| AP4_Q6 | 14 | 22 | 26 | 4 | 34 |  |
| ARNT_01 | 7 | 4 |  |  | 6 |  |
| BRN2_01 | 5 |  |  | 4 |  |  |
| CDPCR3HD_01 |  |  |  | 5 | 8 |  |
| CEBPB_01 |  | 9 | 5 | 13 | 4 |  |
| CETS1P54_01 |  |  |  |  |  | 5 |
| CMYB_01 | 4 |  |  |  |  |  |
| CP2_01 |  | 4 | 5 |  |  |  |
| CREB_02 |  |  |  |  | 4 |  |
| CREB_Q4 |  |  |  |  | 4 |  |
| CREL_01 | 5 | 11 | 11 |  | 7 |  |
| DELTAEF1_01 | 42 | 49 | 67 | 57 | 84 |  |
| E47_01 |  |  | 6 |  | 17 |  |
| FREAC7_01 |  | 4 | 6 |  |  |  |
| GATA1_02 | 6 | 7 | 6 | 9 | 11 |  |
| GATA1_03 | 8 | 7 | 4 | 15 | 5 |  |
| GATA1_04 | 9 | 16 | 10 | 11 | 10 |  |
| GATA1_05 |  | 5 | 7 | 5 |  |  |
| GATA1_06 | 4 | 7 |  |  |  |  |
| GATA2_02 | 7 | 12 | 6 | 8 | 4 |  |
| GATA2_03 |  | 6 |  |  |  |  |
| GATA3_02 | 4 | 6 |  |  |  |  |
| GATA3_03 |  | 4 |  |  |  |  |
| GATA_C | 6 | 13 | 5 | 7 | 7 |  |
| GC_01 |  |  |  |  |  | 7 |
| GFI1_01 |  | 6 |  |  |  |  |
| HFH2_01 |  |  | 4 | 4 |  |  |
| HFH3_01 | 5 |  | 9 | 7 | 4 |  |
| HFH8_01 |  |  |  | 4 | 5 |  |
| IK1_01 |  |  | 4 |  |  |  |
| IK2_01 | 22 | 24 | 34 | 33 | 56 |  |
| LMO2COM_01 | 21 | 33 | 41 | 18 | 57 | 7 |
| LMO2COM_02 | 13 | 15 | 10 | 11 | 14 |  |
| LYF1_01 | 5 | 7 |  | 4 | 6 |  |
| MAX_01 | 4 |  |  |  |  |  |
| MYCMAX_02 | 4 |  |  |  |  |  |
| MYOD_01 |  |  |  |  | 4 |  |
| MYOD_Q6 | 13 | 13 | 22 | 5 | 34 | 11 |
| MZF1_01 | 73 | 106 | 136 | 63 | 211 | 21 |
| NF1_Q6 |  | 5 | 6 |  | 6 |  |
| NFAT_Q6 | 23 | 33 | 20 | 39 | 16 |  |
| NKX25_01 | 6 | 4 | 4 | 7 | 4 |  |
| NKX25_02 |  |  |  | 4 |  |  |
| NMYC_01 | 14 | 15 | 4 | 10 |  |  |
| OCT1_02 |  |  |  | 6 |  |  |
| PADS_C |  |  | 6 |  | 4 |  |
| RORA1_01 |  | 4 |  |  |  |  |
| S8_01 | 5 | 25 | 15 | 23 | 7 |  |
| SOX5_01 | 5 | 9 | 5 | 8 | 11 |  |
| SP1_Q6 | 6 |  |  |  | 11 |  |
| SRY_02 |  | 4 |  | 6 | 9 |  |
| STAT_01 | 5 |  |  |  | 5 |  |
| TATA_01 |  |  |  | 6 |  |  |
| TCF11_01 | 24 | 27 | 27 | 43 | 43 | 9 |
| USF_01 | 14 | 16 | 4 | 10 | 12 | 4 |
| USF_C | 14 | 16 | 4 | 10 | 12 | 6 |
| USF_Q6 |  | 10 |  |  | 6 |  |
| VMYB_02 | 9 | 5 |  | 4 | 11 |  |

Abbreviations: HASH2, human achaete-scute homolog 2; TSSC6, tumor suppressing subtransferable candidate 6; RIBO26, ribosomal protein L26; CD81, cluster of differentiation antigen 81; and TSSC4, tumor suppressing subtransferable candidate 4.

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides
Isolated Polynucleotide Sequences

The human chromosome 11 genomic clone of accession number AC002536 has been discovered to contain the HASH2 gene, the SMS3 gene, the TSSC6 gene, the RIBO26, part of the CD81 gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC002536 was compared to the HASH2 cDNA sequence, accession number U77629, the human SMS3 cDNA sequence accession number AB029488, TSSC6 cDNA sequence accession number NM_005705, and the RIBO26 cDNA sequence, accession number AF083248. The remainder of the CD81 gene and the TSSC4 gene were found by similar means in the downstream clone AC003693. The accession numbers for the CD81 and TSSC4 cDNAs are, respectively, NM_004356 and NM_005706.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: *A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired HASH2 gene, the SMS3 gene, the TSSC6 gene, the RIBO26 gene, the CD81 gene, the TSSC4 gene, SEQ ID NO:13 or SEQ ID NO:14 may be accomplished in a number of ways. For example, if an amount of a portion of the HASH2 gene, the SMS3 gene, the TSSC6 gene, the RIBO26 gene, the CD81 gene or the TSSC4 gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 10, and preferably a 15, nucleotide fragment of the sequences depicted in SEQ ID NOS:7, 8, 9, 10, 11, 12, 13 or 14. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous HASH2, SMS3, TSSC6, or RIBO26 polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:7, 8, 9, 10, 11 or 12 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the HASH2, SMS3, the TSSC6, RIBO26, CD81 or TSSC4 polypeptide.

A gene encoding HASH2, SMS3, TSSC6, RIBO26, CD81 or TSSC4 polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the HASH2 gene (nucleotides 7028-7609 of SEQ ID NO:7), SMS3 gene (nucleotides 18959-21311 of SEQ ID NO:8), TSSC6 gene (nucleotides 5011-20067 of SEQ ID NO:9), RIBO26 gene (nucleotides 11487-11924 of SEQ ID NO:10), CD81 gene (nucleotides 10471-29787 of SEQ ID NO:11) or TSSC4 gene (nucleotides 13982-14971 of SEQ ID NO:12) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 7, 8, 9, 10, 11 or 12 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences which regulate the expression of the polynucleotide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the prokaryotic beta-lactamase gene (Villa-Komaroff et al., 1978, *Proc. Natl. Acad. Sci. USA* 75: 3727-3731), as well as the tac promoter (DeBoer et al., 1983, *Proc. Natl. Acad. of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, *Yeast* 8: 423-488.

Eukaryotic promoters may be obtained from the genomes of viruses such as polyoma virus, fowlpox virus, adenovirus, bovine papilloma virus, avian sarcoma virus, cytomegalovirus, a retrovirus, hepatitis-B virus and SV40. Alternatively, heterologous mammalian promoters, such as the actin promoter or immunoglobulin promoter may be used.

The constructs of the invention may also include enhancers. Enhancers are cis-acting elements of DNA, usually from about 10 to about 300 bp that act on a promoter to increase its transcription. Enhancers from globin, elastase, albumin, alpha-fetoprotein, and insulin enhancers may be used. However, an enhancer from a virus may be used; examples include SV40 on the late side of the replication origin, the cytomegalovirus early promoter enhancer, the polyoma enhancer on the late side of the replication origin and adenovirus enhancers.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

The control sequence may also be a signal peptide coding region, which codes for an amino acid sequence linked to the amino terminus of the polypeptide which can direct the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention.

The control sequence may also be a propeptide coding region, which codes for an amino acid sequence positioned at the amino terminus of a polypeptide. The resultant polypeptide is known as a proenzyme or pro-polypeptide (or a zymogen in some cases). A pro-polypeptide is generally inactive and can be converted to a mature active polypeptide by catalytic or autocatalytic cleavage of the propeptide from the pro-polypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated.

Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. An example of suitable selectable markers for mammalian cells are those that enable the identification of cells competent to take of the nucleic acids of the present invention, such as DHFR or thymidine kinase. An appropriate host cell when wild-type DHFR is employed is the CHO cell line deficient in DHFR activity, prepared and propagated as described by Urlaub et al., Proc. Natl. Acad. Sci. USA, 77:4216 (1980).

The vectors of the present invention preferably contain an element(s) that permits stable integration of the vector into the host cell genome or autonomous replication of the vector in the cell independent of the genome of the cell.

For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, or a *Streptomyces* cell, e.g., *Streptomyces lividans* or *Streptomyces murinus*, or gram negative bacteria such as *E. coli* and *Pseudomonas* sp.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, embryonic kidney cells (293), lung cells, H9 and Jurkat cells, mouse NIH3T3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences by lipid-mediated, calcium phosphate mediated or DEAE-dextran mediated transfection (reviewed in Sambrook and Russell, Molecular Cloning, A Laboratory Manual, Cold Spring Harbor Laboratory Press, Cold Spring Harbor, N.Y., 2001). Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells. The polynucleotide may be directly introduced into the eukaryotic cell via electroporation, bolistics, or polybrene (reviewed in Sambrook and Russell, supra).

The host cell may be a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182-187, Academic Press, Inc., New York; Ito et al., 1983, *Journal of Bacteriology* 153: 163; and Hinnen et al., 1978, *Proc. Natl. Acad. Sci. USA* 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, the presence of the HASH2 and RIBO26 protein may be detected using standard transcription assays. The presence of TSSC4 and TSSC6 may be detected by assaying for tumor suppressor activity in rhabdomyosarcoma cells (Koi et al., 1993, Science 260:361-364). The presence of CD81 may be detected by assaying for binding to E2 hepatitis C protein (Allander et al., 2000, J. Gen. Virol. 81:2451-2459).

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Antibodies

According to the invention, the HASH2, SMS3, TSSC6, RIBO26, CD81 or TSSC4 polypeptides produced according to the method of the present invention may be used as an immunogen to generate any of these antibodies. Such antibodies include but are not limited to polyclonal, monoclonal, chimeric, single chain, Fab fragments, and an Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

For preparation of monoclonal antibodies directed toward the HASH2, SMS3, TSSC6, RIBO26, CD81 or TSSC4 polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the HASH2, SMS3, TSSC6, RIBO26, CD81 or TSSC4 polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the HASH2, SMS3, TSSC6, RIBO26, CD81 or TSSC4 polypeptides.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Uses of Polynucleotides

Diagnostics

Polynucleotides containing noncoding regions of SEQ ID NOS:7, 8, 9, 10, 11, 12, 13 or 14 may be used as probes for detecting mutations from samples from a patient. Genomic DNA may be isolated from the patient. A mutation(s) may be detected by Southern blot analysis, specifically by hybridizing restriction digested genomic DNA to various probes and subjecting to agarose electrophoresis. Alternatively, these polynucleotides may be used as PCR primers and be used to amplify the genomic DNA isolated from the patients. Additionally, primers may be obtained by routine or long range PCR that yield products containing contiguous intron/exon sequence and products containing more than one exon with intervening intron. The sequence of the amplified genomic DNA from the patient may be determined using methods known in the art. Such probes may be between 10-100 nucleotides in length and may preferably be between 20-50 nucleotides in length. Specifically, probes derived from SEQ ID NOS: 13 or 14 may be used to identify mutations duplications, translocations, polysomies and mosaicism associated with Beckwith-Wiedemann syndrome.

Thus the invention is thus directed to kits comprising these polynucleotide probes. In a specific embodiment, these probes are labeled with a detectable substance.

Antisense Oligonucleotides and Mimetics

The antisense oligonucleotides or mimetics of the present invention may be used to decrease levels of a polypeptide. For example, HASH2 is required for development of the trophoblast. Therefore, the HASH2 antisense oligonucleotides of the present invention could be used as an antifertility agent. RIBO26 is expressed in abundance in small cell tumors of the lung. RIBO26 antisense sequences could be used to inhibit small cell tumor growth. CD81 plays a role in T cell activation, and its antisense sequences may help control autoimmune disorders in which T cell activation is uncontrolled. CD81 also binds the human hepatitis C virus; thus CD81 antisense sequences may, by reducing CD81 expression, reduce the infectivity of the human hepatitis C virus. The TSSC4 and 6 proteins act as tumor suppressors. Therefore, antisense sequences may act as antiapoptosis agents.

The HASH2, SMS3, TSSC6, RIBO26, CD81 and TSSC4 genes are all situated in a region of chromosome 11 known to be associated with the Beckwith-Wiedemann Syndrome. Thus, antisense sequences of any of these six genes may provide means of managing patients with the Beckwith-Wiedemann Syndrome. Furthermore, antisense oligonucleotides of SEQ ID NOS:13 or 14 may be used for the same purpose.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, HASH2 is necessary for development of the trophoblast, RIBO26 is a component of the ribosome, TSSC6 and TSSC4 are involved in repressing tumor growth, and CD81 is involved in T cell activation. Therefore, the HASH2 gene may be used to treat some forms of infertility. The CD81 gene may be used in patients whose ability to activate T cells is impaired. CD81 also binds the human hepatitis C virus, thus gene therapy designed to yield a secretable form of CD81 may, by binding the virus in an excretable form, reduce the spread of hepatitis C. Given the tumor suppressing actions of TSSC6 and TSSC4, their genes may be used to prevent tumor growth. RIBO26 may be used to treat disorders in which ribosome assembly is defective. The SMS3 gene is situated within the Beckwith-Wiedemann Syndrome locus and may thus be useful for treatment of patients in which the SMS3 gene is nonfunctional.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes:

a) Biological agents derived from viral, bacterial or other sources.

b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN™ and LIPOFECTACE™, which are formed of cationic lipids such as N-[1-(2,3 dioleyloxy)-propy1]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Felgner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is $N^4$-spermine cholesteryl carbamate (GL-67) disclosed in U.S. Pat. No. 5,767,099. Additional preferred lipids include $N^4$-spermidine cholestryl carbamate (GL-53) and 1-($N^4$-spermidine)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class I molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:

1. An isolated polynucleotide selected from the group consisting of (a) an isolated polynucleotide consisting of a nucleic acid sequence which is at least 99% identical to the polynucleotide shown in SEQ ID NO:12; (b) a polynucleotide fragment of (a) comprising at least nucleotides 13982-14971 of SEQ ID NO:12, wherein (a)-(b) encode a polypeptide which is at least 99% identical to SEQ ID NO:6 and has human tumor suppressing subtransferable candidate 4 (TSSC4) activity or (c): a reverse strand of the polynucleotides of (a) or (b), wherein the isolated polynucleotide is modified.

2. A nucleic acid construct comprising the polynucleotide of claim 1.

3. An expression vector comprising the polynucleotide of claim 1.

4. A recombinant host cell comprising the polynucleotide of claim 1.

5. A method for obtaining human tumor suppressing subtransferable candidate 4 (TSSC4) comprising:
    (a) culturing the recombinant host cell of claim 4 under conditions that provide for the obtaining of human tumor suppressing subtransferable candidate 4 (TSSC4) and
    (b) recovering said human tumor suppressing subtransferable candidate 4 (TSSC4).

6. An isolated polynucleotide at least 50 nucleotides in length identical to a region of SEQ ID NO:12, said region selected from the group consisting of a 5'-noncoding region, a 3'-non-coding region and a contiguous coding and non-coding nucleic acid sequence region of SEQ ID NO:12 or reverse strand of said polynucleotide, wherein the isolated polynucleotide is modified.

7. The isolated polynucleotide of claim 6, wherein said 5'-noncoding region consists of nucleotides 1-13981 of SEQ ID NO:12 and said 3'-non-coding region consists of nucleotides 14968-14972 of SEQ ID NO:12.

8. A composition comprising the polynucleotide of claim 1 and a carrier or diluent.

9. A composition comprising the polynucleotide of claim 6 and a carrier or diluent.

10. A kit comprising the polynucleotide of claim 1.

11. A kit comprising the polynucleotide of claim 6.

12. A method for preparing an antibody specific to human tumor suppressing subtransferable candidate 4 (TSSC4) comprising:
    (a) obtaining a polypeptide according to the method of claim 5;
    (b) optionally conjugating said polypeptide to a carrier protein;
    (c) immunizing a host animal with said polypeptide or polypeptide-carrier protein conjugate of step (b) with an adjuvant and
    (d) obtaining antibody from said immunized host animal.

13. A method for preventing, treating or ameliorating a medical condition, comprising administering to a subject an amount of the composition of claim 1 effective to prevent, treat or ameliorate said medical condition.

14. A method for preventing, treating or ameliorating a medical condition, comprising administering to a subject an amount of the composition of claim 6 effective to prevent, treat or ameliorate said medical condition.

15. A method of identifying variants of SEQ ID NO:12 or its complementary sequence comprising
    (a) isolating genomic DNA from a subject and
    (b) determining the presence or absence of a variant in said genomic DNA using the polynucleotide of claim 6.

16. A method for detecting the presence or absence of a nucleic acid sequence of SEQ ID NO:12 or its complementary sequence in a sample, said method comprising contacting the sample with the polynucleotide of claim 6.

17. A method of detecting the presence or absence of a variant of human tumor suppressing subtransferable candidate 4 (TSSC4) in a sample using the polynucleotide of claim 1.

18. A method of detecting the presence or absence of a nucleotide variant of SEQ ID NO:12, or its complementary sequence comprising:
    (a) isolating genomic DNA from a subject, and
    (b) determining the presence or absence of a nucleotide sequence variation in said genomic DNA by comparing the nucleotide acid sequence of SEQ ID NO:12 with the nucleotide sequence of the isolated genomic DNA of (a) and establishing if and where a difference occurs between the two nucleic acid sequences thereby identifying a nucleotide sequence variant of SEQ ID NO:12, or its complementary sequence.

19. A method for obtaining the polynucleotide of claim 1 comprising
   (a) isolating genomic polynucleotide from a subject;
   (b) providing primers, probes and optionally polymerase, wherein said primers or probes ace at least 50 nucleotides in length identical to a region of SEQ ID NO: 12, said region selected from the group consisting of a 5'-noncoding region, an intron, 3'-non-coding region and a contiguous coding and non-coding, nucleic acid sequence region of SEQ ID NO: 12 reverse strand of said regions and
   (c) incubating (a) and (b) under conditions promoting the isolation of said polynucleotide.

20. A method for obtaining the polynucleotide of claim 6 comprising
   (a) isolating genomic polynucleotide from a subject;
   (b) providing primers, probes and optionally polymerase, wherein said primers or probes are at least 50 nucleotides in length identical to a region of SEQ ID NO: 12 said region selected from the group consisting of a 5'-noncoding region, an intron, a 3'-non-coding region and contiguous coding and non-coding sequence region of SEQ ID NO:12, or reverse strand of said regions and
   (c) incubating (a) and (b) under conditions promoting the isolation of said polynucleotide.

21. The polynucleotide according to claim 1, wherein said polynucleotide is DNA or RNA.

22. An isolated polynucleotide consisting of a 5'-noncoding region, a 3'-non-coding region or a contiguous coding and non-coding nucleic acid sequence region of SEQ ID NO:12, or reverse strand of said polynucleotide, wherein the 5'-non-coding region consists of nucleotides 14969-15540 of SEQ ID NO:12 and the 3'-noncoding region consists of nucleotides 1-13981 of SEQ ID NO:12, wherein the isolated polynucleotide is modified.

23. An isolated polynucleotide fragment of the isolated polynucleotide of claim 22, wherein said fragment is at least 500 nucleotides in length.

24. The method according to claim 19, wherein said polynucleotide is DNA or RNA.

25. The method according to claim 20, wherein said polynucleotide is DNA or RNA.

26. The polynucleotide of claim 6, wherein said polynucleotide is DNA or RNA.

27. The polynucleotide of claim 22, wherein said polynucleotide is DNA or RNA.

28. A kit comprising the polynucleotide of claim 22.

29. A nucleic acid construct comprising an isolated polynucleotide selected from the group consisting of (a) an isolated polynucleotide consisting of a nucleic acid sequence which is at least 99% identical to the polynucleotide shown in SEQ ID NO:12; (b) a polynucleotide fragment of (a) comprising at least nucleotides 13982-14971 of SEQ ID NO:12, wherein (a)-(b) encode a polypeptide which is at least 99% identical to SEQ ID NO:6 and has human tumor suppressing subtransferable candidate 4 (TSSC4) activity or (c) a reverse strand of the polynucleotides of (a) or (b).

30. A recombinant expression vector comprising the nucleic acid construct of claim 29.

31. A recombinant host cell comprising the nucleic acid construct of claim 29.

32. A kit comprising at least one of: (i) an isolated polynucleotide selected from the group consisting of (a) an isolated polynucleotide consisting of a nucleic acid sequence which is at least 99% identical to the polynucleotide shown in SEQ ID NO:12; (b) a polynucleotide fragment of (a) comprising at least nucleotides 13982-14971 of SEQ ID NO:12, wherein (a)-(b) encode a polypeptide which is at least 99% identical to SEQ ID NO:6 and has human tumor suppressing subtransferable candidate 4 (TSSC4) activity or (c) a reverse strand of the polynucleotides of (a) or (b), wherein said isolated polynucleotide is optionally labeled with a detectable substance, (ii) an isolated polynucleotide at least 50 nucleotides in length identical to a region of SEQ ID NO:12, said region selected from the group consisting of a 5'-non-coding region, a 3'-non-coding region and a contiguous coding and non-coding nucleic acid sequence region of SEQ ID NO:12 or reverse strand of said polynucleotide, wherein said isolated polynucleotide is optionally labeled with a detectable substance, or (iii) an isolated polynucleotide consisting of a 5'-non-coding region, a 3'-non-coding region or a contiguous coding and non-coding nucleic acid sequence region of SEQ ID NO:12 or reverse strand of said polynucleotide, wherein the 5'-non-coding region consists of nucleotides 14969-15540 of SEQ ID NO:12 and the 3'-noncoding region consists of nucleotides 1-13981 of SEQ ID NO:12, wherein said isolated polynucleotide is optionally labeled with a detectable substance.

* * * * *

UNITED STATES PATENT AND TRADEMARK OFFICE
CERTIFICATE OF CORRECTION

| | | Page 1 of 1 |
|---|---|---|
| PATENT NO. | : 8,722,865 B2 | |
| APPLICATION NO. | : 13/244468 | |
| DATED | : May 13, 2014 | |
| INVENTOR(S) | : Ryan | |

It is certified that error appears in the above-identified patent and that said Letters Patent is hereby corrected as shown below:

ON THE TITLE PAGE:

Item (73) (Assignee): Replace "Kyoger LLC" with -- Ryogen LLC, Suffern, NY --.

Signed and Sealed this
Twenty-second Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,722,865 B2  Page 1 of 1
APPLICATION NO. : 13/244468
DATED : May 13, 2014
INVENTOR(S) : Ryan It is certified that error appears in the above-identified patent and that said Letters Patent is hereby corrected as shown below:

ON THE TITLE PAGE, ITEM (54) AND IN THE SPECIFICATION, COLUMN 1, LINES 1-7:

(Title): Replace "ISOLATED GENOMIC POLYNUCLEOTIDE FRAGMENTS FROM THE PIS REGION OF ISOLATED GENOMIC POLYNUCLEOTIDE FRAGMENTS FROM THE PIS REGION OF CHROMOSOME 11 ENCODING HUMAN TUMOR SUPPRESSING SUB TRANSFERABLE CANDIDATE 4 (TSSC4)"
with
--ISOLATED GENOMIC POLYNUCLEOTIDE FRAGMENTS FROM THE p15 REGION OF CHROMOSOME 11 ENCODING HUMAN TUMOR SUPPRESSING SUBTRANSFERABLE CANDIDATE 4 (TSSC4)--.

Signed and Sealed this
Twenty-eighth Day of October, 2014

Michelle K. Lee
*Deputy Director of the United States Patent and Trademark Office*